United States Patent [19]

Wing

[11] Patent Number: 5,424,333

[45] Date of Patent: Jun. 13, 1995

[54] ANTHELMINTIC N'-SUBSTITUTED-N,N'-DISUBSTITUTED-HYDRAZINES

[75] Inventor: Keith D. Wing, Lansdale, Pa.

[73] Assignee: Rohm and Haas Company, Philadelphia, Pa.

[21] Appl. No.: 725,925

[22] Filed: Jul. 5, 1991

[51] Int. Cl.$^6$ ............................................ A61K 31/165
[52] U.S. Cl. ...................... 514/615; 514/338; 514/346; 514/353; 514/357; 514/599
[58] Field of Search ............... 514/615, 338, 346, 353, 514/357, 599

[56] References Cited

U.S. PATENT DOCUMENTS

| | | | |
|---|---|---|---|
| 3,481,972 | 12/1969 | Trepanier | 260/468 |
| 3,518,327 | 6/1970 | Fearing | 260/923 |
| 3,636,112 | 1/1972 | Draber et al. | 260/556 B |
| 3,699,111 | 10/1972 | Kaugars | 260/296 R |
| 3,705,928 | 12/1972 | Stolzer et al. | 260/923 |
| 3,721,740 | 3/1973 | Folz | 424/327 |
| 3,721,742 | 3/1973 | Folz | 424/327 |
| 3,809,703 | 5/1974 | Kaugars | 260/332.5 |
| 3,821,261 | 6/1974 | Kaugars | 260/347.7 |
| 3,824,233 | 7/1974 | Friedman | 260/240 G |
| 3,897,559 | 7/1975 | Friedman | 424/275 |
| 4,357,351 | 11/1982 | Fancher et al. | 424/326 |
| 4,564,611 | 11/1986 | Stähler et al. | 514/99 |

FOREIGN PATENT DOCUMENTS 254461 1/1988 European Pat. Off. .

OTHER PUBLICATIONS

*Chemical Abstracts* 84(21): 150–168; (1976).
24 *Journal of Medicinal Chemistry*, 532–538 (1981).

*Primary Examiner*—Marianne M. Cintins
*Assistant Examiner*—William R. A. Jarvis
*Attorney, Agent, or Firm*—Thomas D. Rogerson

[57] ABSTRACT

This invention relates to the anthelmintic use of compositions containing N'-substituted-N,N'-disubstitutedhydrazines. Specifically, the invention relates to methods of controlling helminths by contacting the helminths with a compound having a nucleus of the formula

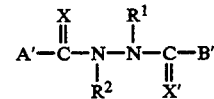

wherein X and X' are the same or different O, S, or NR and A', B', R$^1$ and R$^2$ are a variety of substituents.

14 Claims, 6 Drawing Sheets

ANTHELMINTIC N'-SUBSTITUTED-N,N'-DISUBSTITUTEDHYDRAZINES

BACKGROUND OF THE INVENTION

This application is a continuation of application Ser. No. 07/208,339, filed Jun. 16, 1988, now abandoned, which is a continuation-in-part of application Ser. No. 384,079, filed Jul. 17, 1989, now abandoned, which is a continuation of Ser. No. 91,687, filed Aug. 31, 1987, now abandoned, which is continuation-in-part of application Ser. No. 911,177, filed Sep. 24, 1986, now abandoned, which is a continuation-in-part of application Ser. No. 789,797, filed Oct. 21, 1985, now U.S. Pat. No. 4,985,461, application Ser. No. 858,482, filed May 1, 1986, now abandoned; application Ser. No. 24,660, filed Mar. 11, 1987, now abandoned, which is a continuation-in-part application of application Ser. No. 821,187, filed Jan. 22, 1986, now abandoned; application Ser. No. 207,081, filed Jun. 15, 1988, now abandoned, which is a continuation in part of Ser. No. 5,824, filed Feb. 4, 1987, now abandoned, which is a continuation-in-part of application Ser. No. 835,073, filed Feb. 28, 1986, now abandoned and a continuation-in-part of application Ser. No. 12,380, filed Feb. 19, 1987, now U.S. Pat. No. 5,354,762, which is a continuation-in-part application of application Ser. No. 885,508, filed Jul. 14, 1986, now abandoned; and application Ser. No. 911,928, filed Sep. 26, 1986, now abandoned, which are incorporated by reference.

This invention relates to methods of controlling helminths by contacting the helminths with a N'-substituted-N,N'-disubstitutedhydrazine.

Several hundred million people and animals suffer from helminth infections which are generally not fatal but lead to extreme disability and associated loss of productivity and population vigor. In third world countries, where these diseases pose the greatest problem, the greatest barriers to prevention are ignorance, cultural practices and poor sanitation. However, another shortcoming is the lack of effective chemotherapeutic agents which are both efficacious, safe and inexpensive enough for mass treatments.

The following is a summary of the most important helminthic diseases afflicting man.

| Disease | Organism |
|---|---|
| Bilharziosis or schistosomiasis | *Schistosoma mansoni* <br> *S. japonicum* <br> *S. haematobium* <br> (blood flukes, trematodes) |
| Ancyclostomiasis | *Necator americanus* <br> *Ancylostoma duodenale* <br> (hookworms, nematodes) |
| Ascariasis | *Ascaris lumbricoides* <br> (roundworms, nematodes) |
| Filariasis or elephantiasis | *Wuchereria bancrofti* <br> *Brugia malayi* <br> (nematodes) |
| Onchoceriasis or river blindness | *Onchocerca volvulus* <br> (nematodes) |
| Loiasis | *Loa loa* <br> (eyeworks, nematodes) |

There are a number of drugs used to treat these and related infections in both man and animal. The more common drugs are summarized below.

| Compound | Structure | Disease |
|---|---|---|
| Metrifonate | $(CH_3O)_2\overset{\underset{\|}{O}}{P}CHOHCCl_3$ | Schistosomiasis |
| Oxamniquine | [structure: 6-hydroxymethyl-7-nitro-1,2,3,4-tetrahydroquinoline with CH₂NHCH(CH₃)₂ substituent] | Schistosomiasis |
| Praziquantel | [structure: cyclohexylcarbonyl-tetrahydroisoquinoline-pyrazinone] | Schistosomes, many cestodes and trematodes |
| Mebendazole | [structure: benzoyl-benzimidazole with NHC(O)OCH₃] | Pinworms Hookworms Trichurid Roundworms Echinococcus Trematodes |

-continued

| Compound | Structure | Disease |
| --- | --- | --- |
| Pyrantel pamoate | 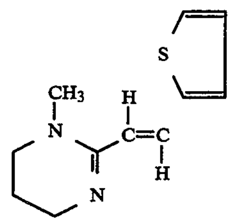 | Ascaris<br>Pinworm |
| Diethylcarbamazine | 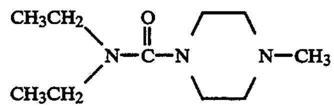 | Filariasis<br>Onchoceriasis<br>Loiasis |
| Niridazole | 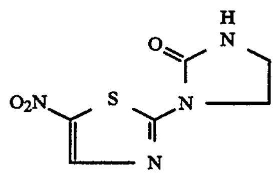 | Schistosomiasis<br>Dracunculinsis |
| Thiabendazole | 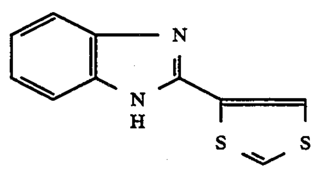 | Strongyloides<br>Trichostrongyl<br>Iasis Cutaneous<br>Larvamigrans<br>Trichinosis<br>Enterobiasis<br>Ascaris |
| Niclosamide | 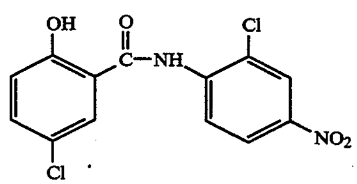 | Diphylobothrium<br>Hymenolepis<br>Cestodes<br>Enterobiasis<br>Dipylidia<br>Tuenia |
| Bunamidine | 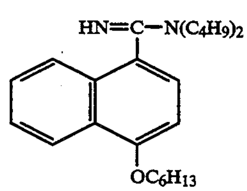 | Dipylidium<br>Taenia<br>Echinococcus |
| Fospirate | 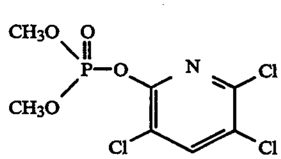 | Echinococcus |
| Albendazole | 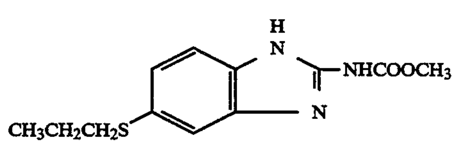 | Cestodes |
| Fenbendazole | 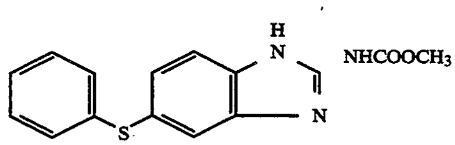 | Nematodes |

| Compound | Structure | Disease |
|---|---|---|
| Dichlorophen | (two phenol rings with OH, joined by CH₂, each with Cl) | Dipylidium Taenia Echinococcus |
| Arecoline | N-methyl tetrahydropyridine-3-carboxylic acid methyl ester | Dipylidium Taenia Echinococcus |
| Bithionol | (two phenol rings with OH, joined by S, each with 2 Cl) | Echinococcus Trematodes |
| Dichlorvos | $(CH_3O)_2P(O)-O-CH=CCl_2$ | Nematodes |
| Disophenol | 2,6-diiodo-4-nitrophenol | Nematodes |
| Tetrachoroethylene | $Cl_2C=CCl_2$ | Nematodes |
| n-Butylchloride | $CH_3CH_2CH_2CH_2Cl$ | Nematodes |
| Clioxanide | (diiodo-acetoxy-benzamide with 4-chlorophenyl) | Trematodes |
| Diamphenethide | $CH_3CONH-C_6H_4-OCH_2CH_2OCH_2CH_2O-C_6H_4-NHCOCH_3$ | Trematodes |
| Menichlopholan | (biphenyl with Cl, HO, NO₂, NO₂, OH, Cl substituents) | Trematodes |
| Rafoxanide | (diiodo-hydroxy-benzamide linked to chloro-(4-chlorophenoxy)phenyl) | Trematodes |

Apart from these recommended drugs, other alternative agents exist. Antimony complexes were commonly used for schistosomiasis, but they are quite toxic. Piperazine is useful only on Ascaris and has mild side effects.

Bephenium is a nicotinic agonist and is only moderately effective on hookworm. The avermectins are by far the most powerful antiparasitics known; on Onchocerus volvulus 50 ug/kg is enough to cause dramatic reduction of microfilaria. They are also effective against Ascaris. However, they are inactive against flukes and tapeworms and the cost of their production by fermentation may make them impractical for third world use.

Certain hydrazine derivatives have been disclosed in the literature. However, none of the prior art literature suggests hydrazine derivatives having insect growth regulating characteristics.

U.S. Pat. No. 3,481,972 discloses 2-(beta-hydroxyethyl)-2-methyl acid hydrazine compounds of the formula ZC(O)NHN(CH₃)CH₂CH₂OH where Z represents furyl, cyclohexyl, phenyl, benzyl, styryl, dihydrostyryl or substituted phenyl. The compounds are stated to be useful as pesticides for the control of such organisms as insects, arachnids, nematodes, fungi, plants and helminth organisms.

U.S. Pat. No. 4,357,351 discloses five specific compounds (Compound Nos. 400 and 402-404) of the formula

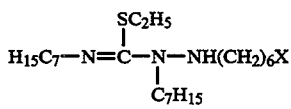

where X is —NCO, —NHC(O)N(CH₂CH₂OH)₂, —NHC(O)(CH₂)₁₁CH₃, —NHC(O)OCH₂CH₂(OCH₂CH₂)ₙOH and

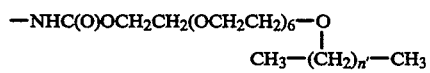

where n averages 7.7 and n' averages 11. These compounds are disclosed to have leptericidal activity. However, they are not claimed and it is not seen how these five compounds are included in the generic formula disclosed in the patent.

U.S. Pat. No. 4,564,611 discloses (di)thiophosphoric and -phosphonic acid derivatives having the formula

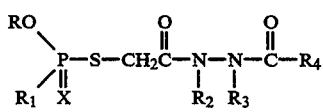

in which R denotes ($C_1$-$C_4$)alkyl; $R_1$ denotes ($C_1$-$C_4$)alkyl, ($C_1$-$C_4$)alkoxy, ($C_1$-$C_4$)alkylmercapto, ($C_1$-$C_4$)alkylamino or di($C_1$-$C_4$)alkylamino; $R_2$ and $R_3$ independently of one another denote hydrogen, ($C_1$-$C_4$)alkyl, ($C_5$-$C_6$)cycloalkyl, benzyl or furylmethyl; $R_4$ denotes ($C_1$-$C_4$)alkyl, ($C_1$-$C_3$)alkoxymethyl, ($C_1$-$C_3$)alkylmercaptomethyl or phenyl and X denotes oxygen or sulfur, which have activity against sucking and biting insects, acarides and nematodes and display good fungicidal activity. Insect growth regulating activity is not disclosed. Further, $R_2$ is not taught to include a tertiary carbon.

The Chemical Abstracts citation CA 84(21):150168j indicates that *Azerb Khim Zh*, 1975, (5), 47-48 discloses Me₂CHCH₂CH=NN(Ac)CH₂CH₂OH, PhCH=NN(Ac)CH₂CH₂OH and Me₂CHCH=NN(Ac)CH₂CH₂OH which have pesticidal activity.

Related U.S. Pat. Nos. 3,699,111, 3,809,703 and 3,821,261 disclose certain heterocyclic acid chloride phenylhydrazones having utility as insecticides, miticides, herbicides, anti-inflammatories and anthelmintics and having the formula

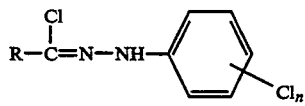

where R is furyl, thienyl or pyridyl and n is 0 to 3.

Related U.S. Pat. Nos. 3,824,233 and 3,897,559 disclose cinnamoyl and thiopheneacryloyl chloride phenylhydrazones, useful as anthelmintics and having the formula

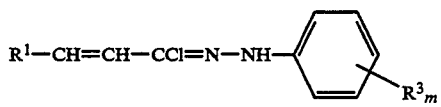

where $R^1$ is phenyl or thienyl; $R^3$ is alkyl, alkoxy, halo, cyano, nitro, trifluoromethyl or two $R^3$ may be taken together to form a methylenedioxy; and m is 0 to 2.

24 *Journal of Medicine Chemistry*, 532-538 (1981), discloses numerous acid chloride phenylhydrazones including a variety of substitutions in the phenyl rings and chloride variations. These compounds have utility as anthelmintics.

SUMMARY OF THE INVENTION

In accordance with the present invention, helminths are controlled by contacting the helminths with a compound having the nucleus of the formula:

where N is nitrogen; where E is an organic or organometallic radical having at least three atoms other than hydrogen and is attached to the nitrogen shown in the formula by a carbon-to-nitrogen single bond; where one $G_1$ is carbon, nitrogen, oxygen or sulfur, and both $G_2$'s and the other $G_1$ are carbon; or one $G_2$ is sulfur or phosphorous, and both $G_1$'s and the other $G_2$ are carbon; where the bond shown as --- is a single or double bond; where an organic radical is a radical comprising at least one carbon atom, but no metal atoms; and where an organometallic radical is a radical containing a carbon-to-metal bond; or a biologically acceptable salt thereof. Preferably, E is a tertiary carbon containing organic radical, and both $G_1$ and $G_2$ are carbon. Most preferably, E is t-butyl and both $G_2$'s are carbon double bonded to oxygen.

DETAILED DESCRIPTION OF THE INVENTION

Figure 1A:
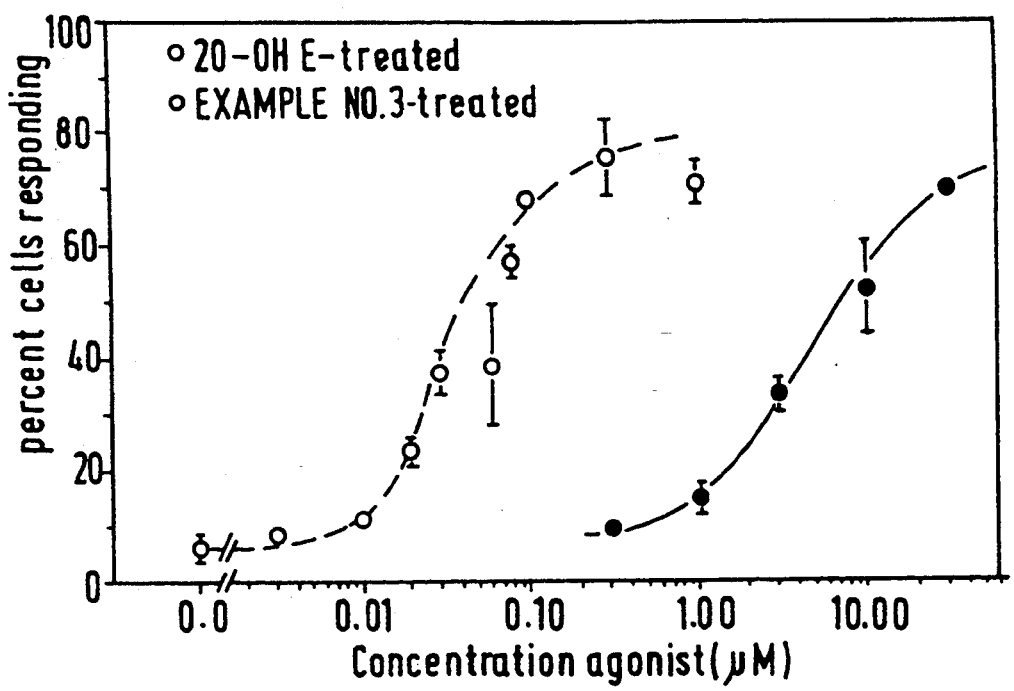
FIG. 1. Both 20-hydroxyecdysone and Example No. 3 induce process elaboration (A) and inhibition of cell proliferation (B) in $K_c$ cells in a dose-dependent manner. Initial cell density was $2 \times 10^6$ cells/ml; after incubation of 1 ml aliquots of the cells with the compound for 48 hours the cells were triturated gently and the percentage of cells responding (with processes longer than approximately 17 μm, see Cherbas et al. 189 Wilhelm Roux's Arch. 1 (1980)) and total cell density was determined by hemocytometer counting, relative to ethanol (1 μl)-treated controls. Determinations were in triplicate for each dose. Data are means ±S.D. For 20-hydroxyecdysone $EC_{50}=0.035$ μM, while for Example No. 3 $EC_{50}=4.8$ μM.

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and where indicated higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "cyanoalkyl" by itself or as part of another group is an alkyl group of the stated number of carbon atoms having one or more cyano groups bonded thereto; "haloalkoxy" by itself or as part of another group is an alkoxy group of the stated number of carbon atoms having one or more halo atoms bonded thereto such as difluoromethoxy, trifluoromethoxy, 2-fluoroethoxy, 2,2,2-trifluoroethoxy and the like. "Alkenyl" and "alkynyl" by themselves or as part of another substituent comprise straight and branched chain groups of the stated number of carbon atoms. "Alkadienyl" is a straight or branched chain alkenyl group comprising two carbon-to-carbon double bonds that can be conjugated such as 1,3-butadienyl, cumulated such as 1,2-propadienyl or isolated such as 1,4-pentadienyl.

The term "organic radical" should be understood to mean a radical comprising at least one carbon atom but no metal atoms. Examples of organic radicals include alkyl, alkenyl, alkynyl, cycloalkyl, cycloalkenyl, cycloalkynyl, aryl, heterocycles, esters, ethers, thio derivatives and amine derivatives.

The term "organometallic radical" should be understood to include radicals containing a carbon-to-metal bond. An example of such radicals include trimethylsilyl.

The term "tertiary carbon" is meant to refer to a carbon having at least three carbon-to-carbon single bonds.

The term "aryl" should be understood to include those molecules which have a ring structure characteristic of benzene, naphthalene, phenanthrene and anthracene, that is either the six-carbon ring of benzene or the condensed six-carbon rings of other aromatic derivatives. Examples of aryl radicals include unsubstituted and substituted phenyl, benzyl and naphthalene.

The term "cyclic aromatic radical" should be understood to mean unsaturated cyclic compounds including heterocyclic compounds. Examples of cyclic aromatic radicals include aryl, indolyl, thienyl, furyl, pyrrolyl, triazolyl and tetrazolyl.

Representative examples of six-membered heterocycles having one, two, three or four nitrogen atoms and two to five nuclear carbon atoms include 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 3-pyrazinyl, 2-(1,3,5-triazinyl), 3-(1,2,4-triazinyl), 5-(1,2,4-triazinyl), 6-(1,2,4-triazinyl), 4-(1,2,3-triazinyl) and 5-(1,2,3-triazinyl).

Representative examples of five-membered heterocycles include 2-furyl; 3-furyl; 2-thienyl; 3-thienyl; 4-(1,2,3-triazolyl); 3-(1,2,4-triazolyl); 5-(1,2,4-triazolyl); 2-pyrrolyl; 2-oxazolyl and the like.

Those N'-substituted-N,N'-diacylhydrazines of Formula I which possess acidic or basic functional groups may be further reacted to form novel salts with appropriate bases or acids. These salts also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula $NR^5R^6R^7R^8$ wherein each of $R^5$, $R^6$, $R^7$ and $R^8$ are independently hydrogen, hydroxy, $(C_1-C_4)$alkoxy, $(C_1-C_{20})$alkyl, $(C_3-C_8)$alkenyl, $(C_3-C_8)$alkynyl, $(C_2-C_8)$hydroxyalkyl, $(C_2-C_8)$alkoxyalkyl, $(C_2-C_6)$aminoalkyl, $(C_2-C_6)$haloalkyl, amino, $(C_1-C_4)$alkyl or $(C_1-C_4)$dialkylamino, substituted or unsubstituted phenyl, substituted or unsubstituted phenylalkyl, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When the $R^5$, $R^6$, $R^7$ or $R^8$ substituent in the ammonium group is a substituted phenyl or substituted phenylalkyl, the substituents on the phenyl and phenalkyl will generally be selected from halo, $(C_1-C_8)$alkyl, $(C_1-C_4)$alkoxy, hydroxy, nitro, trifluoromethyl, cyano, amino, $(C_1-C_4)$alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium and the like. Among the acid addition salts are those in which the anion is a biologically acceptable anion such as hydrochloride, hydrobromide, sulfate, nitrate, perchlorate, acetate, oxalate and the like.

Helminths and arthropods (like insects and crustacea) are members of the Protostomia. However, helminths are not phylogenetically close to insects. There are two different phyla of helminths; the first are nematodes in phylum Nemathelminthes (e.g., intestinal roundworms, hookworms and worms causing elephantiasis and river blindness in humans; roundworms, hookworms, pinworms and heartworms in animals). The second are trematodes (e.g., schistosomes or blood flukes in humans and liver flukes of livestock) and cestodes (e.g., tapeworms of humans and animals), both of which belong to the phylum Plathelminthes.

For insects to successfully grow, that is progress from one larval stage to the next larger larval stage or metamorphose to an adult stage, they must moult or shed the old cuticle. The natural occurring hormones ecdysone or 20-hydroxyecdysone induce the molting. Compounds of this invention are insect growth regulators in that they interfere with this natural moulting and other growth-regulated processes.

Growth regulatory effects are not usually expressed rapidly after treatment. This is contrary to conventional insecticides, such as neurotoxins, respiratory poisons and the like, which affect vital processes and which are noted for rapidity of effect.

For example, compounds such as:

where
- $R^1$ = lower alkyl, alkoxy, thioalkyl and may be identical or different
- $X$ = O or S, $n$ = 0–5 and $R''$ = t-butyl would constitute conventional, fast-acting, cholinesterese-inhibiting neurotoxins with efficacy anticipated against a comparatively broad range of insect orders and acarides as well as non-target organisms such as mammals, fish and birds. By contrast insect growth regulators, as claimed herein, would be somewhat less rapid in effect.

The following parameters are important to yield compounds having the nucleus of Formula Ia which are insect growth regulators. At least one of the moieties attached to one of the $G_1$'s should have at least some bulk, i.e., at least two or three non-hydrogen atoms. However, if the bulk becomes too great, the compounds become less effective as insect growth regulators. Therefore, the moieties attached to the $G_1$'s should be no greater than about 21 non-hydrogen atoms.

The size of the moiety E of Formula I is important. E should have at least 4 non-hydrogen atoms. Oxygen containing radicals have been found to be generally not preferred. If oxygen is present, generally E should be bulkier. Moieties containing two oxygen atoms or one oxygen and one sulfur atom are less preferred. It is preferred that E have no greater than 10 non-hydrogen atoms. Preferably, E does not include a chain of greater than four or five non-hydrogen atoms but is highly branched.

The compounds of this invention or their precursors can be prepared according to the following processes. Process A can be used when preparing compounds according to Formula II below where X and X' are both oxygen and A and B are the same (i.e., both A and B are phenyl or 4-chlorophenyl) or different (i.e., A is 4-methylphenyl and B is 4-chlorophenyl).

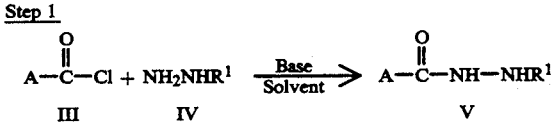

wherein
A and B are organic radicals attached to the carbon shown in Formula II by a carbon-to-carbon single bond and $R^1$ is other than hydrogen.

Process A:
Step 1

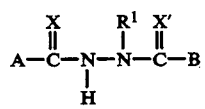

Step 2

Process A:

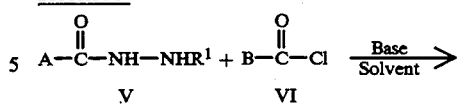

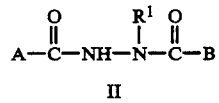

where $R^1$, A and B are as defined above for Formula II and X and X' are oxygen.

When $R^1$ is cyano substituted alkyl, the intermediate Va may be made as follows:

Step 1a

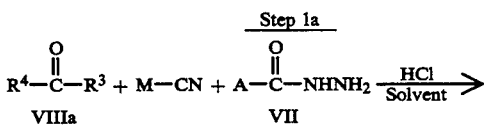

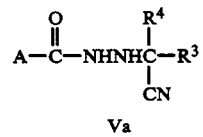

where M is K or Na, X and X' are oxygen, A and B are as defined above for Formula II, and $R_3$ and $R_4$ are the same or different hydrogen or ($C_2$–$C_9$) straight or branched chain unsubstituted or substituted alkyl having one or two of the same or different ($C_3$–$C_6$)cycloalkyl.

Process B can be used when preparing compounds according to Formula II where X and X' are oxygen, and $R^1$, A and B are as defined above for Formula II.

Process B:
Method 1

Step 1

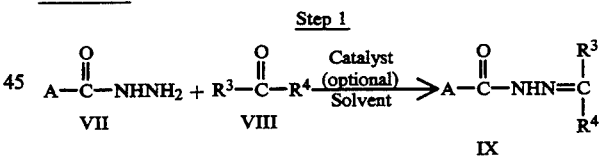

Step 2

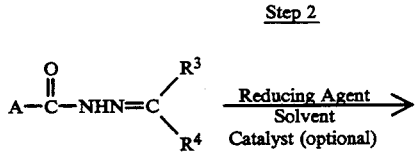

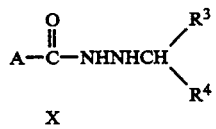

Step 3

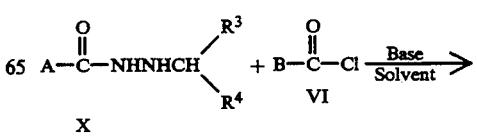

Process B:
Method 1

$$A-\underset{\substack{\|\\O}}{C}-NHN-\underset{\substack{\|\\O}}{\overset{R^3\ H\ R^4}{\underset{|}{C}}}-B$$

XI where X and X' are oxygen, A and B are as defined above for Formula II, and $R^3$ and $R^4$ are the same or different hydrogen or ($C_2$-$C_9$) straight or branched chain unsubstituted or substituted alkyl having one or two of the same or different ($C_3$-$C_6$)cycloalkyl. As can be seen above, the intermediate product of Step 2, the compounds of Formula X, corresponds to the compounds of Formula V. In addition, the compound of Formula XI corresponds to the compounds of Formula II where X and X' are oxygen.

Method 2

$$A-\underset{\substack{\|\\O}}{C}-W + H_2N-\underset{R^1}{\overset{|}{N}}-\underset{\substack{\|\\O}}{C}-B \xrightarrow{\text{Base}}{\text{Solvent}}$$

XII         XIII $$A-\underset{\substack{\|\\O}}{C}-\underset{H}{\overset{|}{N}}-\underset{R^1}{\overset{|}{N}}-\underset{\substack{\|\\O}}{C}-B$$

II or $$A-\underset{\substack{\|\\O}}{C}-\underset{H}{\overset{|}{N}}-NHR^1 + W-\underset{\substack{\|\\O}}{C}-B \xrightarrow{\text{Base}}{\text{Solvent}}$$

XIIIa         XII $$A-\underset{\substack{\|\\O}}{C}-\underset{H}{\overset{|}{N}}-\underset{R^1}{\overset{|}{N}}-\underset{\substack{\|\\O}}{C}-B$$

II where $R^1$, A and B are as defined above for Formula II and W is a good leaving group such as halo, for example, chloro; an alkoxy, for example, ethoxy; methyl sulfonate (—$OSO_2CH_3$); or an ester, for example, acetate (—$OC(O)CH_3$).

Process C can be used when preparing compounds according to Formula II where A, B, and $R^1$ are as defined for Formula II and one or both X and X' are sulfur.

Process C:
Step 1:

$$A-\underset{\substack{\|\\X}}{C}-Y + NH_2NHR^1 \xrightarrow{\text{Base}}{\text{Solvent}} A-\underset{\substack{\|\\X}}{C}-\underset{H}{\overset{|}{N}}-\underset{R^1}{\overset{|}{N}H}$$

XIV      IV          XV

Step 2:

$$A-\underset{\substack{\|\\X}}{C}-\underset{H}{\overset{|}{N}}-NH + B-\underset{\substack{\|\\X'}}{C}-Y \xrightarrow{\text{Base}}{\text{Solvent}} A-\underset{\substack{\|\\X}}{C}-\underset{H}{\overset{|}{N}}-\underset{R^1}{\overset{|}{N}}-\underset{\substack{\|\\X'}}{C}-B$$

XV            XVI              II where A, B and $R^1$ are as defined for Formula II and one or both X and X' are sulfur, and Y is a good leaving group such as carboxyalkylthio, for example, carboxymethylthio and —$SCH_2CO_2H$; alkylthio, for example, methylthio; or halo, for example, chloro.

Process D can be used when preparing compounds according to Formula II where X and X' are oxygen and $R^1$, A and B are as defined above for Formula II.

Process D:
Step 1

$$NH_2NHR^1 + (Z-O)_2C=O \xrightarrow{\text{Base}}{\text{Solvent}} Z-O-\underset{\substack{\|\\O}}{C}-NHNHR^1$$

IV         XVII                    XVIII

Step 2

$$Z-O-\underset{\substack{\|\\O}}{C}-NHNHR^1 + B-\underset{\substack{\|\\O}}{C}-Cl \xrightarrow{\text{Base}}{\text{Solvent}}$$

XVIII                  VI $$Z-O-\underset{\substack{\|\\O}}{C}-NHN-\underset{\substack{\|\\O}}{\underset{R^1}{\overset{|}{C}}}-B$$

XIX

Step 3

$$Z-O-\underset{\substack{\|\\O}}{C}-NH-\underset{R^1}{\overset{|}{N}}-\underset{\substack{\|\\O}}{C}-B \xrightarrow{\text{Acid}}{\text{Solvent}} NH_2\underset{R^1}{\overset{|}{N}}-\underset{\substack{\|\\O}}{C}-B$$

XIX                                XX

Step 4

$$A-\underset{\substack{\|\\O}}{C}-Cl + NH_2\underset{R^1}{\overset{|}{N}}-\underset{\substack{\|\\O}}{C}-B \xrightarrow{\text{Base}}{\text{Solvent}} A-\underset{\substack{\|\\O}}{C}-\underset{H}{\overset{|}{N}}-\underset{R^1}{\overset{|}{N}}-\underset{\substack{\|\\O}}{C}-B$$

III         XX                            II wherein A, B and $R^1$ are as defined above for Formula II and Z is t-butyl; ethyl; phenyl or benzyl.

The starting materials for each process are generally commercially available, or can be prepared generally by customary and known methods.

Other compounds of this invention, or their precursors, can be prepared by reacting a suitably substituted hydrazine (Formula II) with an alkyl halide, allyl halide or phenylmethylhalide in the presence of a base in an inert or substantially inert solvent or mixture of solvents according to the following process:

$$A-\underset{\substack{\|\\X}}{C}-\underset{H}{\overset{|}{N}}-\underset{R^1}{\overset{|}{N}}-\underset{\substack{\|\\X'}}{C}-B + R^2-Hal \xrightarrow{\text{Base}}{\text{Solvent}}$$

II                      XXI

-continued

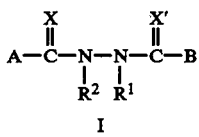

where X, X', R¹,R², A and B are as defined above for Formula II and Hal is halogen (chloro, fluoro or bromo).

Suitable bases for use in the above process include metal hydrides such as sodium hydride or potassium hydride; metal alkoxides such as sodium alkoxides or potassium alkoxides; sodium hydroxide; potassium hydroxide or lithium diisopropyl amide. If desired, mixtures of these bases may be used. The preferred base is potassium t-butoxide.

Suitable solvents for use in the above process include ethers such as tetrahydrofuran (THF), glyme and the like; dimethylformamide (DMF); dimethylsulfoxide (DMSO); acetonitrile or a mixture of water and benzene or toluene. If desired, mixtures of these solvents may be used. The preferred solvent is dimethylformamide.

The above process can be carried out at temperatures between about −20° C. and about 100° C. Preferably, this reaction is carried out between about −5° C. and about 50° C.

Preparation of the compounds of the present invention by the above process is preferably carried out at about atmospheric pressure although higher or lower pressures can be used if desired.

Substantially equimolar amounts of reactants are preferably used although higher or lower amounts can be used if desired.

Generally, one equivalent of base is used per equivalent of starting material of Formula XXI.

The compounds of Formula XXI are generally commercially available or can be prepared by known procedures.

Modifications to the above process may be necessary to accommodate reactive functionalities of particular substitutents. Such modifications would be apparent and known to those skilled in the art.

In process A, a compound of Formula III is reacted with a monosubstituted hydrazine of Formula IV or a corresponding acid addition salt such as the hydrochloride salt or the like in the presence of a base in an inert or substantially inert solvent or mixture of solvents to afford an intermediate product of Formula V which can be isolated or further reacted with a compound of Formula VI in the presence of a base in an inert or substantially inert solvent or mixture of solvents to afford the desired product of Formula II.

When A and B are the same, for example, both A and B are 4-chlorophenyl, two equivalents of a compound of Formula III or VI are reacted with a monosubstituted hydrazine of Formula IV in the presence of a base in an inert or substantially inert solvent or mixture of solvents to afford the desired product of Formula II.

Examples of the compounds of Formula III and/or Formula VI which can be used in the above processes include benzoyl chloride, 4-chlorobenzoyl chloride, 4-methylbenzoyl chloride, 3,5-dichlorobenzoyl chloride, 2-bromobenzoyl chloride, 3-cyanobenzoyl chloride, 3-toluoyl chloride, 4-toluoyl chloride, 4-ethylbenzoyl chloride, 2-nitrobenzoyl chloride, 2,3-dimethylbenzoyl chloride, 2-nitro-5-toluoyl chloride, cyclohexylcarbonyl chloride, n-butanoyl chloride, n-pentanoyl chloride, phenylacetyl chloride, 1-cyclohexenecarbonyl chloride, pivaloyl chloride, trichloroacetyl chloride, methacryloyl chloride and the like. The compounds of Formula III and/or Formula VI are generally commercially available or can be prepared by known procedures.

Examples of the compounds of Formula IV which can be used in the above processes include isopropylhydrazine, t-butylhydrazine, neopentylhydrazine, alpha-methylneopentylhydrazine, isobutylhydrazine, isopentylhydrazine, isooctylhydrazine, 1,1-dimethyl-3-butenylhydrazine, (trimethylsilylmethyl)hydrazine, (1,1,1-trifluoro-2-propyl)hydrazine, (2,2,2-trifluoroethyl)hydrazine, (1-cyano-1-methyl)ethylhydrazine and the like. The compounds of Formula IV are generally commercially available or can be prepared by known procedures. For example, the Grignard reagent addition product of acetone azine in diethyl ether is hydrolyzed by the addition of an acid (such as oxalic acid), in a suitable solvent or mixture of solvents (such as ethanol and diethyl ether, 1:1) to afford the monosubstituted hydrazine of Formula IV.

Suitable solvents for use in the above processes include water; alcohols such as methanol, ethanol, isopropanol and the like; hydrocarbons such as toluene, xylene, hexane, heptane and the like; glyme; tetrahydrofuran; acetonitrile; pyridine or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide or potassium hydroxide. Preferred bases are sodium hydroxide, potassium hydroxide or triethylamine.

In Process B, Method 1, a compound of Formula VII is reacted with a ketone or aldehyde of Formula VIII in an inert or substantially inert solvent or mixture of solvents and optionally in the presence of a catalyst to afford an intermediate product of Formula IX. The intermediate product of Formula IX is then further reacted with a reducing agent in an inert or substantially inert solvent or mixture of solvents to afford a second intermediate product of Formula X which can be isolated or further reacted with a compound of Formula VI in the presence of a base in an inert or substantially inert solvent or mixture of solvents to afford the desired product of Formula XI.

Examples of the compounds of Formula VII which can be used in the above Process B, Method 1, include benzoylhydrazine, 4-chlorobenzoylhydrazine, 2-methylbenzoylhydrazine, 4-methylbenzoylhydrazine, 3,5-dichlorobenzoylhydrazine and the like. The compounds of Formula VII are generally commercially available or can be prepared by known procedures.

Examples of the compounds of Formula VIII which can be used in the above Process B, Method 1, include 1,1,1-trimethylacetaldehyde, methylethylketone, diethylketone, trifluoroacetone, methacrolein, ethyl pyruvate and the like. The compounds of Formula VIII are generally commercially available or can be prepared by known procedures.

Optionally, a catalyst may be used in Step 1, Method 1, of Process B. Suitable catalysts generally include organic acids such as acetic acid, trifluoroacetic acid, oxalic acid and the like; mineral acids such as hydrochloric acid, sulfuric acid, nitric acid and the like; arylsulfonic acids such as toluenesulfonic acid or pyridinium toluenesulfonate. Preferred catalysts are organic acids or arylsulfonic acids. Most preferred catalysts are acetic acid or trifluoroacetic acid.

Suitable solvents for use in the above Process B, Method 1, Step 1, include alcohols such as methanol, ethanol, isopropanol and the like; hydrocarbons such as toluene and benzene; ethers such as tetrahydrofuran (THF), glyme and the like or dimethylformamide. Preferred solvents are alcohols and hydrocarbons. Most preferred solvents are alcohols such as methanol or ethanol.

Examples of suitable reducing agents for use in the above Process B, Method 1, Step 2, include hydrides such as sodium borohydride and derivatives thereof such as sodium cyanoborohydride, lithium aluminum hydride and derivatives thereof and the like or diborane. Preferred reducing agents are sodium borohydride and derivatives thereof or lithium aluminum hydride and derivatives thereof. Most preferred as reducing agents are borane and diborane.

Optionally, in Process B, Method 1, Step 2, a catalyst may be included. Examples of suitable catalysts include organic acids such as acetic acid, trifluoroacetic acid; or mineral acids such as hydrochloric acid, sulfuric acid and the like. Preferred catalysts are organic acids or hydrochloric acid. Most preferred catalysts are acetic acid, trifluoroacetic acid or hydrochloric acid.

Suitable solvents for use in the above Process B, Method 1, Step 2, include alcohols such as methanol, ethanol, isopropanol and the like; ethers such as tetrahydrofuran (THF), diethylether, glyme and the like; or halohydrocarbons such as methylene chloride, chloroform and the like. Preferred solvents are alcohols and most preferred are methanol or ethanol.

Step 3 of Process B, Method 1, corresponds to Step 2 of Process A. Consequently, those bases and solvents suitable for use in Step 2 of Process A are suitable for use in Step 3, Method 1, of Process B including the preferred bases and solvents described above.

In Process B, Method 2, N'-substituted-N'-benzoylhydrazine of Formula XIII or N'-substituted-N-benzoylhydrazine of Formula XIIIa is reacted with a compound of Formula XII in the presence of a base in an inert or substantially inert solvent or mixture of solvents to afford the desired product of Formula II.

The compounds of Formula XII are generally commercially available or can be prepared from commerically available compounds by procedures well known to those skilled in the art as described below.

Examples of the compounds of Formula XIII which can be used in the above Process B, Method 2, include N'-t-butyl-N'-benzoylhydrazine; N'-t-butyl-N'-(3-methylbenzoyl)hydrazine; N'-t-butyl-N'-(4-chlorobenzoyl)hydrazine; N'-t-butyl-N'-(2-fluorobenzoyl)hydrazine; N'-isopropyl-N'-benzoylhydrazine; N'-neopentyl-N'-(4-chlorobenzoyl)hydrazine, N'-isopropyl-N-benzoylhydrazine; N'-sec-butyl-N-benzoylhydrazine; N'-(1-methyl)neopentyl-N-benzoylhydrazine; N'-neopentyl-N-benzoylhydrazine; N'-isobutyl-N-benzoylhydrazine; N'-(1,2,2-trimethylpropyl)-N-benzoylhydrazine; N'-diisopropylmethyl-N-benzoylhydrazine; N'-t-butyl-N-benzoylhydrazine; N'-t-butyl-N-(4-methylbenzoyl)hydrazine; N'-t-butyl-N-(4-chlorobenzoyl)hydrazine; N'(1,1-dimethyl-3-butenyl)-N'-benzoylhydrazine, N'-(trimethylsilylmethyl)-N'-(4-methylbenzoyl)hydrazine, N'-(1,1,1-trifluoro-2-propyl)-N'-(2,4-dichlorobenzoyl)-hydrazine, N'-(1-cyano-1-methyl)ethyl-N'-(2-methylbenzoyl)hydrazine and the like.

Suitable solvents for use in the above Process B, Method 2, include water; hydrocarbons such as toluene, xylene, hexane, heptane and the like; alcohols such as methanol, ethanol, isopropanol and the like; glyme; tetrahydrofuran; acetonitrile; pyridine; haloalkanes such as methylene chloride or mixtures of these solvents. Preferred solvents are water, toluene, methylene chloride or a mixture of these solvents.

Examples of bases suitable for use in the above Process C include tertiary amines such as triethylamine; pyridine; potassium carbonate; sodium carbonate; sodium bicarbonate; sodium hydroxide or potassium hydroxide. Preferred bases are sodium hydroxide or triethylamine.

The compounds of Formula XII are commercially available, such as nicotinoyl chloride hydrochloride, isonicotinoyl chloride hydrochloride and ethyl picolinate or can be prepared from commerically available materials by procedures known to those skilled in the art.

The compounds of Formula XIII can be prepared by procedures known to those skilled in the art from commercially available reactants. By way of example, a suitably substituted hydrazine (such as t-butylhydrazine or (1,1,1-trifluoro-2-propyl)hydrazine) is reacted with an aldehyde or ketone (such as acetone) in the presence of a base (such as triethylamine) to afford a hydrazone which is then reacted with a benzoyl chloride in an inert or substantially inert solvent or mixture of solvents in the presence of a base (such as sodium hydroxide) to afford an N'-substituted-N'-benzoylhydrazone which is then reacted with an acid (such as hydrochloric acid) to afford the compound of Formula XIII. Alternatively, a suitable substituted hydrazine (such as t-butylhydrazine or (trimethylsilylmethyl)hydrazine) is reacted with di-tertbutyldicarbonate in an inert or substantially inert solvent or mixture of solvents (such as toluene/water) to afford an N'-t-butyl-N-t-butoxycarbonylhydrazine or an N'-(trimethylsilylmethyl)-N-t-butoxycarbonylhydrazine which is then reacted with a benzoylchloride in an inert or substantially inert solvent or mixture of solvents to afford N'-t-butyl-N'-benzoyl-N-t-butoxycarbonylhydrazine or an N'-(trimethylsilylmethyl)-N'-benzoyl-N-t-butoxycarbonylhydrazine which is then reacted with an acid to afford the desired compound of Formula XIII.

In Process C, a compound of Formula XIV is reacted with a monosubstituted hydrazine of Formula IV or a corresponding acid addition salt such as the hydrochloride salt or the like in the presence of a base in an inert or substantially inert solvent or mixture of solvents to afford an intermediate compound of Formula XV which can be isolated or further reacted with a compound of Formula XVI in the presence of a base in an inert or substantially inert solvent or mixture of solvents to afford the desired product of Formula I.

In Process D, a monosubstituted hydrazine of Formula IV or a corresponding acid addition salt, such as the hydrochloride salt or the like, is reacted with a compound of Formula XVII in the presence of a base in an inert or substantially inert solvent or mixture of solvents to afford an intermediate product of Formula XVIII. The intermediate product of Formula XVIII is then further reacted with a compound of Formula VI in the presence of a base in an inert or substantially inert solvent or mixture of solvents to afford a second intermediate product of Formula XIX. The second intermediate product of Formula XIX is then further reacted with an acid in an inert or substantially inert solvent or mixture of solvents to afford a third intermediate product of Formula XX. The third intermediate product of Formula XX is then further reacted with a compound of Formula III in the presence of a base in an inert or substantially inert solvent or mixture of solvents to afford the desired product of Formula II.

Examples of the compounds of Formula XVII which can be used in the above Process D include di-t-butyldicarbonate, diethyldicarbonate, diphenyldicarbonate, dibenzyldicarbonate and the like. The compounds of Formula XVII are generally commercially available or can be prepared by known procedures.

Suitable solvents for use in the above Process D, Steps 1, 2 and 4, include water; tetrahydrofuran; dioxane; toluene; alcohols such as methanol, ethanol and isopropanol; hexane; acetonitrile; pyridine and haloalkanes such as methylene chloride or mixtures of these solvents.

Preferred solvents are dioxane; toluene; tetrahydrofuran; pyridine; methylene chloride or water.

Most preferred solvents are dioxane; water or toluene.

Examples of the bases for use in the above Process D, Steps 1, 2 and 4, include tertiary amines such as triethylamine; pyridine; potassium carbonate, sodium carbonate; sodium bicarbonate; sodium hydroxide and potassium hydroxide.

Preferred bases are sodium hydroxide; potassium hydroxide; pyridine or triethylamine.

Suitable solvents for use in the above Process D, Step 3, include alcohols such as methanol, ethanol and isopropanol; water; tetrahydrofuran; dioxane and acetonitrile.

Preferred solvents are methanol or ethanol.

Examples of acids for use in the above Process D, Step 3, include concentrated hydrochloric acid or concentrated sulfuric acid.

When A and B are the same, for example, both A and B are unsubstituted phenyl, two equivalents of a compound Formula XIV or XVI are reacted with a monosubstituted hydrazine of Formula IV in the presence of a base in an inert or substantially inert solvent or mixture of solvents to afford the desired product of Formula II.

Examples of the compounds of Formula XIV and/or Formula XVI which can be used in the above Process C include 3-methyl-methylthio-thiobenzoate, 4-chloromethylthio-thiobenzoate, 4-methyl-methylthio-thiobenzoate, carboxymethylthio-thiobenzoate and the like. The compounds of Formula XIV and/or Formula XVI are generally commercially available or can be prepared by known procedures.

Suitable solvents for use in the above Process C are generally polar high-boiling solvents such as dimethylformamide (DMF); glyme; tetrahydrofuran (THF) and pyridine. The preferred solvent is pyridine.

Suitable bases for use in the above Process C include tertiary amines such as triethylamine and pyridine. The preferred base is pyridine.

The above Processes A and B, Method 1, can be carried out at temperatures between about $-20°$ C. and about $100°$ C. Preferably, these reactions are carried out between about $-5°$ C. and about $50°$ C.

The above Process B, Method 2, can be carried out at temperatures between about $-50°$ C. and about $150°$ C. Preferably when W is a halo radical, the reaction is carried out between about $0°$ C. and about $30°$ C. When W is alkoxy, the reaction is preferably carried out between about $100°$ C. and about $150°$ C. When W is methyl sulfonate, the reaction is preferably carried out between about $-20°$ C. to about $20°$ C. When W is an ester, the reaction is preferably carried out between about $0°$ C. and about $50°$ C.

Process C can be carried out at temperatures between about $10°$ C. and $200°$ C. Preferably, this reaction is carried out between about $70°$ C. and about $100°$ C.

Process D can be carried out at temperatures between about $0°$ C. and $100°$ C. Preferably, these reactions are carried out between about $0°$ C. and about $50°$ C.

Preparation of the compounds of the present invention by processes A, B, C and D are preferably carried out at about atmospheric pressure, although higher or lower pressures can be used if desired.

Substantially equimolar amounts of reactants are preferably used in processes A, B and C, although higher or lower amounts can be used if desired.

Generally, about one equivalent of base is used per equivalent of starting material of Formula III, VI, XII and/or XIV. Where the acid addition salt of the monosubstituted hydrazine of Formula IV is used, one additional equivalent of base is used. For example, in Process A, when substituents A and B are the same and a monosubstituted hydrazine is used, about two equivalents of base are used since about two equivalents of a suitably substituted benzoyl chloride of Formula III or VI are employed. In Process A, when substituents A and B are different and an acid addition salt of the monosubstituted hydrazines of Formula IV is used, about two equivalents of base are used in Step 1 and about one equivalent of base is used in Step 2.

Modifications to the above processes may be necessary to accommodate reactive functionalities of particular A and/or B substituents. Such modifications would be apparent and known to those skilled in the art.

It will be appreciated by those skilled in the art that electronic forces may give rise to more than one isomer of the compounds of Formula II such as enantiomers, conformers and the like. There may be a difference in properties such as physical characteristics and degree of biological activity between such isomers. Separation of a specific isomer can be accomplished by standard techniques well known to those skilled in the art such as silica gel chromatography.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide and the like. When amines are used as reagents, useful solvents include alcohols, such as methanol or ethanol; hydrocarbons, such as toluene, xylene, hexane and the like; tetrahydrofuran; glyme; dioxane or water. When ammonium salts are used as reagents, useful solvents include water; alcohols, such as methanol or ethanol; glyme; tetrahydrofuran or the like. When the ammonium salt is other than a hydroxide or alkoxide, an additional base, such as potassium or sodium hydroxide, hydride or alkoxide is generally used. The particular choice of solvent will depend on the relative solubilities of the starting materials and the resultant salts and slurries rather than solutions of certain reagents which may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acids with a compound of Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents which may be used to obtain the salts. Generally, equivalent molar amounts of starting materials are used and the salt-forming reaction is carried out at from about −10° C. to about 100° C., preferably at about room temperature.

N-t-alkyl-1,2-diacylhydrazines may be prepared by reacting a 1,3,4-oxadiazole with a tertiary alkyl cation precursor in the presence of a strong acid catalyst. The tertiary alkyl cation precursor may be an alcohol, ester, ether, halogen or olefin. The preferred tertiary alkyl cation precursor is an alcohol, acetate, benzoate, methyl ether, ethyl ether, chloride, bromide or olefin. The most preferred precursors are t-butanol, t-butylacetate, t-butylbenzoate, t-butylmethyl ether, t-butylethyl ether and isobutylene.

The strong acid catalyst must be strong enough to open the oxadiazole ring but not so strong as to dehydrate the hydrazine. Acids which include the acid anhydride in excess cause the product hydrazine to revert to the oxadiazole.

The preferred acid catalysts are sulfur containing acids and, more preferably, sulfuric acid. Although hydrogen chloride is a stronger acid than p-toluenesulfonic acid, hydrochloric acid was found not to catalyze the reaction under the conditions tested whereas the p-toluenesulfonic acid was an effective catalyst.

The reaction process is preferably carried out in the presence of a solvent such as a low molecular weight acid, ester, alcohol or ether. "Low molecular weight" is intended to include acids, esters, alcohols and ethers which are liquids at the reaction temperature. The preferred solvents are acetic acid, ethyl acetate, methylbenzoate and diethyl ether. The most preferred solvent is acetic acid.

Depending upon reactants, catalyst and solvent, the process may be carried out between −20° C. and 150° C. The process has been carried out between 0° C. and 118° C. The preferred temperature range is 15° C.–60° C. and the most preferred temperature range is 20° C.–30° C.

The following examples will further illustrate this invention but are not intended to limit it in any way. In Table I, some N'-substituted-N,N'-disubstitutedhydrazines of the present invention that have been made are listed. The structure of these compounds was confirmed by NMR and in some cases by IR and/or elemental analysis. Specific illustrative preparation of the compounds of Examples 1, 3, 16, 44, 102, 103, 148, 220, 295, 324, 625, 635, 636, 637, 638, 639, 642, 646, 648, 654, 656, 659, 660, 682, 683, 688, 689, 691, 699, 702, 722, 723, 724, 727, 729, 733, 737, 738, 739, 743, 754, 755, 764, 765, 766, 767, 772, 778, 787, 802, 809, 822, 829, 837, 853, 855, 864, 870 to 873, 878, 880, 882, 883, 893, 905, 914, 918, 922, 923, 933, 941, 942, 944, 948, 1002, 1008, 1013 and 1015 to 1018 are described after Table I.

TABLE I $$A-G_2 \begin{matrix} X & X' \\ | & | \\ N-N-G_2-B \\ | & | \\ R^2 & R^1 \end{matrix}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 1 | C(O) | C(O) | —C(CH$_3$)$_3$ | H | —C$_6$H$_4$Cl-4 | —C$_6$H$_4$Cl-4 |
| 2 | C(O) | C(O) | —C(CH$_3$)$_3$ | H | —C$_6$H$_4$Cl-3 | —C$_6$H$_4$Cl-3 |
| 3 | C(O) | C(O) | —C(CH$_3$)$_3$ | H | —C$_6$H$_5$ | —C$_6$H$_5$ |
| 4 | C(O) | C(O) | —C(CH$_3$)$_3$ | H | —C$_6$H$_3$Cl$_2$-3,4 | —C$_6$H$_3$Cl$_2$-3,4 |
| 5 | C(O) | C(O) | —C(CH$_3$)$_3$ | H | —C$_6$H$_4$CH$_3$-4 | —C$_6$H$_4$CH$_3$-4 |
| 6 | C(O) | C(O) | —C(CH$_3$)$_3$ | H | —C$_6$H$_4$NO$_2$-4 | —C$_6$H$_4$NO$_2$-4 |
| 7 | C(O) | C(O) | —C(CH$_3$)$_3$ | H | —C$_6$H$_4$OCH$_3$-4 | —C$_6$H$_4$OCH$_3$-4 |
| 8 | C(O) | C(O) | —C(CH$_3$)$_3$ | H | —C$_6$H$_4$NO$_2$-3 | —C$_6$H$_4$NO$_2$-3 |
| 9 | C(O) | C(O) | —C(CH$_3$)$_3$ | H | —C$_6$H$_4$OCH$_3$-3 | —C$_6$H$_4$OCH$_3$-3 |
| 10 | C(O) | C(O) | —C(CH$_3$)$_3$ | H | —C$_6$H$_4$NO$_2$-2 | —C$_6$H$_4$NO$_2$-2 |
| 11 | C(O) | C(O) | —C(CH$_3$)$_3$ | H | —C$_6$H$_4$Cl-2 | —C$_6$H$_4$Cl-2 |
| 12 | C(O) | C(O) | —C(CH$_3$)$_3$ | H | —C$_6$H$_4$OCH$_3$-2 | —C$_6$H$_4$OCH$_3$-2 |
| 13 | C(O) | C(O) | —C(CH$_3$)$_3$ | H | —C$_6$H$_3$Cl$_2$-3,4 | —C$_6$H$_5$ |
| 14 | C(O) | C(O) | —C(CH$_3$)$_3$ | H | —C$_6$H$_4$CN-4 | —C$_6$H$_4$CN-4 |
| 15 | C(O) | C(O) | —C(CH$_3$)$_3$ | H | —C$_6$H$_4$CH$_3$-4 | —C$_6$H$_4$Cl-4 |
| 16 | C(O) | C(O) | —C(CH$_3$)$_3$ | H | —C$_6$H$_5$ | —C$_6$H$_4$Cl-4 |
| 17 | C(O) | C(O) | —C(CH$_3$)$_3$ | H | —C$_6$H$_5$ | —C$_6$H$_4$Cl-3 |
| 18 | C(O) | C(O) | —C(CH$_3$)$_3$ | H | —C$_6$H$_5$ | —C$_6$H$_4$Cl-2 |
| 19 | C(O) | C(O) | —C(CH$_3$)$_3$ | H | —C$_6$H$_4$CH$_3$-3 | —C$_6$H$_4$CH$_3$-3 |
| 20 | C(O) | C(O) | —C(CH$_3$)$_3$ | H | —C$_6$H$_4$CH$_3$-2 | —C$_6$H$_4$CH$_3$-2 |
| 21 | C(O) | C(O) | —C(CH$_3$)$_3$ | H | —C$_6$H$_5$ | —C$_6$H$_4$CH$_3$-4 |
| 22 | C(O) | C(O) | —C(CH$_3$)$_3$ | H | —C$_6$H$_5$ | —C$_6$H$_4$CH$_3$-3 |
| 23 | C(O) | C(O) | —C(CH$_3$)$_3$ | H | —C$_6$H$_5$ | —C$_6$H$_4$CH$_3$-2 |
| 24 | C(O) | C(O) | —C(CH$_3$)$_3$ | H | —C$_6$H$_5$ | —C$_6$H$_4$OCH$_3$-4 |
| 25 | C(O) | C(O) | —C(CH$_3$)$_3$ | H | —C$_6$H$_5$ | —C$_6$H$_4$OCH$_3$-3 |
| 26 | C(O) | C(O) | —C(CH$_3$)$_3$ | H | —C$_6$H$_5$ | —C$_6$H$_4$OCH$_3$-2 |
| 27 | C(O) | C(O) | —C(CH$_3$)$_3$ | H | —C$_6$H$_5$ | —C$_6$H$_4$C(CH$_3$)$_3$-4 |
| 28 | C(O) | C(O) | —C(CH$_3$)$_3$ | H | —C$_6$H$_5$ | —C$_6$H$_4$CN-4 |
| 29 | C(O) | C(O) | —C(CH$_3$)$_3$ | H | —C$_6$H$_5$ | —C$_6$H$_4$NO$_2$-4 |
| 30 | C(O) | C(O) | —C(CH$_3$)$_3$ | H | —C$_6$H$_5$ | —C$_6$H$_4$NO$_2$-3 |
| 31 | C(O) | C(O) | —C(CH$_3$)$_3$ | H | —C$_6$H$_5$ | —C$_6$H$_4$NO$_2$-2 |
| 32 | C(O) | C(O) | —C(CH$_3$)$_3$ | H | —C$_6$H$_4$C(CH$_3$)$_3$-4 | —C$_6$H$_4$C(CH$_3$)$_3$-4 |
| 33 | C(O) | C(O) | —C(CH$_3$)$_3$ | H | —C$_6$H$_4$CH$_3$-4 | —C$_6$H$_3$Cl$_2$-3,4 |
| 34 | C(O) | C(O) | —C(CH$_3$)$_3$ | H | —C$_6$H$_5$ | —C$_6$H$_4$F-4 |
| 35 | C(O) | C(O) | —C(CH$_3$)$_3$ | H | —C$_6$H$_5$ | —C$_6$H$_4$F-3 |
| 36 | C(O) | C(O) | —C(CH$_3$)$_3$ | H | —C$_6$H$_5$ | —C$_6$H$_4$F-2 |
| 37 | C(O) | C(O) | —C(CH$_3$)$_3$ | H | —C$_6$H$_3$Cl$_2$-3,5 | —C$_6$H$_3$Cl$_2$-3,5 |
| 38 | C(O) | C(O) | —C(CH$_3$)$_3$ | H | —C$_6$H$_5$ | —C$_6$H$_3$Cl$_2$-2,4 |
| 39 | C(O) | C(O) | —C(CH$_3$)$_3$ | H | —C$_6$H$_5$ | —C$_6$H$_5$ |
| 40 | C(O) | C(O) | —CH(CH$_3$)$_2$ | H | —C$_6$H$_5$ | —C$_6$H$_4$CF$_3$-4 |
| 41 | C(O) | C(O) | —C(CH$_3$)$_3$ | H | —C$_6$H$_5$ | —C$_6$H$_4$CF$_3$-3 |
| 42 | C(O) | C(O) | —C(CH$_3$)$_3$ | H | —C$_6$H$_5$ | —C$_6$H$_4$CF$_3$-2 |
| 43 | C(O) | C(O) | —C(CH$_3$)$_3$ | H | —C$_6$H$_5$ | —C$_6$H$_3$F$_2$-2,5 |
| 44 | C(O) | C(O) | —CH$_2$C(CH$_3$)$_3$ | H | —C$_6$H$_5$ | —C$_6$H$_5$ |

TABLE I-continued $$A-G_2 \quad N-N-G_2-B$$
$$\phantom{A-G_2 \quad N-}| \quad |$$
$$\phantom{A-G_2 \quad N-N-}R^2 \quad R^1$$

$\phantom{XX}X \phantom{XXXXXXXX} X'$ where $G_2$ N is a single bond when $R^2$ is "H" and is a double bond when $R^2$ is "—"

| Ex. No. | G₂(X) | G₂(X') | R¹ | R² | A | B |
|---|---|---|---|---|---|---|
| 45 | C(O) | C(O) | —C(CH₃)₃ | H | —C₆H₅ | —C₆H₄CN-3 |
| 46 | C(O) | C(O) | —CH(CH₃)CH₂CH₃ | H | —C₆H₅ | —C₆H₅ |
| 47 | C(O) | C(O) | —C(CH₃)₃ | H | —C₆H₅ | —C₆H₃F₂-2,6 |
| 48 | C(O) | C(O) | —C(CH₃)₃ | H | —C₆H₄Cl-4 | —C₆H₅ |
| 49 | C(O) | C(O) | —C(CH₃)₃ | H | —C₆H₅ | —C₆H₃Cl₂-3,4 |
| 50 | C(O) | C(O) | —C(CH₃)₃ | H | —C₆H₅ | —C₆H₃Cl₂-3,5 |
| 51 | C(O) | C(O) | —C(CH₃)₃ | H | —C₆H₅ | —C₆H₃Cl₂-2,6 |
| 52 | C(O) | C(O) | —C(CH₃)₃ | H | —C₆H₄C(CH₃)₃-4 | —C₆H₅ |
| 53 | C(O) | C(O) | —C(CH₃)₃ | H | —C₆H₄Cl-2 | —C₆H₅ |
| 54 | C(O) | C(O) | —C(CH₃)₃ | H | naphthyl | —C₆H₅ |
| 55 | C(O) | C(O) | —C(CH₃)₃ | H | naphthyl | naphthyl |
| 56 | C(O) | C(O) | —C(CH₃)₃ | H | —C₆H₄Cl-3 | —C₆H₅ |
| 57 | C(O) | C(O) | —C(CH₃)₃ | H | —C₆H₄Cl-4 | —C₆H₃Cl₂-3,4 |
| 58 | C(O) | C(O) | —C(CH₃)₃ | H | —C₆H₄Cl-2 | —C₆H₃Cl₂-3,4 |
| 59 | C(O) | C(O) | —C(CH₃)₃ | H | —C₆H₄CH₃-2 | —C₆H₅ |
| 60 | C(O) | C(O) | —C(CH₃)₃ | H | —C₆H₅ | —C₆H₃Cl-2-NO₂-4 |
| 61 | C(O) | C(O) | —C(CH₃)₃ | H | —C₆H₅ | —C₆H₃(NO₂)₂-3,5 |
| 62 | C(O) | C(O) | —C(CH₃)₃ | H | —C₆H₅ | —C₆H₃Cl₂-2,3 |
| 63 | C(O) | C(O) | —CH(CH₃)C(CH₃)₃ | H | —C₆H₅ | —C₆H₅ |
| 64 | C(O) | C(O) | —C(CH₃)₃ | H | —C₆H₅ | —C₆H₃Cl-2-CH₃-5 |
| 65 | C(O) | C(O) | —C(CH₃)₃ | H | —C₆H₅ | —C₆H₃(CH₃)₂-3,5 |
| 66 | C(O) | C(O) | —C(CH₃)₃ | H | —C₆H₅ | —C₆H₃NO₂-2-CH₃-5 |
| 67 | C(O) | C(O) | —C(CH₃)₃ | H | —C₆H₅ | —C₆H₃CH₃-2-Cl-3 |
| 68 | C(O) | C(O) | —C(CH₃)₃ | H | —C₆H₅ | —C₆H₃Cl-3-CH₃-4 |
| 69 | C(O) | C(O) | —C(CH₃)₃ | H | —C₆H₅ | —C₆H₃NO₂-2-Cl-3 |
| 70 | C(O) | C(O) | —C(CH₃)₃ | H | —C₆H₅ | —C₆H₃OCH₃-3-NO₂-4 |
| 71 | C(O) | C(O) | —C(CH₃)₃ | H | —C₆H₅ | —C₆H₃NO₂-2-OCH₃-3 |
| 72 | C(O) | C(O) | —C(CH₃)₃ | H | —C₆H₅ | —C₆H₃(NO₂)₂-2,4 |
| 73 | C(O) | C(O) | —C(CH₃)₃ | H | —C₆H₄Cl-4 | —C₆H₄Cl-2 |
| 74 | C(O) | C(O) | —C(CH₃)₃ | H | —C₆H₄Cl-4 | —C₆H₄Cl-3 |
| 75 | C(O) | C(O) | —C(CH₃)₃ | H | —C₆H₄Cl-4 | —C₆H₄CH₃-4 |
| 76 | C(O) | C(O) | —C(CH₃)₃ | H | —C₆H₄Cl-4 | —C₆H₃Cl₂-3,5 |

TABLE I-continued $$A-G_2 \begin{matrix} X & X' \\ | & | \\ & N-N-G_2-B \\ & | \; | \\ & R^2 \; R^1 \end{matrix}$$

where $G_2$ N is a single bond when $R^2$ is "H" and is a double bond when $R^2$ is "—"

| Ex. No. | $G_2(X)$ | $R^1$ | $G_2(X')$ | $R^2$ | A | B |
|---|---|---|---|---|---|---|
| 77 | C(O) | —C(CH$_3$)$_3$ | C(O) | | —C$_6$H$_4$Cl-4 | —C$_6$H$_3$Cl$_2$-2,4 |
| 78 | C(O) | —C(CH$_3$)$_3$ | C(O) | H | —C$_6$H$_4$Cl-4 | —C$_6$H$_4$CF$_3$-4 |
| 79 | C(O) | —C(CH$_3$)$_3$ | C(O) | H | —C$_6$H$_5$ | —C$_6$H$_4$OSO$_2$CH$_3$-4 |
| 80 | C(O) | —C(CH$_3$)$_3$ | C(O) | H | —C$_6$H$_5$ | —C$_6$H$_4$CH(CH$_3$)$_2$-4 |
| 81 | C(O) | —C(CH$_3$)$_3$ | C(O) | H | —C$_6$H$_5$ | —C$_6$H$_4$OCOCH$_3$-2 |
| 82 | C(O) | —C(CH$_3$)$_3$ | C(O) | H | —C$_6$H$_5$ | —C$_6$H$_4$CH$_2$CH$_3$-4 |
| 83 | C(O) | —C(CH$_3$)$_3$ | C(O) | H | —C$_6$H$_5$ | —C$_6$H$_4$Br-2 |
| 84 | C(O) | —C(CH$_3$)$_3$ | C(O) | H | —C$_6$H$_5$ | —C$_6$H$_4$OH-4 |
| 85 | C(O) | —C(CH$_3$)$_3$ | C(O) | H | —C$_6$H$_4$CH$_3$-4 | —C$_6$H$_4$CH$_3$-2 |
| 86 | C(O) | —C(CH$_3$)$_3$ | C(O) | H | —C$_6$H$_4$CH$_3$-4 | —C$_6$H$_4$CH$_3$-3 |
| 87 | C(O) | —C(CH$_3$)$_3$ | C(O) | H | —C$_6$H$_4$CH$_3$-4 | —C$_6$H$_3$Cl$_2$-2,4 |
| 88 | C(O) | —C(CH$_3$)$_3$ | C(O) | H | —C$_6$H$_4$CH$_3$-4 | —C$_6$H$_3$Cl$_2$-3,5 |
| 89 | C(O) | —C(CH$_3$)$_3$ | C(O) | H | —C$_6$H$_4$CH$_3$-4 | —C$_6$H$_4$Cl-2 |
| 90 | C(O) | —C(CH$_3$)$_3$ | C(O) | H | —C$_6$H$_4$Cl-4 | —C$_6$H$_4$F-4 |
| 91 | C(O) | —C(CH$_3$)$_3$ | C(O) | H | —C$_6$H$_4$Cl-4 | —C$_6$H$_4$CF$_3$-4 |
| 92 | C(O) | —C(CH$_3$)$_3$ | C(O) | H | —C$_6$H$_4$Cl-4 | —C$_6$H$_4$Cl-3 |
| 93 | C(O) | —C(CH$_3$)$_3$ | C(O) | H | —C$_6$H$_4$Cl-4 | —C$_6$H$_4$CH$_2$Cl-3 |
| 94 | C(O) | —C(CH$_3$)$_3$ | C(O) | H | —C$_6$H$_4$Cl-4 | —C$_6$H$_4$CH$_2$Cl-4 |
| 95 | C(O) | —C(CH$_3$)$_3$ | C(O) | H | —C$_6$H$_4$Cl-4 | —C$_6$H$_4$CH$_3$-2 |
| 96 | C(O) | —C(CH$_3$)$_3$ | C(O) | H | —C$_6$H$_4$Cl-4 | —C$_6$H$_4$OCH$_3$-2 |
| 97 | C(O) | —C(CH$_3$)$_3$ | C(O) | H | —C$_6$H$_4$Cl-4 | —C$_6$H$_4$CH$_3$-3 |
| 98 | C(O) | —C(CH$_3$)$_3$ | C(O) | H | —C$_6$H$_4$F-4 | —C$_6$H$_4$F-4 |
| 99 | C(O) | —C(CH$_3$)$_3$ | C(O) | H | —C$_6$H$_4$F-3 | —C$_6$H$_4$F-3 |
| 100 | C(O) | —C(CH$_3$)$_3$ | C(O) | H | —C$_6$H$_4$F-2 | —C$_6$H$_4$F-2 |
| 101 | C(O) | —C(CH$_3$)$_3$ | C(O) | H | 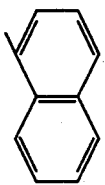 |  |
| 102 | C(S) | —C(CH$_3$)$_3$ | C(S) | H | —C$_6$H$_4$Cl-4 | —C$_6$H$_5$ |
| 103 | C(O) | —C(CH$_3$)$_3$ | C(O) | H | —C$_6$H$_5$ | —C$_6$H$_5$ |
| 104 | C(O) | —C(CH$_3$)$_3$ | C(O) | H | —C$_6$H$_5$ | —C$_6$H$_4$Br-4 |
| 105 | C(O) | —C(CH$_3$)$_3$ | C(O) | H | —C$_6$H$_5$ | —C$_6$H$_4$Br-3 |
| 106 | C(O) | —C(CH$_3$)$_3$ | C(O) | H | —C$_6$H$_4$CH$_2$CH$_3$-4 | —C$_6$H$_4$CH$_2$CH$_2$CH$_2$CH$_3$-4 |
| 107 | C(O) | —C(CH$_3$)$_3$ | C(O) | H | —C$_6$H$_3$Cl$_2$-3,4 | —C$_6$H$_5$ |
| 108 | C(O) | —C(CH$_3$)$_3$ | C(O) | H | —C$_6$H$_5$ | —C$_6$H$_4$COCH$_3$-4 |
| 109 | C(O) | —CH$_2$C(CH$_3$)$_3$ | C(O) | H | —C$_6$H$_5$ | —C$_6$H$_4$Br-2 |
| 110 | C(O) | —CH$_2$C(CH$_3$)$_3$ | C(O) | H | —C$_6$H$_5$ | —C$_6$H$_4$NO$_2$-2 |
| 111 | C(O) | —CH$_2$C(CH$_3$)$_3$ | C(O) | H | —C$_6$H$_5$ | —C$_6$H$_4$OCH$_3$-2 |
| 112 | C(O) | —C(CH$_3$)$_3$ | C(O) | H | —C$_6$H$_5$ | —C$_6$H$_4$I-2 |
| 113 | C(O) | —C(CH$_3$)$_3$ | C(O) | H | —C$_6$H$_5$ | —C$_6$H$_5$ |
| 114 | C(O) | —CH$_2$CH(CH$_3$)$_2$ | C(O) | H | —C$_6$H$_5$ | —C$_6$H$_5$ |

TABLE I-continued $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 115 | C(O) | C(O) | —CH(CH$_3$)$_2$ | H | —C$_6$H$_5$ | —C$_6$H$_4$Br-2 |
| 116 | C(O) | C(O) | —CH(CH$_3$)$_2$ | H | —C$_6$H$_5$ | —C$_6$H$_3$Cl$_2$-3,4 |
| 117 | C(O) | C(O) | —C(CH$_3$)$_3$ | H | —C$_6$H$_5$ | —C$_6$H$_4$OC$_6$H$_5$-4 |
| 118 | C(O) | C(O) | —C(CH$_3$)$_3$ | H | —C$_6$H$_4$CF$_3$-4 | —C$_6$H$_5$ |
| 119 | C(O) | C(O) | —C(CH$_3$)$_3$ | H | —C$_6$H$_4$CF$_3$-4 | —C$_6$H$_3$Cl$_2$-3,4 |
| 120 | C(O) | C(O) | ▷—CH—◁ | H | —C$_6$H$_5$ | —C$_6$H$_5$ |
| 121 | C(O) | C(O) | —C(CH$_3$)$_3$ | H | —C$_6$H$_5$ | —C$_6$H$_3$Cl-2-Br-4 |
| 122 | C(O) | C(O) | —C(CH$_3$)$_3$ | H | —C$_6$H$_5$ | —C$_6$H$_4$C$_6$H$_5$-4 |
| 123 | C(O) | C(O) | —C(CH$_3$)$_3$ | H | —C$_6$H$_5$ | —C$_6$H$_2$(OCH$_3$)$_3$-3,4,5 |
| 124 | C(O) | C(O) | —CH(CH$_3$)C(CH$_3$)$_3$ | H | —C$_6$H$_5$ | —C$_6$H$_4$NO$_2$-2 |
| 125 | C(O) | C(O) | —C(CH$_3$)$_3$ | H | —C$_6$H$_5$ | —C$_6$H$_4$CH$_2$SCN-3 |
| 126 | C(O) | C(O) | —C(CH$_3$)$_3$ | H | —C$_6$H$_5$ | —C$_6$H$_4$CH$_2$CN-3 |
| 127 | C(O) | C(O) | —CH(CH$_3$)C(CH$_3$)$_3$ | H | —C$_6$H$_5$ | —C$_6$H$_5$ |
| 128 | C(O) | C(O) | —CH[CH(CH$_3$)$_2$]$_2$ | H | —C$_6$H$_5$ | —C$_6$H$_5$ |
| 129 | C(O) | C(O) | $\begin{array}{c}H\\|\\-C-\triangleleft\\|\\CH_3\end{array}$ | H | —C$_6$H$_5$ | —C$_6$H$_5$ |
| 130 | C(O) | C(O) | —C(CH$_3$)$_3$ | H | —C$_6$H$_4$CH$_2$CH$_3$-4 | —C$_6$H$_4$CH$_3$-3 |
| 131 | C(O) | C(O) | —C(CH$_3$)$_3$ | H | —C$_6$H$_4$CH$_2$CH$_3$-4 | —C$_6$H$_4$Cl-4 |
| 132 | C(O) | C(O) | —C(CH$_3$)$_3$ | H | —C$_6$H$_4$CH$_2$CH$_3$-4 | —C$_6$H$_4$NO$_2$-2 |
| 133 | C(O) | C(O) | —C(CH$_3$)$_3$ | H | —C$_6$H$_4$CH$_2$CH$_3$-4 | —C$_6$H$_4$CH$_2$CH$_3$-3 |
| 134 | C(O) | C(O) | —C(CH$_3$)$_3$ | H | —C$_6$H$_4$CH$_2$CH$_3$-4 | —C$_6$H$_4$Br-3 |
| 135 | C(O) | C(O) | —CH(CH$_3$)C(CH$_3$)$_3$ | H | —C$_6$H$_5$ | —C$_6$H$_4$I-2 |
| 136 | C(O) | C(O) | —C(CH$_3$)$_3$ | H | —C$_6$H$_5$ | —C$_6$H$_4$Br-2 |
| 137 | C(O) | C(O) | —C(CH$_3$)$_3$ | H | —C$_6$H$_4$Br-2 | —C$_6$H$_4$CO$_2$CH$_3$-4 |
| 138 | C(O) | C(O) | —C(CH$_3$)$_3$ | H | —C$_6$H$_4$CF$_3$-2 | —C$_6$H$_5$ |
| 139 | C(O) | C(O) | —C(CH$_3$)$_3$ | H | —C$_6$H$_5$ | —C$_6$H$_5$ |
| 140 | C(O) | C(O) | —C(CH$_3$)$_3$ | H | —C$_6$H$_5$ | —C$_6$H$_4$I-3 |
| 141 | C(O) | C(O) | —C(CH$_3$)$_3$ | H | —C$_6$H$_5$ | —C$_6$H$_4$CH$_2$CH$_3$-2 |
| 142 | C(O) | C(O) | —C(CH$_3$)$_3$ | H | —C$_6$H$_5$ | —C$_6$H$_4$CH$_2$OCH$_3$-3 |

TABLE I-continued $$\begin{array}{cc} X & X' \\ A-G_2 & N-N-G_2-B \\ & |\ \ | \\ & R^2\ R^1 \end{array}$$

where $G_2\ N$ is a single bond when $R^2$ is "H" and is a double bond when $R^2$ is "—"

| Ex. No. | $G_2(X)$ | $G_2(X')$ | $R^1$ | A | $R^2$ | B |
|---|---|---|---|---|---|---|
| 143 | C(O) | C(O) | —CH(CH$_3$)-cyclohexyl | —C$_6$H$_5$ | H | —C$_6$H$_5$ |
| 144 | C(O) | C(O) | —C(CH$_3$)$_3$ | —C$_6$H$_5$ | H | —C$_6$H$_4$OCH$_2$CH=CH$_2$-4 |
| 145 | C(O) | C(O) | —C(CH$_3$)$_3$ | —C$_6$H$_4$C$_6$H$_5$-4 | H | —C$_6$H$_4$C$_6$H$_5$-4 |
| 146 | C(O) | C(O) | —C(CH$_3$)$_3$ | —C$_6$H$_5$ | H | 2-Cl-4-(4-CF$_3$-2-Cl-phenoxy)-NO$_2$-phenyl |
| 147 | C(O) | C(O) | —C(CH$_3$)$_3$ | 2-Cl-4-(4-CF$_3$-2-Cl-phenoxy)-NO$_2$-phenyl | H | —C$_6$H$_5$ |
| 148 | C(O) | C(O) | —C(CH$_3$)$_3$ | —C$_6$H$_4$(CH$_2$OC(O)C$_6$H$_5$)-2 | H | —C$_6$H$_4$SO$_2$CH$_3$-4 |
| 149 | C(O) | C(O) | —C(CH$_3$)$_3$ | —C$_6$H$_5$ | H | —C$_6$H$_4$OH-2 |
| 150 | C(O) | C(O) | —C(CH$_3$)$_3$ | —C$_6$H$_5$ | H | —C$_6$H$_4$SCH$_3$-4 |
| 151 | C(O) | C(O) | —C(CH$_3$)$_3$ | —C$_6$H$_5$ | H | —C$_6$H$_3$Br-3-CH$_3$-4 |
| 152 | C(O) | C(O) | —C(CH$_3$)$_3$ | —C$_6$H$_5$ | H | —C$_6$H$_3$CH$_3$-3-Br-4 |
| 153 | C(O) | C(O) | —C(CH$_3$)$_3$ | —C$_6$H$_5$ | H | —C$_6$H$_3$Br$_2$-2,4 |
| 154 | C(O) | C(O) | —C(CH$_3$)$_3$ | —C$_6$H$_5$ | H | —C$_6$H$_3$Cl$_2$-2,6 |
| 155 | C(O) | C(O) | —CH(CH$_3$)$_2$ | —C$_6$H$_5$ | H | —C$_6$H$_3$Cl$_2$-3,4 |
| 156 | C(O) | C(O) | —CH$_2$C(CH$_3$)$_3$ | —C$_6$H$_5$ | H | —C$_6$H$_4$CN-4 |
| 157 | C(O) | C(O) | —CH(CH$_3$)C(CH$_3$)$_3$ | —C$_6$H$_5$ | H | —C$_6$H$_4$CH$_2$CH$_3$-4 |
| 158 | C(O) | C(O) | —CH$_2$C(CH$_3$)$_3$ | —C$_6$H$_5$ | H | —C$_6$H$_4$CH$_2$CH$_3$-4 |

TABLE I-continued $$A-G_2 \quad \underset{\underset{R^2}{|}}{N}-\underset{\underset{R^1}{|}}{N}-G_2-B$$
$$\phantom{A-G_2\ }X\phantom{\quad N-N}X'$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 159 | C(O) | C(O) | —C(CH$_3$)$_3$ | H | —C$_6$H$_5$ | ![structure: 3-methylbenzyl 4-methylphenyl sulfide] |
| 160 | C(O) | C(O) | —C(CH$_3$)$_3$ | H | —C$_6$H$_5$ | —C$_6$H$_4$OC$_6$H$_5$-3 |
| 161 | C(O) | C(O) | —C(CH$_3$)$_3$ | H | —C$_6$H$_5$ | —C$_6$H$_4$(CH$_2$)OC(O)CH$_3$)-3 |
| 162 | C(O) | C(O) | —C(CH$_3$)$_3$ | H | —C$_6$H$_5$ | —C$_6$H$_4$CH$_2$OH-4 |
| 163 | C(O) | C(O) | —C(CH$_3$)$_3$ | H | —C$_6$H$_5$ | —C$_6$H$_4$CHO-4 |
| 164 | C(O) | C(O) | —C(CH$_3$)$_3$ | H | —C$_6$H$_5$ | —C$_6$H$_4$CO$_2$H-4 |
| 165 | C(O) | C(O) | —CH(CH$_3$)C(CH$_3$)$_3$ | H | —C$_6$H$_5$ | —C$_6$H$_4$OH-2 |
| 166 | C(O) | C(O) | —C(CH$_3$)$_3$ | H | —C$_6$H$_5$ | —C$_6$H$_4$CH=CCl$_2$-4 |
| 167 | C(O) | C(O) | —CH(CH$_3$)C(CH$_3$)$_3$ | H | —C$_6$H$_5$ | —C$_6$H$_4$(OC(O)CH$_3$)-2 |
| 168 | C(O) | C(O) | —C(CH$_3$)$_3$ | H | —C$_6$H$_3$(OCH$_3$)$_2$-3,4 | —C$_6$H$_5$ |
| 169 | C(O) | C(O) | —C(CH$_3$)$_3$ | H | —C$_6$H$_4$CH$_2$Cl-2 | —C$_6$H$_4$CH$_2$Cl-2 |
| 170 | C(O) | C(O) | —C(CH$_3$)$_3$ | H | —C$_6$H$_4$CH$_2$Cl-2 | —C$_6$H$_5$ |
| 171 | C(O) | C(O) | —C(CH$_3$)$_3$ | H | —C$_6$H$_4$NO$_2$-2 | —C$_6$H$_5$ |
| 172 | C(O) | C(O) | —C(CH$_3$)$_3$ | H | —C$_6$H$_4$CH$_2$CH$_2$CH$_3$-4 | —C$_6$H$_4$CH$_3$-2 |
| 173 | C(O) | C(O) | —C(CH$_3$)$_3$ | H | —C$_6$H$_3$CH$_3$-2-CF$_3$-5 | —C$_6$H$_4$Br-2 |
| 174 | C(O) | C(O) | —C(CH$_3$)$_3$ | H | —C$_6$H$_4$Br-2 | —C$_6$H$_5$ |
| 175 | C(O) | C(O) | —C(CH$_3$)$_3$ | H | —C$_6$H$_4$CH$_2$CH$_3$-4 | —C$_6$H$_4$CH$_2$CH$_3$-3 |
| 176 | C(O) | C(O) | —C(CH$_3$)$_3$ | H | —C$_6$H$_5$ | —C$_6$H$_4$CH$_2$CH$_2$CH$_3$-4 |
| 177 | C(O) | C(O) | —C(CH$_3$)$_3$ | H | —C$_6$H$_4$CH$_3$-4 | —C$_6$H$_4$Br-3 |
| 178 | C(O) | C(O) | —C(CH$_3$)$_3$ | H | —C$_6$H$_4$CH$_3$-4 | —C$_6$H$_3$(CH$_3$)$_2$-3,5 |
| 179 | C(O) | C(O) | —C(CH$_3$)$_3$ | H | —C$_6$H$_4$CH$_2$CH$_3$-4 | —C$_6$H$_4$I-4 |
| 180 | C(O) | C(O) | —C(CH$_3$)$_3$ | H | —C$_6$H$_5$ | —C$_6$H$_4$CH(CH$_3$)$_2$-2 |
| 181 | C(O) | C(O) | —CH(CH$_3$)C(CH$_3$)$_3$ | H | —C$_6$H$_4$CH$_2$CH$_3$-3 | —C$_6$H$_5$ |
| 182 | C(O) | C(O) | —CH$_2$C(CH$_3$)$_3$ | H | —C$_6$H$_5$ | —C$_6$H$_4$NO$_2$-3 |
| 183 | C(O) | C(O) | —CH$_2$C(CH$_3$)$_3$ | H | —C$_6$H$_5$ | —C$_6$H$_4$NO$_2$-3 |
| 184 | C(O) | C(O) | —CH$_2$C(CH$_3$)$_3$ | H | —C$_6$H$_5$ | —C$_6$H$_4$Cl-4 |
| 185 | C(O) | C(O) | —C(CH$_3$)$_3$ | H | —C$_6$H$_5$ | —C$_6$H$_4$Cl-3 |
| 186 | C(O) | C(O) | —C(CH$_3$)$_3$ | H | —C$_6$H$_5$ | —C$_6$H$_3$(NO$_2$)$_2$-2,4 |
| 187 | C(O) | C(O) | —C(CH$_3$)$_3$ | H | —C$_6$H$_3$Cl$_2$-3,4 | —C$_6$H$_3$Cl$_2$-2,4 |
| 188 | C(O) | C(O) | —C(CH$_3$)$_3$ | H | —C$_6$H$_4$(CH$_2$)$_6$CH$_3$-4 | —C$_6$H$_4$Cl-4 |
| 189 | C(O) | C(O) | —C(CH$_3$)$_3$ | H | —C$_6$H$_4$CH$_2$CH$_2$CH$_3$-4 | —C$_6$H$_4$Cl-4 |
| 190 | C(O) | C(O) | —C(CH$_3$)$_3$ | H | —C$_6$H$_4$OCH$_3$-4 | —C$_6$H$_4$CH$_3$—3 |
| 191 | C(O) | C(O) | —C(CH$_3$)$_3$ | H | —C$_6$H$_4$Cl-2 | —C$_6$H$_5$ |
| 192 | C(O) | C(O) | —C(CH$_3$)$_3$ | H | —C$_6$H$_5$ | —C$_6$H$_4$CH$_3$-3 |

TABLE I-continued $$A-G_2 \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 197 | C(O) | C(O) | —C(CH₃)₃ | H | —C₆H₄Cl-2 | —C₆H₄NO₂-2 |
| 198 | C(O) | C(O) | —C(CH₃)₃ | H | —C₆H₄Cl-2 | —C₆H₄Cl-4 |
| 199 | C(O) | C(O) | —C(CH₃)₃ | H | —C₆H₄Cl-2 | —C₆H₄CH₂CH₃-4 |
| 200 | C(O) | C(O) | —C(CH₃)₃ | H | —C₆H₄CH₂CH₃-4 | —C₆H₃(CH₃)₂-3,5 |
| 201 | C(O) | C(O) | —C(CH₃)₃ | H | —C₆H₄CH₂CH₃-4 | —C₆H₃CH₃-3-Cl-6 |
| 202 | C(O) | C(O) | —C(CH₃)₃ | H | —C₆H₅ | —C₆H₄(OC(O)CH₃)-3 |
| 203 | C(O) | C(O) | —C(CH₃)₃ | H | —C₆H₅ | —C₆H₄OH-3 |
| 204 | C(O) | C(O) | —C(CH₃)₃ | H | —C₆H₄CH₂CH₃-4 | —C₆H₃NO₂-2-CH₃-3 |
| 205 | C(O) | C(O) | —C(CH₃)₃ | H | —C₆H₄OCH₃-4 | —C₆H₃(CH₃)₂-3,5 |
| 206 | C(O) | C(O) | —C(CH₃)₃ | H | —C₆H₄OCH₃-4 | —C₆H₃Cl₂-2,4 |
| 207 | C(O) | C(O) | —C(CH₃)₃ | H | —C₆H₄Cl-2 | —C₆H₃Cl₂-2,6 |
| 208 | C(O) | C(O) | —C(CH₃)₃ | H | —C₆H₄Cl-2 | —C₆H₄Br-2 |
| 209 | C(O) | C(O) | —C(CH₃)₃ | H | —C₆H₄Cl-2 | —C₆H₃F₂-2,5 |
| 210 | C(O) | C(O) | —C(CH₃)₃ | H | —C₆H₄Cl-2 | —C₆H₄OCH₃-4 |
| 211 | C(O) | C(O) | —C(CH₃)₃ | H | —C₆H₄Cl-2 | —C₆H₄CH₃-2 |
| 212 | C(O) | C(O) | —C(CH₃)₃ | H | —C₆H₄F-2 | —C₆H₄Cl-4 |
| 213 | C(O) | C(O) | —C(CH₃)₃ | H | —C₆H₃Cl₂-2,4 | —C₆H₄Cl-4 |
| 214 | C(O) | C(O) | —C(CH₃)₃ | H | —C₆H₄Cl-2 | —C₆H₃Cl₂-2,4 |
| 215 | C(O) | C(O) | —C(CH₃)₃ | H | —C₆H₄Cl-2 | —C₆H₄OCH₃-3 |
| 216 | C(O) | C(O) | —C(CH₃)₃ | H | —C₆H₄Cl-2 | —C₆H₄Cl-3 |
| 217 | C(O) | C(O) | —C(CH₃)₃ | H | —C₆H₄Cl-2 | —C₆H₄CF₃-2 |
| 218 | C(O) | C(O) | —C(CH₃)₃ | H | —C₆H₄Cl-2 | —C₆H₄CF₃-3 |
| 219 | C(O) | C(O) | —C(CH₃)₃ | H | —C₆H₄Cl-2 | —C₆H₄CF₃-4 |
| 220 | C(O) | C(O) | —C(CH₃)₃ | H | —C₆H₄CH₃-3 | —C₆H₅ |
| 221 | C(O) | C(O) | —C(CH₃)₃ | H | —C₆H₄NO₂-3 | —C₆H₅ |
| 222 | C(O) | C(O) | —C(CH₃)₃ | H | —C₆H₃Cl₂-2,6 | —C₆H₅ |
| 223 | C(O) | C(O) | —C(CH₃)₃ | H | —C₆H₃F₂-2,4 | —C₆H₅ |
| 224 | C(O) | C(O) | —C(CH₃)₃ | H | —C₆H₄Cl-2 | —C₆H₄CN-4 |
| 225 | C(O) | C(O) | —C(CH₃)₃ | H | —C₆H₄Cl-2 | —C₆H₄F-4 |
| 226 | C(O) | C(O) | —C(CH₃)₃ | H | —C₆H₄Cl-2 | —C₆H₄Br-4 |
| 227 | C(O) | C(O) | —C(CH₃)₃ | H | —C₆H₄Cl-2 | —C₆H₄Cl-4 |
| 228 | C(O) | C(O) | —C(CH₃)₃ | H | —C₆H₄Cl-2 | —C₆H₄OCH₃-2 |
| 229 | C(O) | C(O) | —C(CH₃)₃ | H | —C₆H₄Cl-2 | —C₆H₄NO₂-4 |
| 230 | C(O) | C(O) | —C(CH₃)₃ | H | —C₆H₄Cl-2 | —C₆H₄F-2 |
| 231 | C(O) | C(O) | —C(CH₃)₃ | H | —C₆H₄Cl-2 | —C₆H₃F₂-2,6 |
| 232 | C(O) | C(O) | —C(CH₃)₃ | H | —C₆H₄NO₂-4 | —C₆H₅ |
| 233 | C(O) | C(O) | —C(CH₃)₃ | H | —C₆H₄CN-4 | —C₆H₅ |
| 234 | C(O) | C(O) | —C(CH₃)₃ | H | —C₆H₄OCH₃-3 | —C₆H₄OCH₃-3 |
| 235 | C(O) | C(O) | —C(CH₃)₃ | H | —C₆H₄OCH₃-3 | —C₆H₅ |
| 236 | C(O) | C(O) | —C(CH₃)₃ | H | —C₆H₄OCH₃-3 | —C₆H₄Cl-4 |
| 237 | C(O) | C(O) | —C(CH₃)₃ | H | —C₆H₄OCH₃-2 | —C₆H₃Cl₂-3,4 |
| 238 | C(O) | C(O) | —C(CH₃)₃ | H | —C₆H₄OCH₃-2 | —C₆H₅ |
| 239 | C(O) | C(O) | —C(CH₃)₃ | H | —C₆H₄OCH₃-2 | —C₆H₄CH₃-3 |
| 240 | C(O) | C(O) | —C(CH₃)₃ | H | —C₆H₄OCH₃-2 | —C₆H₃Cl₂-3,4 |

TABLE I-continued $$A-G_2 \quad \begin{array}{cc} X & X' \\ \| & \| \\ N-N-G_2-B \\ | & | \\ R^2 & R^1 \end{array}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 241 | C(O) | C(O) | —C(CH$_3$)$_3$ | H | —C$_6$H$_4$OCH$_3$-2 | —C$_6$H$_4$Cl-4 |
| 242 | C(O) | C(O) | —C(CH$_3$)$_3$ | H | —C$_6$H$_4$OCH$_3$-2 | —C$_6$H$_4$NO$_2$-2 |
| 243 | C(O) | C(O) | —C(CH$_3$)$_3$ | H | —C$_6$H$_5$ | —C$_6$H$_4$OCF$_3$-4 |
| 244 | C(O) | C(O) | —C(CH$_3$)$_3$ | H | —C$_6$H$_4$OCF$_3$-4 | —C$_6$H$_5$ |
| 245 | C(O) | C(O) | —C(CH$_3$)$_3$ | H | —C$_6$H$_4$OCF$_3$-4 | —C$_6$H$_4$CH$_3$-3 |
| 246 | C(O) | C(O) | —C(CH$_3$)$_3$ | H | —C$_6$H$_4$OCF$_3$-4 | —C$_6$H$_4$Cl-4 |
| 247 | C(O) | C(O) | —C(CH$_3$)$_3$ | H | —C$_6$H$_4$OCF$_3$-4 | —C$_6$H$_3$Cl$_2$-3,4 |
| 248 | C(O) | C(O) | —C(CH$_3$)$_3$ | H | —C$_6$H$_4$CF$_3$-4 | —C$_6$H$_4$Cl-4 |
| 249 | C(O) | C(O) | —C(CH$_3$)$_3$ | H | —C$_6$H$_4$CF$_3$-4 | —C$_6$H$_4$CH$_3$-3 |
| 250 | C(O) | C(O) | —C(CH$_3$)$_2$CH$_2$CH$_2$CH$_2$CH$_3$ | H | —C$_6$H$_5$ | —C$_6$H$_5$ |
| 251 | C(O) | C(O) | —C(CH$_3$)$_3$ | H | —C$_6$H$_4$OCH$_2$CH$_3$-4 | —C$_6$H$_4$CH$_3$-3 |
| 252 | C(O) | C(O) | —C(CH$_3$)$_3$ | H | —C$_6$H$_4$OCH$_2$CH$_3$-4 | —C$_6$H$_3$(CH$_3$)$_2$-3,5 |
| 253 | C(O) | C(O) | —C(CH$_3$)$_3$ | H | —C$_6$H$_4$OCH$_2$CH$_3$-4 | —C$_6$H$_5$ |
| 254 | C(O) | C(O) | —C(CH$_3$)$_3$ | H | —C$_6$H$_4$CH$_2$CH$_3$-4 | —C$_6$H$_3$NO$_2$-2-Cl-4 |
| 255 | C(O) | C(O) | —C(CH$_3$)$_3$ | H | —C$_6$H$_3$Cl-3-OCH$_3$-4 | —C$_6$H$_5$ |
| 256 | C(O) | C(O) | —C(CH$_3$)$_3$ | H | —C$_6$H$_4$SCH$_3$-4 | —C$_6$H$_5$ |
| 257 | C(O) | C(O) | —C(CH$_3$)$_3$ | H | —C$_6$H$_4$OCH$_2$CH$_2$CH$_2$CH$_3$-4 | —C$_6$H$_4$Cl-4 |
| 258 | C(O) | C(O) | —C(CH$_3$)$_3$ | H | —C$_6$H$_4$SCH$_3$-4 | —C$_6$H$_5$ |
| 259 | C(O) | C(O) | —C(CH$_3$)$_3$ | H | —C$_6$H$_3$NO$_2$-2-Cl-4 | —C$_6$H$_5$ |
| 260 | C(O) | C(O) | —C(CH$_3$)$_3$ | H | —C$_6$H$_3$NO$_2$-2-Cl-4 | —C$_6$H$_3$NO$_2$-2-Cl-4 |
| 261 | C(O) | C(O) | —C(CH$_3$)$_3$ | H | —C$_6$H$_3$NO$_2$-2-Cl-4 | —C$_6$H$_4$C(CH$_3$)$_3$-4 |
| 262 | C(O) | C(O) | —C(CH$_3$)$_3$ | H | —C$_6$H$_3$NO$_2$-2-Cl-4 | —C$_6$H$_4$Cl-4 |
| 263 | C(O) | C(O) | —C(CH$_3$)$_3$ | H | —C$_6$H$_4$CH$_3$-4 | —C$_6$H$_3$CH$_3$-3-Cl-6 |
| 264 | C(O) | C(O) | —C(CH$_3$)$_3$ | H | —C$_6$H$_3$F$_2$-2,6 | —C$_6$H$_3$F$_2$-2,6 |
| 265 | C(O) | C(O) | —C(CH$_3$)$_3$ | H | —C$_6$H$_4$OC$_6$H$_5$-4 | —C$_6$H$_5$ |
| 266 | C(O) | C(O) | —C(CH$_3$)$_3$ | H | —C$_6$H$_4$OC$_6$H$_5$-4 | —C$_6$H$_4$CH$_3$-4 |
| 267 | C(O) | C(O) | —C(CH$_3$)$_3$ | H | —C$_6$H$_4$CH$_2$CH$_2$CH$_2$CH$_3$-4 | —C$_6$H$_5$ |
| 268 | C(O) | C(O) | —C(CH$_3$)$_3$ | H | —C$_6$H$_4$CH$_2$CH$_2$CH$_2$CH$_3$-4 | —C$_6$H$_4$Cl-4 |
| 269 | C(O) | C(O) | —C(CH$_3$)$_3$ | H | —C$_6$H$_4$CH(CH$_3$)$_2$-4 | —C$_6$H$_5$ |
| 270 | C(O) | C(O) | —C(CH$_3$)$_3$ | H | —C$_6$H$_4$CH(CH$_3$)$_2$-4 | —C$_6$H$_4$OCF$_3$-4 |
| 271 | C(O) | C(O) | —C(CH$_3$)$_3$ | H | —C$_6$H$_4$OH-4 | —C$_6$F$_5$-2,3,4,5,6 |
| 272 | C(O) | C(O) | —C(CH$_3$)$_3$ | H | —C$_6$H$_4$CN-4 | —C$_6$H$_5$ |
| 273 | C(O) | C(O) | —C(CH$_3$)$_3$ | H | —C$_6$H$_4$CN-4 | —C$_6$H$_3$Cl$_2$-3,4 |
| 274 | C(O) | C(O) | —C(CH$_3$)$_3$ | H | —C$_6$H$_3$CH$_3$-2-Cl-4 | —C$_6$H$_4$CN-4 |
| 275 | C(O) | C(O) | —C(CH$_3$)$_3$ | H | —C$_6$H$_4$CH$_2$CH$_3$-4 | —C$_6$H$_4$CH$_3$-3 |
| 276 | C(O) | C(O) | —C(CH$_3$)$_3$ | H | —C$_6$H$_5$ | —C$_6$H$_4$OCF$_3$-4 |
| 277 | C(O) | C(O) | —C(CH$_3$)$_3$ | H | —C$_6$F$_5$-2,3,4,5,6 | —C$_6$H$_5$ |
| 278 | C(O) | C(O) | —C(CH$_3$)$_3$ | H | —C$_6$H$_4$CN-4 | —C$_6$H$_3$Cl$_2$-3,4 |
| 279 | C(O) | C(O) | —C(CH$_3$)$_3$ | H | —C$_6$H$_3$CH$_3$-2-Cl-4 | —C$_6$H$_4$CH$_3$-3 |
| 280 | C(O) | C(O) | —C(CH$_3$)$_3$ | H | —C$_6$H$_4$CF$_3$-4 | —C$_6$H$_4$Cl-4 |
| 281 | C(O) | C(O) | —C(CH$_3$)$_3$ | H | —C$_6$H$_3$CH$_3$-2-Cl-4 | —C$_6$H$_3$(CH$_3$)$_2$-3,5 |
| 282 | C(O) | C(O) | —C(CH$_3$)$_3$ | H | —C$_6$H$_5$ | —C$_6$H$_3$(CH$_3$)$_2$-3,5 |
| 283 | C(O) | C(O) | —C(CH$_3$)$_3$ | H | —C$_6$H$_4$CH$_2$CH$_3$-4 | —C$_6$H$_4$CH=CH$_2$-3 |
| 284 | C(O) | C(O) | —C(CH$_3$)$_3$ | H | —C$_6$H$_4$CF$_3$-4 | —C$_6$H$_4$CH=CH$_2$-3 |

TABLE I-continued $$A-G_2 \begin{array}{c} X \\ \| \\ N-N-G_2-B \\ | \phantom{N} | \\ R^2 \phantom{N} R^1 \end{array} \begin{array}{c} X' \\ \| \\ \end{array}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 285 | C(O) | C(O) | —C(CH₃)₃ | H | —C₆H₄OH-4 | —C₆H₄CH₃-3 |
| 286 | C(O) | C(O) | —C(CH₃)₃ | H | —C₆H₄OCH₂CH=CH₂-4 | —C₆H₄CH₃-3 |
| 287 | C(O) | C(O) | —C(CH₃)₃ | H | —C₆H₄CH₂CH₂CH₃-4 | —C₆H₃Cl₂-3,4 |
| 288 | C(O) | C(O) | —C(CH₃)₃ | H | —C₆H₄CH₂CH₂CH₃-4 | —C₆H₄CH₃-3 |
| 289 | C(O) | C(O) | —C(CH₃)₃ | H | —C₆H₄CH=CH₂-4 | —C₆H₄CH=CH₂-4 |
| 290 | C(O) | C(O) | —C(CH₃)₃ | H | —C₆H₄CH=CH₂-4 | —C₆H₄CH₃-3 |
| 291 | C(O) | C(O) | —C(CH₃)₃ | H | —C₆H₃F₂-2,6 | —C₆H₃Cl₂-3,4 |
| 292 | C(O) | C(O) | —C(CH₃)₃ | H | —C₆H₃F₂-2,6 | —C₆H₄CH₃-3 |
| 293 | C(O) | C(O) | —C(CH₃)₃ | H | —C₆H₄CH₂Cl-2 | —C₆H₄Cl-4 |
| 294 | C(O) | C(O) | —C(CH₃)₃ | H | —C₆H₄CH₂N(CH₂CH₃)₂-2 | |
| 295 | C(O) | C(O) | —C(CH₃)₂CH₂CH₃ | H | —C₆H₅ | —C₆H₅ |
| 296 | C(O) | C(O) | —C(CH₃)₃ | H | —C₆H₄Cl-4 | —C₆H₄Br-2 |
| 297 | C(O) | C(O) | —C(CH₃)₂CH₂CH₃ | H | —C₆H₄CH₃-3 | —C₆H₄CH₃-3 |
| 298 | C(O) | C(O) | —C(CH₃)₂CH₂CH₃ | H | —C₆H₄Br-2 | —C₆H₄Br-2 |
| 299 | C(O) | C(O) | —C(CH₃)₃ | H | —C₆H₄Cl-4 | —C₆H₃(CH₃)₂-3,5 |
| 300 | C(O) | C(O) | —C(CH₃)₃ | H | —C₆H₄OCH₃-3 | —C₆H₃(CH₃)₂-3,5 |
| 301 | C(O) | C(O) | —C(CH₃)₃ | H | —C₆H₄Cl-4 | —C₆H₄F-4 |
| 302 | C(O) | C(O) | —C(CH₃)₃ | H | —C₆H₄CH₂CH₃-4 | —C₆H₃(CH₃)₂-3,5 |
| 303 | C(O) | C(O) | —C(CH₃)₃ | H | —C₆H₄CH=CH₂-4 | —C₆H₃(—CH₃)₂-3,5 |
| 304 | C(O) | C(O) | —C(CH₃)₃ | H | —C₆H₄(OC(O)CH₃)-4 | —C₆H₃(CH₃)₂-3,5 |
| 305 | C(O) | C(O) | —C(CH₃)₃ | H | —C₆H₃(CH₃)₂-3,5 | —C₆H₅ |
| 306 | C(O) | C(O) | —C(CH₃)₃ | H | —C₆H₃(CH₃)₂-3,5 | —C₆H₄CH₃-3 |
| 307 | C(O) | C(O) | —C(CH₃)₃ | H | —C₆H₃(CH₃)₂-3,5 | —C₆H₄CH₂CH₃-4 |
| 308 | C(O) | C(O) | —C(CH₃)₃ | H | —C₆H₃(CH₃)₂-3,5 | —C₆H₄CH₂CH₃-4 |
| 309 | C(O) | C(O) | —C(CH₃)₃ | H | —C₆H₄CH=CHCH₃-4 | —C₆H₄CH=CHCH₃-4 |
| 310 | C(O) | C(O) | —C(CH₃)₃ | H | —C₆H₄CH(CH₃)₂-4 | —C₆H₃(CH₃)₂-3,5 |
| 311 | C(O) | C(O) | —C(CH₃)₃ | H | —C₆H₄CH₂CH₃-4 | —C₆H₄Br-2 |
| 312 | C(O) | C(O) | —C(CH₃)₃ | H | —C₆H₄Cl-3-CH₃-4 | —C₆H₄CH₃-3 |
| 313 | C(O) | C(O) | —C(CH₃)₃ | H | —C₆H₄Cl-3-CH₃-4 | —C₆H₄CH₃-3 |
| 314 | C(O) | C(O) | —C(CH₃)₃ | H | —C₆H₄Cl-3-CH₃-4 | —C₆H₃Cl₂-3,4 |
| 315 | C(O) | C(O) | —C(CH₃)₃ | H | —C₆H₄Cl-3-CH₃-4 | —C₆H₃Cl₂-3,4 |
| 316 | C(O) | C(O) | —C(CH₃)₂CH₂CH₃ | H | —C₆H₄CH₂CH₃-4 | —C₆H₄CH₂CH₃-4 |
| 317 | C(O) | C(O) | —C(CH₃)₃ | H | —C₆H₃F₂-2,6 | —C₆H₄NO₂-2 |
| 318 | C(O) | C(O) | —C(CH₃)₃ | H | —C₆H₃F₂-2,6 | —C₆H₄Cl-3 |
| 319 | C(O) | C(O) | —C(CH₃)₃ | H | —C₆H₃F₂-2,6 | —C₆H₄Cl-4 |
| 320 | C(O) | C(O) | —C(CH₃)₂CH₂CH₃ | H | —C₆H₄CH₂CH₃-4 | —C₆H₃(CH₃)₂-3,5 |
| 321 | C(O) | C(O) | —C(CH₃)₃ | H | —C₆H₄CF₃-3 | —C₆H₃(CH₃)₂-3,5 |
| 322 | C(O) | C(O) | —C(CH₃)₃ | H | —C₆H₄CF₃-3 | —C₆H₄Cl-4 |
| 323 | C(S) | C(S) | —C(CH₃)₃ | H | —C₆H₅ | —C₆H₄Cl-4 |
| 324 | C(S) | C(O) | —C(CH₃)₃ | H | —C₆H₅ | —C₆H₄CH₃-3 |
| 325 | C(O) | C(O) | —C(CH₃)₃ | H | —C₆H₃NO₂-2-OCH₃-3 | —C₆H₄CH₃-3 |
| 326 | C(O) | C(O) | —C(CH₃)₃ | H | —C₆H₃Br-3-CH₃-4 | —C₆H₅ |
| 327 | C(O) | C(O) | —C(CH₃)₃ | H | —C₆H₄Cl-4 | —C₆H₄CO₂CH₃-4 |
| 328 | C(O) | C(O) | —C(CH₃)₃ | H | —C₆H₄CH₂CH₃-4 | —C₆H₄CO₂CH₃-4 |

TABLE I-continued $$A-G_2 \quad \underset{R^2 \; R^1}{N-N-G_2-B}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 329 | C(O) | C(O) | —C(CH₃)₃ | H | —C₆H₅ | —C₆H₄NH₂-3 |
| 330 | C(O) | C(O) | —C(CH₃)₃ | H | —C₆H₅ | —C₆H₄NH₂-2 |
| 331 | C(O) | C(O) | —C(CH₃)₃ | H | —C₆H₄F-4 | —C₆H₅ |
| 332 | C(O) | C(O) | —CH(CH₃)₂C(CH₃)₃ | H | —C₆H₄CH₃-4 | —C₆H₄F-4 |
| 333 | C(O) | C(O) | —C(CH₃)₃ | H | —C₆H₄OH-3 | —C₆H₄NO₂-2 |
| 334 | C(O) | C(O) | —C(CH₃)₃ | H | —C₆H₄CH₂CH₃-4 | —C₆H₃Cl₂-3,5 |
| 335 | C(O) | C(O) | —C(CH₃)₃ | H | —C₆H₄OCH₂CH=CH₂-3 | —C₆H₅ |
| 336 | C(O) | C(O) | —CH(CH₃)C(CH₃)₃ | H | —C₆H₄CH₃-4 | —C₆H₃(CH₃)₂-3,5 |
| 337 | C(O) | C(O) | —CH(CH₃)C(CH₃)₃ | H | —C₆H₄CH₃-4 | —C₆H₃NO₂-2-CH₃-3 |
| 338 | C(O) | C(O) | —CH(CH₃)C(CH₃)₃ | H | —C₆H₄CH₃-4 | —C₆H₃NO₂-2-CH₃-5 |
| 339 | C(O) | C(O) | —CH(CH₃)C(CH₃)₃ | H | —C₆H₄CH₃-4 | —C₆H₄CH₃-3 |
| 340 | C(O) | C(O) | —CH(CH₃)C(CH₃)₃ | H | —C₆H₄CH₃-4 | —C₆H₄I-2 |
| 341 | C(O) | C(O) | —C(CH₃)₃ | H | —C₆H₄Cl-4 | —C₆H₄F-2 |
| 342 | C(O) | C(O) | —C(CH₃)₃ | H | —C₆H₄CH₂CH₃-4 | —C₆H₃Cl₂-3,4 |
| 343 | C(O) | C(O) | —C(CH₃)₃ | H | —C₆H₄CH₂CH₃-4 | —C₆H₄F-2 |
| 344 | C(O) | C(O) | —C(CH₃)₃ | H | —C₆H₄OC(O)N(CH₃)₂-3 | —C₆H₅ |
| 345 | C(O) | C(O) | —C(CH₃)₃ | H | —C₆H₄OCO₂CH₃-4 | —C₆H₅ |
| 346 | C(O) | C(O) | —C(CH₃)₃ | H | —C₆H₄OCO₂CH=CH₂-3 | —C₆H₄Cl-4 |
| 347 | C(O) | C(O) | —C(CH₃)₃ | H | —C₆H₄CO₂CH₃-4 | —C₆H₃(CH₃)₂-3,5 |
| 348 | C(O) | C(O) | —C(CH₃)₃ | H | —C₆H₄CO₂CH₃-4 | —C₆H₄CH₃-3 |
| 349 | C(O) | C(O) | —C(CH₃)₃ | H | —C₆H₄CO₂H-4 | —C₆H₄CH₃-3 |
| 350 | C(O) | C(O) | —C(CH₃)₃ | H | —C₆H₃NH₂-2-OCH₃-3 | —C₆H₄CH₃-3 |
| 351 | C(O) | C(O) | —C(CH₃)₃ | H | —C₆H₄NH₂-4 | —C₆H₄Cl-4 |
| 352 | C(O) | C(O) | —C(CH₃)₃ | H | —C₆H₄NHCO₂CH₃-4 | —C₆H₄Cl-4 |
| 353 | C(O) | C(O) | —C(CH₃)₃ | H | —C₆H₄NHC(O)CH₃-4 | —C₆H₄Cl-4 |
| 354 | C(O) | C(O) | —C(CH₃)₃ | H | —C₆H₃NHC(O)CH₃-2-OCH₃-3 | —C₆H₄CH₃-3 |
| 355 | C(O) | C(O) | —C(CH₃)₃ | H | —C₆H₄OC₆H₅-3 | —C₆H₅ |
| 356 | C(O) | C(O) | —C(CH₃)₃ | H | —C₆H₄OC₆H₅-3 | —C₆H₄CH₃-3 |
| 357 | C(O) | C(O) | —C(CH₃)₃ | H | —C₆H₄OCH₂OCH₃-4 | —C₆H₅ |
| 358 | C(O) | C(O) | —C(CH₃)₃ | H | —C₆H₄OC(O)N(CH₃)₂-4 | —C₆H₅ |
| 359 | C(O) | C(O) | —C(CH₃)₃ | H | —C₆H₄OCH₂CO₂CH₃-4 | —C₆H₅ |
| 360 | C(O) | C(O) | —C(CH₃)₃ | H | —C₆H₄CH₂OC(O)CH₃-4 | —C₆H₅ |
| 361 | C(O) | C(O) | —C(CH₃)₃ | H | —C₆H₄CH₂SCN-4 | —C₆H₄Br-4 |
| 362 | C(O) | C(O) | —C(CH₃)₃ | H | —C₆H₄CH₂OH-4 | —C₆H₅ |
| 363 | C(O) | C(O) | —C(CH₃)₃ | H | —C₆H₄Br-4 | —C₆H₅ |
| 364 | C(O) | C(O) | —C(CH₃)₃ | H | —C₆H₄OCH₂SCH₃-4 | —C₆H₅ |
| 365 | C(O) | C(O) | —C(CH₃)₃ | H | —C₆H₄OCH₂C(CH₃)₂-4 | —C₆H₅ |
| 366 | C(O) | C(O) | —C(CH₃)₃ | H | —C₆H₄OCH₂CN-4 | —C₆H₅ |
| 367 | C(O) | C(O) | —C(CH₃)₃ | H | —C₆H₄CH₂CN-4 | —C₆H₅ |
| 368 | C(O) | C(O) | —C(CH₃)₃ | H | —C₆H₄CH⟶CHCH₃-4 (epoxide O) | —C₆H₅ |
| 369 | C(O) | C(O) | —C(CH₃)₃ | H | —C₆H₄C(CH₃)=NNHC(O)NH₂-4 | —C₆H₄CH₃-3 |
| 370 | C(O) | C(O) | —C(CH₃)₃ | H | —C₆H₄C₆H₅-4 | —C₆H₄CH₃-3 |

TABLE I-continued $$A-G_2 \overset{X}{\underset{R^2}{\|}} N-N-G_2 \overset{X'}{\underset{R^1}{\|}} B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 371 | C(O) | C(O) | —C(CH₃)₃ | H | —C₆H₄CN-3 | —C₆H₄CH₃-3 |
| 372 | C(O) | C(O) | —C(CH₃)₃ | H | —C₆H₄NH₂-3 | —C₆H₄CH₃-3 |
| 373 | C(O) | C(O) | —C(CH₃)₃ | H | —C₆H₄C(O)NHC(CH₃)₂CH₂OH-4 | —C₆H₄CH₃-3 |
| 374 | C(O) | C(O) | —C(CH₃)₃ | H | —C₆H₄CH(OH)CH₃-4 | —C₆H₄CH₃-3 |
| 375 | C(O) | C(O) | —C(CH₃)₃ | H | —C₆H₄NHC(O)C(CH₃)=CH₂-3 | —C₆H₄CH₃ |
| 376 | C(O) | C(O) | —C(CH₃)₃ | H | —C₆H₄CO₂H-3 | —C₆H₄CH₃-3 |
| 377 | C(O) | C(O) | —C(CH₃)₃ | H | —C₆H₄CH₂Cl-3 | —C₆H₄CH₃-3 |
| 378 | C(O) | C(O) | —C(CH₃)₃ | H | —C₆H₄CH₂CH₃-4 | —C₆H₃(CH₃)₂-2,3 |
| 379 | C(O) | C(O) | —C(CH₃)₃ | H | —C₆H₃(CH₃)₂-2,3 | —C₆H₄CH₃-3 |
| 380 | C(O) | C(O) | —C(CH₃)₃ | H | —C₆H₅-4 | —C₆H₃(CH₃)₂-2,3 |
| 381 | C(O) | C(O) | —C(CH₃)₃ | H | —C₆H₄CH₃-4 | —C₆H₃(CH₃)₂-2,3 |
| 382 | C(O) | C(O) | —CH(CH₃)C(CH₃)₃ | H | —C₆H₄CH₃-4 | —C₆H₄CH₂-2 |
| 383 | C(O) | C(O) | —CH(CH₃)C(CH₃)₃ | H | —C₆H₄CH₃-4 | —C₆H₄CF₃-2 |
| 384 | C(O) | C(O) | —CH(CH₃)CH₂C(CH₃)₃ | H | —C₆H₄CH₃-4 | —C₆H₅ |
| 385 | C(O) | C(O) | —C(CH₃)₃ | H | —C₆H₄OCH₃-4 | —C₆H₄CH₃-3 |
| 386 | C(O) | C(O) | —C(CH₃)₃ | H | —C₆H₄C(CH₃)=CH₂-4 | —C₆H₄CH₃-3 |
| 387 | C(O) | C(O) | —C(CH₃)₃ | H | naphthalen-1-yl |  |
| 388 | C(O) | C(O) | —C(CH₃)₃ | H | naphthalen-1-yl | —C₆H₄CH₃-3 |
| 389 | C(O) | C(O) | —C(CH₃)₃ | H | —C₆H₄NCS-4 | —C₆H₄CH₃-3 |
| 390 | C(O) | C(O) | —C(CH₃)₃ | H | —C₆H₃(CH₃)₂-3,5 | —C₆H₃(CH₃)₂-3,5 |
| 391 | C(O) | C(O) | —C(CH₃)₃ | H | —C₆H₃Cl₂-2,4 | —C₆H₃Cl₂-2,4 |
| 392 | C(O) | C(O) | —C(CH₃)₃ | H | —C₆H₄F-2 | —C₆H₄Br-2 |
| 393 | C(O) | C(O) | —C(CH₃)₃ | H | —C₆H₃(CH₃)₂-2,3 | —C₆H₄CH₃-3 |
| 394 | C(O) | C(O) | —C(CH₃)₃ | H | —C₆H₄F-2 | —C₆H₃(CH₃)₂-2,3 |
| 395 | C(O) | C(O) | —C(CH₃)₃ | H | —C₆H₄F-2 | —C₆H₄NO₂-2 |
| 396 | C(O) | C(O) | —C(CH₃)₃ | H | —C₆H₃CH₃-2-Cl₃ | —C₆H₅ |
| 397 | C(O) | C(O) | —C(CH₃)₃ | H | —C₆H₃CH₃-2-Cl-3 | —C₆H₄CH₃-3 |
| 398 | C(O) | C(O) | —C(CH₃)₃ | H | —C₆H₄CH₃-4 | —C₆H₅ |
| 399 | C(O) | C(O) | —CH(CH₃)CH₂C(CH₃)₃ | H | —C₆H₄CH₃-4 | —C₆H₃(CH₃)₂-3,5 |
| 400 | C(O) | C(O) | —CH(CH₃)CH₂C(CH₃)₃ | H | —C₆H₄CH₃-4 | —C₆H₃Cl₂-3,4 |
| 401 | C(O) | C(O) | —C(CH₃)₃ | H | —C₆H₄Br-4 | —C₆H₅ |
| 402 | C(O) | C(O) | —C(CH₃)₃ | H | —C₆H₃Cl₂-2,3 | —C₆H₄Br-2 |
| 403 | C(O) | C(O) | —C(CH₃)₃ | H | —C₆H₃Cl₂-2,3 | —C₆H₅ |

TABLE I-continued $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 404 | C(O) | C(O) | —C(CH$_3$)$_3$ | H | —C$_6$H$_4$F-2 | —C$_6$H$_3$(CH$_3$)$_2$-3,5 |
| 405 | C(O) | C(O) | —C(CH$_3$)$_3$ | H | —C$_6$H$_3$Cl$_2$-2,3 | —C$_6$H$_4$CH$_3$-3 |
| 406 | C(O) | C(O) | —C(CH$_3$)$_3$ | H | —C$_6$H$_5$ | (2-methylnaphthyl) |
| 407 | C(O) | C(O) | —C(CH$_3$)$_3$ | H | (2-methylnaphthyl) | —C$_6$H$_4$CH$_3$-3 |
| 408 | C(O) | C(O) | —C(CH$_3$)$_3$ | H | —C$_6$H$_5$ | —C$_6$H$_4$OCF$_3$-3 |
| 409 | C(O) | C(O) | —C(CH$_3$)$_3$ | H | —C$_6$H$_4$NCS-4 | —C$_6$H$_5$ |
| 410 | C(O) | C(O) | —C(CH$_3$)$_3$ | H | —C$_6$H$_3$F$_2$-2,6 | —C$_6$H$_3$Cl$_2$-2,4 |
| 411 | C(O) | C(O) | —C(CH$_3$)$_3$ | H | —C$_6$H$_3$F$_2$-2,6 | —C$_6$H$_3$Cl$_2$-3,5 |
| 412 | C(O) | C(O) | —C(CH$_3$)$_3$ | H | —C$_6$H$_4$CH$_3$-4 | —C$_6$H$_3$(CF$_3$)$_2$-3,5 |
| 413 | C(O) | C(O) | —C(CH$_3$)$_3$ | H | —C$_6$H$_5$ | —C$_6$H$_3$(CF$_3$)$_2$-3,5 |
| 414 | C(O) | C(O) | —CH(CH$_3$)C(CH$_3$)(CH$_2$CH$_3$)$_2$ | H | —C$_6$H$_4$CH$_3$-4 | —C$_6$H$_5$ |
| 415 | C(O) | C(O) | —CH(CH$_3$)C(CH$_3$)(CH$_2$CH$_3$)$_2$ | H | —C$_6$H$_4$CH$_3$-4 | —C$_6$H$_3$(CH$_3$)$_2$-3,5 |
| 416 | C(O) | C(O) | —CH(CH$_3$)C(CH$_3$)(CH$_2$CH$_3$)$_2$ | H | —C$_6$H$_4$CH$_3$-4 | —C$_6$H$_4$NO$_2$-2 |
| 417 | C(O) | C(O) | —CH(CH$_3$)C(CH$_3$)(CH$_3$)$_3$ | H | —C$_6$H$_4$CH$_2$CH$_3$-4 | —C$_6$H$_3$(CH$_3$)$_2$-3,5 |
| 418 | C(O) | C(O) | —C(CH$_3$)$_3$ | H | —C$_6$H$_4$CH$_2$CH$_3$-4 | —C$_6$H$_3$NO$_2$-2-CH$_3$-5 |
| 419 | C(O) | C(O) | —C(CH$_3$)$_3$ | H | —C$_6$H$_5$ | —C$_6$H$_3$Cl-3-F-4 |
| 420 | C(O) | C(O) | —C(CH$_3$)$_3$ | H | —C$_6$H$_4$Cl-4 | —C$_6$H$_3$Cl-3-F-4 |
| 421 | C(O) | C(O) | —CH(CH$_3$)$_2$ | H | —C$_6$H$_4$CH$_2$CH$_3$-4 | —C$_6$H$_3$(CH$_3$)$_2$-3,5 |
| 422 | C(O) | C(O) | —C(CH$_3$)$_3$ | H | —C$_6$H$_4$Cl-4 | —C$_6$H$_3$(CF$_3$)$_2$-3,5 |
| 423 | C(O) | C(O) | —C(CH$_3$)$_3$ | H | —C$_6$H$_3$(CH$_3$)$_2$-2,3 | —C$_6$H$_3$CH$_3$-3,4 |
| 424 | C(O) | C(O) | —C(CH$_3$)$_3$ | H | —C$_6$H$_4$CH$_3$-4 | —C$_6$H$_3$CH$_3$-2-Cl-3 |
| 425 | C(O) | C(O) | —C(CH$_3$)$_3$ | H | —C$_6$H$_3$Cl-3-F-4 | —C$_6$H$_5$ |
| 426 | C(O) | C(O) | —C(CH$_3$)$_3$ | H | —C$_6$H$_3$(CH$_3$)$_2$-2,6 | —C$_6$H$_4$CH$_3$-3 |
| 427 | C(O) | C(O) | —C(CH$_3$)$_3$ | H | —C$_6$H$_3$(CH$_3$)$_2$-2,6 | —C$_6$H$_3$(CH$_3$)$_2$-3,5 |
| 428 | C(O) | C(O) | —C(CH$_3$)$_3$ | H | —C$_6$H$_3$(CH$_3$)$_2$-2,3 | —C$_6$H$_4$Br-2 |
| 429 | C(O) | C(O) | —C(CH$_3$)$_3$ | H | —C$_6$H$_3$(CH$_3$)$_2$-2,3 | —C$_6$H$_3$(CH$_3$)$_2$-3,5 |
| 430 | C(O) | C(O) | —C(CH$_3$)$_3$ | H | —C$_6$H$_3$(CH$_3$)$_2$-2,3 | —C$_6$H$_4$Cl-3 |
| 431 | C(O) | C(O) | —C(CH$_3$)$_3$ | H | —C$_6$H$_4$OCF$_3$-3 | —C$_6$H$_5$ |
| 432 | C(O) | C(O) | —C(CH$_3$)$_3$ | H | —C$_6$H$_3$(CH$_3$)$_2$-2,3 | —C$_6$H$_4$CH$_3$-3 |
| 433 | C(O) | C(O) | —C(CH$_3$)$_3$ | H | —C$_6$H$_4$CH$_2$CH$_3$-4 | —C$_6$H$_3$CH$_3$-2-Cl-3 |
| 434 | C(O) | C(O) | —C(CH$_3$)$_3$ | H | —C$_6$H$_4$CH$_3$-4 | —C$_6$H$_3$Cl$_2$-2,4 |
| 435 | C(O) | C(O) | —CH(CH$_3$)C(CH$_3$)(CH$_2$CH$_3$)$_2$ | H | —C$_6$H$_4$CH$_3$-4 | —C$_6$H$_3$NO$_2$-2-CH$_3$-5 |
| 436 | C(O) | C(O) | —CH(CH$_3$)C(CH$_3$)(CH$_2$CH$_3$)$_2$ | H | —C$_6$H$_4$CH$_3$-4 | —C$_6$H$_3$NO$_2$-2-CH$_3$-3 |
| 437 | C(O) | C(O) | —C(CH$_3$)$_3$ | H | —C$_6$H$_3$F$_2$-2,6 | —C$_6$H$_4$Br-2 |

TABLE I-continued $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $R^1$ | $G_2(X')$ | $R^2$ | A | B |
|---|---|---|---|---|---|---|
| 438 | C(O) | —C(CH₃)₃ | C(O) | H | —C₆H₃CH₃-2-Cl-3 | —C₆H₃(CH₃)₂-3,5 |
| 439 | C(O) | —C(CH₃)₃ | C(O) | H | —C₆H₃CH₃-2-Cl-3 | —C₆H₃Cl-3-F-4 |
| 440 | C(O) | —C(CH₃)₃ | C(O) | H | —C₆H₃(CH₃)₂-2,3 | —C₆H₃Cl-3-F-4 |
| 441 | C(O) | —C(CH₃)₃ | C(O) | H | —C₆H₄CH₂CH₃-4 | —C₆H₃Cl-3-F-4 |
| 442 | C(O) | —C(CH₃)₃ | C(O) | H | —C₆H₃(CH₃)₂-3,4 | —C₆H₅ |
| 443 | C(O) | —C(CH₃)₃ | C(O) | H | —C₆H₃(CH₃)₂-3,4 | —C₆H₄CH₃-3 |
| 444 | C(O) | —C(CH₃)₃ | C(O) | H | —C₆H₃(CH₃)₂-3,4 | —C₆H₄Cl-2 |
| 445 | C(O) | —C(CH₃)₃ | C(O) | H | —C₆H₃(CH₃)₂-3,4 | —C₆H₃Cl₂-2,4 |
| 446 | C(O) | —C(CH₃)₃ | C(O) | H | —C₆H₃(CH₃)₂-3,4 | —C₆H₄Br-2 |
| 447 | C(O) | —C(CH₃)₃ | C(O) | H | —C₆H₃(CH₃)₂-3,4 | —C₆H₃(CH₃)₂-3,5 |
| 448 | C(O) | —C(CH₃)₃ | C(O) | H | —C₆H₃(CH₃)₂-3,4 | —C₆H₄NO₂-2 |
| 449 | C(O) | —C(CH₃)₃ | C(O) | H | —C₆H₃(CH₃)₂-3,4 | —C₆H₃(CH₃)₂-3,4 |
| 450 | C(O) | —C(CH₃)₃ | C(O) | H | —C₆H₃(*CH₃*)₂-3,4 | —C₆H₃(CH₃)₂-3,4 |
| 451 | C(O) | —C(CH₃)₃ | C(O) | H | —C₆H₅ | —C₆H₄CH₃-3 |
| 452 | C(O) | —CH(CH₂CH₃)C(CH₃)₃ | C(O) | H | —C₆H₄CH₂CH₃-4 | —C₆H₅ |
| 453 | C(O) | —C(CH₃)₃ | C(O) | H | —C₆H₄CH₂Cl-4 | —C₆H₅ |
| 454 | C(O) | —C(CH₃)₃ | C(O) | H | —C₆H₃F-2-Cl-6 | —C₆H₄Cl-4 |
| 455 | C(O) | —C(CH₃)₃ | C(O) | H | —C₆H₄CH₃-4 | —C₆H₄Br-2 |
| 456 | C(O) | —C(CH₃)₃ | C(O) | H | —C₆H₃(OCH₃)₂-2,3 | —C₆H₃Cl₂-3,4 |
| 457 | C(O) | —C(CH₃)₃ | C(O) | H | —C₆H₃(OCH₃)₂-2,3 | —C₆H₃(CH₃)₂-3,4 |
| 458 | C(O) | —C(CH₃)₃ | C(O) | H | —C₆H₃(OCH₃)₂-2,3 | —C₆H₃(CH₃)₂-3,5 |
| 459 | C(O) | —C(CH₃)₃ | C(O) | H | —C₆H₃Cl-3-F-4 | —C₆H₄NO₂-2 |
| 460 | C(O) | —C(CH₃)₃ | C(O) | H | —C₆H₄C(CH₃)₃-4 | —C₆H₄Br-2 |
| 461 | C(O) | —C(CH₃)₃ | C(O) | H | —C₆H₄C(CH₃)₃-4 | —C₆H₄Cl-2 |
| 462 | C(O) | —C(CH₃)₃ | C(O) | H | —C₆H₄C(CH₃)₃-4 | —C₆H₃Cl₂-2,4 |
| 463 | C(O) | —C(CH₃)₃ | C(O) | H | —C₆H₄C(CH₃)₃-4 | —C₆H₄NO₂-2 |
| 464 | C(O) | —C(CH₃)₃ | C(O) | H | —C₆H₄C(CH₃)₃-4 | —C₆H₄Br-2 |
| 465 | C(O) | —C(CH₃)₃ | C(O) | H | —C₆H₄C(CH₃)₃-4 | —C₆H₄CH₃-3 |
| 466 | C(O) | —C(CH₃)₃ | C(O) | H | —C₆H₄C(CH₃)₃-4 | —C₆H₄Cl-2 |
| 467 | C(O) | —C(CH₃)₃ | C(O) | H | —C₆H₄C(CH₃)₃-4 | —C₆H₃Cl₂-3,4 |
| 468 | C(O) | —C(CH₃)₃ | C(O) | H | —C₆H₃(CH₃)₂-3,4 | —C₆H₃Cl₂-3,4 |
| 469 | C(O) | —C(CH₃)₃ | C(O) | H | —C₆H₄C(CH₃)₃-4 | —C₆H₄F-4 |
| 470 | C(O) | —CH(CH₂CH₃)C(CH₃)₃ | C(O) | H | —C₆H₄CH₃-4 | —C₆H₄NO₂-2 |
| 471 | C(O) | —CH(CH₂CH₃)C(CH₃)₃ | C(O) | H | —C₆H₄CH₃-4 | —C₆H₃NO₂-2-CH₃-5 |
| 472 | C(O) | —CH(CH₂CH₃)C(CH₃)₃ | C(O) | H | —C₆H₄F-4 | —C₆H₃(CH₃)₂-3,5 |
| 473 | C(O) | —C(CH₃)₃ | C(O) | H | —C₆H₃NH₂-2-OCH₃-3 | —C₆H₅ |
| 474 | C(O) | —C(CH₃)₃ | C(O) | H |  | —C₆H₃Cl₂-2,4 |

TABLE I-continued $$A-G_2 \quad \overset{X}{N}=\overset{X'}{N}-G_2-B$$
$$\underset{R^2}{|} \underset{R^1}{|}$$

where $G_2$ N is a single bond when $R^2$ is "H" and is a double bond when $R^2$ is "—"

| Ex. No. | G$_2$(X) | G$_2$(X') | R$^1$ | R$^2$ | A | B |
|---|---|---|---|---|---|---|
| 475 | C(O) | C(O) | —C(CH$_3$)$_3$ | H | [naphthyl] | —C$_6$H$_4$Br-2 |
| 476 | C(O) | C(O) | —C(CH$_3$)$_3$ | H | —C$_6$H$_3$CH$_3$-2-NO$_2$-3 | —C$_6$H$_5$ |
| 477 | C(O) | C(O) | —C(CH$_3$)$_3$ | H | —C$_6$H$_3$CH$_3$-2-NO$_2$-3 | —C$_6$H$_4$CH$_3$-3 |
| 478 | C(O) | C(O) | —C(CH$_3$)$_3$ | H | —C$_6$H$_3$CH$_3$-2-NO$_2$-3 | —C$_6$H$_4$Cl-4 |
| 479 | C(O) | C(O) | —C(CH$_3$)$_3$ | H | —C$_6$H$_3$CH$_3$-2-NO$_2$-3 | —C$_6$H$_3$Cl$_2$-2,4 |
| 480 | C(O) | C(O) | —C(CH$_3$)$_3$ | H | —C$_6$H$_3$CH$_3$-2-Br-3 | —C$_6$H$_5$ |
| 481 | C(O) | C(O) | —C(CH$_3$)$_3$ | H | —C$_6$H$_3$CH$_3$-2-Br-3 | —C$_6$H$_4$CH$_3$-3 |
| 482 | C(O) | C(O) | —C(CH$_3$)$_3$ | H | —C$_6$H$_3$CH$_3$-2-Br-3 | —C$_6$H$_4$Cl-4 |
| 483 | C(O) | C(O) | —C(CH$_3$)$_3$ | H | —C$_6$H$_3$CH$_3$-2-Br-3 | —C$_6$H$_3$Cl$_2$-2,4 |
| 484 | C(O) | C(O) | —C(CH$_3$)$_3$ | H | —C$_6$H$_3$CH$_3$-2-NH$_2$-3 | —C$_6$H$_4$CH$_3$-3 |
| 485 | C(O) | C(O) | —C(CH$_3$)$_3$ | H | —C$_6$H$_4$CH$_3$-2 | —C$_6$H$_4$Br-2 |
| 486 | C(O) | C(O) | —C(CH$_3$)$_3$ | H | —C$_6$H$_4$CH$_3$-2 | —C$_6$H$_4$Cl-3 |
| 487 | C(O) | C(O) | —C(CH$_3$)$_3$ | H | —C$_6$H$_4$CH$_3$-2 | —C$_6$H$_4$Cl-4 |
| 488 | C(O) | C(O) | —C(CH$_3$)$_3$ | H | —C$_6$H$_4$CH$_3$-2 | —C$_6$H$_4$CH$_3$-3 |
| 489 | C(O) | C(O) | —C(CH$_3$)$_3$ | H | —C$_6$H$_4$CH$_3$-2 | —C$_6$H$_3$(CH$_3$)$_2$-3,5 |
| 490 | C(O) | C(O) | —C(CH$_3$)$_3$ | H | —C$_6$H$_4$CH$_3$-2 | —C$_6$H$_3$Cl$_2$-3,4 |
| 491 | C(O) | C(O) | —C(CH$_3$)$_3$ | H | —C$_6$H$_4$CH$_3$-2 | —C$_6$H$_3$Cl$_2$-3,5 |
| 492 | C(O) | C(O) | —C(CH$_3$)$_3$ | H | —C$_6$H$_4$CH$_3$-2 | —C$_6$H$_5$ |
| 493 | C(O) | C(O) | —C(CH$_3$)$_3$ | H | —C$_6$H$_3$CH$_3$-2-F-3 | —C$_6$H$_4$CH$_3$-3 |
| 494 | C(O) | C(O) | —C(CH$_3$)$_3$ | H | —C$_6$H$_3$CH$_3$-2-F-3 | —C$_6$H$_5$ |
| 495 | C(O) | C(O) | —C(CH$_3$)$_3$ | H | —C$_6$H$_3$F-2-Cl-6 | —C$_6$H$_3$Cl$_2$-2,4 |
| 496 | C(O) | C(O) | —C(CH$_3$)$_3$ | H | —C$_6$H$_3$F-2-Cl-6 | —C$_6$H$_4$F-4 |
| 497 | C(O) | C(O) | —C(CH$_3$)$_3$ | H | —C$_6$H$_4$CH$_2$CH$_2$Cl-4 | —C$_6$H$_3$(CH$_3$)$_2$-3,5 |
| 498 | C(O) | C(O) | —C(CH$_3$)$_3$ | H | —C$_6$H$_2$F$_3$-2,4,6 | —C$_6$H$_5$ |
| 499 | C(O) | C(O) | —C(CH$_3$)$_3$ | H | —C$_6$H$_2$F$_3$-2,4,6 | —C$_6$H$_3$Cl$_2$-2,4 |
| 500 | C(O) | C(O) | —C(CH$_3$)$_3$ | H | —C$_6$H$_2$F$_3$-2,4,6 | —C$_6$H$_4$Br-2 |
| 501 | C(O) | C(O) | —C(CH$_3$)$_3$ | H | —C$_6$H$_3$NO$_2$-2-Cl-3 | —C$_6$H$_3$(CH$_3$)$_2$-3,5 |
| 502 | C(O) | C(O) | —C(CH$_3$)$_3$ | H | —C$_6$H$_3$NO$_2$-2-Cl-3 | —C$_6$H$_5$ |
| 503 | C(O) | C(O) | —C(CH$_3$)$_3$ | H | —C$_6$H$_3$NO$_2$-2-Cl-3 | —C$_6$H$_4$Br-2 |
| 504 | C(O) | C(O) | —C(CH$_3$)$_3$ | H | | |

TABLE I $$A-G_2 \quad \begin{array}{cc} X & X' \\ N-N-G_2-B \\ | \quad | \\ R^2 \quad R^1 \end{array}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---------|----------|-----------|-------|-------|---|---|
| 505 | C(O) | C(O) | —C(CH₃)₃ | H | —C₆H₄NO₂-Cl-3 | —C₆H₄NO₂-2 |
| 506 | C(O) | C(O) | —C(CH₃)₃ | H | —C₆H₃NO₂-2-Cl-3 | —C₆H₄CH₃-3 |
| 507 | C(O) | C(O) | —C(CH₃)₃ | H | —C₆H₃NO₂-2-Cl-3 | —C₆H₄Cl-3 |
| 508 | C(O) | C(O) | —C(CH₃)₃ | H | —C₆H₃NO₂-2-Cl-3 | —C₆H₃Cl₂-2,4 |
| 509 | C(O) | C(O) | —C(CH₃)₃ | H | —C₆H₃NO₂-2-Cl-3 | —C₆H₃Cl₂-3,5 |
| 510 | C(O) | C(O) | —C(CH₃)₃ | H | —C₆H₃NO₂-2-Cl-3 | —C₆H₃(CH₃)₂-3,5 |
| 511 | C(O) | C(O) | —C(CH₃)₃ | H | —C₆H₄CH₂CH₃-4 | —C₆H₃F₂-2,3 |
| 512 | C(O) | C(O) | —C(CH₃)₃ | H | —C₆H₄CH₂CH₃-4 | —C₆H₃Cl₂-2,3 |
| 513 | C(O) | C(O) | —C(CH₃)₃ | H | —C₆H₃F₂-2,3 | —C₆H₅ |
| 514 | C(O) | C(O) | —C(CH₃)₃ | H | —C₆H₃Cl₂-2,3 | —C₆H₄NO₂-2 |
| 515 | C(O) | C(O) | —C(CH₃)₃ | H | —C₆H₅ | —C₆H₃F₂-2,3 |
| 516 | C(O) | C(O) | —C(CH₃)₃ | H | —C₆H₃Cl 2-2,3 | —C₆H₃(CH₃)₂-3,5 |
| 517 | C(O) | C(O) | —C(CH₃)₃ | H | —C₆H₃Cl₂-2,3 | —C₆H₃Cl₂-2,4 |
| 518 | C(O) | C(O) | —C(CH₃)₃ | H | —C₆H₃Cl₂-2,3 | —C₆H₃Cl₂-3,5 |
| 519 | C(O) | C(O) | —C(CH₃)₃ | H | —C₆H₃Cl₂-2,3 | —C₆H₄Cl-3 |
| 520 | C(O) | C(O) | —C(CH₃)₃ | H | —C₆H₃Cl₂-2,3 | —C₆H₃(CH₃)₂-2,3 |
| 521 | C(O) | C(O) | —C(CH₃)₃ | H | —C₆H₃F₂-2,3 | —C₆H₄Br-2 |
| 522 | C(O) | C(O) | —C(CH₃)₃ | H | —C₆H₃(CH₃)₂-2,3 | —C₆H₄Cl-4 |
| 523 | C(O) | C(O) | —C(CH₃)₃ | H | —C₆H₃(CH₃)₂-2,3 | —C₆H₃Cl₂-2,4 |
| 524 | C(O) | C(O) | —C(CH₃)₃ | H | —C₆H₃(CH₃)₂-2,3 | —C₆H₃F₂-2,6 |
| 525 | C(O) | C(O) | —C(CH₃)₃ | H | —C₆H₃(CH₃)₂-2,3 | —C₆H₃F₂-2,4 |
| 526 | C(O) | C(O) | —C(CH₃)₃ | H | —C₆H₃(CH₃)₂-2,3 | —C₆H₄OCH₃-3 |
| 527 | C(O) | C(O) | —C(CH₃)₃ | H | —C₆H₃(CH₃)₂-2,3 | —C₆H₄OCH₃-2 |
| 528 | C(O) | C(O) | —C(CH₃)₃ | H | —C₆H₃(CH₃)₂-2,3 | —C₆H₄CH₃-2 |
| 529 | C(O) | C(O) | —C(CH₃)₃ | H | —C₆H₃(CH₃)₂-2,3 | —C₆H₄CH₃-4 |
| 530 | C(O) | C(O) | —C(CH₃)₃ | H | —C₆H₃(CH₃)₂-2,3 | —C₆H₃Cl₂-2,4 |
| 531 | C(O) | C(O) | —C(CH₃)₃ | H | —C₆H₄CH₃-2-Cl-3 | —C₆H₅ |
| 532 | C(O) | C(O) | —C(CH₃)₃ | H | —C₆H₄CH₂CH₂Cl-4 | —C₆H₃Cl₂-2,4 |
| 533 | C(O) | C(O) | —C(CH₃)₃ | H | —C₆H₄CH₂CH₃-4 | —C₆H₃(CH₃)₂-3,5 |
| 534 | C(O) | C(O) | —C(CH₃)₃ | H | —C₆H₃F-3-CH₃-4 | —C₆H₃F 2-3,5 |
| 535 | C(O) | C(O) | —C(CH₃)₃ | H | —C₆H₃F-3-CH₃-4 | —C₆H₄CH₃-3 |
| 536 | C(O) | C(O) | —C(CH₃)₃ | H | —C₆H₃F-3-CH₃-4 | —C₆H₃Cl₂-3,5 |
| 537 | C(O) | C(O) | —C(CH₃)₃ | H | —C₆H₃F-3-CH₃-4 | —C₆H₄NO₂-2 |
| 538 | C(O) | C(O) | —C(CH₃)₃ | H | —C₆H₃F-3-CH₃-4 | —C₆H₃Cl₂-2,4 |
| 539 | C(O) | C(O) | —C(CH₃)₃ | H | —C₆H₄CH₂CH₃-4 | —C₆H₃F 2-3,5 |
| 540 | C(O) | C(O) | —C(CH₃)₃ | H | —C₆H₃(CH₃)₂-2,3 | —C₆H₄1-2 |
| 541 | C(O) | C(O) | —C(CH₃)₃ | H | —C₆H₄CH₂CH₂OH-4 | —C₆H₃Cl₂-2,4 |
| 542 | C(O) | C(O) | —C(CH₃)₃ | H | —C₆H₃F₂-2,6-CH₃-3 | —C₆H₅ |
| 543 | C(O) | C(O) | —C(CH₃)₃ | H | —C₆H₃F₂-2,6-CH₃-3 | —C₆H₄CH₃-3 |
| 544 | C(O) | C(O) | —C(CH₃)₃ | H | —C₆H₃F₂-2,6-CH₃-3 | —C₆H₃Cl₂-2,4 |
| 545 | C(O) | C(O) | —C(CH₃)₃ | H | —C₆H₄Cl-4 | —C₆H₃(CH₃)₂-2,3 |
| 546 | C(O) | C(O) | —CH(CH₃)C(CH₃)₃ | H | —C₆H₃(CH₃)₂-2,3 | —C₆H₃(CH₃)₂-3,5 |
| 547 | C(O) | C(O) | —CH(CH₃)C(CH₃)₃ | H | —C₆H₃(CH₃)₂-2,3 | —C₆H₄CH₃-3 |
| 548 | C(O) | C(O) | —C(CH₃)₃ | H | —C₆H₃F-2-Cl-6 | —C₆H₃F₂-2,3 |

-continued
TABLE I $$A-G_2 \overset{X}{\underset{R^2}{N-N}} \overset{X'}{\underset{R^1}{-G_2-B}}$$

where $G_2\text{'N}$ is a single bond when $R^2$ is "H" and is a double bond when $R^2$ is "—"

| Ex. No. | $G_2(X)$ | $G_2(X')$ | $R^1$ | $R^2$ | A | $B_1/93$ |
|---|---|---|---|---|---|---|
| 549 | C(O) | C(O) | —C(CH$_3$)$_3$ | H | —C$_6$H$_3$F$_2$-2,3 | —C$_6$H$_4$NO$_2$-2 |
| 550 | C(O) | C(O) | —C(CH$_3$)$_3$ | H | —C$_6$H$_3$F$_2$-2,3 | —C$_6$H$_4$CH$_3$-3 |
| 551 | C(O) | C(O) | —C(CH$_3$)$_3$ | H | —C$_6$H$_3$F$_2$-2,3 | —C$_6$H$_3$(CH$_3$)$_2$-3,5 |
| 552 | C(O) | C(O) | —C(CH$_3$)$_3$ | H | —C$_6$H$_3$F$_2$-2,3 | —C$_6$H$_3$Cl$_2$-2,4 |
| 553 | C(O) | C(O) | —C(CH$_3$)$_3$ | H | —C$_6$H$_3$(CH$_3$)$_2$-2,3 | —C$_6$H$_3$F$_2$-2,3 |
| 554 | C(O) | C(O) | —C(CH$_3$)$_3$ | H | —C$_6$H$_3$(CH$_3$)$_2$-2,3 | —C$_6$H$_3$Cl$_2$-2,3 |
| 555 | C(O) | C(O) | —C(CH$_3$)$_3$ | H | —C$_6$H$_3$(CH$_3$)$_2$-2,3 | —C$_6$H$_3$(CH$_3$)$_2$-3,4 |
| 556 | C(O) | C(O) | —C(CH$_3$)$_3$ | H | —C$_6$H$_4$CH$_2$CH$_3$-4 | —C$_6$H$_4$NO$_2$-2 |
| 557 | C(O) | C(O) | —C(CH$_3$)$_3$ | H | —C$_6$H$_3$(CH$_3$)$_2$-2,3 | —C$_6$H$_3$CH$_3$-2-Cl-5 |
| 558 | C(O) | C(O) | —C(CH$_3$)$_3$ | H | —C$_6$H$_5$ | —C$_6$H$_5$ |
| 559 | C(O) | C(O) | —C(CH$_3$)$_3$ | H | —C$_6$H$_3$F$_2$-2,6 | —C$_6$H$_3$CH$_3$-2-Cl-5 |
| 560 | C(O) | C(O) | —C(CH$_3$)$_3$ | H | —C$_6$H$_3$(CH$_3$)$_2$-2,3 | —C$_6$H$_3$CH$_3$-2-Cl-5 |
| 561 | C(O) | C(O) | —C(CH$_3$)$_3$ | H | —C$_6$H$_3$CH$_3$-2-Cl-3 | —C$_6$H$_3$CH$_3$-2-Cl-5 |
| 562 | C(O) | C(O) | —C(CH$_3$)$_3$ | H | —C$_6$H$_3$F$_2$-2,6 | —C$_6$H$_3$Cl-2-CH$_3$-5 |
| 563 | C(O) | C(O) | —C(CH$_3$)$_3$ | H | —C$_6$H$_3$(CH$_3$)$_2$-2,3 | —C$_6$H$_3$Cl-2-CH$_3$-5 |
| 564 | C(O) | C(O) | —C(CH$_3$)$_3$ | H | —C$_6$H$_3$CH$_3$-2-Cl-3 | —C$_6$H$_3$Cl-2-CH$_3$-5 |
| 565 | C(O) | C(O) | —C(CH$_3$)$_3$ | H | —C$_6$H$_4$Cl-4 | —C$_6$H$_3$Cl-2-CH$_3$-5 |
| 566 | C(O) | C(O) | —C(CH$_3$)$_3$ | H | —C$_6$H$_4$Cl-4 | —C$_6$H$_3$Cl-2-CH$_3$-5 |
| 567 | C(O) | C(O) | —C(CH$_3$)$_3$ | H | —C$_6$H$_3$F-2-Cl-4 | —C$_6$H$_5$ |
| 568 | C(O) | C(O) | —C(CH$_3$)$_3$ | H | —C$_6$H$_3$F-2-Cl-4 | —C$_6$H$_4$CH$_3$-3 |
| 569 | C(O) | C(O) | —C(CH$_3$)$_3$ | H | —C$_6$H$_3$F-2-Cl-4 | —C$_6$H$_3$(CH$_3$)$_2$-3,5 |
| 570 | C(O) | C(O) | —C(CH$_3$)$_3$ | H | —C$_6$H$_3$F-2-Cl-4 | —C$_6$H$_3$Cl$_2$-3,5 |
| 571 | C(O) | C(O) | —C(CH$_3$)$_3$ | H | —C$_6$H$_3$F-2-Cl-4 | —C$_6$H$_4$Br-2 |
| 572 | C(O) | C(O) | —C(CH$_3$)$_3$ | H | —C$_6$H$_3$F-2-Cl-4 | —C$_6$H$_4$NO$_2$-2 |
| 573 | C(O) | C(O) | —C(CH$_3$)$_3$ | H | —C$_6$H$_3$Cl-2-CH$_3$-3 | —C$_6$H$_3$Cl$_2$-2,4 |
| 574 | C(O) | C(O) | —C(CH$_3$)$_3$ | H | —C$_6$H$_3$Cl-2-CH$_3$-3 | —C$_6$H$_5$ |
| 575 | C(O) | C(O) | —C(CH$_3$)$_3$ | H | —C$_6$H$_3$Cl-2-CH$_3$-3 | —C$_6$H$_4$CH$_3$-3 |
| 576 | C(O) | C(O) | —C(CH$_3$)$_3$ | H | —C$_6$H$_3$Cl-2-CH$_3$-3 | —C$_6$H$_3$(CH$_3$)$_2$-3,5 |
| 577 | C(O) | C(O) | —C(CH$_3$)$_3$ | H | —C$_6$H$_3$Cl-2-CH$_3$-3 | —C$_6$H$_3$Cl$_2$-3,5 |
| 578 | C(O) | C(O) | —C(CH$_3$)$_3$ | H | —C$_6$H$_3$Cl-2-CH$_3$-3 | —C$_6$H$_3$(CH$_3$)$_2$-3,5 |
| 579 | C(O) | C(O) | —C(CH$_3$)$_3$ | H | —C$_6$H$_3$Br-2-CH$_3$-3 | —C$_6$H$_3$Cl$_2$-2,4 |
| 580 | C(O) | C(O) | —C(CH$_3$)$_3$ | H | —C$_6$H$_3$Br-2-CH$_3$-3 | —C$_6$H$_3$Cl$_2$-2,4 |
| 581 | C(O) | C(O) | —C(CH$_3$)$_3$ | H | —C$_6$H$_3$Br-2-CH$_3$-3 | —C$_6$H$_4$CH$_3$-3 |
| 582 | C(O) | C(O) | —C(CH$_3$)$_3$ | H | —C$_6$H$_3$(CH$_3$)$_2$-2,3 | —C$_6$H$_3$(CH$_3$)$_2$-3,5 |
| 583 | C(O) | C(O) | —C(CH$_3$)$_3$ | H | —C$_6$H$_3$(CH$_3$)$_2$-2,3 | —C$_6$H$_4$Br-2 |
| 584 | C(O) | C(O) | —C(CH$_3$)$_3$ | H | —C$_6$H$_3$(CH$_3$)$_2$-2,3 | —C$_6$H$_4$Cl-2 |
| 585 | C(O) | C(O) | —C(CH$_3$)$_3$ | H | —C$_6$H$_3$(CH$_3$)$_2$-2,3 | —C$_6$H$_4$CF$_3$-2 |
| 586 | C(O) | C(O) | —C(CH$_3$)$_3$ | H | —C$_6$H$_3$(CH$_3$)$_2$-2,3 | —C$_6$H$_4$CH$_2$CH$_3$-4 |
| 587 | C(O) | C(O) | —C(CH$_3$)$_3$ | H | —C$_6$H$_3$(CH$_3$)$_2$-2,3 | —C$_6$H$_3$Cl$_2$-3,5 |
| 588 | C(O) | C(O) | —C(CH$_3$)$_3$ | H | —C$_6$H$_3$F$_2$-2,6 | —C$_6$H$_3$Cl-3-F-4 |
| 589 | C(O) | C(O) | —C(CH$_3$)$_3$ | H | —C$_6$H$_4$Cl-4 | —C$_6$H$_3$F$_2$-3,5 |
| 590 | C(O) | C(O) | —C(CH$_3$)$_3$ | H | —C$_6$H$_3$(CH$_3$)$_2$-2,3 | —C$_6$H$_3$F$_2$-3,5 |
| 591 | C(O) | C(O) | —C(CH$_3$)$_3$ | H | —C$_6$H$_3$CH$_3$-2-Cl-3 | —C$_6$H$_3$F$_2$-3,5 |
| 592 | C(O) | C(O) | —C(CH$_3$)$_3$ | H | —C$_6$H$_5$ | —C$_6$H$_3$F$_2$-3,5 |

-continued
TABLE I $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 593 | C(O) | C(O) | —C(CH$_3$)$_3$ | H | —C$_6$H$_4$CH$_2$CH$_3$-4 | —C$_6$H$_3$(CH$_3$)$_2$-2,5 |
| 594 | C(O) | C(O) | —C(CH$_3$)$_3$ | H | —C$_6$H$_3$F$_2$-2,6 | —C$_6$H$_3$F$_2$-3,5 |
| 595 | C(O) | C(O) | —C(CH$_3$)$_3$ | H | —C$_6$H$_3$CH$_3$-2-Cl-3 | —C$_6$H$_3$Cl$_2$-3,5 |
| 596 | C(O) | C(O) | —C(CH$_3$)$_3$ | H | —C$_6$H$_3$(CH$_3$)$_2$-2,3 | —C$_6$H$_3$(CH$_3$)$_2$-2,5 |
| 597 | C(O) | C(O) | —C(CH$_3$)$_3$ | H | —C$_6$H$_4$Br-2 | —C$_6$H$_3$(CH$_3$)$_2$-3,5 |
| 598 | C(O) | C(O) | —C(CH$_3$)$_3$ | H | —C$_6$H$_3$Br-2-CH$_3$-3 | —C$_6$H$_4$Cl-3 |
| 599 | C(O) | C(O) | —C(CH$_3$)$_3$ | H | —C$_6$H$_3$Cl-2-CH$_3$-3 | —C$_6$H$_4$Cl-3 |
| 600 | C(O) | C(O) | —C(CH$_3$)$_3$ | H | —C$_6$H$_3$Br-2-CH$_3$-3 | —C$_6$H$_4$NO$_2$-2 |
| 601 | C(O) | C(O) | —C(CH$_3$)$_3$ | H | —C$_6$H$_3$Cl-2-CH$_3$-3 | —C$_6$H$_4$NO$_2$-2 |
| 602 | C(O) | C(O) | —C(CH$_3$)$_3$ | H | —C$_6$H$_3$(CH$_3$)$_2$-2,3 | —C$_6$H$_3$NO$_2$-2-CH$_3$-3 |
| 603 | C(O) | C(O) | —C(CH$_3$)$_3$ | H | —C$_6$H$_3$(CH$_3$)$_2$-2,3 | —C$_6$H$_3$NO$_2$-2-CH$_3$-5 |
| 604 | C(O) | C(O) | —C(CH$_3$)$_3$ | H | —C$_6$H$_3$F$_2$-2,6 | —C$_6$H$_5$ |
| 605 | C(O) | C(O) | —C(CH$_3$)$_3$ | H | —C$_6$H$_3$(CH$_3$)$_2$-2,6 | —C$_6$H$_3$Cl$_2$-2,4 |
| 606 | C(O) | C(O) | —C(CH$_3$)$_3$ | H | —C$_6$H$_2$(CH$_3$)$_3$-2,4,6 | —C$_6$H$_3$(CH$_3$)$_2$-3,5 |
| 607 | C(O) | C(O) | —C(CH$_3$)$_3$ | H | —C$_6$H$_2$(CH$_3$)$_3$-2,4,6 | —C$_6$H$_3$Cl$_2$-2,4 |
| 608 | C(O) | C(O) | —C(CH$_3$)$_3$ | H | —C$_6$H$_3$F$_2$-2,6 | —C$_6$H$_4$CH$_3$-4 |
| 609 | C(O) | C(O) | —C(CH$_3$)$_3$ | H | —C$_6$H$_3$F$_2$-2,6 | —C$_6$H$_3$Cl$_2$-2,5 |
| 610 | C(O) | C(O) | —C(CH$_3$)$_3$ | H | —C$_6$H$_2$(CH$_3$)$_3$-2,4,6 | —C$_6$H$_4$Cl-4 |
| 611 | C(O) | C(O) | —C(CH$_3$)$_3$ | H | —C$_6$H$_2$(CH$_3$)$_3$-2,4,6 | —C$_6$H$_4$CH$_3$-3 |
| 612 | C(O) | C(O) | —C(CH$_3$)$_3$ | H | —C$_6$H$_3$(CH$_3$)$_3$-2,4,6 | —C$_6$H$_3$Cl$_2$-3,4 |
| 613 | C(O) | C(O) | —C(CH$_3$)$_3$ | H | —C$_6$H$_4$OC(O)CH$_3$-2 | —C$_6$H$_4$OC(O)CH$_3$-2 |
| 614 | C(O) | C(O) | —C(CH$_3$)$_3$ | H | —C$_6$H$_4$OH-2 | —C$_6$H$_4$OH-2 |
| 615 | C(O) | C(O) | —C(CH$_3$)$_3$ | H | —C$_6$H$_3$(CH$_3$)$_2$-2,4 | —C$_6$H$_4$CH$_3$-3 |
| 616 | C(O) | C(O) | —C(CH$_3$)$_3$ | H | —C$_6$H$_3$(CH$_3$)$_2$-2,4 | —C$_6$H$_3$Cl$_2$-2,4 |
| 617 | C(O) | C(O) | —C(CH$_3$)$_3$ | H | —C$_6$H$_3$(CH$_3$)$_2$-2,4 | —C$_6$H$_3$(CH$_3$)$_2$-3,5 |
| 618 | C(O) | C(O) | —C(CH$_3$)$_3$ | H | —C$_6$H$_3$(CH$_3$)$_2$-2,4 | —C$_6$H$_3$Cl$_2$-3,5 |
| 619 | C(O) | C(O) | —C(CH$_3$)$_3$ | H | —C$_6$H$_3$(CH$_3$)$_2$-2,4 | —C$_6$H$_4$Br-3 |
| 620 | C(O) | C(O) | —C(CH$_3$)$_3$ | H | —C$_6$H$_3$(CH$_3$)$_2$-2,4 | —C$_6$H$_3$Cl$_2$-3,4 |
| 621 | C(O) | C(O) | —C(CH$_3$)$_3$ | H | —C$_6$H$_3$Br-2-CH$_3$-3 | —C$_6$H$_5$ |
| 622 | C(O) | C(O) | —C(CH$_3$)$_3$ | H | 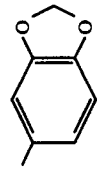 | —C$_6$H$_5$ |
| 623 | C(O) | C(O) | —C(CH$_3$)$_3$ | H | 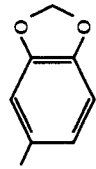 | —C$_6$H$_4$Cl-4 |

TABLE I -continued $$A-G_2-N=N-G_2-B$$
$$\phantom{A-G_2-N-N-G_2-B}|\phantom{-N-G_2-B}|$$
$$\phantom{A-G_2-N-N-G_2-}R^2\phantom{-}R^1$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 624 | C(O) | C(O) | —C(CH$_3$)$_3$ | H | 1,3-benzodioxol-5-yl | —C$_6$H$_4$CH$_3$-3 |
| 625 | C(O) | C(O) | —C(CH$_3$)$_3$ | H | C(CH$_3$)$_2$-N,O-benzoyl-4-methylphenyl | —C$_6$H$_4$CH$_3$-3 |
| 626 | C(O) | C(O) | —C(CH$_3$)$_3$ | H | N-(2-methylphenyl)cyclopentadienyl | —C$_6$H$_5$ |
| 627 | C(O) | C(O) | —C(CH$_3$)$_3$ | H | N-(2-methylphenyl)cyclopentadienyl | —C$_6$H$_4$CH$_3$-3 |
| 628 | C(O) | C(O) | —C(CH$_3$)$_3$ | H | —C$_6$H$_3$(CH$_3$)$_2$-2,3 | —C$_6$H$_3$Br-2-Cl-5 |
| 629 | C(O) | C(O) | —C(CH$_3$)$_3$ | H | —C$_6$H$_3$CH$_3$-2-Cl-3 | —C$_6$H$_4$Cl-3 |
| 630 | C(O) | C(O) | —C(CH$_3$)$_3$ | H | —C$_6$H$_3$CH$_3$-2-Cl-3 | —C$_6$H$_4$F-3 |
| 631 | C(O) | C(O) | —C(CH$_3$)$_3$ | H | —C$_6$H$_3$CH$_3$-2-Cl-3 | —C$_6$H$_4$Br-2 |
| 632 | C(O) | C(O) | —C(CH$_3$)$_3$ | H | —C$_6$H$_3$CH$_3$-2-Cl-3 | —C$_6$H$_3$CH$_3$-2-Cl-3 |
| 633 | C(O) | C(O) | —CH(CH$_3$)C(CH$_3$)$_3$ | H | —C$_6$H$_3$CH$_3$-2-Cl-3 | —C$_6$H$_2$(CH$_3$)$_2$-3,5-Cl-4 |
| 634 | C(O) | C(O) | —C(CH$_3$)$_3$ | H | —C$_6$H$_3$CH$_3$-2-Cl-3 | —C$_6$H$_3$CH$_3$-2-Cl-3 |
| 635 | C(O) | C(O) | —C(CH$_3$)$_3$ | —CH$_3$ | —C$_6$H$_5$ | —C$_6$H$_5$ |
| 636 | C(O) | C(O) | —C(CH$_3$)$_3$ | —CH$_2$C$_6$H$_5$ | —C$_6$H$_5$ | —C$_6$H$_5$ |
| 637 | C(O) | C(O) | —C(CH$_3$)$_3$ | —CH$_2$CH=CH$_2$ | —C$_6$H$_5$ | —C$_6$H$_5$ |
| 638 | C(O) | C(O) | —C(CH$_3$)$_3$ | —CH$_2$OCH$_3$ | —C$_6$H$_5$ | —C$_6$H$_5$ |
| 639 | C(O) | C(O) | —C(CH$_3$)$_3$ | —CH$_2$SCH$_3$ | —C$_6$H$_5$ | —C$_6$H$_5$ |
| 640 | C(O) | C(O) | —C(CH$_3$)$_3$ | —CH$_2$C≡CH | —C$_6$H$_5$ | —C$_6$H$_4$CH$_3$-3 |
| 641 | C(O) | C(O) | —C(CH$_3$)$_3$ | —CH$_2$C≡CH | —C$_6$H$_4$CH$_3$-4 | —C$_6$H$_5$ |
| 642 | C(O) | C(O) | —C(CH$_3$)$_3$ | —CH$_2$C≡CH | —C$_6$H$_5$ | —C$_6$H$_3$(CH$_3$)$_2$-3,5 |
| 643 | C(O) | C(O) | —C(CH$_3$)$_3$ | —CH$_2$C≡CH | —C$_6$H$_5$ | —C$_6$H$_3$Cl$_2$-2,4 |
| 644 | C(O) | C(O) | —C(CH$_3$)$_3$ | —CH$_2$C≡CH | —C$_6$H$_5$ | —C$_6$H$_3$Cl$_2$-3,4 |

TABLE I-continued $$A-G_2 \quad \begin{matrix} X & X' \\ N-N-G_2-B \\ | & | \\ R^2 & R^1 \end{matrix}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 645 | C(O) | C(O) | —C(CH$_3$)$_3$ | —CH$_2$C$_6$H$_4$Br-4 | —C$_6$H$_5$ | —C$_6$H$_5$ |
| 646 | C(O) | C(O) | —C(CH$_3$)$_3$ | H | 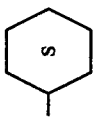 | —C$_6$H$_5$ |
| 647 | C(O) | C(O) | —C(CH$_3$)$_3$ | H | —CH$_2$CH$_2$CH$_3$ | —C$_6$H$_4$Cl-4 |
| 648 | C(O) | C(O) | —C(CH$_3$)$_3$ | H | —CH$_2$CH$_2$CH$_2$CH$_3$ | —C$_6$H$_5$ |
| 649 | C(O) | C(O) | —C(CH$_3$)$_3$ | H | —CH$_2$CH$_2$CH$_2$CH$_3$ | —C$_6$H$_4$Cl-4 |
| 650 | C(O) | C(O) | —C(CH$_3$)$_3$ | H | —CH$_2$CH$_2$CH$_2$CH$_3$ | —C$_6$H$_4$CH$_3$-4 |
| 651 | C(O) | C(O) | —C(CH$_3$)$_3$ | H | —CH$_2$CH$_2$CH$_3$ | —C$_6$H$_5$ |
| 652 | C(O) | C(O) | —C(CH$_3$)$_3$ | H | —CH$_2$CH$_2$CH$_2$CH$_3$ | —C$_6$H$_4$F-4 |
| 653 | C(O) | C(O) | —C(CH$_3$)$_3$ | H | —CH$_2$CH$_2$CH$_2$CH$_3$ | —C$_6$H$_4$CF$_3$-4 |
| 654 | C(O) | C(O) | —C(CH$_3$)$_3$ | H | —CH$_2$C$_6$H$_5$ | —C$_6$H$_5$ |
| 655 | C(O) | C(O) | —C(CH$_3$)$_3$ | H | —C(CH$_3$)$_3$ | —C$_6$H$_4$Cl-4 |
| 656 | C(O) | C(O) | —C(CH$_3$)$_3$ | H | 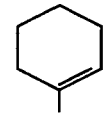 | —C$_6$H$_5$ |
| 657 | C(O) | C(O) | —C(CH$_3$)$_3$ | H | —CH$_2$Cl | —C$_6$H$_5$ |
| 658 | C(O) | C(O) | —C(CH$_3$)$_3$ | H | —CHCl$_2$ | —C$_6$H$_5$ |
| 659 | C(O) | C(O) | —C(CH$_3$)$_3$ | H | —CCl$_3$ | —C$_6$H$_5$ |
| 660 | C(O) | C(O) | —C(CH$_3$)$_3$ | H | —C(CH$_3$)$_2$CH$_2$Cl | —C$_6$H$_5$ |
| 661 | C(O) | C(O) | —C(CH$_3$)$_3$ | H | —C(Cl)=CCl$_2$ | —C$_6$H$_5$ |
| 662 | C(O) | C(O) | —C(CH$_3$)$_3$ | H | —CH$_2$CH$_2$CH$_2$CH$_2$CH$_3$ | —C$_6$H$_3$Cl$_2$-3,4 |
| 663 | C(O) | C(O) | —C(CH$_3$)$_3$ | H | —CH$_2$CH$_2$CH$_2$CH$_2$CH$_3$ | —C$_6$H$_4$CH$_3$-3 |
| 664 | C(O) | C(O) | —C(CH$_3$)$_3$ | H | —C(CH$_3$)=CH$_2$ | —C$_6$H$_5$ |
| 665 | C(O) | C(O) | —C(CH$_3$)$_3$ | H |  | —C$_6$H$_5$ |
| 666 | C(O) | C(O) | —C(CH$_3$)$_3$ | H |  | —C$_6$H$_4$CH$_3$-3 |

TABLE I-continued $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | $B_{1/93}$ |
|---|---|---|---|---|---|---|
| 667 | C(O) | C(O) | —C(CH₃)₃ | H | —⟨cyclohexenyl⟩ | —C₆H₄CH₃-3 |
| 668 | C(O) | C(O) | —C(CH₃)₃ | H | —CH₂C(O)—O—CH₂CH₃ | —C₆H₄Cl₂-3,4 |
| 669 | C(O) | C(O) | —C(CH₃)₃ | H | —CH—C(O)—O—CH₂CH₃ with CH₂OH | —C₆H₄Cl₂-3,4 |
| 670 | C(O) | C(O) | —C(CH₃)₃ | H | —CH₂—⟨cyclobutyl with CH₃, CH₃, C(O)CH₃⟩ | —C₆H₄CH₃-3 |
| 671 | C(O) | C(O) | —C(CH₃)₃ | H | —CH=CHCH₂CH₃ | —C₆H₄CH₃-3 |
| 672 | C(O) | C(O) | —C(CH₃)₃ | H | —CH₂CH₂CH=CH₂ | —C₆H₄CH₃-3 |
| 673 | C(O) | C(O) | —C(CH₃)₃ | H | —CH₂CH₂CH₂COCH₃ | —C₆H₄CH₃-3 |
| 674 | C(O) | C(O) | —C(CH₃)₃ | H | —CH(CH₃)₂ | —C₆H₃(CH₃)₂-3,5 |
| 675 | C(O) | C(O) | —C(CH₃)₃ | H | —C(CH₃)=CH₂ | —C₆H₃(CH₃)₂-3,5 |
| 676 | C(O) | C(O) | —C(CH₃)₃ | H | —CH(CH₃)₂ | —C₆H₄Br-2 |
| 677 | C(O) | C(O) | —C(CH₃)₃ | H | —CH(CH₃)₂ | —C₆H₅ |

TABLE I -continued $$A-G_2\begin{matrix}X & X' \\ | & | \\ N-N-G_2-B \\ | & | \\ R^2 & R^1\end{matrix}$$

where $G_2\ N$ is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 678 | C(O) | C(O) | —C(CH$_3$)$_3$ | H | 4-methylcyclohexane-1,2-diol (cis) | —C$_6$H$_4$CH$_3$-3 |
| 679 | C(O) | C(O) | —C(CH$_3$)$_3$ | H | 4-methylcyclohexane-1,2-diol | —C$_6$H$_4$CH$_3$-3 |
| 680 | C(O) | C(O) | —C(CH$_3$)$_3$ | H | 4-methyl-2,2-dimethyl-1,3-dioxolane cyclohexane | —C$_6$H$_4$—CH$_3$-3 |
| 681 | C(O) | C(O) | —C(CH$_3$)$_3$ | H | 3-methyl-1,3-cyclohexadiene | —C$_6$H$_4$CH$_3$-3 |
| 682 | C(O) | C(O) | —C(CH$_3$)$_3$ | H | —C$_6$H$_5$ | —CH$_2$CH$_2$CH$_2$CH$_2$CH$_3$ |
| 683 | C(O) | C(O) | —C(CH$_3$)$_3$ | H | —C$_6$H$_5$ | tetrahydrothiopyranyl |
| 684 | C(O) | C(O) | —C(CH$_3$)$_3$ | H | —C$_6$H$_3$Cl$_2$-3,5 | —CH$_2$CH$_2$Br |
| 685 | C(O) | C(O) | —C(CH$_3$)$_3$ | H | —C$_6$H$_3$Cl$_2$-3,5 | —CH$_2$Cl |
| 686 | C(O) | C(O) | —C(CH$_3$)$_3$ | H | —C$_6$H$_3$Cl$_2$-3,5 | —CH(CH$_3$)Br |
| 687 | C(O) | C(O) | —C(CH$_3$)$_3$ | H | —C$_6$H$_3$Cl$_2$-3,5 | —CH=CH$_2$ |
| 688 | C(O) | C(O) | —C(CH$_3$)$_3$ | H | —C$_6$H$_5$ | —C(CH$_3$)$_3$ |
| 689 | C(O) | C(O) | —C(CH$_3$)$_3$ | H | —C$_6$H$_5$ | —CH$_2$C$_6$H$_5$ |
| 690 | C(O) | C(O) | —C(CH$_3$)$_3$ | H | —C$_6$H$_3$Cl$_2$-3,4 | —CH$_3$ |

TABLE I -continued $$\begin{array}{cc} X & X' \\ A-G_2 & N-N-G_2-B \\ & \phantom{xx}|\phantom{xx}| \\ & R^2\phantom{x}R^1 \end{array}$$

where $G_2$  N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 691 | C(O) | C(O) | —C(CH$_3$)$_3$ | H | —C$_6$H$_5$ | $B_{1/93}$ —CH=C(CH$_3$)(CF$_3$) |
| 692 | C(O) | C(O) | —C(CH$_3$)$_3$ | H | —C$_6$H$_4$Cl-4 | —C(CH$_3$)$_3$ |
| 693 | C(O) | C(O) | —C(CH$_3$)$_3$ | H | —C$_6$H$_4$Cl-4 | —CH=CC$_6$H$_5$ / H |
| 694 | C(O) | C(O) | —C(CH$_3$)$_3$ | H | —C$_6$H$_4$Cl-4 | —CH$_2$C$_6$H$_5$ |
| 695 | C(O) | C(O) | —C(CH$_3$)$_3$ | H | —C$_6$H$_3$NO$_2$-2-Cl-4 | —CH=CC$_6$H$_4$CF$_3$-3 / H |
| 696 | C(O) | C(O) | —C(CH$_3$)$_3$ | H | —C$_6$H$_3$NO$_2$-2-Cl-4 | —CH=CC$_6$H$_4$CN-4 / H |
| 697 | C(O) | C(O) | —C(CH$_3$)$_3$ | H | —C$_6$H$_3$NO$_2$-2-Cl-4 | —CH=CC$_6$H$_4$CN-4 / H |
| 698 | C(O) | C(O) | —C(CH$_3$)$_3$ | H | —C$_6$H$_5$ | 1-methylcyclohexenyl |
| 699 | C(O) | C(O) | —C(CH$_3$)$_3$ | H | —C$_6$H$_5$ | —C(CH$_3$)=CH$_2$ |
| 700 | C(O) | C(O) | —C(CH$_3$)$_3$ | H | —C$_6$H$_5$ | cyclopropylphenyl |

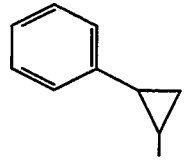

TABLE I -continued $$A-G_2 \quad \begin{array}{c} X \\ | \\ N-N-G_2-B \\ | \quad | \\ R^2 \quad R^1 \end{array} \quad \begin{array}{c} X' \end{array}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---------|----------|-----------|-------|-------|---|---|
| 701 | C(O) | C(O) | —C(CH$_3$)$_3$ | H | —C$_6$H$_3$Cl$_2$-3,4 | △ |
| 702 | C(O) | C(O) | —C(CH$_3$)$_3$ | H | —C$_6$H$_4$Cl-4 | □ |
| 703 | C(O) | C(O) | —C(CH$_3$)$_3$ | H | —C$_6$H$_5$ | —CH=C(H)(furyl) |
| 704 | C(O) | C(O) | —C(CH$_3$)$_3$ | H | —C$_6$H$_5$ | —CH(CH$_2$OH)CO$_2$CH$_2$CH$_3$ |
| 705 | C(O) | C(O) | —C(CH$_3$)$_3$ | H | —C$_6$H$_3$(CH$_3$)$_2$-2,3 | cyclohexenyl |
| 706 | C(O) | C(O) | —C(CH$_3$)$_3$ | H | —C$_6$H$_3$(CH$_3$)$_2$-2,3 | —CH(CH(CH$_3$)$_2$)C$_6$H$_4$Cl-4 |
| 707 | C(O) | C(O) | —C(CH$_3$)$_3$ | H | —C$_6$H$_5$ | methylcyclohexenyl |
| 708 | C(O) | C(O) | —C(CH$_3$)$_3$ | H | —C$_6$H$_5$ | —C≡C—C$_6$H$_5$ |
| 709 | C(O) | C(O) | —C(CH$_3$)$_3$ | H | —C$_6$H$_5$ | —CH(CH$_3$)CH$_2$CH$_3$ |

B1/93

-continued
TABLE I $$A-G_2 \quad \begin{matrix} X & X' \\ N-N-G_2-B \\ | & | \\ R^2 & R^1 \end{matrix}$$

where $G_2$ N is a single bond when $R^2$ is "H" and is a double bond when $R^2$ is "—"

| Ex. No. | G₂(X) | G₂(X') | R¹ | R² | A | B |
|---|---|---|---|---|---|---|
| 710 | C(O) | C(O) | —C(CH₃)₃ | H | —C₆H₅ | B1/93 —CH₃, —CHC₂H₅, —CHC₆H₅ |
| 711 | C(O) | C(O) | —C(CH₃)₃ | H | —C₆H₅ | (cyclobutane with —C(O)CH₃, two —CH₃ groups, and —CH₃) |
| 712 | C(O) | C(O) | —C(CH₃)₃ | H | —C₆H₅ | —CH=CHCH₂CH₃ |
| 713 | C(O) | C(O) | —C(CH₃)₃ | H | —C₆H₅ | —CH₂CH₂CH=CH₂ |
| 714 | C(O) | C(O) | —C(CH₃)₃ | H | —C₆H₅ | —CH₂CH₂CH₂CO₂CH₃ |
| 715 | C(O) | C(O) | —C(CH₃)₃ | H | —C₆H₅ | —CH₂OCH₃ |
| 716 | C(O) | C(O) | —C(CH₃)₃ | H | —C₆H₃(CH₃)₂-2,3 | —C(CH₃)=CH₂ |
| 717 | C(O) | C(O) | —C(CH₃)₃ | H | —C₆H₄CH₂CH₃-4 | —C(CH₃)=CH₂ |
| 718 | C(O) | C(O) | —C(CH₃)₃ | H | —C₆H₃(CH₃)₂-2,3 | —CH(CH₃)₂ |
| 719 | C(O) | C(O) | —C(CH₃)₃ | H | —C₆H₃(CH₃)₂-2,3 | —C(CH₃)₃ |
| 720 | C(O) | C(O) | —C(CH₃)₃ | H | —C₆H₃(CH₃)₂-2,3 | —C(CH₂CH₃)=CH₂ |

-continued
TABLE I
$$A-G_2\underset{R^2\ R^1}{\overset{X\ \ \ \ \ X'}{N-N-G_2-B}}$$
where G$_2$ N is a single bond when R$^2$ is "H" and is a double bond when R$^2$ is "—"
| Ex. No. | G$_2$(X) | G$_2$(X') | R$^1$ | R$^2$ | A | B |
|---|---|---|---|---|---|---|
| 721 | C(O) | C(O) | —C(CH$_3$)$_3$ | H | —C$_6$H$_3$(CH$_3$)$_2$-2,3 | 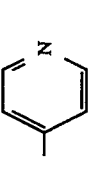 B$_{1/93}$ |
| 722 | C(O) | C(O) | —C(CH$_3$)$_3$ | H | —C$_6$H$_5$ | 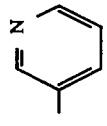 |
| 723 | C(O) | C(O) | —C(CH$_3$)$_3$ | H |  | —C$_6$H$_5$ |
| 724 | C(O) | C(O) | —C(CH$_3$)$_3$ | H | —C$_6$H$_5$ |  |
| 725 | C(O) | C(O) | —C(CH$_3$)$_3$ | H |  | —C$_6$H$_3$Cl$_2$-3,4 |
| 726 | C(O) | C(O) | —C(CH$_3$)$_3$ | H |  | —C$_6$H$_5$ |
| 727 | C(O) | C(O) | —C(CH$_3$)$_3$ | H |  | —C$_6$H$_4$NO$_2$-2 |

TABLE I-continued $$X \quad X'$$
$$A-G_2 \quad \underset{\underset{R^2}{|}}{N}-N-G_2-B$$
$$\phantom{A-G_2 \quad N-N-G_2-}R^1$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 728 | C(O) | C(O) | —C(CH$_3$)$_3$ | H | 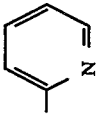 | $B_{1/93}$ |
| 729 | C(O) | C(O) | —C(CH$_3$)$_3$ | H | 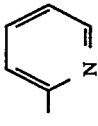 | —C$_6$H$_4$CH$_2$CH$_3$-4 |
| 730 | C(O) | C(O) | —C(CH$_3$)$_3$ | H | —C$_6$H$_4$CH$_2$CH$_3$-4 | —C$_6$H$_4$Br-2 |
| 731 | C(O) | C(O) | —C(CH$_3$)$_3$ | H | —C$_6$H$_4$OCF$_3$-4 |  |
| 732 | C(O) | C(O) | —C(CH$_3$)$_3$ | H |  |  |
| 733 | C(O) | C(O) | —C(CH$_3$)$_3$ | H |  | —C$_6$H$_3$Cl$_2$-3,4 |
| 734 | C(O) | C(O) | —C(CH$_3$)$_3$ | H | CH$_3$(CH$_2$)$_3$— | —C$_6$H$_5$ |

-continued
TABLE I $$\begin{array}{cc} X & X' \\ | & | \\ A-G_2 & N-N-G_2-B \\ & | \quad | \\ & R^2 \quad R^1 \end{array}$$

where $G_2 \cdots N$ is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 735 | C(O) | C(O) | —C(CH$_3$)$_3$ | H | —C$_6$H$_5$ | pyrazinyl, $B_1/93$ |
| 736 | C(O) | C(O) | —C(CH$_3$)$_3$ | H | 2-methylpyridinyl | —C$_6$H$_3$(CH$_3$)$_2$-3,5 |
| 737 | C(O) | C(O) | —C(CH$_3$)$_3$ | H | 3-bromopyridinyl | —C$_6$H$_4$Cl-4 |
| 738 | C(O) | C(O) | —C(CH$_3$)$_3$ | H | 2-methylpyrazinyl | —C$_6$H$_5$ |
| 739 | C(O) | C(O) | —C(CH$_3$)$_3$ | H | 4-methylpyridinyl | —C$_6$H$_5$ |
| 740 | C(O) | C(O) | —C(CH$_3$)$_3$ | H | 2-methylpyridinyl | —C$_6$H$_4$OCH$_3$-4 |

TABLE I -continued $$A-G_2 \quad \begin{matrix} N-N-G_2-B \\ | \quad | \\ R^2 \quad R^1 \end{matrix}$$
$$\phantom{A-G_2}\ \ X \quad\quad X'$$

where $G_2$  N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 741 | C(O) | C(O) | —C(CH$_3$)$_3$ | H | 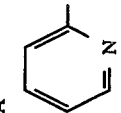 | B$_{1/93}$<br>—C$_6$H$_4$I-2 |
| 742 | C(O) | C(O) | —C(CH$_3$)$_3$ | H | 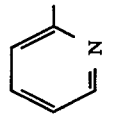 | —C$_6$H$_3$Cl$_2$-2,4 |
| 743 | C(O) | C(O) | —C(CH$_3$)$_3$ | H | 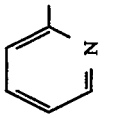 | —C$_6$H$_4$F-4 |
| 744 | C(O) | C(O) | —C(CH$_3$)$_3$ | H | 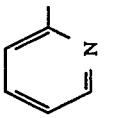 | —C$_6$H$_4$CF$_3$-2 |
| 745 | C(O) | C(O) | —C(CH$_3$)$_3$ | H | 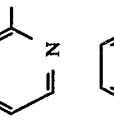 | —C$_6$H$_4$NO$_2$-3 |
| 746 | C(O) | C(O) | —C(CH$_3$)$_3$ | H | 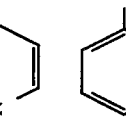 | C$_6$H$_4$CH$_3$-3 |
| 747 | C(O) | C(O) | —C(CH$_3$)$_3$ | H | 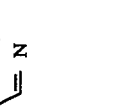 | —C$_6$H$_4$Cl-2 |

TABLE I -continued $$X-G_2 \quad N-N-G_2-B$$
$$A-G_2 \quad | \quad |$$
$$R^2 \quad R^1$$

where G$_2$ N is a single bond when R$^2$ is "H" and is a double bond when R$^2$ is "___"

| Ex. No. | G$_2$(X) | G$_2$(X') | R$^1$ | R$^2$ | A | B |
|---|---|---|---|---|---|---|
| 748 | C(O) | C(O) | —C(CH$_3$)$_3$ | H | 2-methylpyridin-yl | B$_{1/93}$ —C$_6$H$_4$OCH$_3$-3 |
| 749 | C(O) | C(O) | —C(CH$_3$)$_3$ | H | 2-methylpyridin-yl | —C$_6$H$_4$F-4 |
| 750 | C(O) | C(O) | —C(CH$_3$)$_3$ | H | —C$_6$H$_5$ | 6-methylpyridin-2-yl OSO$_2$CH$_3$ |
| 751 | C(O) | C(O) | —C(CH$_3$)$_3$ | H | 4-methylpyrimidin-yl | —C$_6$H$_4$F-4 |
| 752 | C(O) | C(O) | —C(CH$_3$)$_3$ | H | —C$_6$H$_5$ | pyrimidin-yl |
| 753 | C(O) | C(O) | —C(CH$_3$)$_3$ | H | 2-methylpyridin-yl | —C$_6$H$_3$(CH$_3$)$_2$-2,3 |

-continued
TABLE I $$X \quad X'$$
$$A-G_2 \quad N-N-G_2-B$$
$$\phantom{A-G_2 \quad N-N-}|\phantom{G_2}|$$
$$\phantom{A-G_2 \quad N-N-G_2}R^2 \quad R^1$$

where $G_2\!=\!\!=\!\!N$ is a single bond when $R^2$ is "H" and is a double bond when $R^2$ is "—"

| Ex. No. | G₂(X) | G₂(X') | R¹ | R² | A | B |
|---------|-------|--------|-----|-----|-----|-----|
| 754 | C(O) | C(O) | —C(CH₃)₃ | H | 2-pyridyl | 2-pyridyl B₁/93 |
| 755 | C(O) | C(O) | —C(CH₃)₃ | H | —C₆H₅ | —C₆H₄CH₃-3 |
| 756 | C(O) | C(O) | —C(CH₃)₃ | H | —C₆H₅ | 2-chloro-3-methylpyridyl |
| 757 | C(O) | C(O) | —C(CH₃)₃ | H | —C₆H₃(CH₃)₂-2,3 | —C₆H₃Cl-2-CH₃-5 |
| 758 | C(O) | C(O) | —C(CH₃)₃ | H | 2-pyridyl | —C₆H₃Cl-2-CH₃-5 |
| 759 | C(O) | C(O) | —C(CH₃)₃ | H | 2-chloro-3-methylpyridyl | —C₆H₃Cl-2-CH₃-5 |

TABLE I-continued $$A-G_2 \quad \substack{N-N-G_2-B \\ | \quad | \\ R^2 \quad R^1}$$

where G₂ N is a single bond when R² is "H" and is a double bond when R² is "—"

| Ex. No. | G₂(X) | G₂(X') | R¹ | R² | A | B |
|---|---|---|---|---|---|---|
| 760 | C(O) | C(O) | —C(CH₃)₃ | H | 3-methyl-2-(SCH₃)-pyridinyl | —C₆H₄CH₃-3 |
| 761 | C(O) | C(O) | —C(CH₃)₃ | H | 3-methyl-2-(SCH₃)-pyridinyl | —C₆H₃Cl₂-3,4 |
| 762 | C(O) | C(O) | —C(CH₃)₃ | H | 3-methyl-2-Cl-pyridinyl | —C₆H₅ |
| 763 | C(O) | C(O) | —C(CH₃)₃ | H | 2-methylpyridinyl | —C₆H₃Cl-2-F-3 |
| 764 | C(O) | C(O) | —C(CH₃)₃ | H | —C₆H₅ | 2-furyl |
| 765 | C(O) | C(O) | —C(CH₃)₃ | H | —C₆H₅ | 2-thienyl |

-continued
TABLE I $$X \quad X'$$
$$A-G_2 \quad N-N-G_2-B$$
$$\quad\quad\quad\quad R^2 \quad R^1$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---------|----------|-----------|-------|-------|---|---|
| 766 | C(O) | C(O) | —C(CH$_3$)$_3$ | H | 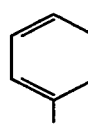 | B1/93 —C$_6$H$_5$ |
| 767 | C(O) | C(O) | —C(CH$_3$)$_3$ | H |  | —C$_6$H$_5$ |
| 768 | C(O) | C(O) | —C(CH$_3$)$_3$ | H | —C$_6$H$_4$CH$_3$-4 |  |
| 769 | C(O) | C(O) | —C(CH$_3$)$_3$ | H |  | —C$_6$H$_4$CH$_3$-4 |
| 770 | C(O) | C(O) | —C(CH$_3$)$_3$ | H |  | —C$_6$H$_4$CH$_3$-3 |
| 771 | C(O) | C(O) | —C(CH$_3$)$_3$ | H | —C$_6$H$_4$CH$_3$-4 |  |
| 772 | C(O) | C(O) | —C(CH$_3$)$_3$ | H | —C$_6$H$_4$CH$_3$-4 |  |

-continued
TABLE I $$X \quad X'$$
$$A-G_2 \quad N-N-G_2-B$$
$$\phantom{A-G_2 \quad N-N-}|\phantom{-}|$$
$$\phantom{A-G_2 \quad N-N-}R^2 \; R^1$$

where $G_2$  N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 773 | C(O) | C(O) | —C(CH$_3$)$_3$ | H | —C$_6$H$_3$Cl$_2$-3,4 | (thiophene) |
| 774 | C(O) | C(O) | —C(CH$_3$)$_3$ | H | (thiophene) | —C$_6$H$_5$ |
| 775 | C(O) | C(O) | —C(CH$_3$)$_3$ | H | (thiophene) | —C$_6$H$_4$CH$_3$-3 |
| 776 | C(O) | C(O) | —C(CH$_3$)$_3$ | H | (thiophene) | —C$_6$H$_3$Cl$_2$-3,4 |
| 777 | C(O) | C(O) | —C(CH$_3$)$_3$ | H | (thiophene) | —C$_6$H$_4$Cl-4 |
| 778 | C(O) | C(O) | —C(CH$_3$)$_3$ | H | (N-methylpyrrole) | —C$_6$H$_5$ |

-continued
TABLE I
$$A-G_2 \quad \begin{matrix} X & X' \\ | & | \\ N-N-G_2-B \\ | & | \\ R^2 & R^1 \end{matrix}$$
where $G_2$ N is a single bond when $R^2$ is "H" and is a double bond when $R^2$ is "—"
| Ex. No. | $G_2(X)$ | $G_2(X')$ | $R^1$ | $R^2$ | A | B1/93 |
|---|---|---|---|---|---|---|
| 779 | C(O) | C(O) | —C(CH$_3$)$_3$ | H | 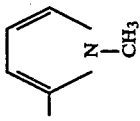 | —C$_6$H$_4$Cl-4 |
| 780 | C(O) | C(O) | —C(CH$_3$)$_3$ | H | 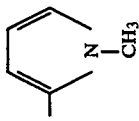 | —C$_6$H$_4$CH$_3$-3 |
| 781 | C(O) | C(O) | —C(CH$_3$)$_3$ | H | 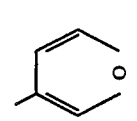 | —C$_6$H$_5$ |
| 782 | C(O) | C(O) | —C(CH$_3$)$_3$ | H | 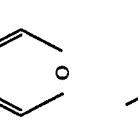 | —C$_6$H$_4$CH$_3$-2 |
| 783 | C(O) | C(O) | —C(CH$_3$)$_3$ | H | 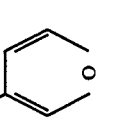 | —C$_6$H$_4$Cl-4 |

TABLE I-continued $$A-G_2 \overset{X}{\underset{\underset{R^2}{|}}{N}}-N-\overset{X'}{\underset{\underset{R^1}{|}}{G_2}}-B$$

where $G_2$ N is a single bond when $R^2$ is "H" and is a double bond when $R^2$ is "—".

| Ex. No. | $G_2(X)$ | $G_2(X')$ | $R^1$ | $R^2$ | A | B |
|---|---|---|---|---|---|---|
| 784 | C(O) | C(O) | —C(CH$_3$)$_3$ | H | (4-pyranyl) | —C$_6$H$_3$Cl$_2$-2,4 |
| 785 | C(O) | C(O) | —C(CH$_3$)$_3$ | H | (4-pyranyl) | —C$_6$H$_4$CH$_3$-3 |
| 786 | C(O) | C(O) | —C(CH$_3$)$_3$ | H | —C$_6$H$_3$F$_2$-2,6 | (2-thienyl) |
| 787 | C(O) | C(O) | —C(CH$_3$)$_3$ | H | (4-methyl-1,2,3-triazolyl-NH) | —C$_6$H$_4$CH$_3$-3 |
| 788 | C(O) | C(O) | —C(CH$_3$)$_3$ | H | —C$_6$H$_3$Cl-2-OCH$_3$-3 | (4-pyranyl) |
| 789 | C(O) | C(O) | —C(CH$_3$)$_3$ | H | (3-methyl-2-thienyl) | —C$_6$H$_4$CH$_3$-3 |

TABLE I-continued $$X-X'$$
$$A-G_2\quad N-N-G_2-B$$
$$\qquad\qquad |\quad |$$
$$\qquad\qquad R^2\ R^1$$

where $G_2$ N is a single bond when $R^2$ is "H" and is a double bond when $R^2$ is "—"

| Ex. No. | $G_2(X)$ | $G_2(X')$ | $R^1$ | $R^2$ | X | X' |
|---|---|---|---|---|---|---|
| 790 | C(O) | C(O) | —C(CH$_3$)$_3$ | H | A (methyl-thiophene structure, B$_1$/93, CH$_3$) | —C$_6$H$_5$ |
| 791 | C(O) | C(O) | —C(CH$_3$)$_3$ | H | (dimethyl isoxazole structure) | —C$_6$H$_5$ |
| 792 | C(O) | C(O) | —C(CH$_3$)$_3$ | H | —C$_6$H$_4$CH$_2$CH$_3$-4 | (N-phenyl pyrazole structure) |
| 793 | C(O) | C(O) | —C(CH$_3$)$_3$ | H | —C$_6$H$_5$ | (oxazoline structure with CH$_3$, CH$_3$) |
| 794 | C(O) | C(O) | —C(CH$_3$)$_3$ | H | H$_3$CS—CH=CH—N=S—SCH$_3$ | —C$_6$H$_5$ |
| 795 | C(O) | C(O) | —CH(CH$_3$)CF$_3$ | H | —C$_6$H$_3$(CH$_3$)$_2$-2,3 | —C$_6$H$_3$Cl$_2$-2,4 |
| 796 | C(O) | C(O) | —CH(CH$_3$)CF$_3$ | H | —C$_6$H$_3$(CH$_3$)$_2$-2,3 | —C$_6$H$_3$(CH$_3$)$_2$-3,5 |
| 797 | C(O) | C(O) | —CH(CH$_3$)CF$_3$ | H | —C$_6$H$_3$(CH$_3$)$_2$-2,3 | —C$_6$H$_3$NO$_2$-2-CH$_3$-5 |
| 798 | C(O) | C(O) | —CH(CH$_3$)CF$_3$ | H | —C$_6$H$_5$ | —C$_6$H$_5$ |
| 799 | C(O) | C(O) | —CH$_2$CF$_3$ | H | —C$_6$H$_3$Cl$_2$-3,4 | —C$_6$H$_3$Cl$_2$-3,4 |
| 800 | C(O) | C(O) | —CH$_2$CF$_3$ | H | —C$_6$H$_4$Cl-4 | —C$_6$H$_4$Cl-4 |
| 801 | C(O) | C(O) | —CH$_2$CF$_3$ | H | —C$_6$H$_5$ | —C$_6$H$_5$ |
| 802 | C(O) | C(O) | —C(CH$_3$)$_2$CN | H | —C$_6$H$_5$ | —C$_6$H$_5$ |

TABLE I -continued $$A-G_2 \overset{X}{\underset{R^2}{N-N}}\overset{X'}{\underset{R^1}{G_2-B}}$$

where $G_2$ N is a single bond when $R^2$ is "H" and is a double bond when $R^2$ is "—"

| Ex. No. | $G_2(X)$ | $R^1$ | $G_2(X')$ | $R^2$ | A | $B_1/93$ |
|---|---|---|---|---|---|---|
| 803 | C(O) | —C(CH$_3$)$_2$CN | C(O) | H | —C$_6$H$_5$ | —C$_6$H$_4$Cl-4 |
| 804 | C(O) | —C(CH$_3$)$_2$CN | C(O) | H | —C$_6$H$_4$CH$_3$-4 | —C$_6$H$_4$CH$_3$-3 |
| 805 | C(O) | —C(CH$_3$)$_2$CN | C(O) | H | —C$_6$H$_5$ | —C$_6$H$_4$CH$_3$-3 |
| 806 | C(O) | —C(CH$_3$)$_2$CN | C(O) | H | —C$_6$H$_4$Cl-4 | —C$_6$H$_4$Cl-4 |
| 807 | C(O) | —C(CH$_3$)$_2$CN | C(O) | H | —C$_6$H$_4$CH$_3$-4 | —C$_6$H$_3$(CH$_3$)$_2$-3,5 |
| 808 | C(O) | —C(CH$_3$)$_2$CN | C(O) | H | —C$_6$H$_4$CH$_3$-4 | —C$_6$H$_4$F-4 |
| 809 | C(O) | —C(CH$_3$)$_2$CN | C(O) | H | —C$_6$H$_4$CH$_3$-4 | —C$_6$H$_4$CH$_3$-4 |
| 810 | C(O) | —C(CH$_3$)(CH$_2$CH$_3$)CN | C(O) | H | —C$_6$H$_5$ | —C$_6$H$_5$ |
| 811 | C(O) | —C(CH$_3$)$_2$CN | C(O) | H | 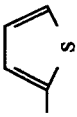 | —C$_6$H$_4$CH$_3$-3 |
| 812 | C(O) | —C(CH$_3$)$_2$CN | C(O) | H | —C$_6$H$_4$C$_2$H$_5$-4 | —C$_6$H$_3$(CH$_3$)$_2$-3,5 |
| 813 | C(O) | —C(CH$_3$)$_2$CN | C(O) | H | —C$_6$H$_4$CH$_3$-2 | —C$_6$H$_3$(CH$_3$)$_2$-3,5 |
| 814 | C(O) | —C(CH$_3$)$_2$CN | C(O) | H | —C$_6$H$_4$Cl-4 | —C$_6$H$_4$CH$_3$-3 |
| 815 | C(O) | —C(CH$_3$)$_2$CN | C(O) | H | —C$_6$H$_3$F$_2$-2,6 | —C$_6$H$_4$Cl-4 |
| 816 | C(O) | —C(CH$_3$)$_2$CN | C(O) | H | —C$_6$H$_4$CH$_3$-2 | —C$_6$H$_4$CH$_3$-3 |
| 817 | C(O) | —C(CH$_3$)$_2$CN | C(O) | H | —C$_6$H$_4$NO$_2$-2 | —C$_6$H$_4$CH$_3$-3 |
| 818 | C(O) | —C(CH$_3$)$_2$CN | C(O) | H | —C$_6$H$_4$Cl-2 | —C$_6$H$_4$CH$_3$-3 |
| 819 | C(O) | —C(CH$_3$)$_2$CO$_2$CH$_3$ | C(O) | H | —C$_6$H$_5$ | —C$_6$H$_5$ |
| 820 | C(O) | —C(CH$_3$)$_2$CH$_2$CH=CH$_2$ | C(O) | H | —C$_6$H$_4$CH$_3$-4 | —C$_6$H$_4$CH$_3$-4 |
| 821 | C(O) | —C(CH$_3$)$_2$CH$_2$CH=CH$_2$ | C(O) | H | —C$_6$H$_4$CH$_3$-3 | —C$_6$H$_4$CH$_3$-3 |
| 822 | C(O) | —C(CH$_3$)$_2$CH$_2$CH=CH$_2$ | C(O) | H | —C$_6$H$_5$ | —C$_6$H$_5$ |
| 823 | C(O) | —CH$_2$Si(CH$_3$)$_3$ | C(O) | H | —C$_6$H$_4$C$_2$H$_5$-4 | —C$_6$H$_3$NO$_2$-2-CH$_3$-5 |
| 824 | C(O) | —CH$_2$Si(CH$_3$)$_3$ | C(O) | H | —C$_6$H$_4$Cl-4 | —C$_6$H$_4$Cl-4 |
| 825 | C(O) | —CH$_2$Si(CH$_3$)$_3$ | C(O) | H | —C$_6$H$_4$CH$_3$-2 | —C$_6$H$_4$CH$_3$-2 |
| 826 | C(O) | —CH$_2$Si(CH$_3$)$_3$ | C(O) | H | —C$_6$H$_4$NO$_2$-2 | —C$_6$H$_4$NO$_2$-2 |
| 827 | C(O) | —CH$_2$Si(CH$_3$)$_3$ | C(O) | H | —C$_6$H$_5$ | —C$_6$H$_5$ |
| 828 | C(O) | —CH$_2$Si(CH$_3$)$_3$ | C(O) | H | —C$_6$H$_4$C$_2$H$_5$-4 | —C$_6$H$_3$(CH$_3$)$_2$-3,5 |
| 829 | CH$_2$ | —C(CH$_3$)$_3$ | C(O) | H | —C$_6$H$_5$ | —C$_6$H$_5$ |
| 830 | CH$_2$ | —C(CH$_3$)$_3$ | C(O) | H | —C$_6$H$_5$ | —C$_6$H$_4$Cl-4 |
| 831 | CH$_2$ | —C(CH$_3$)$_3$ | C(O) | H | —C$_6$H$_5$ | —C$_6$H$_3$Cl$_2$-2,4 |
| 832 | CH$_2$ | —C(CH$_3$)$_3$ | C(O) | H | —C$_6$H$_5$ | —C$_6$H$_3$Cl$_2$-3,4 |
| 833 | CH$_2$ | —C(CH$_3$)$_3$ | C(O) | H | —C$_6$H$_5$ | —C$_6$H$_4$CF$_3$-4 |
| 834 | CH$_2$ | —C(CH$_3$)$_3$ | C(O) | H | —C$_6$H$_5$ | —C$_6$H$_4$CO$_2$CH$_3$-4 |
| 835 | CH$_2$ | —C(CH$_3$)$_3$ | C(O) | H | —C$_6$H$_5$ | —C$_6$H$_4$NO$_2$-2 |
| 836 | CH$_2$ | —C(CH$_3$)$_3$ | C(O) | H | —C$_6$H$_5$ | —C$_6$H$_4$F-4 |

TABLE I -continued $$A-G_2\begin{matrix}X & X' \\ | & | \\ N-N-G_2-B \\ | & | \\ R^2 & R^1\end{matrix}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 837 | C(O) | CH$_2$ | —C(CH$_3$)$_3$ | H | furyl | —C$_6$H$_5$ |
| 838 | C(O) | CH$_2$ | —C(CH$_3$)$_3$ | H | —C$_6$H$_5$ | —C$_6$H$_4$Br-2 |
| 839 | C(O) | CH$_2$ | —C(CH$_3$)$_3$ | H | —C$_6$H$_5$ | —C$_6$H$_4$CN-2 |
| 840 | C(O) | CH$_2$ | —C(CH$_3$)$_3$ | H | thienyl | —C$_6$H$_5$ |
| 841 | C(O) | CH$_2$ | —C(CH$_3$)$_3$ | H | —C$_6$H$_4$CH$_3$-4 | —C$_6$H$_4$CN-4 |
| 842 | C(O) | CH$_2$ | —C(CH$_3$)$_3$ | H | —C$_6$H$_4$CH$_3$-4 | —C$_6$H$_5$ |
| 843 | C(O) | CH$_2$ | —C(CH$_3$)$_3$ | H | —C$_6$H$_5$ | —C$_6$H$_4$NO$_2$-3 |
| 844 | C(O) | CH$_2$ | —C(CH$_3$)$_3$ | H | —C$_6$H$_5$ | —C$_6$H$_4$OCH$_3$-4 |
| 845 | C(O) | CH$_2$ | —C(CH$_3$)$_3$ | H | —C$_6$H$_5$ | —C$_6$H$_4$OCH$_3$-3 |
| 846 | C(O) | CH$_2$ | —C(CH$_3$)$_3$ | H | —C$_6$H$_5$ | —C$_6$H$_4$CH$_3$-3 |
| 847 | C(O) | CH$_2$ | —C(CH$_3$)$_3$ | H | —C$_6$H$_4$CH$_3$-4 | —C$_6$H$_4$CH$_3$-3 |
| 848 | C(O) | CH$_2$ | —C(CH$_3$)$_3$ | H | —C$_6$H$_5$ | —C$_6$H$_4$CH$_3$-4 |
| 849 | C(O) | CH$_2$ | —C(CH$_3$)$_3$ | H | —C$_6$H$_5$ | —C$_6$H$_4$CH$_3$-4 |
| 850 | C(O) | CH$_2$ | —C(CH$_3$)$_3$ | H | —C$_6$H$_3$Cl$_2$-3,4 | —C$_6$H$_5$ |
| 851 | C(O) | CH$_2$ | —C(CH$_3$)$_3$ | H | —C$_6$H$_3$Cl$_2$-3,4 | —C$_6$H$_4$CH$_3$-4 |
| 852 | C(O) | CH$_2$ | —C(CH$_3$)$_3$ | H | —C$_6$H$_5$ | —C$_6$H$_5$ |
| 853 | C(O) | CH$_2$ | —C(CH$_3$)$_3$ | H | pyridyl | pyridyl |
| 854 | C(O) | CH$_2$ | —C(CH$_3$)$_3$ | H | —C$_6$H$_5$ | —C$_6$H$_4$CH$_3$-2 |
| 855 | CH$_2$ | C(O) | —C(CH$_3$)$_3$ | H | —C$_6$H$_5$ | —C$_6$H$_5$ |
| 856 | CH$_2$ | C(O) | —C(CH$_3$)$_3$ | H | —C$_6$H$_5$ | —C$_6$H$_4$F-4 |
| 857 | CH$_2$ | C(O) | —C(CH$_3$)$_3$ | H | —C$_6$H$_5$ | —C$_6$H$_4$Br-2 |
| 858 | CH$_2$ | C(O) | —C(CH$_3$)$_3$ | H | —C$_6$H$_5$ | —C$_6$H$_3$Cl$_2$-3,4 |
| 859 | CH$_2$ | C(O) | —C(CH$_3$)$_3$ | H | —C$_6$H$_5$ | —C$_6$H$_4$CH$_3$-2 |

TABLE I-continued $$A-G_2\quad \underset{\underset{R^2}{|}}{N}-N-\underset{\underset{R^1}{|}}{G_2}-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 860 | $CH_2$ | C(O) | —C(CH$_3$)$_3$ | H | —C$_6$H$_4$CH$_3$-3 | —C$_6$H$_3$Cl$_2$-2,3 |
| 861 | $CH_2$ | C(O) | —C(CH$_3$)$_3$ | H | —C$_6$H$_4$CH$_3$-3 | —C$_6$H$_5$ |
| 862 | $CH_2$ | C(O) | —C(CH$_3$)$_3$ | H | —C$_6$H$_4$CH$_3$-3 | 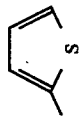 |
| 863 | $CH_2$ | C(O) | —C(CH$_3$)$_3$ | H |  | —C$_6$H$_5$ |
| 864 | C(H) | C(O) | —C(CH$_3$)$_3$ | — | —C$_6$H$_5$ | —C$_6$H$_5$ |
| 865 | C(H) | C(O) | —C(CH$_3$)$_3$ | — | —C$_6$H$_5$ | —C$_6$H$_4$F-4 |
| 866 | C(H) | C(O) | —C(CH$_3$)$_3$ | — | —C$_6$H$_5$ | —C$_6$H$_3$Cl$_2$-3,4 |
| 867 | C(H) | C(O) | —C(CH$_3$)$_3$ | — | —C$_6$H$_5$ | —C$_6$H$_4$Br-2 |
| 868 | C(H) | C(O) | —C(CH$_3$)$_3$ | — | —C$_6$H$_4$CH$_3$-3 | —C$_6$H$_5$ |
| 869 | C(H) | C(O) | —C(CH$_3$)$_3$ | — | —C$_6$H$_5$ | 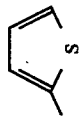 |
| 870 | C(O) | $CH_2$ | —C(CH$_3$)$_3$ | H | —C$_6$H$_5$ | —CH$_2$C$_6$H$_5$ |
| 871 | C(O) | $CH_2$ | —C(CH$_3$)$_3$ | H | —C$_6$H$_5$ | —CO$_2$CH$_2$CH$_3$ |
| 872 | C(O) | C(O) | —C(CH$_3$)$_3$ | H | —N(H)C$_6$H$_5$CH$_3$-4 | —C$_6$H$_5$ |
| 873 | C(O) | C(O) | —C(CH$_3$)$_3$ | H | —C(O)C$_6$H$_5$ | —C$_6$H$_5$ |
| 874 | C(O) | C(O) | —C(CH$_3$)$_3$ | H | —C(O)C$_6$H$_5$ | —C$_6$H$_4$CH$_3$-3 |
| 875 | C(O) | C(O) | —C(CH$_3$)$_3$ | H | —C$_6$H$_3$(CH$_3$)$_2$-2,3 | —C(O)C$_6$H$_5$ |
| 876 | C(O) | C(O) | —C(CH$_3$)$_3$ | H | —C$_6$H$_4$CH$_3$-4 | —C(O)C$_6$H$_5$ |
| 877 | C(O) | C(O) | —C(CH$_3$)$_3$ | H | —C$_6$H$_4$C$_2$H$_5$-4 | —C(O)C$_6$H$_5$ |
| 878 | C(O) | C(O) | —C(CH$_3$)$_3$ | H | —C$_6$H$_5$ | —C(O)C$_6$H$_5$ |
| 879 | C(O) | C(O) | —C(CH$_3$)$_3$ | H | —C$_6$H$_3$(CH$_3$)$_2$-2,3 | $\underset{\text{—CHC}_6\text{H}_5}{\overset{\text{CH}_3}{\text{HCCH}_3}}$ |

TABLE I-continued $$A-G_2 \quad \overset{X}{\underset{R^2}{N}}-\overset{X'}{\underset{R^1}{N}}-G_2-B$$

where $G_2$ N is a single bond when $R^2$ is "H" and is a double bond when $R^2$ is "—"

| Ex. No. | $G_2(X)$ | $G_2(X')$ | $R^1$ | $R^2$ | A | $B_1/93$ |
|---|---|---|---|---|---|---|
| 880 | C(O) | C(O) | —C(CH$_3$)$_3$ | H | [2-methyl-1,2,3,4-tetrahydronaphthyl] | —C$_6$H$_4$CH$_3$-3 |
| 881 | C(O) | C(O) | —C(CH$_3$)$_3$ | H | —C$_6$H$_4$Cl-4 | —CH$_2$C$_6$H$_5$ |
| 882 | C(O) | C(O) | —C(CH$_3$)$_3$ | H | —C$_6$H$_5$ | —CHClC$_6$H$_5$ |
| 883 | C(O) | C(O) | —C(CH$_3$)$_3$ | H | —C$_6$H$_5$ | —CH$_2$C$_6$H$_5$ |
| 884 | C(O) | C(O) | —C(CH$_3$)$_3$ | H | —C$_6$H$_4$Cl-4 | —CHClC$_6$H$_5$ |
| 885 | C(O) | C(O) | —C(CH$_3$)$_3$ | H | —C$_6$H$_3$(CH$_3$)$_2$-2,3 | —CH$_2$C$_6$H$_5$ |
| 886 | C(O) | C(O) | —C(CH$_3$)$_3$ | H | —C$_6$H$_4$C$_2$H$_5$-4 | —CH$_2$C$_6$H$_5$ |
| 887 | C(OC(O)CH$_3$ | C(O) | —C(CH$_3$)$_3$ | — | —C$_6$H$_5$ | —C$_6$H$_5$ |
| 888 | C(OC(O)CH$_2$CH$_3$ | C(O) | —C(CH$_3$)$_3$ | — | —C$_6$H$_5$ | —C$_6$H$_5$ |
| 889 | C(OC(O)CH(CH$_3$) | C(O) | —C(CH$_3$)$_3$ | — | —C$_6$H$_5$ | —C$_6$H$_5$ |
| 890 | C(OC(O)CH$_2$OCH$_3$ | C(O) | —C(CH$_3$)$_3$ | — | —C$_6$H$_5$ | —C$_6$H$_5$ |
| 891 | C(OC(O)CH=CHCH$_3$ | C(O) | —C(CH$_3$)$_3$ | — | —C$_6$H$_5$ | —C$_6$H$_5$ |
| 892 | C(OC(O)CH=C(CH$_3$)$_2$) | C(O) | —C(CH$_3$)$_3$ | — | —C$_6$H$_5$ | —C$_6$H$_5$ |
| 893 | C(OC(O)—[furanyl] | C(O) | —C(CH$_3$)$_3$ | — | —C$_6$H$_5$ | —C$_6$H$_5$ |
| 894 | C(OC(O)CH(CH$_3$)=CH$_2$) | C(O) | —C(CH$_3$)$_3$ | — | —C$_6$H$_4$C$_2$H$_5$-4 | —C$_6$H$_3$(CH$_3$)$_2$-3,5 |
| 895 | C(OC(O)CH$_3$ | C(O) | —C(CH$_3$)$_3$ | — | —C$_6$H$_4$C$_2$H$_5$-4 | —C$_6$H$_3$(CH$_3$)$_2$-3,5 |
| 896 | C(OC(O)CH(CH$_3$) | C(O) | —C(CH$_3$)$_3$ | — | —C$_6$H$_4$C$_2$H$_5$-4 | —C$_6$H$_3$(CH$_3$)$_2$-3,5 |
| 897 | C(OC(O)CH$_2$OCH$_3$ | C(O) | —C(CH$_3$)$_3$ | — | —C$_6$H$_4$C$_2$H$_5$-4 | —C$_6$H$_3$(CH$_3$)$_2$-3,5 |
| 898 | C(OC$_2$CH=CH$_2$) | C(O) | —C(CH$_3$)$_3$ | — | —C$_6$H$_4$C$_2$H$_5$-4 | —C$_6$H$_3$(CH$_3$)$_2$-3,5 |
| 899 | C(OC(O)—[furanyl] | C(O) | —C(CH$_3$)$_3$ | — | —C$_6$H$_4$C$_2$H$_5$-4 | —C$_6$H$_3$(CH$_3$)$_2$-3,5 |
| 900 | C(OC(O)CH$_2$CH$_3$ | C(O) | —C(CH$_3$)$_3$ | — | —C$_6$H$_3$(CH$_3$)$_2$-2,3 | —C$_6$H$_4$CH$_3$-3 |
| 901 | C(OC(O)CH$_3$ | C(O) | —C(CH$_3$)$_3$ | — | —C$_6$H$_3$(CH$_3$)$_2$-2,3 | —C$_6$H$_4$CH$_3$-3 |
| 902 | C(OC$_2$CH$_3$ | C(O) | —C(CH$_3$)$_3$ | — | —C$_6$H$_3$(CH$_3$)$_2$-2,3 | —C$_6$H$_4$CH$_3$-3 |
| 903 | C(OC(O)—[furanyl] | C(O) | —C(CH$_3$)$_3$ | — | —C$_6$H$_3$(CH$_3$)$_2$-2,3 | —C$_6$H$_4$CH$_3$-3 |

TABLE I-continued $$\begin{array}{cc} X & X' \\ A-G_2 & N-N-G_2-B \\ & \phantom{XX} | \phantom{X} | \\ & \phantom{XX} R^2 \phantom{X} R^1 \end{array}$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 904 | $C(OC_2H_5)$ | $C(O)$ | $-C(CH_3)_3$ | — | $-C_6H_3(CH_3)_2$-2,4 | $-C_6H_3Cl_2$-2,4 |
| 905 | $C(OCH_3)$ | $C(O)$ | $-C(CH_3)_3$ | — | $-C_6H_3(CH_3)_2$-2,3 | $-C_6H_3Cl_2$-2,4 |
| 906 | $C(OCH_3)$ | $C(O)$ | $-C(CH_3)_3$ | — | $-C_6H_5$ | $-C_6H_5$ |
| 907 | $C(OC(O)CH=CH_2)$ | $C(O)$ | $-C(CH_3)_3$ | — | $-C_6H_4C_2H_5$-4 | $-C_6H_3(CH_3)_2$-2,3 |
| 908 | $C(OC(O)CH=CH_2)$ | $C(O)$ | $-C(CH_3)_3$ | — | $-C_6H_5$ | $-C_6H_5$ |
| 909 | $C(OC(O)C_6H_4C_2H_5$-4) | $C(O)$ | $-C(CH_3)_3$ | — | $-C_6H_5$ | $-C_6H_5$ |
| 910 | $C(OC(O)CH_2CH=CH_2)$ | $C(O)$ | $-C(CH_3)_3$ | — | $-C_6H_5$ | $-C_6H_5$ |
| 911 | $C(OC(O)CH=C(CH_3)_2)$ | $C(O)$ | $-C(CH_3)_3$ | — | $-C_6H_5$ | $-C_6H_5$ |
| 912 | $C(OC(O)CH_3)$ | $C(O)$ | $-C(CH_3)_3$ | — | $-C_6H_5$ | $-C_6H_3Cl_2$-2,4 |
| 913 | $C(OC(O)CCH_3=CH_2)$ | $C(O)$ | $-C(CH_3)_3$ | — | $-C_6H_5$ | $-C_6H_3Cl_2$-2,4 |
| 914 | $SO_2$ | $C(O)$ | $-C(CH_3)_3$ | H | $-C_6H_5$ | $-C_6H_5$ |
| 915 | $SO_2$ | $C(O)$ | $-C(CH_3)_3$ | H | $-C_6H_5CH_3$-4 | $-C_6H_5$ |
| 916 | $SO_2$ | $C(O)$ | $-C(CH_3)_3$ | H | $-C_6H_4F$-4 | $-C_6H_4F$-4 |
| 917 | $C(O)$ | $SO_2$ | $-C(CH_3)_3$ | H | $-C_6H_5$ | $-C_6H_5$ |
| 918 | $C(O)$ | $SO_2$ | $-C(CH_3)_3$ | H | $-C_6H_5$ | $-C_6H_5$ |
| 919 | $C(O)$ | $SO_2$ | $-C(CH_3)_3$ | H | $-C_6H_5$ | $-C_6H_4CH_3$-4 |
| 920 | $C(O)$ | $SO_2$ | $-C(CH_3)_3$ | H | 2-methylpyridyl | $-C_6H_5$ |
| 921 | $C(O)$ | $SO_2$ | $-C(CH_3)_3$ | H | $-C_6H_5$ | thienyl |
| 922 | $C(O)CH_3$ | $P(O)CH_3$ | $-C(CH_3)_3$ | H | $-C_6H_5$ | $-NHC_6H_4Cl$-2 |
| 923 | $P(O)CH_3$ | $C(O)$ | $-C(CH_3)_3$ | H | $-C_6H_5$ | $-C_6H_5$ |
| 924 | $C(O)$ | $C(O)$ | $-CH_3$ | H | $-C_6H_4Cl$-4 | $-C_6H_4Cl$-4 |
| 925 | $C(O)$ | $C(O)$ | $-CH_3$ | H | $-C_6H_3Cl_2$-3,5 | $-C_6H_3Cl_2$-3,5 |
| 926 | $C(O)$ | $C(O)$ | $-C(CH_3)_3$ | H | $-CH_2CH_2CH_2CH_3$ | $-CH_2CH_2CH_2CH_3$ |
| 927 | $C(O)$ | $C(O)$ | $-C(CH_3)_3$ | H | $-CH_2CH_2CH_2CH_3$ | $-CH_2CH_2CH_2CH_2CH_3$ |
| 928 | $C(O)$ | $C(O)$ | $-C(CH_3)_3$ | H | $-CH_2Cl$ | $-CH_2Cl$ |
| 929 | $C(O)$ | $C(O)$ | $-C(CH_3)_3$ | H | $-OCH_2CH_3$ | $-OCH_2CH_2CH_2CH_3$ |
| 930 | $C(O)$ | $C(O)$ | $-C(CH_3)_3$ | H | $-OCH_2CH_3$ | $-C_6H_4Cl$-4 |
| 931 | $C(O)$ | $C(O)$ | $-C(CH_3)_3$ | H | $-C_6H_5$ | $-OCH_2CH_3$ |
| 932 | $C(O)$ | $C(O)$ | $-C(CH_3)_3$ | H | $-CH(C_6H_5)CH(CH_3)CH_2CH_3$ | $-C_6H_4CH_3$-3 |
| 933 | $C(O)$ | $C(O)$ | $-C(CH_3)_3$ | H | $-OC_6H_5$ | $-C_6H_5$ |
| 934 | $C(O)$ | $C(O)$ | $-C(CH_3)_3$ | H | $-C_6H_5$ | $-OC_6H_5$ |
| 935 | $C(O)$ | $C(O)$ | $-C(CH_3)_3$ | H | $-C_6H_5$ | $B_1/93$ |

-continued
TABLE I $$X \quad X'$$
$$A-G_2 \quad N-N-G_2-B$$
$$\qquad\quad R^2 \quad R^1$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 936 | C(O) | C(O) | —C(CH₃)₃ | H | —C₆H₅ | —OC₆H₄NO₂-4 |
| 937 | C(O) | C(O) | —C(CH₃)₃ | H | —CH=C(CH₃)₂ | —CH=C(CH₃)₂ |
| 938 | C(O) | C(O) | —C(CH₃)₃ | H | —CCl=CCl₂ | —CCl=CCl₂ |
| 939 | C(O) | C(O) | —C(CH₃)₃ | H | —CH=CHC₆H₅ | —CH=CHC₆H₅ |
| 940 | C(O) | C(O) | —C(CH₃)₃ | H | —C₆H₄CH₃-4 | —C≡CC₆H₅ |
| 941 | C(O) | C(O) | —C(CH₃)₃ | H | —C≡CC₆H₅ | —C₆H₄-3 |
| 942 | C(O) | C(O) | —C(CH₃)₃ | H | —C₆H₃(CH₃)₂-2,3 | —C≡CC₆H₅ |
| 943 | C(O) | C(O) | —C(CH₃)₃ | H |  | 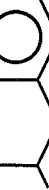 |
| 944 | C(O) | C(O) | —C(CH₃)₃ | H |  —C₆H₄Cl-4 | —C₆H₄C₆H₅-4 |
| 945 | C(O) | C(O) | —C(CH₃)₃ | H | —C₆H₅ |  |
| 946 | C(O) | C(O) | —C(CH₃)₃ | H | —C₆H₅ | |
| 947 | C(O) | C(O) | —C(CH₃)₃ | H |  | —C₆H₄CH₃-3 |
| 948 | C(O) | C(O) | —C(CH₃)₃ | H |  | —CH₄CH₃-3 |

TABLE I -continued $$A-G_2 \quad \begin{array}{c} X \\ | \\ N-N-G_2-B \\ | \quad | \\ R^2 \quad R^1 \end{array} \quad X'$$

where $G_2$ N is a single bond when $R^2$ is "H" and is a double bond when $R^2$ is "—"

| Ex. No. | $G_2(X)$ | $G_2(X')$ | $R^1$ | $R^2$ | A | B |
|---|---|---|---|---|---|---|
| 949 | C(O) | C(O) | —C(CH$_3$)$_3$ | H | | B$_{1/93}$ |
| 950 | C(O) | C(O) | —C(CH$_3$)$_3$ | H | 2-furyl | 2-furyl |
| 951 | C(O) | C(O) | —C(CH$_3$)$_3$ | H | 2-thienyl | 2-thienyl |
| 952 | C(O) | C(O) | —C(CH$_3$)$_3$ | H | pyrrolidinyl | —N(CH$_2$CH$_3$)$_2$ |
| 953 | C(O) | C(O) | —C(CH$_3$)$_3$ | H | —C$_6$H$_5$ | —NHC$_6$H$_4$Cl-4 |
| 954 | C(O) | C(O) | —C(CH$_3$)$_3$ | H | —N(CH$_2$CH$_3$)$_2$ | —N(CH$_2$CH$_3$)$_2$ |
| 955 | C(O) | C(O) | —CH(C$_6$H$_5$)CH$_2$C$_6$H$_5$ | H | —C$_6$H$_5$ | —C$_6$H$_5$ |
| 956 | C(O) | C(O) | 2-thienyl (5-mem) | H | —C$_6$H$_5$ | —C$_6$H$_5$ |
| 957 | C(O) | C(O) | 2-thianyl (6-mem) | H | —C$_6$H$_5$ | —C$_6$H$_5$ |

-continued
TABLE I $$X - X'$$
$$A-G_2 \quad N-N-G_2-B$$
$$\quad\quad\quad | \quad |$$
$$\quad\quad\quad R^2 \; R^1$$

where $G_2$ N is a single bond when $R^2$ is "H" and is a double bond when $R^2$ is "—"

| Ex. No. | G₂(X) | G₂(X') | R¹ | R² | A | B |
|---|---|---|---|---|---|---|
| 958 | C(O) | C(O) | [2-methylthiacyclohexyl] | H | —C₆H₅ | —C₆H₅ |
| 959 | C(O) | C(O) | [2-methylphenyl] | H | —C₆H₅ | —C₆H₅ |
| 960 | C(O) | C(O) | CH(C₆H₅)[thiophene] | H | —C₆H₅ | —C₆H₅ |
| 961 | C(O) | C(O) | —C₆H₅ | H | —C₆H₅ | —C₆H₅ |
| 962 | C(O) | C(O) | —C₆H₅ | H | C₆H₃Cl₂-3,5 | —C₆H₃Cl₂-3,5 |
| 963 | C(O) | C(O) | —C₆H₄Cl-2 | H | —C₆H₅ | —C₆H₅ |
| 964 | C(O) | C(O) | —C₆H₄Cl-4 | H | —C₆H₅ | —C₆H₅ |
| 965 | C(O) | C(O) | —CH₂C₆H₅ | H | —C₆H₅ | —CH₂Cl |
| 966 | C(O) | C(O) | —CH₂C₆H₅ | H | —C₆H₃Cl₂-3,5 | —C₆H₃Cl₂-3,5 |
| 967 | C(O) | C(O) | [2-chloro-5-methylpyridazinyl] | H | —C₆H₅ | —C₆H₅ |
| 968 | C(O) | C(O) | —CH₂C(CH₃)=CH₂ | H | —C₆H₄CH₃-4 | —C₆H₅ |
| 969 | C(O) | C(O) | —CH₂C(CH₃)=CH₂ | H | —C₆H₄CH₃-4 | —C₆H₄CH₃-3 |
| 970 | C(O) | C(O) | —C(CH₃)=CHCH₂CH₂CH₂CH(CH₃)CH₂CH₃ | H | —C₆H₄CH₃-4 | —C₆H₄Br-2 |
| 971 | C(O) | C(O) | —C(CH₃)=CHCH₂CH₂CH(CH₃)CH₂CH₃ | H | —C₆H₅ | —C₆H₄NO₂-2 |
| 972 | C(O) | C(O) | —CH₂C(CH₃)₂Br | H | —C₆H₅ | —C₆H₄CH₃-3 |
| 973 | C(O) | C(O) | —CH(CH₃)CO₂CH₂CH₃ | H | —C₆H₄CH₃-4 | —C₆H₅ |
| 974 | C(O) | C(O) | —CH(CH₃)CO₂CH₂CH₃ | H | —C₆H₄CH₃-4 | —C₆H₅ |
| 975 | C(O) | C(O) | —CH(CH₃)CH₂CH₂CH₃ | H | —C₆H₄CH₃-4 | —C₆H₄NO₂-2 |
| 976 | C(O) | C(O) | —CH(CH₃)CH₂N(CH₃)₂ | H | —C₆H₄CH₃-4 | —C₆H₃(CH₃)₂-3,5 |

TABLE I -continued $$A-G_2 \quad \begin{array}{c} X \\ | \\ N-N-G_2-B \\ | \quad | \\ R^2 \quad R^1 \end{array}$$

where $G_2$ N is a single bond when $R^2$ is "—"
"H" and is a double bond when $R^2$ is "—"

| Ex. No. | $G_2(X)$ | $G_2(X')$ | $R^1$ | $R^2$ | A | B |
|---|---|---|---|---|---|---|
| 977 | C(O) | C(O) | —CH(CH$_3$)C(CH$_3$)$_2$OH | H | —C$_6$H$_4$CH$_3$-4 | —C$_6$H$_5$ |
| 978 | C(O) | C(O) | —CH(CH$_3$)C(CH$_3$)$_2$OH | H | —C$_6$H$_4$CH$_3$-4 | —C$_6$H$_3$(CH$_3$)$_2$-3,5 |
| 979 | C(S) | C(O) | —C(CH$_3$)$_3$ | H | —C$_6$H$_5$ | —C$_6$H$_5$ |
| 980 | C(S) | C(O) | —C(CH$_3$)$_3$ | H | —C$_6$H$_5$ | —C$_6$H$_4$Br-2 |
| 981 | C(S) | C(O) | —C(CH$_3$)$_3$ | H | —C$_6$H$_5$ | —C$_6$H$_3$Cl$_2$-2,4 |
| 982 | C(S) | C(O) | —C(CH$_3$)$_3$ | H | —C$_6$H$_5$ | —C$_6$H$_3$Cl$_2$-3,4 |
| 983 | C(S) | C(O) | —C(CH$_3$)$_3$ | H | —C$_6$H$_5$ | —C$_6$H$_3$F$_2$-2,6 |
| 984 | C(S) | C(O) | —C(CH$_3$)$_3$ | H | —C$_6$H$_5$ | —C$_6$H$_3$CH$_3$-4 |
| 985 | C(S) | C(O) | —C(CH$_3$)$_3$ | H | —C$_6$H$_5$ | (thiophene ring) |
| 986 | C(S) | C(O) | —C(CH$_3$)$_3$ | H | —C$_6$H$_5$ | —OC$_2$H$_5$ |
| 987 | C(S) | C(O) | —C(CH$_3$)$_3$ | H | —C$_6$H$_5$ | —NHCH$_2$CH$_3$ |
| 988 | C(S) | C(O) | —C(CH$_3$)$_3$ | H | —C$_6$H$_5$ | —NHCH$_2$CH$_2$CH$_3$ |
| 989 | C(S) | C(O) | —C(CH$_3$)$_3$ | H | —CH$_2$CH$_2$CH$_3$ | —NHCH$_2$CH$_2$CH$_3$ |
| 990 | C(O) | C(O) | —C(CH$_3$)$_3$ | H | —C$_6$H$_5$ | —CH$_2$CH$_2$CH$_3$ |
| 991 | C(O) | C(O) | —C(CH$_3$)$_3$ | H | —C(CH$_3$)$_3$ | —CH$_2$Cl |
| 992 | C(O) | C(O) | —C(CH$_3$)$_3$ | H | —CH$_2$CH$_2$CH$_3$ | —CH$_2$Cl |
| 993 | C(O) | C(O) | —C(CH$_3$)$_3$ | H | —CH$_2$CH$_2$CH$_3$ | —C$_6$H$_5$ |
| 994 | C(O) | C(O) | —C(CH$_3$)$_3$ | H | —C$_6$H$_4$Cl-4 | —OC$_2$H$_5$ |
| 995 | C(O) | C(O) | —C(CH$_3$)$_3$ | H | —C$_6$H$_3$F$_2$-2,6 | —C$_2$H$_5$ |
| 996 | C(O) | C(O) | —C(CH$_3$)$_3$ | H | —C$_6$H$_5$ | —OC$_2$H$_5$ |
| 997 | C(O) | C(O) | —C(CH$_2$)$_2$C$_6$H$_5$ | H | —C$_6$H$_5$ | —C$_6$H$_5$ |
| 998 | C(O) | C(O) | —C(CH$_2$)$_2$C$_6$H$_5$ | H | —C$_6$H$_5$ | —C$_6$H$_4$Cl-4 |
| 999 | C(O) | C(O) | —C(CH$_2$)$_2$C$_6$H$_5$ | H | —NH$_2$ | —C$_6$H$_4$Cl-4 |
| 1000 | C(O) | C(O) | —C(CH$_3$)$_3$ | H | —NHSO$_2$C$_6$H$_5$ | —C$_6$H$_3$Cl$_2$-3,4 |
| 1001 | C(O) | C(O) | —C(CH$_3$)$_3$ | H | —NHSO$_2$C$_6$H$_4$Cl-2 | —C$_6$H$_4$CH$_3$-3 |
| 1002 | C(O) | C(O) | —C(CH$_3$)$_3$ | H | —NHSO$_2$C$_6$H$_4$Cl-4 | —C$_6$H$_4$CH$_3$-3 |
| 1003 | C(O) | C(O) | —C(CH$_3$)$_3$ | H | —NHSO$_2$C$_6$H$_4$CH$_3$-4 | —C$_6$H$_4$CH$_3$-3 |
| 1004 | C(O) | C(O) | —C(CH$_3$)$_3$ | H | —C$_6$H$_5$ | —NHCH$_2$CH$_2$CH$_3$ |
| 1005 | C(O) | C(O) | —C(CH$_3$)$_3$ | H | —C$_6$H$_5$Cl-3 | —NHCH$_2$CH$_2$CH$_3$ |
| 1006 | C(O) | C(O) | —C(CH$_3$)$_3$ | H | —C$_6$H$_4$CH$_3$-3 | —NHC$_6$H$_5$ |
| 1007 | C(O) | C(O) | —C(CH$_3$)$_3$ | H | —C$_6$H$_4$CH$_3$-3 | —NHCH$_2$CH$_2$CH$_3$ |
| 1008 | C(O) | C(O) | —C(CH$_3$)$_2$C(O)NH$_2$ | H | —NHC(O)C$_6$H$_4$Cl-4 | —C$_6$H$_4$CH$_3$-3 |
| 1009 | C(O) | C(O) | —C(CH$_3$)$_2$C(O)NH$_2$ | H | —NHC(O)C$_6$H$_4$CH$_3$-2 | —C$_6$H$_4$CH$_3$-3 |
| 1010 | C(O) | C(O) | —C(CH$_3$)$_2$C(O)NH$_2$ | H | —C$_6$H$_4$NO$_2$-2 | —C$_6$H$_4$CH$_3$-3 |
| 1011 | C(O) | C(O) | —C(CH$_3$)$_2$C(O)NH$_2$ | H | —C$_6$H$_4$Cl-2 | —C$_6$H$_4$CH$_3$-3 |
| 1012 | C(O) | C(O) | —C(CH$_3$)$_3$ | — | —C$_6$H$_5$Cl-2 | —NHCH$_2$CH$_2$CH$_3$ |
| 1013 | C(H) | C(O) | —C(CH$_3$)$_3$ | — | —C(Cl)=C(Cl)CO$_2$H | —C$_6$H$_4$CH$_3$-3 |
| 1014 | C(H) | C(O) | —C(CH$_3$)$_3$ | — | —C(Br)=C(Br)CO$_2$H | —C$_6$H$_4$CH$_3$-3 |

TABLE I-continued $$A-G_2\underset{X}{\phantom{-}}\quad \underset{X'}{N-N-G_2-B}$$
$$\phantom{A-G_2\quad}\underset{\phantom{X}}{R^2}\phantom{N-N-}R^1$$

where $G_2$ N is a single bond when $R^2$ is "H" and is a double bond when $R^2$ is "—"

| Ex. No. | $G_2(X)$ | $R^1$ | $G_2(X')$ | $R^2$ | A | B$_{1/93}$ |
|---|---|---|---|---|---|---|
| 1015 | C(CH$_3$)O | —C(CH$_3$)$_3$ | C(O) | — | —C(O)OC$_2$H$_5$ | —C$_6$H$_4$CH$_3$-3 |
| 1016 | C(CH$_3$) | —C(CH$_3$)$_3$ | C(O) | — | —CH$_3$ | —C$_6$H$_4$CH$_3$-3 |
| 1017 | CH(CH$_3$) | —C(CH$_3$)$_3$ | C(O) | H | —CH$_3$ | —C$_6$H$_4$CH$_3$-3 |
| 1018 | C(CH$_3$)$_2$ | —C(CH$_3$)$_3$ | C(O) | H | —CN | —C$_6$H$_5$ |

EXAMPLE NO. 1

Preparation of N'-t-butyl-N,N'-(4-chlorobenzoyl)hydrazine

A suspension of t-butylhydrazine hydrochloride (12.5 g, 0.1 mole) in toluene (100 ml) at 0°–5° C. was treated slowly with 1 equivalent of NaOH solution, prepared from diluting 8 g of 50% NaOH commercially available solution to 20 ml of the volume with $H_2O$. At 0° to 5° C. with mechanical stirring, 2 equivalents of 4-chlorobenzoyl chloride (35.9 g, 0.2 mole) and 2 equivalents of NaOH (16 g of 50% NaOH diluted with $H_2O$ to 40 ml) were added dropwise separately and simultaneously from dropping funnels. The exothermic reaction was cooled down by an ice-water bath through the entire addition. After the addition was completed, the resulting suspension was stirred at room temperature (RT) for one hour. The white precipitate (p.p.t.) was collected by suction-filtration and washed with a small amount of toluene and 100 ml of $H_2O$. The material was then air-dried, then crystallized from 95% aqueous $CH_3OH$ to afford 24.65 g of N'-t-butyl-N,N'-(4-chlorobenzoyl)hydrazine as needles: m.p. 246°–248° C.

Additional product can be obtained by concentrating the mother liquor of crystallization.

EXAMPLE NO. 3

Preparation of N'-t-butyl-N,N'-dibenzoylhydrazine

To a stirred suspension of t-butylhydrazine hydrochloride (1.24 g, 10 mmoles) in toluene (50 ml) at room temperature, was added dropwise a solution of 50% aqueous sodium hydroxide (0.8 g, 10 ml). After 15 minutes, the reaction mixture was cooled to 5° C. and solutions of benzoyl chloride (2.82 gm, 20 ml) in toluene (7 ml) and 50% aqueous sodium hydroxide (1.6 g) were added dropwise and simultaneously from separate addition funnels while maintaining the temperature below 10° C. Following the addition, the reaction mixture was warmed to room temperature and stirred for 1 hr. The reaction mixture was diluted with ether and the product isolated by filtration. The product was washed with water and ether and dried. The product was recrystallized from ether-methanol to afford N'-t-butyl-N,N'-dibenzoylhydrazine as a white powder: m.p. 174°–176° C.

EXAMPLE NO. 16

Preparation of N'-t-butyl-N'-(4-chlorobenzoyl)-N-benzoylhydrazine

To a stirred suspension of t-butylhydrazine hydrochloride (1.24 g, 10 mmoles) in toluene (30 ml) at room temperature was added dropwise a 50% aqueous solution of sodium hydroxide (0.8 g, 10 mmole). After 15 min., the reaction mixture was cooled to 5° C. and a solution of benzoyl chloride (1.42 g, 10 mmoles) in toluene (5 ml) and a solution of aqueous 50% sodium hydroxide (0.8 g, 10 mmole) were added dropwise simultaneously from separate addition funnels while maintaining the temperature at or below 10°. Following the addition, the reaction mixture was warmed to room temperature and stirred for 1 hr. The reaction mixture was diluted with toluene washed with water. The organic layer was separated, dried over anhydrous magnesium sulfate and the solvent removed under vacuum to afford a yellow oil which slowly solidifies on standing. The product was recrystallized from ether-hexane to afford white crystals.

To a stirred solution of the monobenzoylated compound (1.92 g, 10 mmoles) in toluene (30 ml) at 5° C. as added dropwise simultaneously from separate addition funnels, solutions of p-chlorobenzoyl chloride (1.75 g, 10 mmoles) in toluene (5 ml) and aqueous 50% sodium hydroxide solution (0.8 g) while maintaining the temperature below 10° C. Following the addition, the reaction mixture was warmed to room temperature and stirred for 1 hr. The mixture was then diluted with hexane and the precipitated product isolated by filtration. The product was washed with water and hexane and dried. The crude product was recrystallized from ether-methanol to afford N'-t-butyl-N'-(4-chlorobenzoyl)-N-benzoylhydrazine as a white powder: m.p. 201°–204° C.

EXAMPLE NO. 44

Preparation of N'-neopentyl-N,N'-dibenzoylhydrazine

A solution of benzoylhydrazine (1.36 g, 10 mmoles), 1,1,1-trimethylacetaldehyde (0.86 g, 10 mmoles) and acetic acid (catalytic amount) in methanol are stirred at room temperature until hydrazone formation is complete. The reaction mixture is brought to a pH of 4 and sodium cyanoborohydride (0.75 g, 12.5 mmoles) is added slowly portionwise (the reaction is connected to an aqueous sodium hydroxide trap). Upon completion, the reaction is diluted with excess aqueous sodium hydroxide and the methanol is removed under vacuum. The product is partitioned into methylene chloride and washed with aqueous base and water. The organic layer is separated and dried over anhydrous magnesium sulfate. The magnesium sulfate is filtered and the methylene chloride removed under vacuum to afford the product as a yellow oil which solidifies on standing. The crude 2-neopentyl-1-benzoylhydrazine is benzoylated directly.

To a stirred solution of the 2-neopentyl-1-benzoylhydrazine in toluene (40 ml) at 5° C. were added dropwise and simultaneously solutions of benzoyl chloride (1.4 g, 10 mmoles) in toluene (5 ml) and aqueous 50% sodium hydroxide solution (0.8 g) while maintaining the temperature below 10° C. After the addition, the reaction mixture was warmed to room temperature and stirred for 1 hour. The reaction mixture was diluted with hexane and the precipitated product isolated by filtration. The product was washed with water and hexane and dried. The crude product was recrystallized from methanol to afford N'-neopentyl-N,N'-dibenzoylhydrazine as a white powder: m.p. 237°–239° C.

EXAMPLE NO. 102

Preparation of N'-t-butyl-N'-benzoyl-N-4-chlorothiobenzoylhydrazine

A mixture of 4-chloro-methylthio-thiobenzoate (3.0 g, 0.015 mol) and t-butyl hydrazine hydrochloride (2.0 g, 0.016 mol) in 5 ml of pyridine was heated at 90° C. for 18 hours. The mixture was poured into 0.1N HCl/ether. The layers were separated and the organic extracts were washed with 3 portions of 0.1N HCl followed by saturated aqueous NaHCO. After the extracts were dried over anhydrous magnesium sulfate, the solvents were removed under vacuum to afford 1.9 g of a brown solid. Chromatography on silica gel using ether (25%)-methylene chloride (25%)-hexane as eluant afforded 0.8 g of a golden yellow solid. The solid was dissolved in 3 ml of methylene chloride and treated with pyridine (1 ml) and benzoyl chloride (0.6 ml). After 24 hours at 23° C., the reaction mixture was poured onto 0.1N HCl/ether. The organic layer was washed with saturated aqueous sodium bicarbonate and was dried over anhydrous magnesium sulfate. Evaporation of solvents gave a yellow oil which was chromatographed on silica gel using ether (25%)-methylene chloride (25%)-hexane as eluant to give 0.15 g of N'-t-butyl-N'-benzoyl-N-4-chlorothiobenzoylhydrazine as a yellow solid: m.p. 160°–162° C.

EXAMPLE NO. 103

Preparation of N'-t-butyl-N'-thiobenzoyl-N-benzoylhydrazine

A mixture of N'-t-butyl-N-benzoyl hydrazine (60% purity, 1.0 g, 0.0031 mol) and S-(thiobenzoyl)-thioglycolic acid (1.0 g, 0.0047 mol) in 3 ml of pyridine was heated at about 90° C. for 24 hours. The dark colored mixture was cooled and poured into 0.1N HCl/ether. The organic layer was washed with three 15 ml portions of 0.1N HCl followed by saturated aqueous sodium bicarbonate. The organic extracts were dried over anhydrous magnesium sulfate. Evaporation of the solvents afforded 0.5 g of a brown oil which was recrystallized from ether-hexane to yield 0.2 g of N'-t-butyl-N'-thiobenzoyl-N-benzoylhydrazine as a tan solid: m.p. 169°–171° C.

EXAMPLE NO. 148

Preparation of N'-t-butyl-N-(2-hydroxy-methylbenzoyl)-N'-benzoylhydrazine t-Butylhydrazine (0.1 mol) in 75 ml ethanol was treated with 50% aqueous sodium hydroxide (0.11 mol). Phthalide (0.1 mol) was added and the mixture was refluxed for 5 days. After cooling, water was added and the crude product was isolated by filtration. Filtration through silica gel afforded N'-t-butyl-N-(2-hydroxymethylbenzoyl)hydrazine (3.0 g): m.p. 116°–118° C.

0.7 g of N'-t-butyl-N-(2-hydroxymethylbenzoyl)hydrazine and 1.1 g benzoyl chloride are combined in 10 ml of 5% NaOH and stirred at room temperature for 1.5 hours. The solids are filtered off, washed with water and then ether to afford 0.6 g of white solid N'-t-butyl-N-(2-(benzoyloxymethyl)benzoyl)-N'-benzoylhydrazine: m.p. 190°–191° C.

EXAMPLE NO. 220

Preparation of N-(3-toluoyl)-N'-t-butyl-N'-benzoylhydrazine

Step 1

To a stirred suspension of t-butylhydrazine (51 g) in a mixture of dioxane and water (2:1) (150 ml) was added sodium hydroxide (32 g of a 50% aqueous solution). After 10 min., the solution was cooled to 5° C. and di-t-butyldicarbonate (42 g) was added dropwise so as to maintain the reaction temperature below 10° C. The reaction mixture was warmed and stirred 2 hours at room temperature. The reaction mixture was filtered, washed with water and dried to afford N-t-butyloxycarbonyl-N'-t-butylhydrazine (74 g) as a white crystalline solid: m.p. 69°–71° C.

Step 2

To a stirred solution of N-t-butyloxycarbonyl-N'-t-butylhydrazine (61 g) in toluene (120 ml) was added benzoyl chloride (45 g) and sodium hydroxide (31 g of a 50% aqueous sodium hydroxide solution) dropwise and simultaneously. After stirring for 1 hour at room temperature, the solid N-t-butyloxycarbonyl-N'-t-butyl-N'-benzoylhydrazine was filtered, washed with water, hexane and dried to afford 52 g of product: m.p. 167°–170° C.

Step 3

The N-t-butoxycarbonyl-N'-t-butyl-N'-benzoylhydrazine (52 g, 0.18 mol) was stirred at room temperature in a methanolic hydrochloric acid solution for 4 days. The reaction mixture was neutralized with saturated aqueous sodium bicarbonate. The white precipitate was filtered, washed with water and dried in vacuo to give 30 g of N'-t-butyl-N'-benzoylhydrazine: m.p. 124°–125° C.

Step 4

To a stirred mixture of N'-t-butyl-N'-benzoylhydrazine (1.0 g) in 15 ml toluene and aqueous sodium hydroxide (0.5 g of 50% NaOH) was added 3-toluoylchloride (0.9 g). After stirring for 2 hours, the product was isolated by filtration to give N'-t-butyl-N-(3-toluoyl)-N'-benzoylhydrazine in good yield: m.p. 111°–114° C.

EXAMPLE NO. 295

Preparation of N'-(1,1-dimethylethyl)-N,N'-dibenzoylhydrazine

To a gently refluxing solution of ethyl magnesium bromide (150 ml of 1M solution) was added acetone azine (20 g) dissolved in diethyl ether (80 ml). The solution was refluxed for three days. Upon cooling, a saturated solution of ammonium chloride (75 ml) was added. The aqueous layer was separated and washed twice with diethyl ether (150 ml). The combined ether extracts were dried over anhydrous magnesium sulfate, filtered and the ether removed at reduced pressure. The product was distilled through a vigreux column at 3 torr and collected in a dry ice/acetone cooled receiving flask. The boiling point was 40°–50°. 15 g of product was collected.

Oxalic acid (17 g) was dissolved in a solution of ethanol:diethyl ether (1:1) (150 ml) and water (3.3 g) was added. To this acid solution was added the hydrazone (13 g) dissolved in diethyl ether (30 ml). The solution was stirred for 24 hours then filtered. The solid is washed once with diethyl ether. The filtrate was concentrated and combined with the solid to afford a 77% yield (16.3 g) of the hydrazine oxalate.

The 1,1-dimethylethylhydrazine oxalate (2 g) was dissolved in toluene and neutralized with 50% aqueous sodium hydroxide. To this solution was added benzoyl chloride (4.02 g) and sodium hydroxide (50% Aq. solution) (2.45 g) at 25° C. The reaction mixture was warmed to room temperature and stirred 3 hours. The mixture was diluted with hexane and filtered to afford the product as a white solid (0.5 g).

EXAMPLE NO. 324

Preparation of N'-t-butyl-N-(thiobenzoyl)-N'-(3-toluoyl)hydrazine

S-(thiobenzoyl)thioglycolic acid (3.0 g) was dissolved in 20 ml pyridine, treated with t-butyl hydrazine hydrochloride (excess, ca. 4 g) and then was heated at ca. 120° C. for 14 hours. Water (120 ml) was added and the mixture was extracted with ether. The organic extracts were dried over anhydrous magnesium sulfate, filtered and evaporated to give crude N'-t-butyl-N-(thiobenzoyl)hydrazine as a viscous yellow oil.

N'-t-butyl-N-(thiobenzoyl)hydrazine (ca. 1 g), m-toluoyl chloride (approx. 0.7 g) and 50% aqueous sodium hydroxide (6 drops) were mixed in 1 ml water and 10 ml toluene at 23° C. After stirring for 3 hours, ether-hexane was added and the product was isolated by filtration (0.25 g): m.p. 165°–168° C.

EXAMPLE NO. 344

Preparation of N'-t-butyl-N-[3-(N,N-dimethylcarbamoyl)benzoyl])-'-benzoylhydrazine N-(3-hydroxybenzoyl)-N'-t-butyl-N'-benzoylhydrazine (0.2 g) was stirred in tetrahydrofuran (15 ml) at 23° C. Solid potassium t-butoxide (0.1 g) was added and the solution went from clear colorless to cloudy yellow. After stirring 10 minutes at room temperature, N,N-dimethylcarbamoyl chloride was added dropwise (0.1 g). With the addition the solution turned colorless and a precipitate appeared. Saturated aqueous NaHCO$_3$ and ether were added, the layers separated and the organic dried over magnesium sulfate, filtered and rotavapped to afford an oily solid.

EXAMPLE NO. 625

Preparation of N'-t-butyl-N-(4-4,4-dimethyloxazol-2-yl)benzoyl)-N'-(3-toluoyl)hydrazine 1.2 g of N'-t-butyl-N-(4-carbomethoxybenzoyl-N'-(3-toluoyl)hydrazine was heated in 2 ml of 2-amino-2-methyl-1-propanol at 90°–100° C. for 5 hours. After cooling, the mixture was diluted with ether/methylene chloride and washed with 0.1N HCl. The organic layer was evaporated to afford 1.0 g of the corresponding amide.

The amide in 10 ml of chloroform was treated with 0.25 g of thionyl chloride and stirred at 23° C. for 1.5 hours. Saturated aqueous sodium bicarbonate was added and the layers separated. Evaporation of the organic layer afforded the product as a foam.

EXAMPLE NO. 635

Preparation of N-methyl-N'-t-butyl-N,N'-dibenzoylhydrazine

To a stirred solution of N'-t-butyl-N,N'-dibenzoylhydrazine (2.5 g, 0.008M) in dimethylformamide (DMF) (30 ml) at room temperature under nitrogen was added portionwise sodium hydride (60% oil dispersion) (0.4 g, 0.009M). The mixture was stirred at room temperature for 0.5 hours, and then methyl iodide (1.0 g, 0.008M) was added dropwise. The reaction mixture was allowed to stir for 1 hour. The mixture was then diluted with water (50 ml), neutralized with 10% HCl and the product extracted into methylene chloride (50 ml). The methylene chloride layer was washed with water (5×20 ml), dried over anhydrous magnesium sulfate and the methylene chloride removed under vacuum to afford N-methyl-N'-t-butyl-N,N'-dibenzoylhydrazine as an oil.

EXAMPLE NO. 636

Preparation of N-benzyl-N'-t-butyl-N,N'-dibenzoylhydrazine

To a stirred solution of N'-t-butyl-N,N'-dibenzoylhydrazine (2 g, 0.006M) in DMF (25 ml) at room temperature under nitrogen was added portionwise sodium hydride (60% oil dispersion) (0.3 g, 0.007M). The mixture was stirred at room temperature for 0.5 hours, and then benzyl bromide (1.2 g, 0.007M) was added dropwise. The reaction mixture was warmed to 60° C. and allowed to stir for 2 hours. The mixture was then diluted with water (50 ml), neutralized with 10% HCl and the product extracted into methylene chloride (50 ml). The methylene chloride layer was washed with water (5×20 ml), dried over anhydrous magnesium sulfate and the methylene chloride removed under vacuum to afford N-benzyl-N'-t-butyl-N,N'-dibenzoylhydrazine as an oil.

EXAMPLE NO. 637

Preparation of N-allyl-N'-t-butyl-N,N'-dibenzoylhydrazine

To a stirred solution of N'-t-butyl-N,N'-dibenzoylhydrazine (3 g, 0.011M) in DMF (30 ml) at room temperature under nitrogen was added portionwise sodium hydride (60% oil dispersion) (0.5 g, 0.012M). The mixture was stirred at room temperature for 0.5 hours, and then allyl iodide (1.8 g, 0.01M) was added dropwise. The reaction mixture was warmed to 60° C. and stirred for 2 hours. The mixture was then diluted with water (50 ml), neutralized with 10% HCl and the product extracted into methylene chloride (50 ml). The methylene chloride layer was washed with water (5×20 ml), dried over anhydrous magnesium sulfate and the methylene chloride removed under vacuum to afford N-allyl-N'-t-butyl-N,N'-dibenzoylhydrazine as an oil.

EXAMPLE NO. 638

Preparation of N-methoxymethyl-N'-t-butyl-N-N'-dibenzoylhydrazine

N'-t-butyl-N,N'-dibenzoylhydrazine (2 g, 0.007M) was stirred at room temperature in a two phase system of toluene-50% sodium hydroxide with 100 mg of phase transfer catalyst (tetra-n-butylammonium hydrogen sulfate). Methoxymethyl chloride (1.2 g, 0.015M) was added dropwise and the mixture was stirred 3 hours. The layers were separated and the toluene layer was washed several times with water (until the water washes were neutral). The toluene solution was dried over anhydrous magnesium sulfate and the toluene removed under vacuum to afford N-methoxymethyl-N'-t-butyl-N,N'-dibenzoylhydrazine as a thick oil.

EXAMPLE NO. 639

Preparation of N-methylthiomethyl-N'-t-butyl-N,N'-dibenzoylhydrazine

To a stirred suspension of sodium hydride (a 50% oil dispersion washed 2 times with 20 ml pentane) (0.21 g, 0.0043M) in dry DMF (20 ml) under nitrogen at room temperature was added N'-t-butyl-N,N'-dibenzoylhydrazine (1 g, 0.0034M) portionwise as a solid. The mixture was stirred at room temperature for ½ hour and methylthiomethylchloride (0.34 g, 0.0035M) was added dropwise. The resulting mixture was heated at 50° C. overnight, cooled, diluted with methylene chloride and washed repeatedly with water. The organic layer was dried over anhydrous magnesium sulfate and the methylene chloride removed under vacuum. The oily residue was chromatographed on silica gel using methylene chloride to afford N-methylthiomethyl-N'-t-butyl-N,N'-dibenzoylhydrazine as an oil (60% yield).

EXAMPLE NO. 642

Preparation of N-(2-propynyl)-N'-t-butyl-N-benzoyl-N'-(3,5-dimethylbenzoyl)hydrazine To a stirred suspension of N'-t-butyl-N-benzoyl-N'-(3,5-dimethylbenzoyl)hydrazine (1.5 g) in dimethylformamide (DMF) (20 ml) was added sodium hydride (200 mg of 60% oil dispersion) portionwise. After 15 min., propargyl bromide (0.6 g) was added to the reaction mixture dropwise and the reaction stirred for 1 hour. The reaction mixture was diluted with ethyl acetate (50 ml) and washed with water (5×20 ml). The organic layer was then dried over magnesium sulfate and the solvent removed under vacuum to afford N-(2-propynyl)-N'-(3,5-dimethylbenzoyl)hydrazine as a yellow amorphous solid. The product, N-(2-propynyl)-N'-t-butyl-N-benzoyl-N'-(3,5-dimethylbenzoyl)hydrazine, was purified by column chromatography on silica gel (solvent system: methylene chloride) to afford a 70% yield as a white solid.

EXAMPLE NO. 646

Preparation of N'-t-butyl-N-cyclohexylcarbonyl-N'-benzoylhydrazine

To a stirred suspension of t-butylhydrazine hydrochloride (2.0 g, 0.016M) in toluene (30 ml) was added 50% sodium hydroxide (1.3 g, 0.016M). After 15 minutes, the mixture was cooled to 5° C. and cyclohexanecarbonylchloride (2.4 g, 0.016M) and 50% sodium hydroxide (1.3 g, 0.016M) were added separately and simultaneously so as to maintain the reaction temperature below 10° C. After the addition, the reaction mixture was allowed to warm to room temperature and stirred for 1 hour. The mixture was diluted with hexane and the solid product isolated by filtration. This product (1.5 g, 0.008M) was dissolved in a stirred mixture of toluene (30 ml) and cooled on ice. To this mixture was added benzoylchloride (1.1 g, 0.008M) and 50% sodium hydroxide (0.6 g, 0.008M) simultaneously. After addition, the mixture was stirred for ½ hour, diluted with hexane and the solid product, N'-t-butyl-N-cyclohexylcarbonyl-N'-benzoylhydrazine, isolated by filtration.

EXAMPLE NO. 648

Preparation of N'-t-butyl-N-valeryl-N'-benzoylhydrazine

To a stirred suspension of t-butylhydrazine hydrochloride (24.8 g, 0.20 mole) in toluene (150 ml) at 5° C. was added one equivalent of NaOH, prepared by diluting 16 g of 50% aqueous (aq.) NaOH to 30 ml. After addition, valeryl chloride (24 g, 0.2 mole) and another one equivalent of NaOH solution (30 ml) were dropwise added separately and simultaneously. The reaction mixture was warmed to room temperature and stirred for 40 minutes. The two phase mixture was separated and the organic layer was washed with water and brine. The organic layer was dried over $Na_2SO_4$ and concentrated under vacuum to give a colorless oil.

To a stirred solution of 1-t-butyl-2-valerylhydrazine (4 g, 0.023M) in toluene (40 ml) at 5° C. was added benzoyl chloride (3.4 g, 0.024M) and 50% aq. sodium hydroxide (0.98 g, 0.024M). After addition, the mixture was warmed to room temperature and stirred 2.5 hour. The mixture was diluted with ethylacetate (50 ml) and washed with water (2×25 ml) and brine (1×25 ml). The organic layer was dried over magnesium sulfate and concentrated under vacuum to afford N'-t-butyl-N-valeryl-N'-benzoylhydrazine as a yellow oil.

EXAMPLE NO. 654

Preparation of N'-t-butyl-N-phenylacetyl-N'-benzoylhydrazine

To a stirred suspension of t-butylhydrazine hydrochloride (2.0 g, 0.016M) in toluene (30 ml) was added 50% sodium hydroxide (1.3 g, 0.016M). After 15 minutes, the mixture was cooled to 5° C. and phenylacetyl chloride (2.4 g, 0.016M) and 50% sodium hydroxide (1.3 g, 0.016M) were added separately and simultaneously so as to maintain the reaction temperature below 10° C. After the addition, the reaction mixture was allowed to warm to room temperature and stirred for 1 hour. The mixture was diluted with hexane and the solid product isolated by filtration. This product (3.2 g, 0.015M) was dissolved in a stirred mixture of toluene (30 ml) and cooled on ice. To this mixture was added benzoylchloride (2.2 g, 0.016M) and 50% sodium hydroxide (1.3 g, 0.016M) simultaneously. After addition, the mixture was stirred for ½ hour, diluted with hexane and the solid product, N'-t-butyl-N-phenylacetyl-N'-benzoylhydrazine, isolated by filtration.

EXAMPLE NO. 656

Preparation of N'-t-butyl-N-cyclohexenylcarbonyl-N'-benzoylhydrazine

To a stirred suspension of t-butylhydrazine hydrochloride (0.86 g, 0.007M) in toluene (30 ml) was added 50% sodium hydroxide (0.55 g, 0.007M). After 15 minutes, the mixture was cooled to 5° C. and cyclohexenylcarbonyl chloride (1.0 g, 0.007M) and 50% sodium hydroxide (0.55 g, 0.007M) were added separately and simultaneously so as to maintain the reaction temperature below 10° C. After the addition, the reaction mixture was allowed to warm to room temperature and stirred for 1 hour. The mixture was diluted with hexane and the solid product isolated by filtration. This product (1.2 g, 0.006M) was dissolved in toluene (30 ml) and cooled on ice while stirring. To this mixture was added benzoylchloride (1.0 g, 0.007M) and 50% sodium hydroxide (1.3 g, 0.007M) simultaneously. After addition, the mixture was stirred for ½ hour, diluted with hexane and the solid product, N'-t-butyl-N-cyclohexenylcarbonyl-N'-benzoylhydrazine, was isolated by filtration.

EXAMPLE NO. 659

Preparation of N'-t-butyl-N-beta-chloropivaloyl-N'-benzoylhydrazine

To a stirred suspension of t-butylhydrazine hydrochloride (200 g, 1.61 mole) in acetone (400 ml) was dropwise added triethylamine (200 g, 1.98 mole). After addition, the mixture was refluxed for 3 hours while periodically adding magnesium sulfate (100 g total). The mixture was cooled to room temperature and funnel filtered. The filtrate was dried over magnesium sulfate and concentrated under vacuum at 5° C. until a slurry formed. The mixture was diluted with ethyl acetate (100 ml) and was filtered. The filtrate was distilled yielding a yellow oil: b.p. 121°–127° C.

Into a stirred suspension of 1-t-butyl-2-acetonehydrazone (43 g, 0.34 mole) in toluene (250 ml) at 5° C. was added 10% aq. sodium hydroxide (200 ml, 0.50 mole). After addition, benzoylchloride (70 g, 0.50 mole) was added dropwise to this mixture. Stirring was continued for 2 hours at 5° C. and 72 hours at room temperature. The mixture was diluted with ethyl acetate (300 ml) and washed with water (3×200 ml) and brine (200 ml). The organic layer was dried over magnesium sulfate and concentrated at 35° C. under vacuum to afford a yellow oil.

A mixture of 1-t-butyl-1-benzoyl-2-acetone hydrazone (90 g, approximately 60% pure, approximately 0.3 mole), ethanol (500 ml, 200 proof) and 10% aq. hydrochloric acid (500 ml) was stirred overnight at room temperature. The mixture was concentrated under vacuum to a thick slurry. The slurry was suction filtered with a water wash (400 ml). The solids were air-dried overnight.

The solids were dissolved in a water (200 ml) and methanol (100 ml) solution on a steam bath. The mixture stood at room temperature overnight. The mixture was suction filtered and rinsed with cold water (100 ml) and the solids were air dried overnight. The solids were dissolved in 10% aq. hydrochloric acid (300 ml) and were washed with ethyl acetate (3×300 ml). The ethyl acetate washes were combined and extracted with 10% aq. hydrochloric acid (250 ml). The 10% aq. hydrochloric acid layers were combined and were neutralized with 50% aq. sodium hydroxide while being stirred. Stirring was continued for 1 hour at room temperature. The mixture was suction filtered and rinsed with water (100 ml) and the solids were air-dried yielding a white solid: m.p. 125°–126° C.

To a stirred solution of 1-t-butyl-1-benzoylhydrazine (1 g, 0.005M) in toluene (40 ml) cooled to 5° C. was added 3-chloro-2,2-dimethylpropionylchloride (1.2 g, 0.007M) and 50% aq. sodium hydroxide (0.45 g, 0.0056M) so as to maintain the temperature below 10° C. The mixture was warmed to room temperature and stirred 1 hour. The mixture was diluted with hexane (40 ml) and water (10 ml). The white solid product N'-t-butyl-N-(beta-chloropivaloyl)-N'-benzoylhydrazine was isolated by suction filtration, washed with 50 ml hexane and 50 ml water and dried.

EXAMPLE NO. 661

Preparation of N'-t-butyl-N-(1,2,2-trichlorovinyl)carbonyl-N'-benzoylhydrazine

To a stirred suspension of t-butylhydrazine hydrochloride (200 g, 1.61 mole) in acetone (400 ml) was dropwise added triethylamine (200 g, 1.98 mole). After addition, the mixture was refluxed for 3 hours while periodically adding magnesium sulfate (100 g total). The mixture was cooled to room temperature and funnel filtered. The filtrate was dried over magnesium sulfate and concentrated under vacuum at 5° C. until a slurry formed. The mixture was diluted with ethylacetate (100 ml) and was filtered. The filtrate was distilled yielding a lightly yellow tinted oil: b.p. 121°–127° C.

To a stirred suspension of 1-t-butyl-2-acetonehydrazone (43 g, 0.34 mole) in toluene (250 ml) at 5° C. was added 10% aq. sodium hydroxide (200 ml, 0.50 mole). After addition, benzoylchloride (70 g, 0.50 mole) was added dropwise to the mixture. Stirring was continued for 2 hours at 5° C. and 72 hours at room temperature. The mixture was diluted with ethyl acetate (300 ml) and washed with water (3×200 ml) and brine (200 ml). The organic layer was dried over magnesium sulfate and concentrated at 35° C. under vacuum yielding a yellow oil.

A mixture of 1-t-butyl-1-benzoyl-2-acetone hydrazone (90 g, approximately 60% pure, approximately 0.3 mole), ethanol (500 ml, 200 proof) and 10% aq. hydrochloric acid (500 ml) was stirred overnight at room temperature. The mixture was concentrated under vacuum to a thick slurry. The slurry was suction filtered and washed with water (400 ml). The solids were air-dried overnight.

The solids were dissolved in a water (200 ml) and methanol (100 ml) solution on a steam bath. The mixture stood at room temperature overnight. The mixture was suction filtered and rinsed with cold water (100 ml) and the solids were air dried overnight. The solids were dissolved in 10% aq. hydrochloric acid (300 ml) and were washed with ethyl acetate (3×300 ml). The ethyl acetate washes were combined and extracted with 10% aq. hydrochloric acid (250 ml). The 10% aq. hydrochloric acid layers were combined and were neutralized with 50% aq. sodium hydroxide while being stirred. Stirring was continued for 1 hour at room temperature. The mixture was suction filtered and rinsed with water (100 ml) and the solids were air-dried yielding a white solid: m.p. 125°–126° C.

To a stirred solution of 1-t-butyl-1-benzoylhydrazine (1.5 g, 0.008M) in methylene chloride at 5° C. was added, simultaneously and separately, trichloroacryloylchloride (1.7 g, 0.009M) and triethylamine (0.9 g, 0.009M). After addition, the reaction was warmed to room temperature and stirred for 3 hours. The flask's contents were diluted with 50 ml methylene chloride and washed with water (3×75 ml) and brine solution (1×75 ml). The organic layer was dried over magnesium sulfate and the solvent removed under vacuum to afford N'-t-butyl-N-(1,2,2-trichlorovinyl)carbonyl-N'-benzoylhydrazine as a white solid product.

EXAMPLE 682

Preparation of N'-t-butyl-N-benzoyl-N'-n-pentanecarbonylhydrazine

To a stirred suspension of t-butylhydrazine hydrochloride (1 g, 0.008M) in toluene (30 ml) at room temperature was added dropwise a 50% aqueous solution of sodium hydroxide (0.64 g, 0.008M). After 15 minutes, the reaction mixture was cooled to 5° C. and a solution of benzoyl chloride (1.12 g, 0.008M) in toluene (5 ml) and a solution of aqueous 50% sodium hydroxide (0.64 g, 0.008M) were added dropwise simultaneously from separate addition funnels while maintaining the temperature at or below 10° C. Following the addition, the reaction mixture was warmed to room temperature and stirred for 1 hour. The reaction was diluted with hexane and the solid N'-t-butyl-N'-benzoylhydrazine was isolated by filtration.

To a stirred solution of the monobenzoylated compound (1.4 g, 0.0073M) in toluene (30 ml) at 5° C. were added dropwise simultaneously from separate addition funnels, solutions of hexanoyl chloride (1 g, 0.0073M) in toluene (5 ml) and aqueous 50% sodium hydroxide solution (0.58 g, 0.0073M) while maintaining the temperature below 10° C. Following the addition, the reaction mixture was warmed to room temperature and stirred for 1 hour. The mixture was then diluted with hexane and the solid product isolated by filtration. The product was washed with water and hexane and dried. The crude product was recrystallized from ether-methanol to afford N'-t-butyl-N-benzoyl-N'-n-pentanecarbonylhydrazine as a white powder: m.p. 117°–118° C.

EXAMPLE 683

Preparation of N'-t-butyl-N-benzoyl-N'-cyclohexanecarbonylhydrazine

To a stirred suspension of t-butylhydrazine hydrochloride (1 g, 0.008 M) in toluene (30 ml) at room temperature was added dropwise a 50% aqueous solution of sodium hydroxide (0.64 g, 0.008M). After 15 minutes, the reaction mixture was cooled to 5° C. and a solution of benzoyl chloride (1.12 g, 0.008M) in toluene (5 ml) and a solution of aqueous 50% sodium hydroxide (0.64 g, 0.008M) were added dropwise and simultaneously from separate addition funnels while maintaining the temperature at or below 10° C. Following the addition, the reaction mixture was warmed to room temperature and stirred for 1 hour. The reaction was diluted with hexane and the solid N'-t-butyl-N-benzoylhydrazine was isolated by filtration.

To a stirred solution of the monobenzoylated compound (1.4 g, 0.0073M) in toluene (30 ml) at 5° C. were added dropwise and simultaneously from separate addition funnels, solutions of cyclohexanecarbonyl chloride (1.1 g, 0.0073M) in toluene (5 ml) and aqueous 50% sodium hydroxide solution (0.58 g, 0.0073M) while maintaining the temperature below 10° C. Following the addition, the reaction mixture was warmed to room temperature and stirred for 1 hour. The mixture was then diluted with hexane and the solid product isolated by filtration. The product was washed with water and hexane and dried. The crude product was recrystallized from ether-methanol to afford N'-t-butyl-N-benzoyl-N'-cyclohexanecarbonylhydrazine as a white powder: m.p. 202°–204° C.

EXAMPLE 688

Preparation of N'-t-butyl-N-benzoyl-N'-pivaloylhydrazine

To a stirred suspension of t-butylhydrazine hydrochloride (2 g, 0.016M) in toluene (50 ml) at room temperature was added dropwise a 50% aqueous solution of sodium hydroxide (1.28 g, 0.016M). After 15 minutes, the reaction mixture was cooled to 5° C. and a solution of benzoyl chloride (2.3 g, 0.017M) in toluene (5 ml) and a solution of aqueous 50% sodium hydroxide (1.36 g, 0.017M) were added dropwise simultaneously from separate addition funnels while maintaining the temperature at or below 10° C. Following the addition, the reaction mixture was warmed to room temperature and stirred for 1 hour. The reaction mixture was diluted with hexane and the solid N'-t-butyl-N-benzoylhydrazine was isolated by filtration.

To a stirred solution of the monobenzoylated compound (2 g, 0.010M) in pyridine (15 ml) was added pivaloyl chloride (1.8 g, 0.015M) and a catalytic amount of 4-dimethylamino pyridine. The mixture was heated to 60° C. and stirred for approximately 1 hour, cooled and diluted with methylene chloride. The organic layer was washed with 10% HCl (3×25 ml) and water (50 ml), dried over magnesium sulfate and the solvent removed under vacuum. The solid product was recrystallized from methanol-ether to afford N'-t-butyl-N-benzoyl-N'-pivaloylhydrazine in 60% yield as a white solid: m.p. 217°–220° C.

EXAMPLE 689

Preparation of N'-t-butyl-N-benzoyl-N'-phenylacetylhydrazine

To a stirred suspension of t-butylhydrazine hydrochloride (1 g, 0.008M) in toluene (30 ml) at room temperature was added dropwise a 50% aqueous solution of sodium hydroxide (0.64 g, 0.008M). After 15 minutes, the reaction mixture was cooled to 5° C. and a solution of benzoyl chloride (1.12 g, 0.008M) in toluene (5 ml) and a solution of aqueous 50% sodium hydroxide (0.64 g, 0.008M) were added dropwise simultaneously from separate addition funnels while maintaining the temperature at or below 10° C. Following the addition, the reaction mixture was warmed to room temperature and stirred for 1 hour. The reaction was diluted with hexane and the solid N'-t-butyl-N-benzoylhydrazine was isolated by filtration.

To a stirred solution of the monobenzoylated compound (1.5 g, 0.0078M) in toluene (30 ml) at 5° C. were added dropwise and simultaneously from separate addition funnels, solutions of phenylacetyl chloride (1.2 g, 0.008M) in toluene (5 ml) and aqueous 50% sodium hydroxide solution (0.63 g, 0.0078M) while maintaining the temperature below 10° C. Following the addition, the reaction mixture was warmed to room temperature and stirred for 1 hour. The mixture was then diluted with hexane and the solid product isolated by filtration. The product was washed with water and hexane and dried. The crude product was recrystallized from ether-methanol to afford N'-t-butyl-N-benzoyl-N'-phenylacetylhydrazine as a white powder: m.p. 167°–169° C.

EXAMPLE 691

Preparation of N'-t-butyl-N-benzoyl-N'-(beta-trifluoromethylcrotonyl)hydrazine

N'-t-butyl-N-benzoylhydrazine (1.0 g,) in 2 ml toluene was added dropwise to a solution of beta-trifluoromethylcrotonyl chloride (prepared by addition of oxalyl chloride (1.3 g) to a solution of 1.5 g beta-trifluoromethylcrotonic acid in 5 ml toluene at 23° C.). After 30 minutes at 23° C., the reaction mixture was partitioned between saturated aqueous sodium bicarbonate (20 ml) and ether (20 ml). The ether layer was evaporated under reduced pressure to about 10 ml and the excess hydrazine was removed by filtration. The filtrate was evaporated to give N'-t-butyl-N-benzoyl-N'-(beta-trifluoromethylcrotonyl)hydrazine as a colorless oil.

EXAMPLE 699

Preparation of N'-t-butyl-N-benzoyl-N'-methacryloylhydrazine

N'-t-butyl-N-benzoylhdyrazine (0.9 g) suspended in 10 ml toluene and 1 ml H$_2$O containing 0.3 g 50% sodium hydroxide was treated with 1.2 g of methacryloyl chloride at 23° C. After 18 hours, 5 ml of hexane was added and N'-t-butyl-N-benzoyl-N'-methacryloylhydrazine was collected by filtration: m.p. 148°–152° C.

EXAMPLE 702

Preparation of N'-t-butyl-N'-cyclobutanecarbonyl-N-(4-chlorobenzoyl)hydrazine

To a stirred solution of N'-t-butyl-N-(4-chlorobenzoyl)hydrazine (2.0 g, 8.8 mmole) in toluene (35 ml) at 5° C. was added cyclobutanecarboxylic acid chloride (1.25 g, 10.5 mmole) in one portion. To the above mixture was dropwise added 50% NaOH solution (0.85 g, 10.6 mmole). After addition, the ice water bath was removed and the reaction mixture was stirred at room temperature overnight.

The mixture was diluted with hexane (30 ml) and H$_2$O (30 ml) and stirred for another 30 minutes. The solid product was collected by suction-filtration and washed with water (100 ml) and hexane (100 ml) to yield 1.5 g of N'-t-butyl-N'-cyclobutanecarbonyl-N-(4-chlorobenzoyl)hydrazine.

EXAMPLE 722

Preparation of N'-t-butyl-N-benzoyl-N'-isonicotinoylhydrazine

N'-t-butyl-N-benzoylhydrazine (1.0 g, 0.0052 mol) was suspended in 20 ml of toluene. Isonicotinoyl chloride hydrochloride (0.93 g, 0.0052 mol) was added and then a solution of sodium hydroxide (1.25 g of 50% aqueous NaOH) in 5 ml of water was added dropwise. After stirring at 23° C. for 2 hours, the solids were removed by filtration, washed with water and dried in air. The crude product was chromatographed on silica gel using 5% methanol/methylene chloride as eluant to afford pure N'-t-butyl-N-benzoyl-N'-isonicotinoylhydrazine: m.p. >210° C.

EXAMPLE 723

Preparation of N'-t-butyl-N-(2-pyridinecarbonyl)-N'-benzoylhydrazine

A solution of N'-t-butyl-N-(2-pyridinecarbonyl)hydrazine (1.0 g, 0.00518 mol) in 20 ml of toluene at 23° C. was treated sequentially with 50% sodium hydroxide (1.3 g) and benzoyl chloride (0.728 g). The mixture was stirred overnight. The solids were removed by filtration and washed with water to afford N'-t-butyl-N-(2-pyridinecarbonyl)-N'-benzoylhydrazine.

EXAMPLE 724

Preparation of N'-t-butyl-N-benzoyl-N'-nicotinoylhydrazine

A solution of N'-t-butyl-N-benzoylhydrazine (2.0 g) and nicotinoyl chloride hydrochloride in 20 ml of methylene chloride at 23° C. was treated dropwise with triethylamine (4 ml). The reaction mixture was stirred at 23° C. for 0.5 hours. Solids were removed by filtration. The filtrate was diluted with 10N HCl and ether. The layers were separated and the organic layer was washed with 10N HCl. The aqueous layer was neutralized with solid sodium bicarbonate and extracted with ether. The ether extracts were treated with charcoal and then dried with magnesium sulfate. Evaporation of solvents afforded a yellow oil which was chromatographed on silica gel using as eluant a mixture of 10% $CH_3OH$, 40% $CH_2Cl_2$, 50% $Et_2O$ to afford N'-t-butyl-N-benzoyl-N'-nicotinoylhydrazine as a yellow foam: m.p. 60°–63° C.

EXAMPLE 727

Preparation of N'-t-butyl-N-(2-pyridinecarbonyl)-N'-(2-nitrobenzoyl)hydrazine

A solution of N'-t-butyl-N-(2-pyridinecarbonyl)hydrazine (1.0 g, 0.00518 mol) in 20 ml of toluene was treated dropwise simultaneously with a solution of sodium hydroxide (1.24 g of 50% aqueous solution) in 5 ml of water and 2-nitrobenzoyl chloride (0.96 g). The resulting mixture was stirred at 23° C. overnight. Water was added and the mixture was extracted with ether. A second extraction was performed with methylene chloride and the combined organic extracts were dried over magnesium sulfate. Evaporation afforded 0.4 g of N'-t-butyl-N-(2-pyridinecarbonyl)-N'-(2-nitrobenzoyl)hydrazine as a yellow solid: m.p. 137°–140° C.

EXAMPLE 727

Preparation of N'-t-butyl-N-(2-pyridinecarbonyl)-N'-(2-bromobenzoyl)hydrazine

An aqueous solution of sodium hydroxide (1.24 g of 50% NaOH diluted with 5 ml of water) was added to a solution of N'-t-butyl-N-(2-pyridinecarbonyl)hydrazine (1.0 g, 0.00518 mol) in 20 ml of toluene at 23° C. The mixture was cooled and treated with 2-bromobenzoyl chloride (1.137 g, 0.00518 mol). The mixture was then stirred at 23° C. overnight. The solids were removed by filtration, washed with water and dried to afford 0.96 g of N'-t-butyl-N-(2-pyridinecarbonyl)-N'-(2-bromobenzoyl)hydrazine as a white solid: m.p. 179°–180° C.

EXAMPLE 733

Preparation of N'-t-butyl-N-(2-pyridinecarbonyl)-N'-(3,4-dichlorobenzoyl)hydrazine A solution of N'-t-butyl-N-(2-pyridinecarbonyl)hydrazine (0.5 g) in 10 ml of toluene was treated with 50% sodium hydroxide (0.61 g). 3,4-Dichlorobenzoyl chloride (0.6 g) was added and the mixture was stirred rapidly for 4 hours at 23° C. and then was allowed to stand for 48 hours. The solids were removed by filtration and washed with water to afford 0.75 g of N'-t-butyl-N-(2-pyridinecarbonyl)-N'-(3,4-dichlorobenzoyl)hydrazine as a white solid: m.p. 175°–178° C.

EXAMPLE 737

Preparation of N'-t-butyl-N-(5-bromonicotinoyl-N'-(4-chlorobenzoyl)hydrazine

N'-t-butyl-N'-(4-chlorobenzoyl)hydrazine was prepared substantially according to the procedure for preparing N'-t-butyl-N'-benzoylhydrazine described for Example 220, Step 3, except 4-chlorobenzoyl chloride was used in place of benzoyl chloride.

A solution of N'-t-butyl-N'-(4-chlorobenzoyl)hydrazine (0.5 g, 0.0022 mol) and 5-bromonicotinic acid (0.44 g, 0.0022 mol) in 10 ml of methylene chloride containing triethylamine (0.33 g) was added to a solution of methanesulfonyl chloride (0.25 g, 0.0022 mol) in 10 ml of methylene chloride at 0° C. The resulting mixture was stirred at 23° C. for 2 hours and then was allowed to stand overnight at 23° C. Aqueous sodium bicarbonate was added and the layers were separated. The aqueous layer was re-extracted with methylene chloride. The organic extracts were evaporated to give a yellow solid which was triturated with hexane/methylene chloride to afford N'-t-butyl-N-(5-bromonicotinoyl)-N'-(4-chlorobenzoyl)hydrazine as an off-white solid: m.p. 193°–197° C.

EXAMPLE 738

Preparation of N'-t-butyl-N-(pyrazinecarbonyl)-N'-benzoylhydrazine

A mechanically stirred solution of t-butyl-hydrazine hydrochloride (51 g, 0.41 mol) in dioxane (100 ml) and water (50 ml), cooled in an ice bath, was treated with 50% sodium hydroxide (32 g). The resulting mixture was treated dropwise with di-t-butyl-dicarbonate (92 g, 0.42 mol) over about one-half of an hour. After complete addition, the reaction mixture was warmed to room temperature and stirred for 2 hours. The resulting white solid was filtered off, washed with water and air-dried to afford 74 g of N'-t-butyl-N-t-butoxycarbonylhydrazine: m.p. 69°–71° C.

A mechanically stirred solution of N'-t-butyl-N-t-butoxycarbonylhydrazine (61 g, 0.32 mol) in toluene (120 ml) cooled in an ice bath, was treated dropwise and simultaneously with 50% sodium hydroxide (31 g) in water (50 ml) and benzoyl chloride (45 g). The addition was complete in 20 minutes and the resulting mixture was warmed to room temperature and allowed to stir for 1 hour. The resulting white solid was filtered, washed with water and air dried to afford 94 g of N-t-butoxycarbonyl-N'-benzoyl-N'-t-butylhydrazine: m.p. 167°–170° C.

To a mechanically stirred solution of N-t-butoxycarbonyl-N'-benzoyl-N'-t-butylhydrazine (52 g, 0.18 mol) in methanol (100 ml) was added concentrated hydrochloric acid (35 ml). The resulting mixture was stirred at room temperature for 4 days and then neutralized with saturated aqueous sodium bicarbonate. The resulting white solid was filtered, washed with water and dried under vacuum to afford N'-t-butyl-N'-benzoylhydrazine (39 g): m.p. 124°–125° C.

Triethylamine (1.0 g, 0.01 mol) was added to a solution of N'-t-butyl-N'-benzoylhydrazine (0.86 g, 0.0031 mol) and pyrazine carboxylic acid (0.56 g, 0.0045 mol) in 10 ml of methylene chloride at 23° C. This mixture was added to a solution of methanesulfonyl chloride (0.6 g, 0.0052 mol) in 10 ml of methylene chloride at 0° C. The mixture was stirred at 23° C. for 3 hours and then allowed to stand at 23° C. overnight. Aqueous sodium bicarbonate was added and the layers were separated. The organic extracts were evaporated to give crude product which was triturated with ether to afford N'-t-butyl-N-(pyrazinecarbonyl)-N'-benzoylhydrazine as a white solid: m.p. 181°–183° C.

EXAMPLE 739

Preparation of N'-t-butyl-N-isonicotinoyl-N'-benzoylhydrazine

A solution of N'-t-butyl-N'-benzoylhydrazine (0.5 g, 0.00026 mol) in 10 ml of toluene was treated with 50% sodium hydroxide (0.6 g) followed by isonicotinyl chloride hydrochloride (0.47 g, 0.0026 mol). The mixture was stirred at 23° C. overnight. The solids were removed by filtration and washed with water followed by ether to afford N'-t-butyl-N-isonicotinyl-N'-benzoylhydrazine.

EXAMPLE 743

Preparation of N'-t-butyl-N-(2-pyridinecarbonyl)-N'-(4-fluorobenzoyl)hydrazine

By substantially following the procedures described above for Example 2, except using 4-fluorobenzoyl chloride rather than benzoyl chloride, N'-t-butyl-N-(2-pyridinecarbonyl)-N'-(4-fluorobenzoyl)hydrazine was afforded.

EXAMPLES 754 AND 755

Preparation of N'-t-butyl-N'-(2-pyridinecarbonyl)-N-benzoylhydrazine

To a suspension of 2-picolinic acid (12.8 g, 0.104 mol) in methylene chloride (80 ml) were added dropwise triethylamine (14 g, 0.139 mol) in 10 ml methylene chloride followed by methanesulfonyl chloride (13 g, 0.113 mol) in 10 ml methylene chloride at 0° C. The resulting mixture was stirred for one-half of an hour before the dropwise addition of N'-t-butyl-N-benzoylhydrazine (20.0 g, 0.10 mol) in 80 ml methylene chloride at 0° C. to 23° C. The final dark brown mixture was allowed to stir at 23° C. for one hour, and to stand at 23° C. overnight.

Aqueous sodium bicarbonate was added and the layers were separated. The aqueous layer was re-extracted with methylene chloride. The organic extracts were combined and dried over magnesium sulfate. Evaporation under reduced pressure gave 25 g of a light green, brown solid. Recrystalization on a steam bath with ethyl acetate:hexane (80:20 v/v) afforded a light yellow solid.

Column chromatography on silica gel, eluted first with methylene chloride and ether and then with ethyl acetate afforded two separate isomers of N'-t-butyl-N'-(2-pyridinecarbonyl)-N-benzoylhydrazine.

EXAMPLE 764

Preparation of N'-t-butyl-N-benzoyl-N'-(2-furoyl)hydrazine

N'-t-butyl-N-benzoylhydrazine (1 g) was dissolved in 20 ml toluene. Water (5 ml) and 50% aqueous sodium hydroxide (1.25 g) was added followed by 2-furoylchloride (0.68 g). After stirring for 7 hours at room temperature, 0.3 g 2-furoylchloride was added and the mixture stirred for a further 6 hours. The solid product, N'-t-butyl-N-benzoyl-N'-(2-furoyl)hydrazine, was removed by filtration and washed with water: m.p. 155°–175° C.

EXAMPLE 765

Preparation of N'-t-butyl-N-benzoyl-N'-(2 2-thiophenecarbonyl)hydrazine

N'-t-butyl-N-benzoylhydrazine (1.0 g) was dissolved in 20 ml toluene. 50% aqueous sodium hydroxide (1.25 g) was added followed by 2-thiophenecarbonylchloride (0.76 g). The mixture was stirred at room temperature for 14 hours. The solid product, N'-t-butyl-N-benzoyl-N'-(2-thiophenecarbonyl)hydrazine, was removed by filtration and washed with water: m.p. >200° C.

EXAMPLE 766

Preparation of N'-t-butyl-N-(2-thiophenecarbonyl)-N'-benzoylhydrazine

N'-t-butyl-N-(2-thiophenecarbonyl)hydrazine (1 g) was dissolved in 10 ml toluene and treated with 50% aqueous sodium hydroxide (1.0 g) and water (2 ml) followed by benzoylchloride (0.8 g). After stirring for 14 hours at room temperature, the solid product, N'-t-butyl-N-(2-thiophenecarbonyl)-N'-benzoylhydrazine, was removed by filtration and washed with water: m.p. >190° C.

EXAMPLE 767

Preparation of N'-t-butyl-N-(2-furoyl)-N'-benzoylhydrazine

N'-t-butyl-N-(2-furoyl)hydrazine (1.0 g) was dissolved in 10 ml toluene and 2 ml water. 50% aqueous sodium hydroxide (1.0 g) was added followed by benzoylchloride (0.8 g). After stirring for 14 hours at room temperature, the solid product, N'-t-butyl-N-(2-furoyl)-N'-benzoylhydrazine, was removed by filtration and washed with water: m.p. 160°–162° C.

EXAMPLE 772

Preparation of N'-t-butyl-N-(4-methylbenzoyl)-N'-(2,5-dichlorothiophene-3-carbonyl)hydrazine N'-t-butyl-N-4-methylbenzoylhydrazine (0.7 g) was dissolved in 35 ml toluene. Water (5 ml) and 50% aqueous sodium hydroxide (0.8 g) were added followed by 2,5-dichlorothiophene-3-carbonylchloride (2.0 g). After stirring for 3 hours at room temperature, ether was added and the organic layer separated. Evaporation afforded a solid which was triturated with 10% ether-hexane to afford N'-t-butyl-N-(4-methylbenzoyl)-N'-(2,5-dichlorothiophene-3-carbonyl)hydrazine: m.p. 163°–165° C.

EXAMPLE 778

Preparation of N'-t-butyl-N-(N-methyl-2-pyrrolecarbonyl)-N'-benzoylhydrazine

N'-t-butyl-N-(N-methyl-2-carbonylpyrrole)hydrazine (0.8 g) was dissolved in 10 ml toluene and 1 ml water. 50% aqueous sodium hydroxide (10 drops) was added followed by benzoylchloride (1.2 g). After 14 hours stirring at room temperature, ether was added and the product, N'-t-butyl-N-(N-methyl-2-pyrrolecarbonyl)-N'-benzoylhydrazine, was isolated by filtration and washed with ether: m.p. 182°–185° C.

EXAMPLE 787

Preparation of N'-t-butyl-N-(1,2,3-triazole-4-carbonyl)-N'-(3-methylbenzoyl)hydrazine 1,2,3-triazole-4-carboxylic acid (1.0 g) and triethylamine (0.9 g) were dissolved in 40 ml methylene chloride and cooled in an ice bath. Methanesulfonylchloride (1.0 g) was added dropwise. After addition was complete, the reaction mixture was stirred for 0.5 hours. N'-t-butyl-N'-(3-methylbenzoyl)hydrazine (1.84 g) in 10 ml CH$_2$Cl$_2$ was added dropwise. The resulting mixture was allowed to stand for 14 hours. Aqueous sodium bicarbonate was added. The organic layer was dried over anhydrous magnesium sulfate, filtered and evaporated to give a yellow oil. Chromatography on silica gel using acetone as eluant afforded N'-t-butyl-N-1,2,3-triazole-4-carbonyl-N'-(3-methylbenzoyl)hydrazine.

EXAMPLE NO. 802

Preparation of N'-(1-cyano-1-methyl)ethyl-N,N'-dibenzoylhydrazine

To a suspension of benzoylhydrazine (13.6 g, 0.1 mol) in deionized water (50 ml) at 5° C. with stirring was dropwise added concentrated hydrogen chloride (9.8 g, 0.1 mol). To the resulting clear solution was added sodium cyanide (5.2 g, 0.1 mol) and acetone (6.5 g, 0.11 mol). A white and thick precipitate appeared. The cooling bath was removed and the reaction flask was stoppered tightly. The reaction mixture was stirred for 18 hours. The precipitate was collected by suction-filtration and was washed with a small amount of water to give 17.5 g (86.2% yielded) of the desired intermediate, N'-(1-cyano-1-methyl)ethyl-N-benzoic acid hydrazide, as the starting material for the next step: m.p. 82°-92° C.

To the solution of N'-(1-cyano-1-methyl)ethyl-N-benzoic acid hydrazide (2 g, 0.01 mol) in dry methylene chloride (25 ml) under nitrogen at room temperature with stirring was added benzoyl chloride (2.02 g, 0.014 mol). To the above mixture was dropwise added triethylamine (1.31 g, 0.013 mol). The reaction mixture was stirred at room temperature for 5 hours. The reaction mixture was diluted with methylene chloride (50 ml) and washed with water and brine. The organic layer was dried over MgSO$_4$ and the solvent was evaporated at reduced pressure to give a residue. The residue was treated with ethyl acetate/hexane mixture (1:1) affording a crude solid product which was collected by suction-filtration (1 g, 33% yield). An analytical sample was obtained by crystallization from ethyl acetate/hexane (4:1): m.p. 202°-204° C. NMR and IR spectra showed the desired product.

EXAMPLE NO. 809

Preparation of N'-(1-cyano-1-methyl)ethyl-N,N'-di-4-toluoylhydrazine

To the suspension of 4-toluic acid hydrazide (15 g, 0.1 mol) in water (150 ml) and ethanol (20 ml) at 5° C. with stirring was dropwise added concentrated hydrogen chloride (10 g, 0.1 mol). To the above suspension was carefully added sodium cyanide (5.3 g, 0.1 mol) and acetone (6.6 g, 0.11 mol). The reaction flask was stoppered tightly and the cooling bath was removed. The resulting viscous reaction mixture was stirred at room temperature for more than 24 hours. The precipitate was collected by suction-filtration and was washed with a small amount of diluted hydrogen chloride and water affording 14.6 g. (64.8%) of N'-(1-cyano-1-methyl)ethyl-4-toluic acid hydrazide as the starting material for the next step. Analytical sample was obtained by crystallization from ethyl acetate/hexane (3:1): m.p. 146°-148° C.

To the solution of N'-(1-cyano-1-methyl)ethyl-4-toluic acid hydrazide (2.17 g, 0.01 mol) in dry methylene chloride (65 ml) under nitrogen with magnetic stirring was added 4-dimethylaminopyridine catalyst (1.34 g, 0.011 mol) followed by 4-methylbenzoyl chloride (2.52 g, 0.017 mol). To the above mixture was dropwise added triethylamine (1.1 g, 0.011 mol). The reaction mixture was slightly exothermic. After stirring at room temperature for 40 minutes, the reaction mixture was diluted with methylene chloride (50 ml), washed with diluted HCl solution (2×50 ml), dil NaOH (50 ml), H$_2$O (50 ml) and brine. The organic layer was dried over MgSO$_4$, and the solvent was evaporated under reduced pressure to give a residue. The residue was treated with ethyl acetate/hexane mixture (1:1) and the resulting solid was collected by suction-filtration and affording 2.75 g (82% yield) of almost pure product: m.p. 192°-198° C. NMR and IR spectra showed the desired product.

EXAMPLE NO. 822

Preparation of N'-(1,1-dimethyl-3-butenyl)-N,N'-dibenzoylhydrazine

To a gently refluxing solution of allyl magnesium bromide (380 ml of 1M solution) was added acetone azine (20 g) dissolved in diethyl ether (200 ml). The solution was refluxed for 3 days. Upon cooling, a saturated solution of ammonium chloride (50 ml) was added. The aqueous layer was separated and washed twice with diethyl ether (200 ml). The combined ether extracts were dried over anhydrous magnesium sulfate, filtered and the ether removed at reduced pressure. The product was distilled through a vigreux column at 3.1 torr and collected in a dry ice/acetone cooled receiving flask. The boiling point was 60°-65° C. 15 g of product was collected.

Oxalic acid (16.7 g) was dissolved in a solution of ethanol:diethyl ether (1:1) (150 ml) and water (3.3 g) was added. To this acid solution was added the hydrazone (13 g) dissolved in diethyl ether (75 ml). The solution was stirred for 24 hours then filtered. The solid is washed once with diethyl ether. The filtrate was concentrated and combined with the solid to afford a 71% yield (17.2 g) of the hydrazine oxalate.

The 1,1-dimethyl-3-butenylhydrazine oxalate (2 g) was dissolved in toluene and neutralized with 50% aqueous sodium hydroxide. To this solution was added benzoyl chloride (2.8 g) and sodium hydroxide (50% Aq. solution) (3.2 g) at 25° C. The reaction mixture was warmed to room temperature and stirred. The mixture was diluted with hexane and filtered to afford an oily product which solidified upon standing: m.p. 105°-112° C.

EXAMPLE NO. 829

Preparation of N'-t-butyl-N-benzoyl-N'-benzylhydrazine

Benzyl bromide (0.9 g), 1-benzoyl-2-t-butyl hydrazine (1 g) and triethylamine (0.52 g) were warmed in dimethylformamide (50 ml) at 50° C. for 2 hours. The reaction mixture was cooled to room temperature, diluted with diethylether (100 ml) and washed three times with 25 ml of water. The organic layer was dried over magnesium sulfate, filtered and the solvent removed in vacuo to afford the product as a white solid. The product was chromatographed on silica gel (G:70 to 230 mesh) using methylene chloride as eluant to afford a 75% yield of a white solid: m.p. 147-149.

EXAMPLE NO. 837

Preparation N'-t-butyl-N-furoyl-N'-benzylhydrazine

Benzyl bromide (1.8 g), 1-furoyl-2-t-butyl hydrazine (2 g) and excess powdered potassium carbonate were stirred in dimethylformamide (50 ml) at 50° C. for 2 hours. The reaction mixture was cooled to room temperature, diluted with diethyl ether and washed several times with water. The organic layer was dried over magnesium sulfate, filtered and the solvent removed in vacuo. The white solid product was chromatographed on silica gel (G:70–230 mesh) using methylene chloride as eluant to afford the product in good yield: m.p. 152–153.

EXAMPLE NO. 853

Preparation of N'-t-butyl-N-benzoyl-N'-methylpyridinylhydrazine

N'-t-butyl-N-benzoyl hydrazine (1.2 g), 2-chloromethyl pyridine (1.0 g) and triethylamine (2 equivalents) were stirred in dimethyl sulfoxide (15 ml) at room temperature for 2 hours. The reaction mixture was then warmed to 50° C. for 2 hours. The mixture was diluted with ether and washed with water. The organic layer was dried over magnesium sulfate, filtered and rotavapped to afford a yellow oil. The oil was chromatographed on silica gel (G:70–230 mesh) using a methylene chloride-ether mixture (1:1) as eluant to afford the purified product as a yellow gum in approximately 20% yield.

EXAMPLE NO. 855

Preparation of N'-t-butyl-N-benzyl-N'-benzoylhydrazine

N'-t-butyl-N'-benzoyl benzaldehyde hydrazone (1.8 g) and sodium cyanoborohydride (1.5 equivalents) were stirred in dry methanol (30 ml) at room temperature. Ten percent HCl was added to bring the pH of the reaction mixture to pH 3–4 and stirred at room temperature for 1 hour. The methanol was removed in vacuo and the residue was dissolved in methylene chloride. The methylene chloride layer was washed with saturated aqueous sodium bicarbonate and then with water. The organic layer was dried over magnesium sulfate, filtered and the solvent removed in vacuo to afford in good yield a white solid: m.p. 110–115.

EXAMPLE NO. 864

Preparation of N'-t-butyl-N'-benzoylbenzaldehyde hydrazone

Benzaldehyde (10.6 g), t-butylhydrazine, hydrochloride (12.4 g) and triethylamine (10.1 g) were stirred in toluene (150 ml) at room temperature. The reaction mixture was washed with water and dried over magnesium sulfate. The mixture was filtered and the solvent was removed in vacuo to afford N'-t-butyl benzaldehyde hydrazone as a yellow oil in good yield.

The N'-t-butyl benzaldehyde hydrazone (1.76 g) and benzoyl chloride (1.4 g) were stirred in a pyridine-methylene chloride solvent system (1:1, 50 ml), diluted with methylene chloride and washed several times with 10% HCl. The organic layer was dried over magnesium sulfate, filtered and the solvent removed in vacuo to afford a low melting solid in good yield: m.p. 69°–72° C.

EXAMPLE NO. 870

Preparation of N-benzoyl-N'-t-butyl-N'-phenylethylhydrazine

N'-t-butyl-N-benzoylhydrazine (2.2 g), powdered potassium carbonate (5 g) and beta-phenethyl bromide (1.8 g) were stirred in dimethylformamide (15 ml) at 60° for 18 hours. The reaction mixture was cooled and diluted with ether and water. The white solid product was filtered off and recrystallized from ether/hexane to afford 0.3 g of product: m.p. 150°–152° C.

EXAMPLE NO. 871

Preparation of N-benzoyl-N'-t-butyl-N'-(ethoxycarbonyl)methylhydrazine

N'-t-butyl-N-benzoylhydrazine (2.0 g), powdered potassium carbonate (5 g) and bromoethyl acetate (1.6 g) were stirred in dimethylformamide (20 ml) at 60° C. for 14 hours. The reaction mixture was diluted with water and ether, and the organic layer was separated. The organic layer was washed several times with water, dried over magnesium sulfate and rotavapped to afford an oil. Chromatographic purification gave the pure oil product (0.25 g).

EXAMPLE NO. 872

Preparation of N'-t-butyl-N'-benzoyl-N-[N-(4-tolyl)aminocarbonyl]hydrazine

N't-butyl-N'-benzoylhydrazine (0.8 g) and p-methylphenylisocyanate (0.9 g) were stirred in diethylether (10 ml) at 23° C. for 15 hours. The reaction mixture was diluted with ether and filtered to afford 0.5 g of solid product: m.p. 208°–210° C.

EXAMPLE NO. 873

Preparation of N'-t-butyl-N'-benzoylcarbonyl-N-benzoylhydrazine

N'-t-butyl-N'-benzoylhydrazine (1 g), benzoyl formic acid (0.7 g) and methanesulfonyl chloride (0.7 g) were stirred in toluene (30 ml) and saturated sodium bicarbonate (10 ml) at approximately 5° C. Triethylamine was added slowly, dropwise to the reaction mixture and stirred 1 hour at room temperature. After stirring for 1 hour, the reaction mixture was diluted with toluene (25 ml) and washed with water several times. The organic layers were dried over magnesium sulfate, filtered and the toluene rotavapped off to afford a white solid. After column chromatography, the product was obtained as a white solid in approximately 70% yield.

EXAMPLE NO. 878

Preparation of N'-t-butyl-N-benzoylcarbonyl-N'-benzoylhydrazine

N'-t-butyl-N-benzoylhydrazine (1 g), benzoyl formic acid (1 g) and methanesulfonyl chloride (0.7 g) were stirred in toluene (35 ml) and saturated sodium bicarbonate (15 ml) at approximately 5° C. Triethylamine was added slowly, dropwise to the reaction mixture, and slowly warmed to room temperature. After stirring for 1 hour, the reaction mixture was diluted with toluene (20 ml) and the organic layer was washed several times with water. The organic layers were dried over magnesium sulfate, filtered and the toluene rotavapped off to afford a white gum. The crude product was chromatographed on silica gel (G:230–400 mesh) using a methylene chloride ether solvent system as eluant to afford a 65% yield of a white solid.

EXAMPLE NO. 880

Preparation of N'-t-butyl-N-(1,2,3,4-tetrahydronaphtyl-2-carbonyl)-N'-(3-toluoyl)hydrazine To a stirred suspension of N'-t-butyl-N'-(3-toluoyl)-hydrazine (1.2 g) in toluene (10 ml) and aqueous sodium hydroxide (3 ml of 50% solution) was added 1,2,3,4-tetrahydronaphthyl-2-carbonyl chloride (0.007 mol). After stirring 1 hour, hexane and ether were added and the solids filtered off and dried by vacuum oven at 45° C.

EXAMPLE NO. 882

Preparation of N'-t-butyl-N-benzoyl-N'-(alpha-chlorophenylacetylhydrazine)

N'-t-butyl-N-benzoylhydrazine (10 g) was stirred in toluene (100 ml) and saturated sodium bicarbonate (50 ml) at approximately 5°-10° C. Alpha-chlorophenylacetylchloride (9.8 g) in toluene (20 ml) was added slowly, dropwise to the cooled reaction mixture, warmed to room temperature and stirred several hours. Hexane (100 ml) was added to the reaction mixture and the solid product was filtered. The filter cake was washed several times with hexane and then water. The product was air dried to afford a 92% yield.

EXAMPLE NO. 883

Preparation of N'-t-butyl-N-benzoyl-N'-phenylacetylhydrazine

N'-t-butyl-N-benzoylhydrazine (2 g) was stirred in toluene (35 ml) and 50% aqueous sodium hydroxide (1 g) at 5° C. Phenylacetylchloride (1.5 g) was added slowly, dropwise to the reaction mixture, warmed to room temperature and stirred 1 hour. The reaction mixture was diluted with hexane (50 ml) and filtered off to yield a solid product. The filter cake was washed with hexane and water and allowed to air dry. The white solid product obtained in 90% yield melted at 167°-169° C.

EXAMPLE NO. 893

Preparation of N'-t-butyl-N'-benzoylalpha-furoyloxybenzaldehyde hydrazone

N'-benzoyl-N'-t-butyl hydrazine (1.5 g) was stirred in a two-phase solvent system consisting of toluene (20 ml) and 50% aqueous sodium hydroxide (10 ml). First, a phase transfer catalyst, (n-Bu)$_4$N+-I (25-50 mg) was added and then 2-furoyl chloride was added dropwise. After the addition, the suspended white solid hydrazine went slowly into solution as it reacted to form the acylated product. After stirring at room temperature for 1 hour, the reaction mixture was diluted with 35 ml water and 30 ml of ethyl acetate. The layers were separated and the organic layer was washed several times with water, dried over magnesium sulfate, filtered and concentrated in vacuo to afford the product as a clear oil. The product was chromatographed on silica gel (G:230-400 mesh) using methylene chloride as the eluting solvent affording a clear, colorless oil (85% yield).

EXAMPLE NO. 905

Preparation of N'-t-butyl-N'-2,4-dichlorobenzoyl-alpha-methoxy-2,3-dimethylbenzaldehyde hydrazone To a stirred solution of N'-t-butyl-N-(2,3-dimethylbenzoyl)hydrazine (4.2 g) and triphenylphosphine (5.5 g) in dry acetonitrile (60 ml) at room temperature under nitrogen was dropwise added carbon tetrachloride (3.5 g). The reaction mixture was stirred overnight at room temperature. The acetonitrile was removed in vacuo and the crude reaction mixture was chromatographed on silica gel (6, 230-400 mesh) using hexane/ethyl acetate (3:1) to afford the corresponding hydrazinoyl chloride as a yellow oil.

To a stirred suspension of powdered potassium carbonate (2 g) in methanol (75 ml) was added dropwise a solution of the above hydrazinoyl chloride (2.2 g) in methanol (40 ml). The reaction mixture was stirred overnight at room temperature, concentrated in vacuo and the carbonate was filtered off. The filtrate was rotavapped to afford methoxyhydrazine as a white solid (1.9 g).

To a stirred solution of the methoxyhydrazine (1.5 g) in toluene (25 ml) and 50% sodium hydroxide (2 g diluted with 8 g of water) was added 2,4-dichlorobenzoyl chloride (2.5 g) dropwise while the reaction mixture was kept at approximately 0° C. After warming to room temperature, the reaction mixture was diluted with ether and the layers separated. The organic layer was washed twice with water, once with saturated sodium chloride solution and dried over sodium sulfate. Concentration of the reaction gave a product which was chromatographed on silica gel (6, 230-400 mesh) using a hexane/ethyl acetate (4:1) solvent system.

EXAMPLE NO. 914

Preparation of N'-t-butyl-N-benzenesulfonyl-N'-benzoylhydrazine

N'-t-butyl-N'-benzoylhydrazine (0.4 g) was stirred in pyridine (3 ml) at room temperature. Benzenesulfonyl chloride (0.5 g) was added slowly, dropwise and stirred for 2 hours, diluted with diethyl ether (20 ml) and washed several times with a 10% HCl solution and then water. The organic layer was dried over magnesium sulfate, filtered and the solvent rotavapped off to afford a white solid in good yield.

EXAMPLE NO. 918

Preparation of N'-t-butyl-N-benzoyl-N'-benzenesulfonylhydrazine

N-benzoyl-N'-t-butyl hydrazine (0.8 g) was stirred in pyridine (2 ml) at room temperature. Benzenesulfonyl chloride (0.8 g) was added slowly dropwise, stirred about 1 hour, diluted with diethyl ether (10 ml) and washed several times with a 10% HCl solution and then water. The organic layer was dried over magnesium sulfate. The mixture was filtered and the solvent rotavapped off to afford a white solid in good yield.

EXAMPLE NO. 922

Preparation of N'-t-butyl-N'-[methyl-(2-chlorophenylamino)phosphinyl]-N-benzoylhydrazine Methyl dichlorophosphine (1.3 g) in ether (10 ml) and triethylamine (2 ml) were added to a stirred solution of N-benzoyl-N'-t-butyl hydrazine (1.0 g) in methylene chloride (3 ml). After stirring 5 minutes at room temperature, o-chloroaniline was added neat producing a mild exotherm. The reaction was quenched 2 minutes later with water (20 ml) and ether (20 ml), separated and the organic washed with 0.1N HCl, dried over MgSO$_4$, filtered and rotavapped to a colorless oil weighing 0.5 g.

EXAMPLE NO. 923

Preparation of N'-t-butyl-N-methylphenylphosphinyl-N'-benzoylhydrazine

Triethylamine (7 ml) and t-butyl hydrazine .HCl (4 g) were stirred in methylene chloride (20 ml) at about 0° C. To this was added, slowly, methylphenylphosphinyl chloride (0.03 mol). The mixture was stirred at 0° C. for 15 minutes and quenched with a sodium bicarbonate solution. The reaction mixture was extracted with diethyl ether, washed with water and dried over magnesium sulfate. After filtering the drying agent, the solvent was removed in vacuo to afford an oily product which was used directly in the subsequent step.

N'-t-butyl-N-(methylphenyl)phosphinylhydrazine (0.7 g) and triethylamine (3 ml) were stirred in diethyl ether (30 ml) at room temperature. Slowly, benzoyl chloride (1.2 g) was added dropwise to the reaction mixture. After stirring 1 hour at room temperature, the reaction mixture was diluted with hexane and the solid product filtered off. The white solid melted at 175°–178° C.

EXAMPLE NO. 933

Preparation of N'-t-butyl-N-(2-phenyl-3-methylpentanoyl)-N'-(3-toluoyl)hydrazine To a stirred suspension of N'-t-butyl-N'-(3-toluoyl)-hydrazine (0.7 g) in toluene (10 ml) and aqueous sodium hydroxide (12 drops of 50% aqueous sodium hydroxide) was added dropwise 2-phenyl-3-methyl-pentanoyl chloride (1.0 g). The reaction mixture was stirred overnight, diluted with hexanes and the solids filtered. The solids were washed with hexane and air dried.

EXAMPLE NO. 941

Preparation of N'-t-butyl-N-phenylpropiolyl-N'-(3-hydrazine

To a stirred solution of N'-(3-toluoyl)-N'-t-butyl hydrazine (1.0 g) in toluene (15 ml) and aqueous sodium hydroxide was added phenylpropiolyl chloride (0.01 mol) dropwise at room temperature. After stirring the reaction mixture for 3 hours, hexane and ether were added and the solids filtered. The solids were vacuum dried at 60° C.

EXAMPLE NO. 942

Preparation of N'-t-butyl-N-(2,3-dimethylbenzoyl)-N'-phenylpropiolylhydrazine

To a stirred solution of N-(2,3-dimethylbenzoyl)-N'-t-butyl hydrazine (1.0 g) in toluene (15 ml) and aqueous sodium hydroxide was added phenylpropiolyl chloride (0.006 mol) dropwise. After stirring 15 minutes at room temperature, ether and hexane were added and the solid product was filtered off.

EXAMPLE NO. 944

Preparation of N'-t-butyl-N-(3,4-epoxy-cyclohexane carbonyl)-N'-(3-toluoyl)hydrazine To a stirred solution of N'-t-butyl-N'-(3-toluoyl)hydrazine (20 g) in toluene (150 ml) and aqueous sodium hydroxide at 10° C. was added 3-cyclohexenecarbonyl chloride (14.3 g) dropwise at a rate which maintained the temperature at or below 10° C. After stirring at room temperature for 2 hours, hexane was added and the solids filtered. The filler cake was washed with hexane and water and dried overnight.

A mixture of N-(3-cyclohexenecarbonyl)-N'-t-butyl-N'-(3-toluoyl)hydrazine (2 g) and m-chloroperbenzoic acid (1.1 mol equivalents of 80% material) was stirred in methylene chloride (50 ml) overnight. The reaction mixture was diluted with methylene chloride (50 ml) and washed with saturated aqueous sodium bicarbonate solution (3×25 ml), dried over magnesium sulfate, filtered and rotavapped to afford the white solid epoxide in 78% overall yield.

EXAMPLE NO. 948

Preparation of N'-t-butyl-N-pyrenonecarbonyl-N'-(3-toluoyl)hydrazine

To a stirred suspension of t-butyl hydrazine hydrochloride (0.02 mol) in toluene (20 ml) and aqueous hydroxide (5 ml of 50% solution) at room temperature was added pyrenonecarbonyl chloride (0.01 mol). After stirring the reaction mixture for 20 minutes, ether and hexane were added and the solid product was filtered and washed with water. The solid product (0.5 g) was stirred in toluene (10 ml) and aqueous sodium hydroxide and m-toluoyl chloride (0.8 g) was added dropwise. After stirring for 5 hours, hexane and ether were added and the solid product filtered and air dried.

EXAMPLE NO. 1002

Preparation of 1-t-butyl-1-(3-toluoyl)-4-(4-chlorobenzenesulfonyl)semicarbazide

To a solution of N'-t-butyl-N'-3-toluoyl hydrazine (4.03 g, 0.02 mol) in methylene chloride (25 ml) under nitrogen was added 4-chlorobenzenesulfonyl isocyanate (5 g, 80%, 0.02 mol) at room temperature. The exothermic reaction mixture was stirred at room temperature for 30 minutes. The solvent was evaporated under reduced pressure to give an oil. A precipitate appeared after treating with ether. The pure product was collected by suction-filtration and washed with a small amount of ether affording 4.8 g of 1-t-butyl-1-(3-toluoyl)-4-(4-chlorobenzenesulfonyl)semicarbazide as a white solid: m.p. 184°–188° C.

EXAMPLE NO. 1008

Preparation of N'-(1-methyl-1-carbamyl)ethyl-N'-3-toluoyl-N-4-chlorobenzoyl hydrazine To a concentrated hydrochloric acid (10 ml) at 0°–5° C. was added N'-(1-methyl-1-cyano)ethyl-N'-3-toluoyl-N-4-chlorobenzoyl hydrazine (0.8 g, 2.25 mmol) in one portion with stirring. After stirring for 40 minutes at a temperature below 20° C., the reaction mixture was diluted with water (50 ml) and hexane (50 ml). The resultant suspension was suction-filtered to give the product, N'-(1-methyl-1-carbamyl)ethyl-N'-3-toluoyl-N-4-chlorobenzoyl hydrazine, as a white solid: m.p. 213°–218° C. Yield is 0.5 g (59%).

EXAMPLE NO. 1013

Preparation of N'-t-butyl-N'-3-toluoyl-mucochloric acid hydrazone

To a solution of N'-t-butyl-N'-3-toluoylhydrazine (1.03 g, 5 mmol) in 80% methanol (25 ml) was added mucochloric acid (0.85 g, 5 mmole). The reaction mixture was held at room temperature for 2 hours with occasional shaking. The resultant viscous suspension was suction-filtered and washed with water. After airdrying overnight, the product, N'-t-butyl-3-toluoyl mucochloric acid hydrazone, weighed 1.50 g: m.p. 167°–168° C.

EXAMPLE NO. 1015

Preparation of N'-t-butyl-N'-3-toluoyl-ethylpyruvate hydrazone

To a solution of N'-t-butyl-N'-3-toluoyl hydrazine (2.06 g, 10 mmole) in methylene chloride (20 ml) and water (20 ml) at room temperature with stirring was added ethylpyruvate (2.4 g, 21 mmol). The reaction mixture was stirred at room temperature for 16 hours. The reaction mixture turned to two phases. The aqueous phase was extracted with methylene chloride (2×50 ml), and the extracts were combined with the organic phase. The combined organic solution was washed with water and brine, dried over magnesium sulfate, filtered and evaporated to give a liquid product. The product was further dried in vacuum to give 1.9 g of N'-t-butyl-N'-3-toluoyl ethylpyruvate hydrazone as an oil.

EXAMPLE NO. 1016

Preparation of N'-t-butyl-N'-3-toluoyl-acetone hydrazone

To a solution of t-butyl acetone hydrazone (5 g, 39 mmole) in methylene chloride (50 ml) at 0° C. under nitrogen was added 3-toluoyl chloride (6.1 g, 39 mmole), followed by slowly adding triethylamine (3.94 g, 39 mmole). After the addition the reaction mixture was stirred at between 0°–5° C. for one hour. The reaction mixture was diluted with methylene chloride (100 ml) and washed subsequently with water, dilute HCl, water and brine. The organic layer was dried over MgSO₄ and filtered. The solvent was evaporated under a reduced pressure to give a light brown liquid. The desired product, N'-t-butyl-N'-3-toluoyl acetone hydrazone, was obtained (2.45 g) by a vacuum distillation: b.p. 96°–104° C. at 0.05 mm Hg.

EXAMPLE NO. 1017

Preparation of N'-t-butyl-N'-3-toluoyl-N-isopropylhydrazine

To a solution of N'-t-butyl-N'-3-toluoyl acetone hydrazone (1.5 g, 6.08 mmole) in methanol (50 ml) at room temperature with stirring was added, in small portions, sodium borocyanohydride (0.5 g, 8 mmole). To the above reaction mixture was added 10% HCl (5 ml) and the mixture was stirred for 10 minutes. A white precipitate appeared. To this was added water (50 ml) and dilute NaOH until the solution turned basic. The resultant white solid was collected by suction-filtration and washed with water. The product was further dried in vacuum to give 0.9 g (60%) of N'-t-butyl-N'-3-toluoyl-N-isopropylhydrazine as a fluffy white powder: m.p. 107°–109° C.

EXAMPLE NO. 1018

Preparation of N'-t-butyl-N'-benzoyl-N-(1-cyano-1-methyl)ethylhydrazine

To a suspension of N'-t-butyl-N'-benzoylhydrazine (1.92 g, 10 mmole) in water (30 ml) at 0°–5° C. was added concentrated HCL (1 g, 10 mmole), followed by NaCN (0.52 g, 10.6 mmole) and acetone (0.75 g, 12.9 mmole). After the addition, the reaction flask was stoppered tightly and the reaction mixture was stirred at room temperature for 16 hours. The resultant suspension was suction-filtered and washed with water. The product, N'-t-butyl-N'-benzoyl-N-(1-cyano-1-methyl)ethylhydrazine, was further dried in vacuum to give 2.1 g as white powder: m.p. 117°–120° C.

By following substantially the procedures in Examples 1 and 3 and using the appropriately substituted reactants, the products of Example Nos. 2, 4 through 12, 14, 19, 20, 32, 37, 55, 98 through 101, 145, 169, 174, 181, 234, 250, 260, 264, 289, 295, 298, 308, 364, 390, 391, 394, 449, 613, 632, 924 through 928, 937, 938, 939, 943, 949, 950, 951, 954, 959, 961, 963, 964, 965, 967, 968, 990 and 996 were prepared.

By following substantially the procedures in Example 16 and using the appropriately substituted reactants, the products of Example Nos. 13, 15, 17, 18, 21, through 31, 33 through 36, 38, 40 through 43, 45, 47 through 54, 56, 57 through 62, 64 through 97, 104 through 109, 113, 117, 118, 119, 121, 122, 123, 125, 126, 130 through 135, 137 through 142, 146, 147, 150, 152 through 154, 160, 163, 167, 173, 175 through 180, 182, 183, 184, 190, 194 through 202, 204 through 211, 214 through 219, 224 through 231, 235 through 249, 251 through 259, 261 through 263, 265 through 270, 272 through 284, 287, 288, 290 through 292, 296, 297, 299 through 307, 309 through 322, 325, 327, 328, 334, 341 through 343, 346 through 348, 355 through 357, 370, 371, 377, 378, 380, 381, 387 through 389, 392, 393, 395, 396, 401 through 413, 419, 420, 422 through 424, 426 through 433, 437 through 448, 450 through 452, 454 through 457, 459 through 469, 474 through 483, 485 through 540, 542 through 545, 548 through 612, 615 through 624, 626 through 631, 633, 929 through 932, 934, 935, 936, 940, 946, 947, 952, 953, 962, 966, 993, 994, 995, 997 and 998 were prepared.

By following substantially the procedures in Example 44 and using the appropriately substituted reactants, the products of Example Nos. 39, 46, 63, 110, 111, 112, 114, 115, 116, 120, 124, 127, 128, 129, 136, 143, 155 through 158, 185 through 189, 332, 336 through 340, 382, 383, 384, 399 400, 414 through 418, 421, 434, 435, 436, 453, 470, 471, 472, 546, 547, 634 and 955 through 960 were prepared.

By following substantially the procedures in Example 220 and using the appropriately substituted reactants, the products of Examples 168, 170, 171, 172, 191, 192, 193, 212, 213, 221 through 223, 232, 233, 293, 326, 331, 379, 397, 398, 425 and 458 were prepared.

By following substantially the procedures in Example 324 but using the appropriately substituted reactants, the compounds of Examples 323 and 979 to 989 were prepared.

Using a nitrobenzoyl compound of Formula II as a reactant and reducing it, followed in certain cases by an addition reaction (such as alkylation), the products of Examples 329, 330, 350 through 354, 372, 375, 473 and 484 were prepared.

Using a chloromethylbenzoyl compound of Formula II as a reactant and performing a substitution reaction, the products of Examples 159, 161, 162, 294, 361, 362, 363 and 367 were prepared.

Using an acetyloxybenzoyl compound of Formula II as a reactant and performing a hydrolysis, the products of Examples 151, 165, 203, 271, 285, 333, 349 and 614 were prepared.

Using a hydroxybenzoyl compound of Formula II as a reactant and performing an alkylation or esterification, the products of Examples 144, 286, 335, 345, 358, 359, 360, 365, 366 and 385 were prepared.

Using a compound of Formula II as a reactant and performing the stated reaction under the conditions (additional reactant, base or acid and solvent) set forth in Table II, the products of Examples 149, 164, 166, 368, 369, 373, 374, 376, 386 and 541 were prepared.

TABLE II

| Example No. | Compound Prepared, Reactants, Reaction Conducted and Conditions |
| --- | --- |
| 149 | N-benzoyl-N'-t-butyl-N'-(4-methanesulfonylbenzoyl)hydrazine was prepared from N-benzoyl-N'-t-butyl-N'-(4-methyl thiobenzoyl)hydrazine using metachloro perbenzoic acid in methylene chloride in an oxidation reaction. |

TABLE II-continued

| Example No. | Compound Prepared, Reactants, Reaction Conducted and Conditions |
|---|---|
| 164 | N-benzoyl-N'-t-butyl-N'-(4-carboxybenzoyl)hydrazine was prepared from N-benzoyl-N'-t-butyl-N'-(4-methoxycarbonylbenzoyl)hydrazine sodium hydroxide as a base and methanol as solvent in a hydrolysis reaction. |
| 166 | N-benzoyl-N'-t-butyl-N'-(4-(2,2-dichloroethenyl)benzoyl)hydrazine was prepared from N-benzoyl-N'-t-butyl-N'-(4-formylbenzoyl)hydrazine using triphenylphosphine in carbon tetrachloride as solvent in a Wittig-type reaction. |
| 376 | N-(3-carboxybenzoyl)-N'-t-butyl-N'-(3-toluoyl)hydrazine was prepared from N-(3-cyanobenzoyl)-N'-t-butyl-N'-(3-toluoyl)hydrazine using potassium hydroxide as base in methanol solvent in a hydrolysis reaction. |
| 386 | N-(4-(1-methylethenyl)benzoyl)-N'-t-butyl-N'-(3-toluoyl)hydrazine was prepared from N-(4-acetylbenzoyl)-N'-t-butyl-N'-(3-toluoyl)hydrazine using methyltriphenylphosphonium bromide and n-butyl lithium as base and tetrahydrofuran solvent in a Wittig reaction. |
| 541 | N-(4-(2-hydroxyethyl)benzoyl)-N'-t-butyl-N'-(3,5-dimethylbenzoyl)hydrazine was prepared from N-(4-(2-acetoxyethyl)benzoyl)-N'-t-butyl-N'-(3,5-dimethylbenzoyl)hydrazine using sodium hydroxide as base and methanol as solvent in a hydrolysis. |

By following substantially the processes for preparing the compounds of the present invention as described above and as exemplified by the illustrative preparation the compounds of Examples 635 to 639 and 642 and using the appropriately substituted reactants, the compounds of Examples 640, 641 and 643 to 645 were prepared.

By following substantially the processes for preparing the compounds as described above and as exemplified by the illustrative preparation of the compounds of Examples 646, 648, 654, 656, 659 and 660 and using the appropriately substituted reactants, the compounds of Examples 647, 649 to 653, 655, 657, 658 and 661 and 681 were prepared.

By following substantially the procedures in processes described above as exemplified above by the preparation of the compounds of Examples 682, 683, 688, 689, 691, 699 and 702 and using the appropriately substituted reactants, the compounds of Examples 684 to 687, 690, 692 to 698, 700, 701, 703 to 721 and 991 were prepared.

By following substantially the procedures in the processes described above and as exemplified by the preparation of the compounds of Examples 722, 723, 724, 727, 729, 733, 737, 738, 739, 743, 754 and 755 and using the appropriately substituted reactants, the compounds of Examples 725, 726, 728, 730 to 732, 734 to 736, 740 to 753, 756 and 992 were prepared.

By following substantially the procedures in the processes described above and as exemplified by the preparation of the compounds of Examples 764, 765, 766, 767, 772, 778 and 787 and using the appropriately substituted reactants, the compounds of Examples 768 to 771, 773 to 777, 779 to 786 and 788 to 794 were prepared.

By following substantially the procedures in Example 802 (without catalyst) or 809 (with catalyst) and using the reactants shown below in Table XI, the products of Examples 802 to 818 were prepared.

Examples 820 and 821 were made generally in accordance with the procedures for Example 822 above.

The (trimethylsilylmethyl)hydrazine, trifluoroalkyl hydrazine and (2-carbomethoxy-2-propyl)hydrazine were made generally in accordance with the procedures from Noll, J. E.; Sprier, J. L.; Daubert, B. F.; JACS 73, 3867, (1951); Hung, S. C.; Le; Breton, G. C.; JOC 46, 5413, (1981); and Organic Synthesis Vol 5, pg. 43, respectively. From these starting materials, Examples 795–801, 819 and 823–828 were made generally in accordance with the procedure for Example 822 above.

The reactants shown below in Table III were used to prepare Examples 795–801, 819–828 and 969–978.

TABLE III

| Ex. No. | Compound of Formula III | Compound of Formula IV | Compound of Formula VI |
|---|---|---|---|
| 795 | 2,3-dimethyl benzoylchloride | (1-methyl-2,2,2-trifluoroethyl) hydrazine | 2,4-dichloro benzoylchloride |
| 796 | 2,3-dimethyl benzoylchloride | (1-methyl-2,2,2-trifluoroethyl) hydrazine | 3,5-dimethyl benzoylchloride |
| 797 | 2,3-dimethyl benzoylchloride | (1-methyl-2,2,2-trifluoroethyl) hydrazine | 2-nitro-5-toluoylchloride |
| 798 | benzoylchloride hydrazine | (1-methyl-2,2,2-trifluoroethyl) | benzoylchloride |
| 799 | 3,4-dichloro benzoylchloride | (2,2,2-trifluoroethyl) hydrazine | 3,4-dichloro benzoylchloride |
| 800 | 4-chlorobenzoyl chloride | (2,2,2-trifluoroethyl) hydrazine | 4-chlorobenzoyl chloride |
| 801 | benzoylchloride | (2,2,2-trifluoroethyl) hydrazine | benzoylchloride |

By following substantially the procedures in Examples 829, 837 and 853, the products of Example Nos. 830 to 836, 838 to 852 and 854 were prepared.

By following substantially the procedures in Example 855, the products of Example Nos. 856 to 863 were prepared.

By following substantially the procedures in Example 864, the products of Example Nos. 865 to 869 were prepared.

Example No. 874 was prepared by following substantially the procedures in Example 873 and using N'-t-butyl-N'-benzoylhydrazine, 3-methylbenzoyl formic acid, methanesulfonyl chloride in toluene and saturated sodium bicarbonate.

By following substantially the procedures in Example 878, the products of Example Nos. 875 to 877 were prepared.

By following substantially the procedure in Example Nos. 882 and 883, the products of Example Nos. 879 to 881 and 884 to 886 were prepared.

In general, for the control of helminths, the compounds of the present invention may be used at a dosage corresponding to from about 0.1 to 200 mg/kg body weight. The exact amount of dosage for a given situation can be routinely determined and depends on a variety of factors, for example, the substance used, the kind of helminth, the formulation used and the state of the human or animal infested with the helminth.

The term "anthelmintic" as employed in the specification and claims of this application is to be construed as any means which adversely affect the existence or growth of the target helminths at any stage in their life cycle. Such means can comprise a complete killing action, eradication, arresting in growth, inhibition, reducing in number, reproductive inhibition (such as ovicidal or chemisterilant) or any combination thereof.

The term "control" as employed in the specification and claims of this application is to be construed as meaning "anthelminticidal" or protecting humans or animals from helminth damage. By "anthelmintically effective amount" is meant that dosage of active substance sufficient to exert helminth "control."

The compounds of the present invention, for practical applications, can be utilized in the form of compositions or formulations. Examples of the preparation of compositions and formulations can be found in *Controlled Action Drug Forms* by J. C. Colbert, Noyes Data Corp., Park Ridge, N.J. (1974).

The steroid molting hormone 20-hydroxyecdysone is the physiological inducer of molting and metamorphosis in insects. Certain insect cell lines retain sensitivity to the hormone and respond by proliferative and differentiative transformation. Such responses in Drosophilia $K_c$ cells have been used to demonstrate that N-t-butyl-N,N'-dibenzoylhydrazine (Example No. 3) mimics the action of 20-hydroxyecdysone by causing the formation of neuron-like processes, an inhibition of cell proliferation and induction of acetylcholinesterase. Example No. 3 also competes with $^3$H-ponasterone A for high affinity ecdysone receptor sites from $K_c$ cell extracts. Resistant cell populations selected by growth in the continued presence of either Example No. 3 or 20-hydroxyecdysone are insensitive to both compounds and exhibit a decreased titer of measurable ecdysone receptors. Example No. 3 thus represents the first known non-steroidal ecdysone agonist. Although it is less potent than 20-hydroxyecdysone in both whole cell and cell-free receptor assays, this insecticide and its analogs possess useful ecdysone type action.

The two non-peptide hormones known to regulate insect metamorphosis and development are the sesquiterpenoid juvenile hormone and the steroid molting hormone 20-hydroxyecdysone having the following formula:

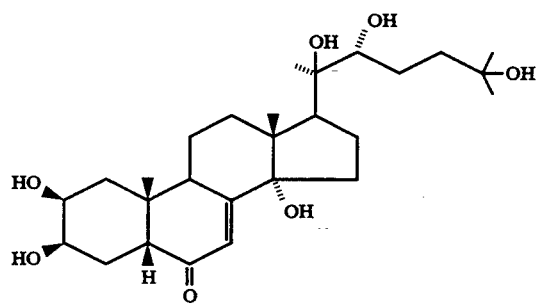

Juvenile hormone, which is responsible for maintenance of a larval or nymphal state in immature molting insects, has been the subject of intensive chemical research and has served as a model for an entire class of structurally diverse juvenoid mimics. By contrast, while the use of edysones as insecticides has been considered, progress has been hampered by the structural complexity and synthetic inaccessibility of the active steroids for commercial scale field application. In addition, insects have developed powerful mechanisms for catabolizing and clearing ecdysones between molts. Thus the molting hormones have received little attention from the pesticide industry.

The discovery made over 50 years ago that ketophenanthrenes can have estrogenic effects has spawned both an active area of basic biomedical research and an approach to novel drug development. However, the absence of such non-steroidal ecdysone agonists and antagonists has prevented similar advances in the field of insect endocrinology. Example No. 3 is a non-steroidal ecdysone agonist in Drosophila $K_c$ cell extracts, whole cells and in larval Lepidoptera.

Figure 1B:
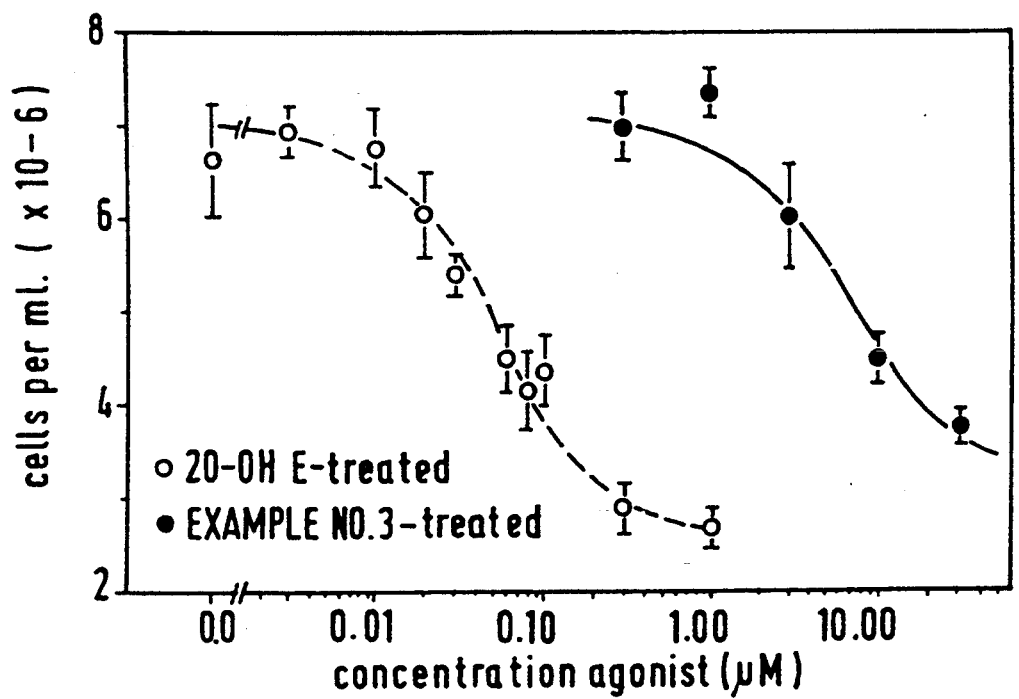

The $K_c$ cell line, originally derived from Drosophila embryos, has proven to be an excellent model system for the study of ecdysone action on differentiation and morphogenesis and early events in genomic regulation of protein synthesis. Naive $K_c$ cells divide every 24 hours and are roughly spherical; however, they differentiate after exposure for two days or more to active ecdysones by halting their proliferation, clumping tightly and forming long, branched processes. Cells treated with Example No. 3 are in all respects indistinguishable morphologically from 20-hydroxyecdysone-treated cells. However, the hormone ($EC_{50}=0.035$ uM) is about 137-fold more potent than Example No. 3 ($EC_{50}=4.8$ uM) at initiating process elaboration and inhibiting proliferation (FIG. 1). These characteristic responses have heretofore been restricted to active ecdysones, and cannot be induced by cyclic nucleotides, dimethyl sulfoxide, various mammalian growth factors or serum deprivation.

Figure 2:
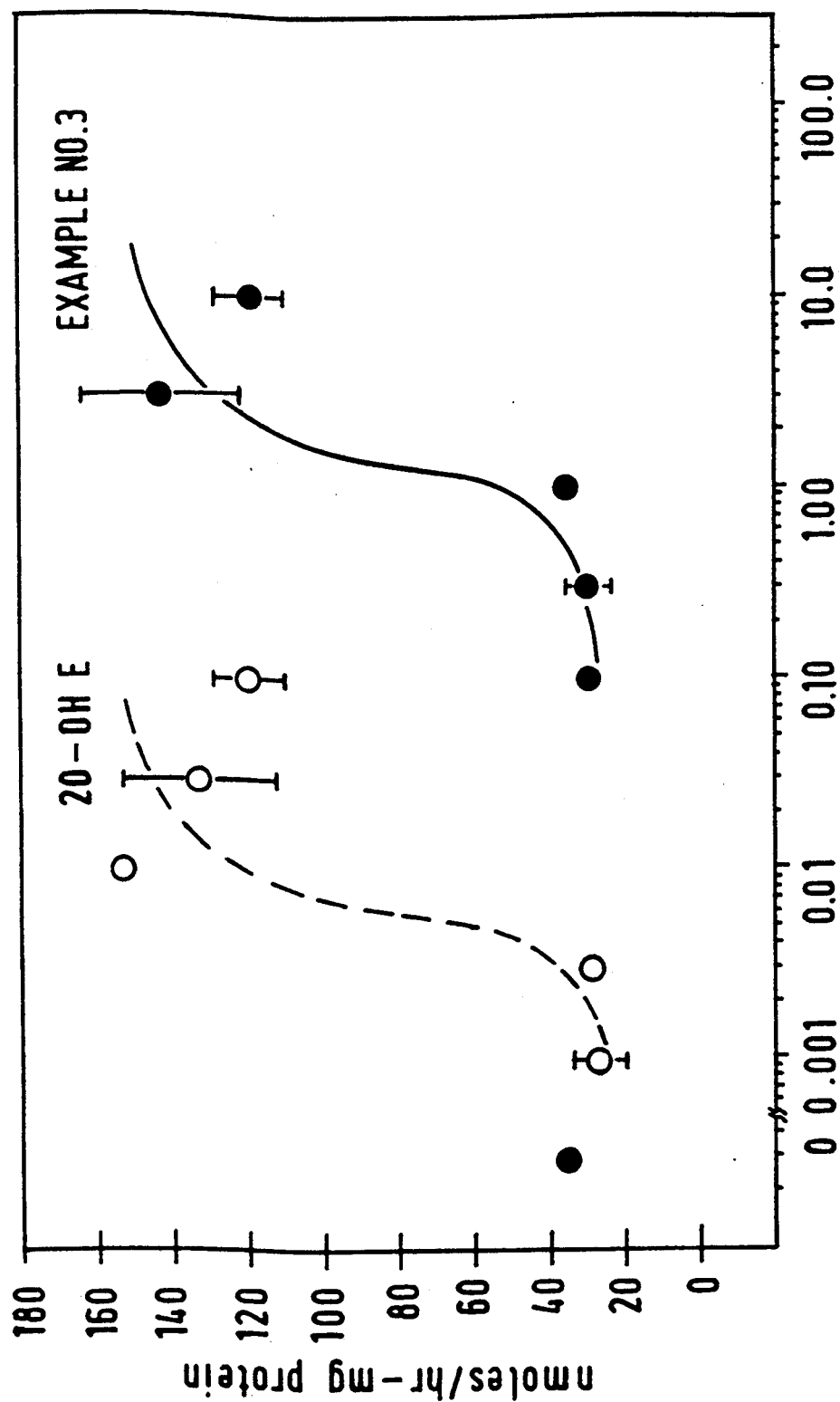
FIG. 2. Induction of acetylcholinesterase by varying concentrations of 20-hydroxyecdysone and Example No. 3. $K_c$ cells at an initial density of $3\times 10^6$ cells/ml (10 ml per sample) were incubated with the agonist for three days. After harvesting by centrifugation at $3000\times g$, the cell pellets were washed with Robb's Drosophila saline (18, 2×5 ml) at 4° C., then lysed by sonication in 1 ml of phosphate buffer (pH 7.4, I=0.1M) containing 0.5M NaCl, 0.25M EDTA and 0.5% TRITON ® X-100. See Cherbas, 197 Science 275 (1977). Triton is a registered trademark of Rohm and Haas Company for a alkylaryl polyoxyethylene glycol surfactant. After centrifugation at $16,000\times g$, the supernatants were assayed for acetylcholinesterase activity by an adaptation of the method of Ellman et al., 7 Biochem. Pharmacol. 88 (1961), by subtracting out any 412 nm absorbance observed in incubations in the presence of $2\times 10^{-5}$ eserine sulfate. Thus reaction mixtures contained 50 μl of enzyme extract, 20 μl eserine (blank tubes only) and 1.0 ml of 0.5 mM acetylthiocholine, 0.3 mM dithiobisnitrobenzoic acid in phosphate buffer (pH 7.4, I=0.1M). Incubations were at 25° C. for two hours; reactions in active tubes were terminated by addition of eserine. Absorbance at 412 nm was then measured. Protein concentration in extracts was measured by the Biorad method. Data are means of triplicate cell incubations ±S.D. After substraction for eserine-sensitive acetylcholinesterase activity in non-treated cells (30 nmol/hr-mg protein) the $EC_{50}$ for 20-hydroxyecdysone and Example No. 3 were determined to be 0.007 and 1.05 μM, respectively.

In addition, both 20-hydroxyecdysone ($EC_{50}=0.007$ uM) and Example No. 3 ($EC_{50}=1.05$ uM) cause an increase in the specific activity of acetylcholinesterase (FIG. 2), again a response previously restricted to the ecdysones. Thus 20-hydroxyecdysone is 150-fold more potent in this assay than is Example No. 3. The slopes of the process elaboration, cell density and acetylcholinesterase induction dose-response curves are roughly parallel for both compounds, indicating that although the chemical structures are totally different, the action of both the steroid and Example No. 3 is at the same receptor, but with different affinities.

Figure 3A:
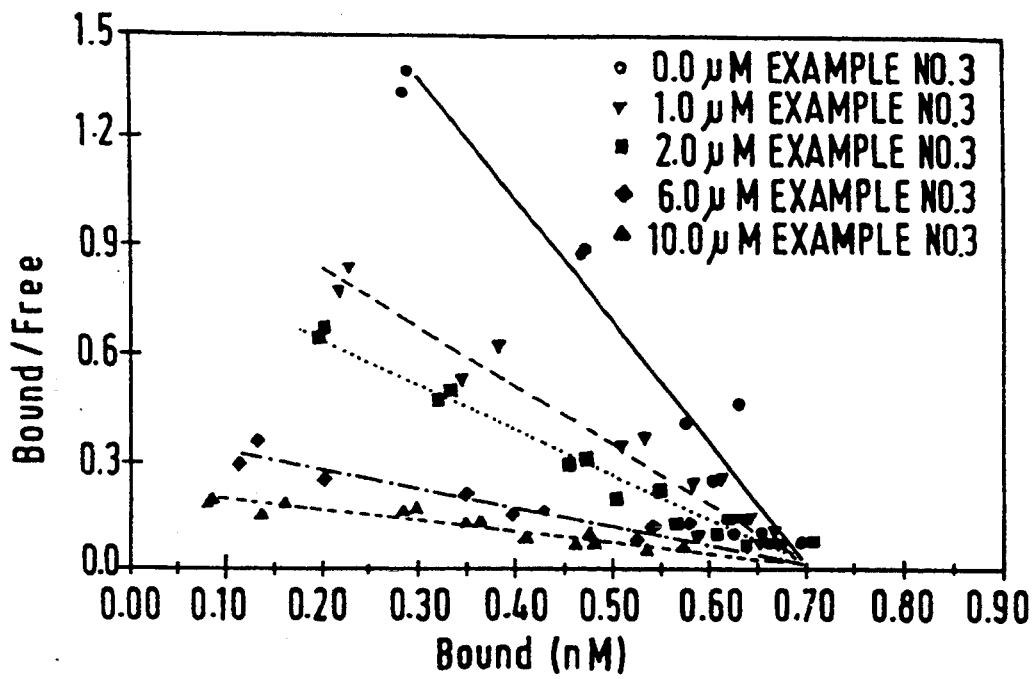
FIG. 3A. Scatchard plot of $^3$H-ponasterone A binding to $K_c$ cell cytosolic receptor extracts in the presence of differing concentrations of Example No. 3. Cytosolic extract preparation and ecdysteroid receptor assays were essentially as described in Sage, 111 Meth. in Enzymol. 458 (1985). Example No. 3 was added in 1 ul DMSO to 50 ul of radioligand in 10 mM Tris buffer (pH 7.2) and 50 ul of undiluted cytosol extract. After incubation overnight at 0.5° C., bound label was separated from free by addition of 300 ul 1% HCl-washed charcoal (Sigma) and 0.1% Dextran T70 (Pharmacia) in Tris buffer, centrifugation ($13,000\times g$, 3 min, 4° C.) and liquid scintillation counting of a 300 ul aliquot of the supernatant in 15 ml Hydrofluor (National Diagnostics). Points are means of duplicate determinations. For incubations in the absence of Example No. 3 $K_d=0.29$ nM and $B_{max}=0.79$ nM.
Figure 3B:
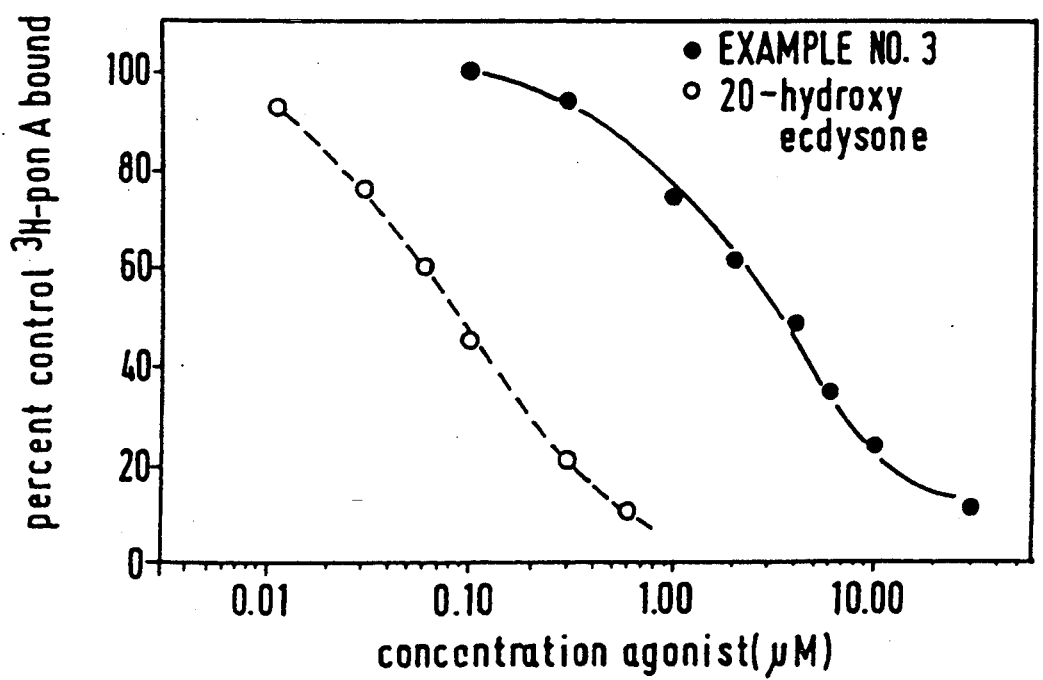
FIG. 3B. Relative ability of 20- hydroxyecdysone and Example No. 3 to displace $^3$H-ponasterone A from cytosolic receptor extracts. Conditions were as in FIG. 3 except that only 0.5 nM ponasterone A was used. Points are means of duplicate determinations. For 20-hydroxyecdysone $EC_{50}=0.1$ μM while for Example No. 3 $EC_{50}=3.0$ μM. Control binding=10 femtomoles $^3$H-ponasterone A bound per mg cytosol protein.

Biochemical evidence for the action of Example No. 3A on an ecdysone receptor is shown in FIG. 3A. These data show a Scatchard plot of $^3$H-ponasterone A binding to $K_c$ cell cytosol extracts in the presence of Example No. 3; increasing concentrations of Example No. 3 lead to an increase in the equilibrium dissociation constant $K_d$ while the value of $B_{max}$ remains the same. The binding thermodynamics observed indicate a competitive mode of inhibition of $^3$H-ponasterone A binding and imply that ponasterone A and Example No. 3 share a common binding domain in the receptor. The experimentally determined values $K_d=0.29$ nM and $B_{max}=0.71$ nM calculated from the binding isotherm in the absence of Example No. 3A compare favorably with values obtained by other workers. FIG. 3B shows the relative ability of 20-hydroxyecdysone and Example No. 3 to displace 0.5 nM $^3$H-ponasterone A from the receptor; the hormone ($IC_{50}=0.1$ uM) has 30-fold greater apparent affinity than Example No. 3 ($IC_{50}=3.0$ uM).

When $K_c$ cells are incubated for four weeks in either $1 \times 10^{-6}$M 20-hydroxyecdysone or $1 \times 10^{-4}$M Example No. 3, the surviving cells do not respond to either compound by elaborating processes or slowing their proliferation. Both of these resistant populations also show a dramatically reduced capacity to bind $^3$H-ponasterone A relative to untreated cells.

Resistant $K_c$ cell populations were reared by incubating cells at an initial density of $8 \times 10^6$ cells/ml with hormone or Example No. 3. The cells killed by treatment provide a feeder layer for the resistant populations. When tested for ecdysteroid receptor activity, it was found that cell populations reared in the presence of $1\times10^{-6}$M 20-hydroxyecdysone, $1\times10^{-4}$M Example No. 3 and solvent controls bind 1.5, 1.4 and 10.1 femtomoles $^3$H-ponasterone A per mg cytosolic protein, respectively. Ponasterone binding was assayed as described below and protein concentrations were determined using the Biorad method. This cross-resistance is compelling evidence that 20-hydroxyecdysone and Example No. 3 act through the ecdysone receptor.

The benzoylphenylurea insect growth regulators 1-(4-chloro-phenyl)-3-(2,6-difluorobenzoyl)urea and 1-(3,5-dichloro-4-(3-chloro-5-trifluoromethyl-2-pyridyloxy)phenyl)-3-(2,6-difluorobenzoyl)urea at saturating concentrations failed to produce ecdysone-like responses in whole $K_c$ cells and did not displace $^3$H-ponasterone A from cytosolic receptor extracts. Thus, at the biochemical and cellular levels Example No. 3 is distinct in its actions from the benzoylphenylureas.

Example No. 3 causes the premature initiation of molting at all stages of larval development of the tobacco hornworm, *Manduca sexta*. This phenomenon occurs without an increase in the endogenous ecdysone titers. Example No. 3 likewise provokes the initiation of molting in larval abdomens in the absence of a source of endogenous hormone. Though substantially less active than 20-hydroxyecdysone in Drosophila cell assays, Example No. 3 was 30 to >670-fold as active as the authentic molting hormone in bioassays utilizing isolated larval abdomens or intact hornworms. This reversal in potency can be attributed to the superior transport properties and metabolic stability of Example No. 3 relative to 20-hydroxyecdysone.

The following 25 examples were tested to determine their ability to induce rapid molting in *M. sexta* larvae which correlates well with their relative apparent $K_c$ cell receptor affinities: 3, 10, 13, 16, 24, 27, 28, 30, 45, 60, 80, 83, 104, 107, 138, 172, 200, 379, 428, 481, 489, 529, 724 and 835. Example No. 3 and its analogs are relatively persistent ecdysone agonists which halt feeding in larval Lepidoptera by forcing an ultimately lethal, developmentally premature molt.

As described previously, in in vitro bioassays where differential metabolic and transport effects were inconsequential, Example No. 3 was consistently less active than 20-hydroxyecdysone. However, Example No. 3 is extraordinarily potent at promoting molting in larvae of the tobacco hornworm. This is due to a direct action of the compound on target tissues and not via elevation of endogenous ecdysone titers. This is the insecticidally significant mode of action of Example No. 3 and many of its analogs in lepidopteran larvae.

Lepidoptera display the onset of a larval molt by slippage of the head capsule down over the mandibles during formation of an underlying pharate head capsule; this morphological marker accompanies epidermal apolysis which ordinarily occurs at or near peak molting hormone titers. Example No. 3 causes a rapid, premature apolysis in newly ecdysed fifth instar day 0 (L5DO) *M. sexta* larvae. Clear signs of head capsule apolysis are evident 24 hours after the initiation of feeding.

Figure 4A:
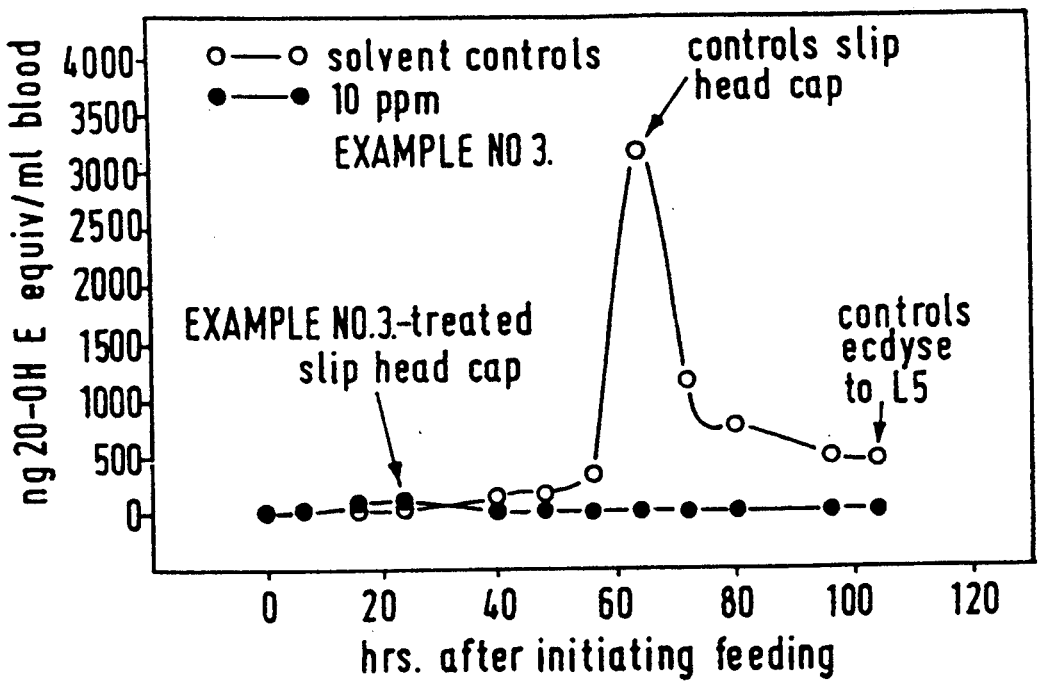
FIG. 4. Effects of 10 ppm Example No. 3 administered in artificial diet to newly ecdysed fourth instar (L4) M. sexta, monitoring (A)immunoreactive hemolymph ecdysteroid titers and (B)weight gain. Ecdysteroid titers were measured by a radioimmunoassay adapted from Warren et al., 40 Experientia 393 (1984) with Protein A-Staph. aureus suspension (Sigma) used as the reagent to separate bound from free ligand. The antiecdysone antiserum was formed by reaction of 20-hydroxyecdysone with carboxymethoxyamine resulting in the corresponding ecdysteroid 6-oxime acid. The antiserum recognizes alpha-ecdysone with a 2.7-fold greater affinity than 20-hydroxyecdysone, using commercially available $^3$H-alpha ecdysone as the radioligand (New England Nuclear). Data are expressed in 20-hydroxyecdysone equivalents, for which the log-logit standard curve commonly had a correlation coefficient r>0.99. All samples were diluted appropriately in borate buffer pH 8.0 and assayed in duplicate. For both ecdysteroid titer and weight determinations 10 individuals per time point were used, and all data points are means. All larvae described in this paper were reared in a long day photoperiod (16L:8D) at 25° C., and were purchased as eggs (Carolina Biological Supply Co.).
Figure 4B:
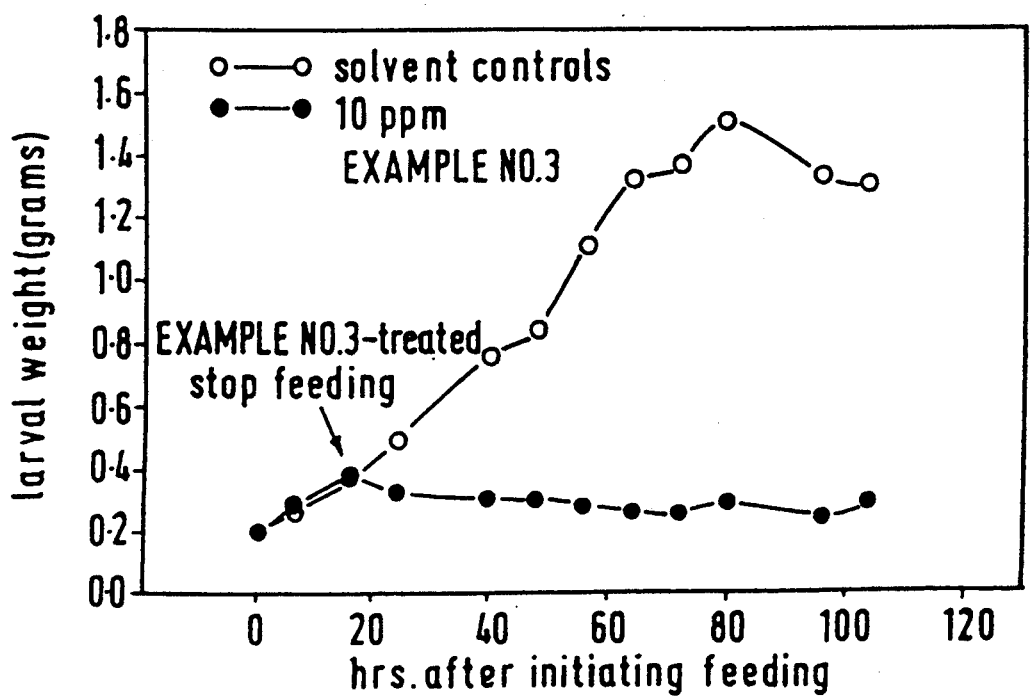

The effect of Example No. 3 on immunoreactive ecdysone titers and weights of developing L4 *M. sexta* larvae are shown in FIG. 4. It may be observed that the treated larvae undergo head capsule slippage after only 24 hours, without any elevation of ecdysone titers; simultaneously further feeding and weight gain ceases.

Larvae treated with Example No. 3 are unable to ecdyse (shed their old cuticle) successfully; hemorrhage of hemolymph and molting fluid took place and the pharate larvae eventually died without completing the molt.

The relative potency of 20-hydroxyecdysone and Example No. 3 at initiating development in isolated abdomen or intact hornworm assays is shown in Table IV.

TABLE IV

Relative potency of 20-hydroxyecdysone and Example No. 3 at inducing the onset of-molting in ligated *M. sexta* abdomens and L5Do whole larvae.

| Bioassay | 50% effective dose | |
|---|---|---|
| | 20-hydroxyecdysone | Example No. 3 |
| L4D1 abdomens (ug inject./abdomen) | 35.2 | 1.3 |
| L5D3 abdomens (ug inject./abdomen) | 30.7 | 1.1 |
| L5D0 larvae, injected (ug/g body wt.) | 181.0 | 3.4 |
| L5D0 larvae, oral (ppm in diet) | >2000 | 3.0 |

L4D1 means fourth instar, first day after molting. L4 animals 36 hours after ecdysis were ligated, decapitated and next day injected with varying doses of compound in 1-2 ul DMSO. They were scored as follows: 0=normal L4 abdomens with no L5 crochets or spiracle apolysis; 1=exposed dorsal vessel (response to moderate levels of molting hormone in the presence of low JH levels); 2=L5 crochets formed but no spiracle apolysis; 3=L5 crochets formed and mild spiracle apolysis; 4=strong molting response, both L5 crochets and spiracle cuticle synthesized. These methods are an adaptation of the method of J. W. Truman, L. M. Riddiford, L. Safranek, 39 Dev. Biol 247 (1974). Injection and scoring of L5D3 abdomens (weighing 6.5-7.5 g) are also adaptations of previous methods in H. F. Nijhout, 22 J. Insect Physiol. 453 (1976). Mature feeding stage fifth instar animals weighing 8.5-9.5 g were ligated and decapitated, and immediately injected with Example No. 3 in 2-5 ul DMSO. Animals were held over moistened filter paper at 25° C. and were scored after three days. Scoring was as follows: 0=normal undeveloped blue-green L5D3 abdomen; 1=light dorsal vessel exposure; 2=dorsal vessel well-exposed with mild cuticular blanching, abdominal contraction; 3=complete prepupal cuticle formation with strong abdominal contraction and strong cuticular blanching. For both L4 and L5 abdomens, 50% effective doses were determined by plotting the mean score for all individuals vs. dose, then determining the dose which gives a score of 2.0 and 1.5 respectively. Intact L5D0 hornworms were either allowed to feed on treated commercial black cutworm diet or injected into a proleg and scored after 48 hours. The 50% effective dose was calculated by plotting percentage of the population bearing a prematurely apolysed head capsule vs. dose. For all experiments in this table at least 5 different doses with 10 animals per dose were used.

The prothoracic glands are the only known source of 20-hydroxyecdysone precursors in hornworm larvae, and after ligation and removal of the thorax the abdomens are convenient preparations of target tissues. When injected into L4D1 abdomens 20-hydroxyecdysone elicited apolysis of spiracular cuticle and the formation of new fifth instar larval crochets (sclerotized hooks at the bottom of the proleg). However, Example No. 3 is 30-fold more potent in this assay than the molting hormone.

When injected into L5D3 abdomens, Example No. 3 was again 30 times as potent as 20-hydroxyecdysone at initiating events related to pupal formation. These results imply that Example No. 3 is capable of stimulating the epidermal cells to undergo apolysis and to synthesize the appropriate proteins necessary for either larval or pupal cuticle formation under the modulating influence of juvenile hormone, in a manner precisely analogous to stimulation by 20-hydroxyecdysone.

The dosage differences between the two compounds was even more dramatic in bioassays on intact (unligated) L5D0 hornworms. If the compounds are injected, Example No. 3 was 67-fold as effective as 20-hydroxyecdysone, while if administered orally, it was over 670-fold as potent.

Figure 5:
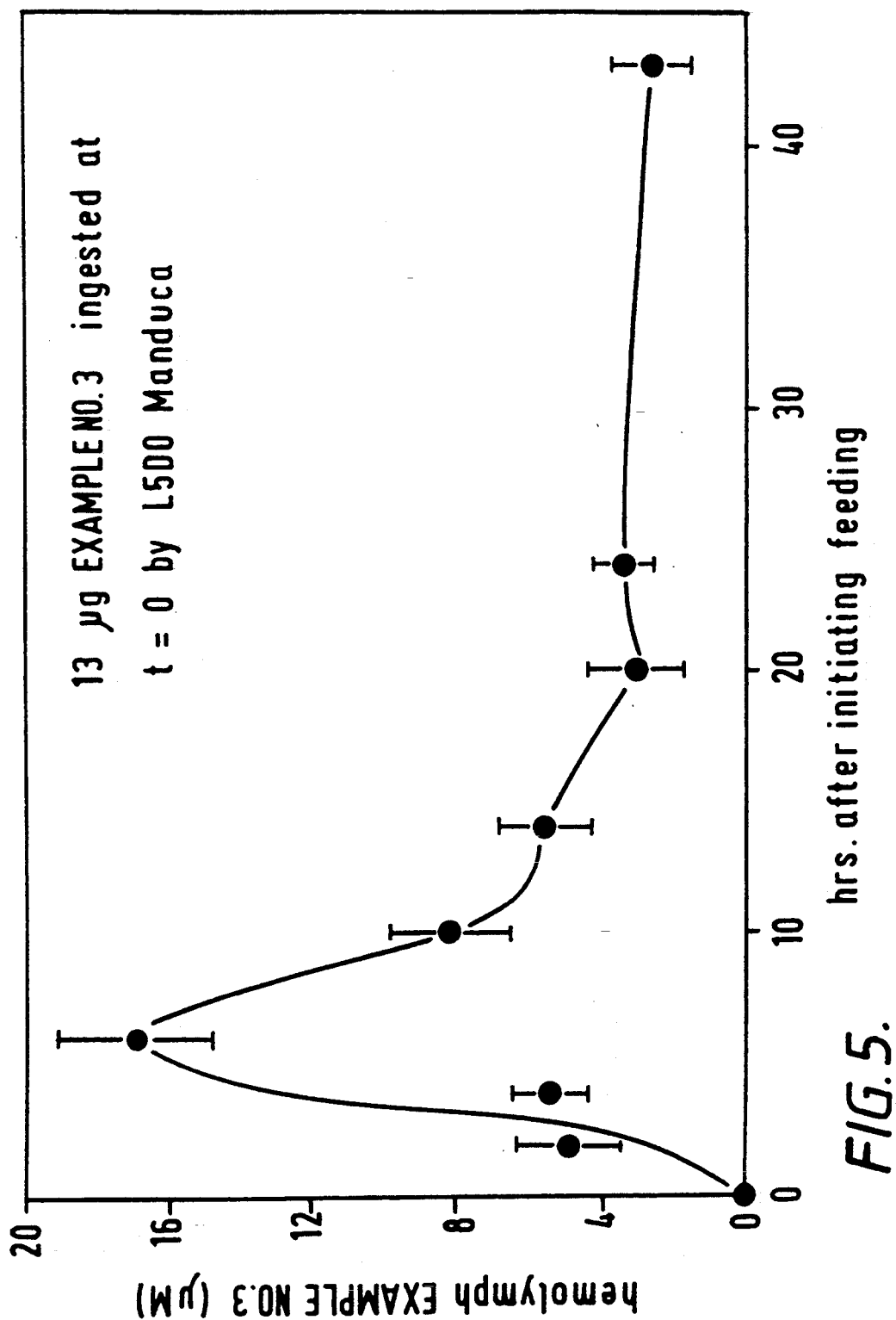
FIG. 5. Hemolymph titers of $^{14}$C-Example No. 3 in L5 hornworms after feeding on 10 μg/gr of the radiolabelled compound. Newly ecdysed L5 M. sexta larvae were starved for 12 hours and then offered 350 mg chunks of artificial diet containing 13 μg of the radiolabelled Example No. 3 (1-$^{14}$C-carbonyl, >99% radiochemically pure, spec. act. 3.09 mCi/mmole, synthesized at Rohm and Haas Research Laboratories). At specified times thereafter larvae were bled into calibrated tubes and the hemolymph volume measured. Example No. 3 was recovered from the hemolymph by adding excess NaCl in 500 μl of 1% aqueous HCl and extracting with 3×1 ml ethyl acetate/acetonitrile (2:1), using vigorous vortexing and centrifugation between washes. The pooled organic layers were evaporated to dryness and spotted on 500 μm normal phase silica gel thin layer chromatography plates (Analtech), and developed in dichloromethane/acetonitrile/acetic acid (67:33:1). Radioactivity was analyzed by either autoradiography, scraping the spot corresponding to parent compound and liquid scintillation counting or using a Berthold LB 2842 Linear Analyzer and comparison to a $^{14}$C-Example No. 3 calibration curve. When the radioactivity corresponding to the parent Example No. 3 on TLC was scraped, extracted and run on reversed phase HPLC (35% acetonitrile in water, 35° C., Alltech Applied Sciences 3 μm particle size C18 Adsorbosphere column), the radioactivity almost quantitatively eluted with authentic Example No. 3 standard. Data are means of five to eight individuals ±S.E.M.

Hemolymph concentrations of $^{14}$C-Example No. 3 were measured by feeding L5D0 hornworm larvae artificial diet containing the labelled compound. At specified intervals thereafter measured volumes of hemolymph were collected, extracted and analyzed by thin layer chromatography and high performance liquid chromatography. FIG. 5 shows that administration of 10 ug/g of the compound (about a 95% effective dose for premature molting at this stage) resulted in peak hemolymph concentrations of 16 uM, at six hours after the initiation of feeding. Blood levels then declined rapidly, but remained at a residual level of about 3 uM for at least 36 hours thereafter. By contrast, feeding up to 2000 ppm 20-hydroxyecdysone failed to elicit head capsule slippage in L5D0 hornworm larvae, indicating that hemolymph ecdysone titers were well below those usually observed during a molt (about 6 uM).

Although the apparent binding affinity of Example No. 3 to $K_c$ cell extracts was 30-fold lower than that of 20-hydroxyecdysone, Example No. 3 is clearly much more potent at eliciting whole animal effects, apparently due to its longevity in the hemocoele after ingestion. The peak concentrations of Example No. 3 in the hemolymph at 10 ug/g oral dose exceeded by 3 to 5 fold those required for a 50% response in process elaboration in whole $K_c$ cells and in displacement of $^3$H-ponasterone A from its receptor in $K_c$ cell extracts. By contrast orally administered 20-hydroxyecdysone is probably metabolized and cleared rapidly.

Figure 6:
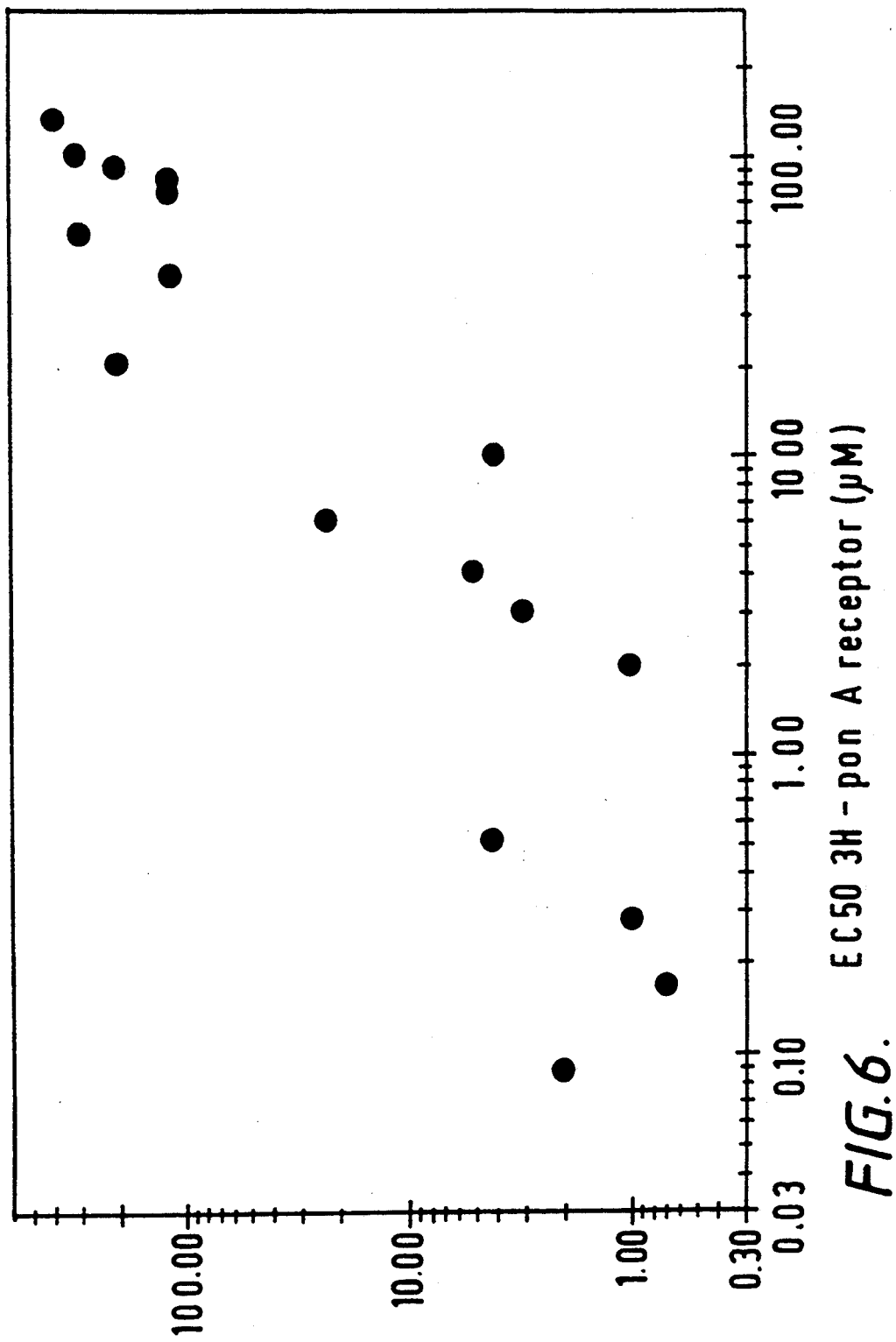
FIG. 6. Correlation of apparent $K_c$ cell ecdysteroid receptor affinity and induction of premature molting in L3D0 M. sexta larvae for Example No. 3 analogs. $^3$H-ponasterone A receptor displacement assays were as described herein. Premature molt induction of L3D0 hornworms was measured by admixing different concentrations of analogs in 0.5% DMSO:acetone (1:1) into artificial diet, then allowing the larvae to feed for 48 hours (10 individuals per treatment). The $EC_{50}$ was determined by plotting percentage of the treatment population bearing a prematurely slipped head capsule vs. dose in the diet.

The relative potencies of the previously listed 24 analogs of Example No. 3 were tested in vitro on Drosophila $K_c$ cell receptor binding and compared with their ability to promote premature head capsule apolysis in L3D0 hornworm larvae (FIG. 6). Apparent receptor binding affinity correlates highly with insecticidal activity in vivo (r=0.88). These data argue that at least for this population of compounds the toxicologically significant mode of action is ecdysonergic, and that the N-alkyl-N,N'-diacyl hydrazine binding domains of both the dipteran $K_c$ cell receptor and the lepidopteran epidermal receptors are similar.

In parallel tests the two benzoylphenylurea insecticides previously mentioned failed to elicit premature molting in intact hornworms or isolated abdomens. These results corroborate those described for Drosophila $K_c$ cells and their ecdysone receptor extracts and provide further evidence that Example No. 3 and the benzoylphenylureas differ markedly in their mode of action. Although both compound classes cause ecdysis failure, the benzoylphenylureas disrupt normal cuticle lamellar deposition, while it appears that Example No. 3 causes a forced, ill-timed synthesis of cuticle before the animal is developmentally competent to molt. In addition, high residual levels of an ecdysone agonist may inhibit the release of and sensitivity to eclosion hormone, which requires a peak of 20-hydroxyecdysone followed by its precipitous decline.

The relative potencies of some 373 of the analogs of Example No. 3 were tested in vitro of Drosophila $K_c$ cell receptor binding $EC_{50}$ (uM) and compared with their Southern Armyworm activity $LC_{50}$(ppm). There is an excellent correlation between apparent receptor binding affinity and Southern Armyworm activity (R=0.79).

Example No. 3 at $1 \times 10^{-4}$M is not significantly bound by our antiecdysone antiserum (representing a >>3125-fold lower binding affinity than 20-hydroxyecdysone). Consequently, Example No. 3 can be used as an agonist in physiological systems, while using ecdysone-specific immunoassays to measure steroid levels. For example, we have observed that ecdysone titers in L4D0 animals treated with Example No. 3 are significantly depressed relative to control levels within four hours after the initiation of feeding. These findings imply that in hornworm larvae ecdysone agonists exert a negative feedback inhibition on hormone biosynthesis, as has been suggested for *Pieris brassicae* pupae.

We have observed the induction of premature head capsule apolysis by Example No. 3 in all larval stages of *M. sexta*. This phenomenon has also been observed in larval Lepidoptera of the families Noctuidae, Pyralidae and Pieridae. Example No. 3 controls dipteran larvae (both houseflies and mosquitoes) and certain coleopteran larvae, and has been shown to inhibit ovariole development in all three orders. This latter activity is consistent with its putative ecdysonergic mechanism of action.

It is known that ecdysteroids occur in helminths, and they are thought to play an important role in molting and development, as they do in insects. (See J. Koolman et al., in *Biosynthesis Metablism and Mode of Action of Invertebrate Hormines*, ed. by J. Hoffmann and M. Porchet, Springer-Verlag Berlin Heidelbery 1984, p. 323–345. Also see H. H. Rees and A. W. H. mendis, ibid., p. 331.)

It is known that 20-hydroxyecdysone controls helminths. It has been shown that Example No. 3 has a mode of action similar to 20-hydroxyecdysone, the apparent receptor binding affinity of 24 analogs of Example No. 3 correlates highly with hornworm activity in vivo and the apparent receptor binding affinity of 373 of the analogs of Example No. 3 correlates excellently with Southern Armyworm activity in vivo. Therefore one would anticipate that each of the Example No. 3 analogs would control helminths.

The N-alkyl-N,N'-diacyl hydrazines are thus a novel class of "ecdysonoids" and are representative members of the "third generation insecticides" having their genesis in insect hormones. C. M. Williams coined the term "hyperecdysonism", an experimentally induced state first described in *Samia cynthia* pupae; clearly, many of the phenomena reported here for Example No. 3 are aptly described by this term. Other modes of action may be encountered in these compounds; for example, significant neurotoxic symptoms in certain Coleoptera in vivo and housefly larval muscle in vitro. However, it is clear that Example No. 3 and its analogs are behaving as nonsteroidal ecdysone agonists in Drosophila $K_c$ cells and in hornworm larvae, and it is anticipated that these findings will extend to other invertebrate systems utilizing ecdysones such as helminths.

I claim:

1. A method of controlling helminths which comprises contacting the helminths with a compound having the formula

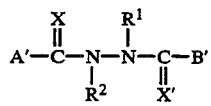

wherein

X and X' are the same or different O, S or NR;

$R^1$ is unsubstituted ($C_3$-$C_{10}$) branched alkyl or ($C_1$-$C_{10}$)alkyl substituted with one to four of the same or different ($C_3$-$C_6$)cycloaklyl, fluoro, straight chain ($C_2$-$C_4$)alkenyl, carboxyl, ($C_1$-$C_3$)alkoxycarbonyl, cyano, cyano substituted ($C_1$-$C_4$)alkyl, tri($C_1$-$C_4$alkylsilyl having independently the stated number of carbon atoms in each alkyl group or tri($C_1$-$C_2$)alkylsilylmethyl having independently the stated number of carbon atoms in each alkyl group;

$R^2$ is hydrogen; ($C_1$-$C_6$)alkyl; ($C_1$-$C_6$)alkoxy($C_1$-$C_6$)alkyl having independently the stated number of carbon atoms in each alkyl group; ($C_1$-$C_6$)alkylthio($C_1$-$C_6$)alkyl having independently the stated number of carbon atoms in each alkyl group; ($C_2$-$C_6$)alkenyl; ($C_2$-$C_6$)alkynyl or phen($C_1$-$C_4$)alkyl where the phenyl ring is unsubstituted or substituted with one to three of the same or different halo, cyano, nitro, hydroxy, ($C_1$-$C_4$)alkyl, halo($C_1$-$C_4$)alkyl, ($C_1$-$C_4$)alkoxy, halo($C_1$-$C_4$)alkoxy, carboxy, ($C_1$-$C_4$)alkoxycarbonyl, ($C_1$-$C_4$)alkanoyloxy, amino, ($C_1$-$C_4$)alkyl amino or ($C_1$-$C_4$)dialkylamino having independently the stated number of carbon atoms in each alkyl group; and A' and B' are the same or different unsubstituted naphthyl or substituted naphthyl where the substituents can be from one to three of the same or different halo; cyano; nitro; hydroxy; ($C_1$-$C_4$)alkoxy; ($C_1$-$C_4$)alkyl; carboxy; ($C_1$-$C_4$)alkoxycarbonyl; ($C_1$-$C_4$)alkanoyloxy; amino; ($C_1$-$C_4$)alkylamino; or ($C_1$-$C_4$)dialkylamino having independently the stated number of carbon atoms in each alkyl group; or unsubstituted phenyl or substituted phenyl where the substituents can be from one to five of the same or different halo; nitro; cyano; hydroxy; ($C_1$-$C_6$)alkyl; ($C_1$-$C_6$)haloalkyl; ($C_1$-$C_6$)cyanoalkyl; ($C_1$-$C_6$)hydroxyalkyl; ($C_1$-$C_6$)alkoxy; ($C_1$-$C_6$)haloalkoxy; ($C_1$-$C_6$)epoxialkyl; ($C_1$-$C_6$)alkoxyalkyl having independently the stated number of carbon atoms in each alkyl group; ($C_1$-$C_6$)alkoxyalkoxy having independently the stated number of carbon atoms in each alkyl group; carboxyoxy; ($C_1$-$C_6$)alkylthioalkoxy having independently the stated number of carbon atoms in each alkyl group; ($C_1$-$C_6$)alkanoyloxyalkyl having independently the stated number of carbon atoms in each alkyl group; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; carboxy; ($C_1$-$C_6$)carboxyalkyl; ($C_1$-$C_6$)alkoxycarbonylalkyl having independently the stated number of carbon atoms in each alkyl group; —COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; alkanoyloxy; amino; ($C_1$-$C_6$)alkylamino; ($C_1$-$C_6$)dialkylamino having independently the stated number of carbon atoms in each alkyl group; amino or ($C_1$-$C_6$)alkylamino where the N of the amino or ($C_1$-$C_6$)alkylamino is substituted with hydroxy, ($C_1$-$C_4$)alkoxy or ($C_1$-$C_4$)alkylthio groups; phenylamino; diphenylamino; —CONRR'; —OCONRR'; —C(NR)NR'R''; —N=NR; —NRCOR'; —NRCO$_2$R'; —N(COR)COR'; —OCONRCOR; sulfhydryl; phenylazo; halothio; ($C_1$-$C_6$)alkylthio; ($C_1$-$C_6$)haloalkylthio; ($C_1$-$C_6$)alkylsulfinyl; ($C_1$-$C_6$)alkylsulfonyl; phenylsulfonyl; ($C_1$-$C_6$)alkylsulfonate; ($C_1$-$C_6$)haloalkylsulfonyloxy; —SO$_2$NRR'; —NRSOR'; —NRSO$_2$R'; —CSR; —CS$_2$R; —NRCSR'; —SCOR; unsubstituted phenyl; phenyl substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; —CR=N—$R^3$ where $R^3$ is hydroxy, ($C_1$-$C_4$)alkyl, ($C_1$-$C_4$)alkoxy, amino, ($C_1$-$C_4$)alkylamino, ($C_1$-$C_4$)dialkylamino having independently the stated number of carbon atoms in each alkyl group, phenylamino, —COR, carboxy, ($C_1$-$C_4$)alkoxycarbonyl, ($C_1$-$C_4$)alkanoyloxy, benzoyl, phenoxycarbonyl or —CONRR'; or when two adjacent positions on the phenyl ring are substituted with alkoxy groups, these groups may be joined to form a 5- or 6-membered dioxolano or dioxano heterocyclic ring; unsubstituted six-membered heterocycle or substituted six-membered heterocycle having one, two, three or four nitrogen atoms and two to five nuclear carbon atoms where the substituents can be from one to three of the same or different halo;

nitro; hydroxy; (C$_1$-C$_6$)alkyl; (C$_1$-C$_6$)alkoxy; (C$_1$-C$_6$)thioalkoxy; carboxy; (C$_1$-C$_6$)alkoxycarbonyl; (C$_1$-C$_6$)carboxyalkyl; (C$_1$-C$_6$)alkoxycarbonylalkyl having independently the stated number of carbon atoms in each alkyl group; —CONRR'; amino; (C$_1$-C$_6$)alkylamino; (C$_1$-C$_6$)dialkylamino having independently the stated number of carbon atoms in each alkyl group; —NRCOR'; (C$_1$-C$_6$)alkylthio; unsubstituted phenyl; or substituted phenyl having one to three of the same or different halo, nitro, (C$_1$-C$_6$)alkyl, (C$_1$-C$_6$)haloalkyl, (C$_1$-C$_6$)alkoxy, (C$_1$-C$_6$)haloalkoxy, carboxy, (C$_1$-C$_4$)alkoxycarbonyl, amino, (C$_1$-C$_4$)alkylamino or (C$_1$-C$_4$)dialkylamino having independently the stated number of carbon atoms in each alkyl group; unsubstituted or substituted five-membered heterocycle selected from furyl, thienyl, triazolyl, pyrrolyl, isopyrrolyl, pyrazolyl, isoimidazolyl, thiazolyl, isothiazolyl, oxazolyl and isooxazolyl where the substituents can be from one to three of the same or different halo; nitro; hydroxy; (C$_1$-C$_6$)alkyl; (C$_1$-C$_6$)alkoxy; carboxy; (C$_1$-C$_6$)alkoxycarbonyl; (C$_1$-C$_6$)carboxyalkyl; (C$_1$-C$_6$)alkoxycarbonylalkyl having independently the stated number of carbon atoms in each alkyl group; —CONRR'; amino; (C$_1$-C$_6$)alkylamino; (C$_1$-C$_6$)dialkylamino having independently the stated number of carbon atoms in each alkyl group; —NRCOR'; (C$_1$-C$_6$)alkylthio; unsubstituted phenyl; or substituted phenyl having one to three of the same or different halo, nitro, (C$_1$-C$_6$)alkyl, (C$_1$-C$_6$)haloalkyl, (C$_1$-C$_6$)alkoxy, (C$_1$-C$_6$)haloalkoxy, carboxy, (C$_1$-C$_4$)alkoxycarbonyl; amino; (C$_1$-C$_4$)alkylamino or (C$_1$-C$_4$)dialkylamino having independently the stated number of carbon atoms in each alkyl group; unsubstituted (C$_1$-C$_{10}$)alkyl or substituted (C$_1$-C$_{10}$)alkyl having one to four of the same or different halo, cyano, nitro, hydroxy, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; unsubstituted (C$_3$-C$_8$)cycloalkyl or substituted (C$_3$-C$_8$)cycloalkyl having one to four of the same or different halo, cyano, nitro, hydroxy, (C$_1$-C$_4$)alkyl, (C$_1$-C$_4$)haloalkyl, (C$_1$-C$_4$)alkoxy, (C$_1$-C$_4$)haloalkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; unsubstituted (C$_2$-C$_8$)alkenyl or substituted (C$_2$-C$_8$)alkenyl or unsubstituted (C$_3$-C$_8$)alkadienyl or substituted (C$_3$-C$_8$)alkadienyl having one to four of the same or different halo, cyano, nitro, hydroxy, (C$_1$-C$_4$)alkyl, (C$_3$-C$_6$)cycloalkyl, (C$_1$-C$_4$)haloalkyl, (C$_1$-C$_4$)alkoxy, (C$_1$-C$_4$)haloalkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; unsubstituted (C$_3$-C$_8$)cycloalkenyl or substituted (C$_3$-C$_8$)cycloalkenyl or unsubstituted (C$_3$-C$_8$)cycloalkadienyl or substituted (C$_3$-C$_8$)cycloalkadienyl having one to four of the same or different halo, cyano, nitro, hydroxy, (C$_1$-C$_4$)alkyl, (C$_1$-C$_4$)haloalkyl, (C$_1$-C$_4$)alkoxy, (C$_1$-C$_4$)haloalkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; or unsubstituted (C$_2$-C$_8$)alkynyl or substituted (C$_2$-C$_8$)alkynyl having one to four of the same or different halo, cyano, nitro, hydroxy, (C$_1$-C$_4$)alkyl, (C$_1$-C$_4$)haloalkyl, (C$_1$-C$_4$)alkoxy, (C$_1$-C$_4$)haloalkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group;

where R, R' and R" are hydrogen or (C$_1$-C$_6$)alkyl; and agronomically acceptable salts thereof.

2. The method according to claim 1 wherein X and X' are oxygen.

3. The method according to claim 1 wherein R$^1$ is a tertiary carbon containing (C$_4$-C$_{10}$)alkyl.

4. The method according to claim 3 wherein R$^1$ is t-butyl.

5. The method according to claim 1 wherein A' and B' are the same or different unsubstituted naphthyl or substituted naphthyl where the substituents can be from one to three of the same or different halo, nitro, (C$_1$-C$_4$)alkoxy, (C$_1$-C$_4$)alkyl, amino, (C$_1$-C$_6$) alkylamino or (C$_1$-C$_6$)dialkylamino having independently the stated number of carbon atoms in each alkyl group; or unsubstituted phenyl or substituted phenyl where the substituents can be from one to five of the same or different halo; nitro; cyano; hydroxy; (C$_1$-C$_6$)alkyl; (C$_1$-C$_6$)haloalkyl; (C$_1$-C$_6$)cyanoalkyl; (C$_1$-C$_6$)hydroxyalkyl; (C$_1$-C$_6$)epoxialkyl; (C$_1$-C$_6$)alkoxy; (C$_1$-C$_6$)haloalkoxy; (C$_1$-C$_6$)alkoxyalkyl having independently the stated number of carbon atoms in each alkyl group; (C$_1$-C$_6$)alkoxyalkoxy having independently the stated number of carbon atoms in each alkyl group; (C$_1$-C$_6$)alkylthioalkoxy having independently the stated number of carbon atoms in each alkyl group; (C$_1$-C$_6$)alkoxycarbonyloxy; (C$_1$-C$_6$)alkanoyloxyalkyl having independently the stated number of carbon atoms in each alkyl group; unsubstituted (C$_2$-C$_6$)alkenyl; (C$_2$-C$_6$)alkenyl substituted with halo, cyano, (C$_1$-C$_4$)alkyl or (C$_1$-C$_4$)alkoxy; (C$_2$-C$_6$)alkenyloxy; (C$_2$-C$_6$)alkenylcarbonyl; (C$_2$-C$_6$)alkenyloxycarbonyloxy; unsubstituted (C$_2$-C$_6$)alkynyl; (C$_2$-C$_6$)alkynyl substituted with halo or (C$_1$-C$_4$)alkyl; carboxy; (C$_1$-C$_6$)carboxyalkyl; (C$_1$-C$_6$)alkoxycarbonylalkyl having independently the stated number of carbon atoms in each alkyl group; —COR; (C$_1$-C$_6$)haloalkylcarbonyl; (C$_1$-C$_6$)alkoxycarbonyl; (C$_1$-C$_6$)haloalkoxycarbonyl; (C$_1$-C$_6$)alkanoyloxy; (C$_1$-C$_6$)alkoxycarbonylalkoxy having independently the stated number of carbon atoms in each alkyl group; amino; (C$_1$-C$_6$)alkylamino; (C$_1$-C$_6$)dialkylamino having independently the stated number of carbon atoms in each alkyl group; —CONRR'; (C$_2$-C$_6$)alkenylcarbonylamino; (C$_1$-C$_6$)hydroxyalkylaminocarbonyl; —OCONRR'; —NRCOR'; —NRCO$_2$R'; —CR=NHNC(O)NH$_2$; thiocyanato; isothiocyanato; (C$_1$-C$_6$)thiocyanatoalkyl; (C$_1$-C$_6$)alkylthio; —S(O)R; (C$_1$-C$_6$)alkylsulfonyl; (C$_1$-C$_6$)alkylsulfonyloxy; —SO$_2$NRR'; (C$_1$-C$_6$)alkylthiocarbonyl; —NRCSR'; unsubstituted phenyl; substituted phenyl having one to three of the same or different halo, cyano, nitro, (C$_1$-C$_4$)alkyl, (C$_1$-C$_4$)haloalkyl, (C$_1$-C$_4$)alkoxy, carboxy, amino, (C$_1$-C$_4$)alkylamino or (C$_1$-C$_4$)dialkylamino having independently the stated number of carbon atoms in each alkyl group; phenoxy where the phenyl ring is unsubstituted or substituted with one to three of the same or different halo, cyano, nitro, (C$_1$-C$_4$)alkyl, (C$_1$-C$_4$)haloalkyl, (C$_1$-C$_4$)alkoxy, carboxy, amino, (C$_1$-C$_4$)alkylamino or (C$_1$-C$_4$)dialkylamino having independently the stated number of carbon atoms in each alkyl group; benzoyl where the phenyl ring is unsubstituted or substituted with one to three of the same or different halo, cyano, nitro, ($C_1$-$C_4$)alkyl, ($C_1$-$C_4$)haloalkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; benzoyloxy($C_1$-$C_6$)alkyl; phenylthio($C_1$-$C_6$)alkyl where the phenyl ring is unsubstituted or substituted with one to three of the same or different halo, cyano, nitro, ($C_1$-$C_4$)alkyl, ($C_1$-$C_4$)haloalkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; —CR=N—$R^3$ where $R^3$ is hydroxy, ($C_1$-$C_4$)alkyl, ($C_1$-$C_4$)alkoxy, amino, ($C_1$-$C_4$)alkylamino or ($C_1$-$C_4$)dialkylamino having independently the stated number of carbon atoms in each alkyl group, phenylamino, —COR or benzoyl; ($C_2$-$C_6$)oxiranyl; acetylthiosemicarbazone; pyrrolyl; oxazolyl, unsubstituted or substituted with one or two methyl groups; or when two adjacent positions on the phenyl ring are substituted with alkoxy groups, these groups may be joined to form together with the carbon atoms to which they are attached a 5- or 6-membered dioxolano or dioxano heterocyclic ring; where the stated number of carbon atoms in the A and B substituents refers to the number of carbon atoms in the alkyl, alkoxy, alkanoyl, alkenyl or alkenyloxy portion of the substituent and where R and R' are independently hydrogen or ($C_1$-$C_6$)alkyl; and salts thereof.

6. The method according to claim 5 wherein
X and X' are O or S;
$R^1$ is unsubstituted ($C_3$-$C_8$) branched alkyl or ($C_1$-$C_4$) straight chain alkyl substituted with one or two of the same or different ($C_3$-$C_4$)cycloalkyl; and
A' and B' are the same or different unsubstituted naphthyl; or unsubstituted phenyl or substituted phenyl where the substituents can be from one to three of the same or different halo; nitro; cyano; ($C_1$-$C_4$)alkyl; ($C_1$-$C_4$)haloalkyl; ($C_1$-$C_4$)cyanoalkyl; ($C_2$-$C_4$)epoxialkyl; ($C_1$-$C_4$)alkoxy; ($C_1$-$C_4$)alkoxyalkyl having independently the stated number of carbon atoms in each alkyl group; —COZ; carboxy; ($C_1$-$C_4$)alkoxycarbonyl; ($C_1$-$C_4$)alkanoyloxy; ($C_2$-$C_6$)alkenyl; ($C_2$-$C_6$)alkynyl; amino; ($C_1$-$C_4$)alkylamino; ($C_1$-$C_4$)dialkylamino having independently the stated number of carbon atoms in each alkyl group; —CH=NNHC(O)NH$_2$; —C(CH$_3$)=NNHC(O)NH$_2$; —C(C$_2$H$_5$)=NNHC(O)NH$_2$; thiocyanato; ($C_1$-$C_4$)alkylthio; alkylthiocarbonyl; unsubstituted phenyl; substituted phenyl having one to two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one or two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; or when two adjacent positions on the phenyl ring are substituted with alkoxy groups, these groups may be joined to form a 5- or 6-membered dioxolano or dioxano heterocyclic ring; where Z is hydrogen or ($C_1$-$C_4$)alkyl; and 7. The method according to claim 6 wherein
X and X' are O or S;
$R^1$ is branched ($C_3$-$C_8$)alkyl; and
A' and B' are the same or different unsubstituted naphthyl; or unsubstituted phenyl or substituted phenyl having one to three of the same or different halo; nitro; cyano; ($C_1$-$C_4$)alkyl; ($C_1$-$C_4$)haloalkyl; ($C_1$-$C_4$)cyanoalkyl; ($C_1$-$C_4$)alkoxy; ($C_1$-$C_4$)alkoxyalkyl having independently the stated number of carbon atoms in each alkyl group; —COZ; ($C_1$-$C_4$)alkoxycarbonyl; ($C_1$-$C_4$)alkanoyloxy; thiocyanato; unsubstituted phenyl; substituted phenyl having one or two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alky group; and salts thereof.

8. The method according to claim 7 wherein X and X' are oxygen.

9. The method according to claim 8 wherein $R^1$ is t-butyl, $R^2$ is hydrogen and A' and B' are unsubstituted phenyl.

10. A method of controlling helminths which comprises contacting the helminths with a compound having the formula

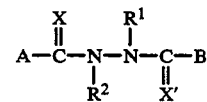

wherein
X and X' are the same or different O, S or NR; provided at least one of X and X' is O;
$R^1$ is unsubstituted ($C_3$-$C_{10}$) branched alkyl or ($C_1$-$C_{10}$)alkyl substituted with one to four of the same or different ($C_3$-$C_6$)cycloalkyl, fluoro, straight chain ($C_2$-$C_4$)alkenyl, carboxyl, ($C_1$-$C_3$)alkoxycarbonyl, cyano, cyano substituted ($C_1$-$C_4$)alkyl, tri($C_1$-$C_4$)alkylsilyl having independently the stated number of carbon atoms in each alkyl group or tri($C_1$-$C_2$)alkylsilylmethyl having independently the stated number of carbon atoms in each alkyl group;
$R^2$ is hydrogen; or ($C_1$-$C_6$)alkyl; and
A and B are the same or different unsubstituted naphthyl or substituted naphthyl where the substituents can be from one to three of the same or different halo; cyano; nitro; hydroxy; ($C_1$-$C_4$)alkoxy; ($C_1$-$C_4$)alkyl; carboxy; ($C_1$-$C_4$)alkoxycarbonyl; ($C_1$-$C_4$)alkanoyloxy; amino; ($C_1$-$C_4$)alkylamino; or ($C_1$-$C_4$)dialkylamino having independently the stated number of carbon atoms in each alkyl group; or
unsubstituted phenyl or substituted phenyl where the substituents can be from one to five of the same or different halo; nitro; cyano; hydroxy; ($C_1$-$C_6$)alkyl; ($C_1$-$C_6$)haloalkyl; ($C_1$-$C_6$)cyanoalkyl; ($C_1$-$C_6$)hydroxyalkyl; ($C_1$-$C_6$)alkoxy; ($C_1$-$C_6$)haloalkoxy; ($C_1$-$C_6$)epoxialkyl; ($C_1$-$C_6$)alkoxyalkyl having independently the stated number of carbon atoms in each alkyl group; ($C_1$-$C_6$)alkoxyalkoxy having independently the stated number of carbon atoms in each alkyl group; carboxyoxy; ($C_1$-$C_6$)alkylthioalkoxy having independently the stated number of carbon atoms in each alkyl group; ($C_1$-$C_6$)alkanoyloxyalkyl having independently the stated number of carbon atoms in each alkyl group;

($C_1$–$C_6$)alkoxycarbonyloxy; ($C_2$–$C_6$)alkenyl optionally substituted with halo, cyano, ($C_1$–$C_4$)alkyl, ($C_1$–$C_4$)alkoxy, ($C_1$–$C_4$)haloalkoxy or ($C_1$–$C_4$)alkylthio; carboxy; ($C_1$–$C_6$)carboxyalkyl; ($C_1$–$C_6$)alkoxycarbonylalkyl having independently the stated number of carbon atoms in each alkyl group; —COR; ($C_1$–$C_6$)haloalkylcarbonyl; ($C_1$–$C_6$)cyanoalkylcarbonyl; ($C_1$–$C_6$)nitroalkylcarbonyl; ($C_1$–$C_6$)alkoxycarbonyl; ($C_1$–$C_6$)haloalkoxycarbonyl; alkanoyloxy; amino; ($C_1$–$C_6$)alkylamino; ($C_1$–$C_6$)dialkylamino having independently the stated number of carbon atoms in each alkyl group; amino or ($C_1$–$C_6$)alkylamino where the N of the amino or ($C_1$–$C_6$)alkylamino is substituted with hydroxy, ($C_1$–$C_4$)alkoxy or ($C_1$–$C_4$)alkylthio groups; phenylamino; diphenylamino; —CONRR'; —OCONRR'; —C(NR)NR'R''; —N=NR; —NRCOR'; —NRCO$_2$R'; —N(COR)COR'; —OCONRCOR'; sulfhydryl; phenylazo; halothio; ($C_1$–$C_6$)alkylthio; ($C_{1-6}$)haloalkylthio; ($C_1$–$C_6$)alkylsulfinyl; ($C_1$–$C_6$)alkylsulfonyl; phenylsulfonyl; ($C_1$–$C_6$)alkylsulfonate; ($C_1$–$C_6$)haloalkylsulfonyloxy; —SO$_2$NRR'; —NRSOR'; —NRSO$_2$R'; —CSR; —CS$_2$R; —NRCSR'; —SCOR; unsubstituted phenyl; phenyl substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$–$C_4$)alkyl, ($C_1$–$C_4$)alkoxy, carboxy, ($C_1$–$C_4$)alkoxycarbonyl, ($C_1$–$C_4$)alkanoyloxy, amino, ($C_1$–$C_4$)alkylamino or ($C_1$–$C_4$)dialkylamino having independently the stated number of carbon atoms in each alkyl group; —CR=N—R$^3$ where R$^3$ is hydroxy, ($C_1$–$C_4$)alkyl, ($C_1$–$C_4$)alkoxy, amino, ($C_1$–$C_4$)alkylamino, ($C_1$–$C_4$)dialkylamino having independently the stated number of carbon atoms in each alkyl group, phenylamino, —COR, carboxy, ($C_1$–$C_4$)alkoxycarbonyl, ($C_1$–$C_4$)alkanoyloxy, benzoyl, phenoxycarbonyl or —CONRR'; or when two adjacent positions on the phenyl ring are substituted with alkoxy groups, these groups may be joined to form a 5- or 6-membered dioxolano or dioxano heterocyclic ring;

where R, R' and R'' are hydrogen or ($C_1$–$C_6$)alkyl; and agronomically acceptable salts thereof.

11. The method according to claim 10 wherein X and X' are oxygen.

12. The method according to claim 11 wherein

A and B are the same or different unsubstituted naphthyl or substituted naphthyl where the substituents can be from one to three of the same or different halo, nitro, ($C_1$–$C_4$)alkoxy, ($C_1$–$C_4$)alkyl, amino, ($C_1$–$C_6$)alkylamino or ($C_1$–$C_6$)dialkylamino having independently the stated number of carbon atoms in each alkyl group; or unsubstituted phenyl or substituted phenyl where the substituents can be from one to five of the same or different halo; nitro; cyano; hydroxy; ($C_1$–$C_6$)alkyl; ($C_1$–$C_6$)haloalkyl; ($C_1$–$C_6$)cyanoalkyl; ($C_1$–$C_6$)hydroxyalkyl; ($C_1$–$C_6$)epoxialkyl; ($C_1$–$C_6$)alkoxy; ($C_1$–$C_6$)haloalkoxy; ($C_1$–$C_6$)alkoxyalkyl having independently the stated number of carbon atoms in each alkyl group; ($C_1$–$C_6$)alkoxyalkoxy having independently the stated number of carbon atoms in each alkyl group; ($C_1$–$C_6$)alkylthioalkoxy having independently the stated number of carbon atoms in each alkyl group; ($C_1$–$C_6$)alkoxycarbonyloxy; ($C_1$–$C_6$)alkanoyloxyalkyl having independently the stated number of carbon atoms in each alkyl group; unsubstituted ($C_2$–$C_6$)alkenyl; ($C_2$–$C_6$)alkenyl substituted with halo, cyano, ($C_1$–$C_4$)alkyl or ($C_1$–$C_4$)alkoxy; ($C_2$–$C_6$)alkenyloxy; ($C_2$–$C_6$)alkenylcarbonyl; ($C_2$–$C_6$)alkenyloxycarbonyloxy; unsubstituted ($C_2$–$C_6$)alkynyl; ($C_2$–$C_6$)alkynyl substituted with halo or ($C_1$–$C_4$)alkyl; carboxy; ($C_1$–$C_6$)carboxyalkyl; ($C_1$–$C_6$)alkoxycarbonylalkyl having independently the stated number of carbon atoms in each alkyl group; —COR; ($C_1$–$C_6$)haloalkylcarbonyl; ($C_1$–$C_6$)alkoxycarbonyl; ($C_1$–$C_6$)haloalkoxycarbonyl; ($C_1$–$C_6$)alkanoyloxy; ($C_1$–$C_6$)alkoxycarbonylalkoxy having independently the stated number of carbon atoms in each alkyl group; amino; ($C_1$–$C_6$)alkylamino; ($C_1$–$C_6$)dialkylamino having independently the stated number of carbon atoms in each alkyl group; —CONRR'; ($C_2$–$C_6$)alkenylcarbonylamino; ($C_1$–$C_6$)hydroxyalkylaminocarbonyl; —OCONRR'; —NRCOR'; —NRCO$_2$R'; —CR=NHNC(O)NH$_2$; thiocyanato; isothiocyanato; ($C_1$–$C_6$)thiocyanatoalkyl; ($C_1$–$C_6$)alkylthio; —S(O)R; ($C_1$–$C_6$)alkylsulfonyl; ($C_1$–$C_6$)alkylsulfonyloxy; —SO$_2$NRR'; ($C_1$–$C_6$)alkylthiocarbonyl; —NRCSR'; unsubstituted phenyl; substituted phenyl having one to three of the same or different halo, cyano, nitro, ($C_1$–$C_4$)alkyl, ($C_1$–$C_4$)haloalkyl, ($C_1$–$C_4$)alkoxy, carboxy, amino, ($C_1$–$C_4$)alkylamino or ($C_1$–$C_4$)dialkylamino having independently the stated number of carbon atoms in each alkyl group; phenoxy where the phenyl ring is unsubstituted or substituted with one to three of the same or different halo, cyano, nitro, ($C_1$–$C_4$)alkyl, ($C_1$–$C_4$)haloalkyl, ($C_1$–$C_4$)alkoxy, carboxy, amino, ($C_1$–$C_4$)alkylamino or ($C_1$–$C_4$)dialkylamino having independently the stated number of carbon atoms in each alkyl group; benzoyl where the phenyl ring is unsubstituted or substituted with one to three of the same or different halo, cyano, nitro, ($C_1$–$C_4$)alkyl, ($C_1$–$C_4$)haloalkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; benzoyloxy($C_1$-$C_6$)alkyl; phenylthio($C_1$-$C_6$)alkyl where the phenyl ring is unsubstituted or substituted with one to three of the same or different halo, cyano, nitro, ($C_1$-$C_4$)alkyl, ($C_1$-$C_4$)haloalkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; —CR=N—$R^3$ where $R^3$ is hydroxy, ($C_1$-$C_4$)alkyl, ($C_1$-$C_4$)alkoxy, amino, ($C_1$-$C_4$)alkylamino or ($C_1$-$C_4$)dialkylamino having independently the stated number of carbon atoms in each alkyl group, phenylamino, —COR or benzoyl; ($C_2$-$C_6$)oxiranyl; acetylthiosemicarbazone; pyrrolyl; oxazolyl, unsubstituted or substituted with one or two methyl groups; or when two adjacent positions on the phenyl ring are substituted with alkoxy groups, these groups may be joined to form together with the carbon atoms to which they are attached a 5- or 6-membered dioxolano or dioxano heterocyclic ring;

where the stated number of carbon atoms in the A and B substituents refers to the number of carbon atoms in the alkyl, alkoxy, alkanoyl, alkenyl or alkenyloxy portion of the substituent and where R and R' are independently hydrogen or ($C_1$-$C_6$)alkyl; and salts thereof.

13. The method according to claim 12 wherein $R^1$ is unsubstituted ($C_3$-$C_8$) branched alkyl or ($C_1$-$C_4$) straight chain alkyl substituted with one or two of the same or different ($C_3$-$C_4$)cycloalkyl; and A and B are the same or different unsubstituted naphthyl; or unsubstituted phenyl or substituted phenyl where the substituents can be from one to three of the same or different halo; nitro; cyano; ($C_1$-$C_4$)alkyl; ($C_1$-$C_4$)haloalkyl; ($C_1$-$C_4$)cyanoalkyl; ($C_2$-$C_4$)epoxialkyl; ($C_1$-$C_4$)alkoxy; ($C_1$-$C_4$)alkoxyalkyl having independently the stated number of carbon atoms in each alkyl group; —COR; carboxy; ($C_1$-$C_4$)alkoxycarbonyl; ($C_1$-$C_4$)alkanoyloxy; ($C_2$-$C_6$)alkenyl; ($C_2$-$C_6$)alkynyl; amino; ($C_1$-$C_4$)alkylamino; ($C_1$-$C_4$)dialkylamino having independently the stated number of carbon atoms in each alkyl group; —CH=NNHC(O)NH$_2$; —C(CH$_3$)=NNHC(O)NH$_2$; —C(C$_2$H$_5$)=NNHC(O)NH$_2$; thiocyanato; ($C_1$-$C_4$)alkylthio; alkylthiocarbonyl; unsubstituted phenyl; substituted phenyl having one to two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one or two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alkyl group; or when two adjacent positions on the phenyl ring are substituted with alkoxy groups, these groups may be joined to form a 5- or 6-membered dioxolano or dioxano heterocyclic ring;

where R is hydrogen or ($C_1$-$C_4$)alkyl; and agronomically acceptable salts thereof.

14. The method according to claim 13 wherein $R^1$ is branched ($C_3$-$C_8$)alkyl; and A and B are the same or different unsubstituted naphthyl; or unsubstituted phenyl or substituted phenyl having one to three of the same or different halo; nitro; cyano; ($C_1$-$C_4$)alkyl; ($C_1$-$C_4$)haloalkyl; ($C_1$-$C_4$)cyanoalkyl; ($C_1$-$C_4$)alkoxy; ($C_1$-$C_4$)alkoxyalkyl having independently the stated number of carbon atoms in each alkyl group; —COR; ($C_1$-$C_4$)alkoxycarbonyl; ($C_1$-$C_4$)alkanoyloxy; thiocyanato; unsubstituted phenyl; substituted phenyl having one or two of the same or different halo, nitro, ($C_1$-$C_4$)alkyl, ($C_1$-$C_4$)alkoxy, carboxy, amino, ($C_1$-$C_4$)alkylamino or ($C_1$-$C_4$)dialkylamino having independently the stated number of carbon atoms in each alky group;

and agronomically acceptable salts thereof.

* * * * *